US012480951B2

(12) United States Patent
Bot et al.

(10) Patent No.: US 12,480,951 B2
(45) Date of Patent: Nov. 25, 2025

(54) METHODS AND COMPOSITIONS FOR T CELL THERAPY

(71) Applicant: Kite Pharma, Inc., Santa Monica, CA (US)

(72) Inventors: Adrian I. Bot, Beverly Hills, CA (US); Justin Budka, Fishers, IN (US); Szu-Ting Chou, Los Angeles, CA (US); Francesca Milletti, Manhattan Beach, CA (US); Vicki Plaks, Santa Monica, CA (US); John M. Rossi, Newbury Park, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 330 days.

(21) Appl. No.: 17/570,917

(22) Filed: Jan. 7, 2022

(65) Prior Publication Data

US 2022/0221463 A1 Jul. 14, 2022

Related U.S. Application Data

(60) Provisional application No. 63/135,711, filed on Jan. 10, 2021.

(51) Int. Cl.

| | |
|---|---|
| ***A61P 35/00*** | (2006.01) |
| ***A61K 40/11*** | (2025.01) |
| ***A61K 40/31*** | (2025.01) |
| ***A61K 40/42*** | (2025.01) |
| ***C12N 5/0783*** | (2010.01) |
| ***G01N 33/50*** | (2006.01) |
| ***G01N 33/574*** | (2006.01) |

(52) U.S. Cl.

CPC ........ *G01N 33/57492* (2013.01); *A61K 40/11* (2025.01); *A61K 40/31* (2025.01); *A61K 40/4211* (2025.01); *A61P 35/00* (2018.01); *C12N 5/0636* (2013.01); *G01N 33/5094* (2013.01)

(58) Field of Classification Search

CPC ......... G01N 33/57492; G01N 33/5094; A61K 35/17; A61K 39/4611; A61K 39/4631; A61K 39/464412; A61P 35/00; C12N 5/0636

USPC ....................................................... 424/93.71

See application file for complete search history.

(56) References Cited

U.S. PATENT DOCUMENTS

| | | | | |
|---|---|---|---|---|
| 5,595,756 A * | 1/1997 | Bally | A61K 9/1272 264/4.1 |
| 2019/0144825 A1 | 5/2019 | Waller et al. | |
| 2021/0023134 A1 | 1/2021 | Go et al. | |

FOREIGN PATENT DOCUMENTS

| | | |
|---|---|---|
| WO | WO-2019/213282 A1 | 11/2019 |
| WO | WO-2019/232510 A1 | 12/2019 |
| WO | WO-2020/193045 A1 | 2/2020 |
| WO | WO-2020/047452 A2 | 3/2020 |
| WO | WO-2020/102770 A1 | 5/2020 |
| WO | WO-2021/168375 A1 | 8/2021 |

OTHER PUBLICATIONS

Heppner et al. (Cancer Metastasis Review 2:5-23; 1983) (Year: 1983).*

Sporn et al ("Chemoprevention of Cancer," Carcinogenesis, vol. 21 (2000), 525-530 (Year: 2000).*

Auerbach et al (Cancer and Metastasis Reviews, 2000, 19: 167-172) (Year: 2000).*

Gura T (Science, 1997, 278(5340): 1041-1042, encloses 1-5) (Year: 1997).*

Lindner et al., Sci. Adv. 2020; 6 : May 20, 2020, p. 6, paragraph 2 (Year: 2020).*

Dagar et al. Journal of Translational Medicine (2023) 21:449 (Year: 2023).*

Levstek L, Janzic L,(2024) Biomarkers for prediction of CAR T therapy outcomes: current and future perspectives. Front. Immunol. 15:1378944. pp. 1-19 (Year: 2024).*

Jain RK (Scientific American, Jul. 1994,58-65 (Year: 1994).*

Gravanis Submitted Mar. 4, 2014. Accepted for publication May 19, 2014. doi: 10.3978/j.issn.2304-3865.2014.05.08 (Year: 2014).*

Hait (Nature Reviews/Drug Discovery, 2010, 9, pp. 253-254) (Year: 2010).*

Worel et al (Blood (2019) 134 (Supplement_1); published Nov. 13, 2019) (Year: 2019).*

Wang et al (Oncotarget, vol. 8, (No. 3), published Dec. 27, 2016) (Year: 2016).*

American Cancer Society "CAR T-cell therapy and its side effects", downloaded from https://www.cancer.org/cancer/managing-cancer/treatment-types/immunotherapy/car-t-cell1.html on Mar. 20, 2024; last revised Dec. 20, 2023) (Year: 2023).*

Guzman et al (Current Oncology Reports (2023) 25:479-489), CAR-T therapy has shown success in treating hematological malignancies (see e.g. p. 480, left column, second paragraph) (Year: 2023).*

Beans (PNAS 2018; 115(50): 12539-12543) (Year: 2018).*

Budka, J. et al. (2021) "Abstract CT661: Pretreatment (PreTx) immune cell phenotypes in peripheral blood associated with the tumor immune contexture, product attributes, and durable clinical efficacy in patients with large B-cell lymphoma (LBCL) teated with axicabtagene ciloleucel (axi-cel)" Cancer Research 81(13)(Suppl):CT166.

(Continued)

*Primary Examiner* — Yan Xiao

(57) ABSTRACT

The disclosure relates to methods of diagnosis and prognosis, compositions for immunotherapies, methods of improving said compositions, and immunotherapies using the same.

15 Claims, 54 Drawing Sheets

Specification includes a Sequence Listing.

(56) References Cited

OTHER PUBLICATIONS

Fraietta, J.A. et al. (2018) "Determinants of response and resistance to CD19 chimeric antigen receptor (Car) T cell therapy of chronic lymphocytic leukemia" Nature 24(5):563-571.
Jain, M.D. et al. (2017) "Concise Review: Emerging Principles from the Clinical Application of Chimeric Antigen Receptor T Cell Therapies for B Cell Malignancies : Principles of CAR T Therapy" Stem Cells 36(1):36-44.
Locke, F.L. et al. (2020) "Tumor burden, inflammation, and product attributes determine outcomes of axicabtagene ciloleucel in large B-cell lymphoma", Blood Advances 4(19):4898-4911.
Petersen, C.T. et al. (2018) "Improving T-cell expansion and function for adoptive T-cell therapy using ex vivo treatment with PI3K[delta] inhibitors and VIP antagonists" Blood Advances 2(3):210-223.
Intl. Search Report-Written Opinion dated May 12, 2022 for Intl. Appl. No. PCT/US2022/011606.
Office Action dated Apr. 20, 2023 for Taiwanese Appl. No. 111100953.
Office Action dated Sep. 12, 2023 for Taiwanese Appl. No. 111100953.
Office Action dated May 14, 2024 for Taiwanese Appl. No. 111100953.
Office Action dated May 21, 2024 for Japanese Appl. No. 2023-541537.
Office Action dated Jan. 13, 2025 for Australian Appl. No. 2022205653.
Office Action dated May 30, 2025 for Korean Appl. No. 10-2023-7026771.
Mousset, C.M. et al. (2019) "Comprehensive Phenotyping of T Cells Using Flow Cytometry" Cytometry Part A, 95A:647-654.

* cited by examiner

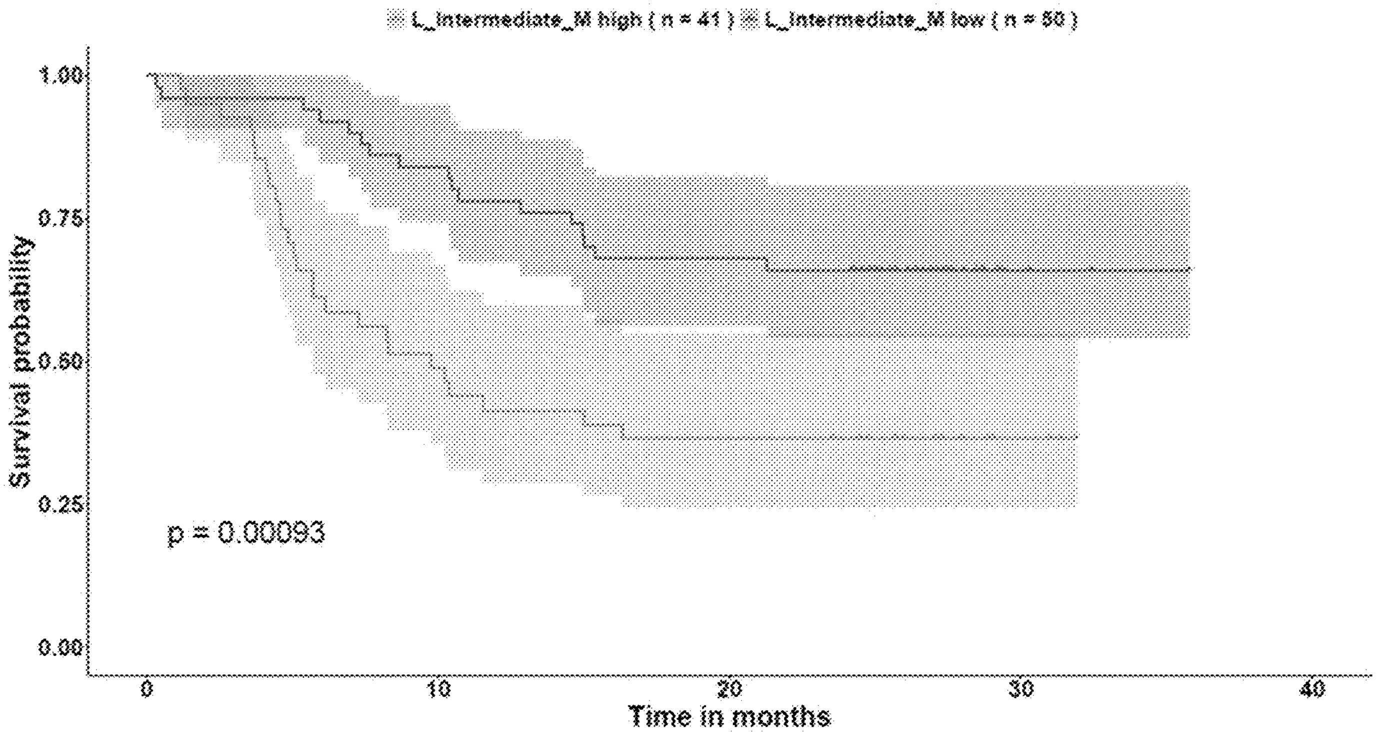

cut-off = 1.922262238 %
Complete Response Rate (High Group) 20 / 41 ( 48.78 % )
Complete Response Rate (Low Group) 34 / 50 ( 68 % )
Obj. Response Rate (High Group) 31 / 41 ( 75.61 % )
Obj. Response Rate (Low Group) 44 / 50 ( 88 % )
Ong. Response (High Group) 12 / 41 ( 29.27 % )
Ong. Response (Low Group) 26 / 50 ( 52 % )
Gd3+ Ntox (High Group) 11 / 41 ( 26.83 % )
Gd3+ Ntox (Low Group) 14 / 50 ( 28 % )
Gd3+ CRS (High Group) 5 / 41 ( 12.2 % )
Gd3+ CRS (Low Group) 6 / 50 ( 12 % )
CARpeak (High Group) 34.40622706 (median)
CARpeak (Low Group) 35.27328 (median)
CARpeak/TumorBurden (High Group) 0.00871919431279621 (median)
CARpeak/TumorBurden (Low Group) 0.0120340722495895 (median)

FIG. 8A cut-off = 0.170504120651575 %
Complete Response Rate (High Group) 42 / 65 ( 64.62 % )
Complete Response Rate (Low Group) 12 / 26 ( 46.15 % )
Obj. Response Rate (High Group) 56 / 65 ( 86.15 % )
Obj. Response Rate (Low Group) 19 / 26 ( 73.08 % )
Ong. Response (High Group) 32 / 65 ( 49.23 % )
Ong. Response (Low Group) 6 / 26 ( 23.08 % )

CARpeak (High Group) = 42.12 (average = 99.74)
CARpeak (Low Group) = 20.95 (average = 53.58)
CARpeak/TumorBurden (High Group) = 0.0492 (average = 0.0121)
CARpeak/TumorBurden (Low Group) = 0.0274 (average = 0.00757)

| | IPI Score <=2 | IPI Score >=3 |
|---|---|---|
| Count | 56 | 45 |
| Median | 0.0746401 | -0.719049 |
| Outliers | 0 | 1 |

P=0.268 (Wilcoxon)

P=0.042 (Wilcoxon)

| | SPDhi | SPDlo |
|---|---|---|
| Count | 50 | 51 |
| Median | 2.15438 | 1.53296 |
| Outliers | 4 | 1 |

P=0.022 (Wilcoxon)

METHODS AND COMPOSITIONS FOR T CELL THERAPY

CROSS REFERENCE TO RELATED APPLICATIONS

This application claims priority to U.S. Provisional Patent Application No. 63/135,711 filed Jan. 10, 2021, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jan. 26, 2022, is named K-1104-US-NP_SL.txt and is 744 bytes in size.

FIELD

The disclosure relates to methods of diagnosis and prognosis, compositions for immunotherapies, methods of improving said compositions, and immunotherapies using the same.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens may be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and T cell receptors (TCR) which comprise binding domains capable of interacting with a particular tumor antigen, allow T cells to target and kill cancer cells that express the particular tumor antigen.

There is a need to understand how attributes of CAR-positive T cells, TCR-positive T cells and other cell-based immunotherapies and patients' immunological status correlate with clinical outcomes.

SUMMARY

In one embodiment, the disclosure provides that collection of apheresis materials from cancer patients prior to any cancer therapy may provide an improved source of cells for immunotherapy, such as CAR T cell immunotherapy. In one embodiment, the disclosure provides that immunotherapy (e.g., CAR T cell immunotherapy) may be administered as part of an early if not earliest line of therapy to maximize efficacy of the immunotherapy, wherein there is a negative impact of other therapies on the quality of the immune cells from apheresis products that may be used to produce the immunotherapy (e.g., CAR T cells). In one embodiment, the method provides for collection of apheresis materials from cancer patients at the diagnostic stage, wherein the method improves the quality of immunotherapies that are derived from apheresis materials. In one embodiment, the disclosure provides predictive biomarkers that allow for pre-treatment blood tests to be done on immunotherapy patients that help stratify the patients based on anticipated response (e.g., objective and ongoing response) to immunotherapy (e.g., CAR T cell therapy). In one embodiment, the method allows for the identification of patients who are likely to achieve durable response with CAR T cell treatment alone. In one embodiment, the method allows for the identification of patients who may benefit from combination therapy. In one embodiment, the combination therapy is given upfront to maximize efficacy (and not after primary/secondary treatment failure). In one embodiment, the method allows for the identification of patients who may benefit from a modified manufacturing process for CAR T cell product production, in which the modifications to the process result in a T cell product that is more fit for immunotherapy. In one embodiment, allows for the identification of patients who may be better candidates for allogeneic or off-the-shelf CAR T cells.

In one embodiment, the disclosure provides methods for optimization of immunotherapy products. In one embodiment, the immunotherapy product comprises CAR T cells. In one embodiment, levels of pre-treatment biomarkers in the patient's blood (e.g., apheresis sample) are correlated with features of the immunotherapy product (e.g., CAR T cell product) prepared from the patient's blood that are associated with immunotherapy response. In one embodiment, the levels of pre-treatment biomarkers in the patient's blood are used to inform modifications to the manufacturing process for the immunotherapy cells (e.g., CAR T cell). In one embodiment, the modifications to the manufacturing process result in an enrichment of certain T cells in the immunotherapy product, which in turn result in an immunotherapy product with better CAR T cell efficacy. In one embodiment, the immunotherapy product comprises autologous CAR T cells. In one embodiment, the immunotherapy product comprises allogeneic CAR T cells. In one embodiment, the immunotherapy comprises T-Cell Receptor-modified T cells. In one embodiment, the immunotherapy comprises tumor infiltrating lymphocytes (TILs). In one embodiment, the immunotherapy product comprises Induced Pluripotent Stem Cells (iPSCs). In one embodiment, the immunotherapy is used to treat cancer. In one embodiment, the cancer is a leukemia or lymphoma. In one embodiment, the cancer is a solid tumor.

In one embodiment, the manufacturing process is adjusted to increase the input material. In one embodiment, the manufacturing process is adjusted to cell selection processes to enrich the immunotherapy product in T cells with specific phenotypes. In one embodiment, the manufacturing process is adjusted to deplete the immunotherapy product of myeloid cells. In one embodiment, the myeloid cells are intermediate monocytes. In one embodiment, the adjustments to the manufacturing process comprise adjustments to the immune cell growth media composition. In some embodiments, the adjustments to the manufacturing process comprise adjustments to the length of the manufacturing process. In one embodiment, the adjustments to the process help overcome negative product factors such as low lymphocyte counts and/or low percentage of specialized cell subsets such as such as CD4+ CD27+ CD28+ T cells and CD4+ CD127+ CD25dim CD27+ CD28+ CCR7+ CD45RA+ T cells, and/or lower intermediate monocytes CD14+ CD16+ cells, or combinations thereof in blood or apheresis cell population.

In one embodiment, the method provides for adjustments to the infused T cell dose that are based on pre-treatment biomarkers to overcome potential mechanisms of treatment resistance. In one embodiment, the pre-treatment biomarkers measured by flow cytometry that comprise levels of pre-manufactured PBMC populations such as CD3+ CD4+ CD127+ CD25dim CCR7+ CD45RA+ CD27+ CD28+ (CD27+ CD28+ Naïve Th); CD3− CD19− CD56− CD11c+ CD14+ CD16+ (intermediate monocytes); CD3+ CD4+ CD127dim CD25+ CCR7+ CD45RA− CD27− CD28+ (CD27− CD28+ TEMRA Treg); lymphocytes to leukocytes/ ratio (hematology baseline cell count); and/or lymphocyte to monocyte ratio (hematology baseline cell count.

In one embodiment, the disclosure provides treatment methods that integrate post-CAR T cell infusion with other treatments aimed at overcoming mechanisms of treatment resistance associated with negative predictive biomarkers. In one embodiment, the biomarkers comprise CD3+ CD4+ CD127+ CD25dim CCR7+ CD45RA+ CD27+ CD28+ (CD27+ CD28+ Naïve Th); CD3− CD19− CD56− CD11c+ CD14+ CD16+ (intermediate monocytes); CD3+ CD4+ CD127dim CD25+ CCR7+ CD45RA− CD27− CD28+ (CD27− CD28+ TEMRA Treg); lymphocytes to leukocytes ratio (hematology baseline cell count); lymphocyte to monocyte ratio (hematology baseline cell count). In one embodiment, the other treatment(s) comprises gamma chain receptor cytokines (e.g., IL-15), myeloid cell modulators (e.g., JAK/STAT inhibitors, agents that modulate detrimental myeloid cell subsets such as intermediate monocytes), bispecific engagers, monoclonal antibodies (e.g., anti-CD20) with or without immune modulators such as iMiDs (e.g., lenalidomide, pomalidomide), CD47 blockade with or without anti-CD20 antibodies.

In some embodiments, the population of T cells is obtained from apheresis material. In some embodiments, the method further comprises engineering the population of T cells to express a CAR. In some embodiments, the CAR T cells are engineered to express a chimeric antigen receptor that targets a tumor antigen. In some embodiments, the chimeric antigen receptor targets a tumor antigen selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGFI)-1, intestinal carboxyl esterase, kappa chain, LAGA-la, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the Al domain of tenascin-C (TnC Al), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens.

In some embodiments, the malignancy is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T-cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma)), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

In some embodiments, the therapeutically effective dose is between 75-200×$10^6$ engineered T cells. In some embodiments, the therapeutically effective dose is 2×$10^6$ CAR T cells per kilogram of body weight. In some embodiments, the engineered T cells are autologous or allogeneic T cells. In some embodiments, the response is measured within about 1 month, about 3 months, about 6 months, about 9 months, or about 12 months after administration of the engineered T cells.

Further exemplary embodiments are provided below:

1. A method of optimization of immunotherapy product (e.g., CAR T cells) manufacturing, wherein product T cell population fitness is improved by increasing the level of CD27+ CD28+ Th cells of naïve phenotype (CCR7+ CD45RA+) in the pre-manufacturing PBMC population.

2. The method of embodiment 1, wherein this may be achieved by enriching for CD27+ CD28+ Th cells of naïve phenotype (CCR7+ CD45RA+) following subject apheresis, by increasing the amount of apheresis material collected until a threshold of CD27+ CD28+ Th cells of naïve phenotype (CCR7+ CD45RA+) is achieved to start the manufacturing process, by selecting the administered dose of CAR T-cells not through the total CAR count per kg but instead by utilizing a count of CD27+ CD28+ Th cells of naïve phenotype (CCR7+ CD45RA+) per kg, and/or by adjusting the T cells product manufacturing conditions (such as, without limitation, length of manufacturing and/or composition of growth media) to increase the levels of the CD27+ CD28+ Th cells of naïve phenotype (CCR7+ CD45RA+).

3. A method to stratify cancer patients as better candidates for allogeneic/off-the-shelf CAR or TCR T-cells to overcome the lack of sufficient positive factors such as CD27+ CD28+ Th cells of naïve phenotype (CCR7+ CD45RA+) in the pre-manufacturing PBMC population obtained from the patient.

4. A method to stratify patients who may be better candidates for combination therapies which could enhance the activity of their CAR or TCR T-cells or reduce the impact of negative factors to improve on the clinical efficacy of the CAR T therapy to overcome the lack of sufficient positive factors such as CD27+ CD28+ Th cells of naïve phenotype (CCR7+ CD45RA+) in the pre-manufacturing PBMC population obtained from the patient.

5. The method of embodiment 4, wherein the combination therapies may be selected from but not limited to immunotherapies (including checkpoints inhibitors anti-PD-1, anti-PD-L1, anti-CTLA-4, etc or any combination thereof), SRC kinase inhibitors (such as dasatinib), T cell bi-specific antibodies, anti-CD20 monoclonal antibody (such as rituximab), anti-4-1BB, anti-CD47, TGF-beta inhibitors or dominant negative TGF-beta, mTOR/AKT agonists, histone deacetylase inhibitors, cyclophosphamide, fluorouracil, gemcitabine, doxorubicin, taxanes and any other form of chemo- or radio-therapies, small molecule inhibitors or antibodies targeted towards enhancing anti-tumor immunity.

6. The method of any one of embodiments 3 through 5, wherein the patient is stratified for manufacturing optimization based on the percentage of CD27+ CD28+ Th cells of naïve phenotype (CCR7+ CD45RA+) in the pre-manufacturing PBMC population and/or identified as a patient that would benefit from allogeneic/off-the-shelf CAR or TCR T cells or combination therapies to maximize the efficacy of the cell therapy.

7. A method of predicting the inflammatory state of a cancer patient and/or the clinical efficacy of the patient's CAR or TCR T cells by quantifying intermediate monocytes and/or total monocytes in the patients' pre-manufacturing PBMC product.

8. The method of embodiment 7, wherein this method is used as an indicator of potential use of anti-inflammatory medications to negate the inflammatory signaling in the periphery.

9. The method of embodiment 8, wherein the anti-inflammatory medications are selected from but not limited to antibodies against IL-6 pathway (such as tocilizumab and siltuximab), corticosteroids (such as dexamethasone), antibodies inhibiting TNF pathway (such as etanercept, infliximab), anakinra, and anti-GM-CSF (such as lenzilumab).

10. A method of predicting IPI score in a cancer patient, wherein the level of intermediate monocytes (% of leukocytes) in the pre-manufacturing PBMCs population is enriched in, and is a marker for, patients with higher IPI scores.

11. A method of estimating clinical efficacy of CAR and TCR T cells comprising quantifying intermediate monocytes and/or total monocytes in the pre-manufacturing PBMC product, which allow for estimation of the patient's tumor burden, which has been shown to be a negative indicator of clinical efficacy of CAR T-cells.

12. The method of embodiment 11, wherein the level of intermediate monocytes and/or total monocytes indicates the use of additional therapeutics to help overcome larger estimated tumor burden such as chemo-, radio-antibody and small molecule based therapies, immunotherapies (including by not limited to checkpoint inhibitors, bispecific engagers), and cell therapies (including but limited to CAR-T, TCR-based and tumor infiltrating lymphocytes) in which tumor burden had shown to be a negative prognostic and/or predictive biomarker.

13. A method of quantifying biomarkers (e.g., intermediate monocytes and/or total monocytes) that allow for the estimation of the patient's hypoxic state, which has been shown to be a negative indicator of clinical efficacy of CAR or TCR T-cells.

14. The method of embodiment 13, wherein the level of intermediate monocytes and/or total monocytes is used as an indicator of supplemental therapeutics to overcome the hypoxic tumor microenvironment (TME).

15. The method of any one of embodiments 13 and 14, wherein the supplemental therapeutics are selected from but not limited to metabolic modulators, VEGF inhibitors (such as bevacizumab), HIF inhibitors, and LDH inhibitors that establish a more normoxic TME.

16. A method of predicting response to immunotherapy (e.g., CAR T cell treatment), wherein monocytes, particularly intermediate monocytes, in pre-manufacturing PBMC population negatively associated with T-cell features in the TME while CD27+CD28+ Naïve Th cells and lymphocytes positively associate with T-cell features in the TME that have been associated with response.

17. The method of embodiment 16, wherein the T-cell features in the TME that have been associated with response include but not limited to activated CD8+T cell subsets (CD3+ CD8+ PD-1+Lag3+/−Tim3− cells) as well as genes associated with activated T cell signature (for example CXCL10, CXC11, GZMA, GZMB, GZMK and Immunosign21).

18. A method of elucidating the overall status of the TME in a cancer patient, wherein the levels of peripheral blood biomarkers, allow for estimation of the tumor immune contexture into varying classes such as immune desert, myeloid imbalanced, immunosuppressive, etc within the TME.

19. The method of embodiment 18, wherein these biomarkers are used to select potential combinatory therapies that may be selected from but not limited to immunotherapies (including checkpoints inhibitors anti-PD-1, anti-PD-L1, anti-CTLA-4, etc or any combination thereof), SRC kinase inhibitors (such as dasatinib), T cell bi-specific antibodies, anti-CD20 monoclonal antibody (such as rituximab), anti-4-1BB, anti-CD47, TGF-beta inhibitors or dominant negative TGF-beta, mTOR/AKT agonists, histone deacetylase inhibitors, cyclophosphamide, fluorouracil, gemcitabine, doxorubicin, taxanes and any other form of chemo- or radio-therapies, small molecule inhibitors or antibodies targeted towards enhancing anti-tumor immunity.

20. A method of quantifying simple biomarkers (CD27+ CD28+ naïve Th) which allow for estimation of the patients eventual infusion bag naïve state following manufacturing and a T-cell rich tumor immune contexture, these have both been shown to be positive indicators of clinical efficacy of CAR T-cells, wherein low levels of these CD27+CD28+ Naïve Th cells indicate for potential use of anti-inflammatory medications, off-the-shelf/allogeneic CAR or TCR T cells, manufacturing optimization, or combination therapies which help modify the tumor microenvironment to improve CAR T cell efficacy.

21. A method of predicting inflammatory state, wherein intermediate monocytes in the pre-manufacturing PBMC population, associate positively with pre-treatment inflammatory (INTL8, Ferritin, CRP, Amyloid A)/tumor hypoxic state (LDH), and negatively with a T-cell rich tumor immune contexture (e.g., activated T cell signatures, CD3+CD8+ PDI+LAG3−TIM3− cells; GZMA, TGIT, LAG3, CXCL10, GZMB, PRF1, STAT1, EOMES, CXCL9, GZMK, CXCL11, HAVCR2, CD3D, IS21) defined pre-treatment.

22. A method where high level of intermediate monocytes indicate the use of anti-inflammatory medications (such as corticosteroids or tocilizumab) and/or immunomodulatory drugs that help overcome the poor TIC (for example, TME modulatory drugs [such as checkpoint inhibitors, drugs that target suppressive myeloid cells and enhance antigen presentation, drugs that stabilize the vasculature, or drugs that normalize tumor metabolism.

23. The method of embodiment 22, wherein, the drugs are administered pre-, during and/or after immunotherapy.

24. A method of predicting whether a patient is likely to respond to CAR or TCR T cell therapy based on the level of intermediate monocytes in the pre-manufacturing PBMC population, wherein the level of intermediate monocytes in the pre-manufacturing PBMC population has a positive association with pretreatment tumor burden which itself is negatively associated with response.

25. A method of using the level of intermediate monocytes and/or total monocytes in the pre-manufacturing PBMC population to estimate the patient's tumor burden, which in turn has been shown to be a negative indicator of clinical efficacy of CAR T-cells, wherein the level of intermediate monocytes serves as an indicator to the use of additional therapeutics to help overcome larger estimated tumor burden such as chemo-, radio-antibody and small molecule based therapies, immunotherapies (including by not limited to check point inhibitors, bispecific engagers), and cell therapies (including but limited to CAR-T, TCR-based and tumor infiltrating lymphocytes) in which tumor burden had shown to be a negative prognostic and/or predictive biomarker.

26. A method of predicting the likelihood of survival of a patient in need of CAR T cell therapy based on the level of CD27+CD28+ Naïve Th cells (% of leukocytes) in the apheresis product that is used to prepare the CAR T cell product, wherein the level of CD27+CD28+ Naïve Th cells (% of leukocytes) in the apheresis product/pre-manufacturing PBMC population is a predictive marker for improved overall survival (OS) and progression free survival (PFS) (optimal cutoff) (i.e., there is a positive association between them, i.e., subjects with pre-treatment CD27+CD28+ naïve Th cells above the listed cutoff have a higher likelihood of survival than those below the selected cutoff).

27. A method of predicting PFS of a patient in need of CAR or TCR T cell therapy based on the level of CD27+ CD28+ Naïve Th cells (% of leukocytes) in the apheresis product that is used to prepare the CAR or TCR T cell product, wherein there are improvements in complete response rates, objective response rates, and CAR or TCR T cell expansion for those subjects above a selected cutoff.

28. A method of stratification whereby subjects with low levels (such as below 0.27%) of CD27+CD28+ naïve Th cells may benefit from another form of therapy (combination therapy, allogeneic CAR T cells, etc) or manufacturing optimization to improve their likelihood of survival.

29. The method of embodiment 28, wherein the low levels are levels below the median of evaluable clinical study subjects, or below between 0.1 and 0.5%, 0.5-1.0%, 1-1.5%, 1.5-2%, 2-5%, 5-10%, 10-15%, 15-20%, 20-25%, 25-50-% etc., or 95-100%.

30. A method whereby subjects with intermediate monocyte levels in the apheresis product (% of leukocytes) below a cutoff of around 1%, 2%, 3%, 4%, 5%, 6%, 7%, 8%, 9%, 10%, 15%, or 20%, preferably between 1 and 5%, even more preferably below around 3% are predicted to have a higher likelihood of survival than those above the cutoff.

31. A method of predicting OS and PFS in a subject in need of CAR or TCR T cell therapy comprising measuring the level of intermediate monocytes in the apheresis product (% of leukocytes) used to prepare the CAR or TCR T cell product and determining whether the level is above or below the cutoff, wherein there are improvements in complete response rates and objective response rates, as well as CAR or TCR T expansion for those subjects below a cutoff of around 3%.

32. A method of patient stratification whereby subjects with high levels of intermediate monocytes (levels above around 1%, 2%, 3%, 4%, 5%, 6%, 7%, 8%, 9%, 10%, 15%, or 20%, preferably between 1 and 5%, even more preferably above around 3%) may benefit from another form of therapy (such as combination therapy with immunotherapies, allogeneic CAR T cells, etc) or manufacturing optimization to improve their likelihood of survival.

33. A method of predicting OS and PFS, response, and CAR or TCR T cell expansion rates in a subject in need of CAR T cell therapy comprising measuring the ratio of CD27+CD28p+Naïve Th cells in the apheresis product (% of leukocytes) to intermediate monocytes (% of leukocytes) used to prepare the CAR or TCR T cell product and determining whether the level is above or below the cutoff of around 0.1, 0.2, 0.3, 0.4, 0.5, 0.6, 0.7, 0.8, 0.9, 1, 1-5, 5-10, 10-20, preferably between 0.05-0.2, 0.2-0.25, 0.25-0.5, 0.5-0.6, 0.6-0.7, 0.7-0.8, 0.8-0.9, 0.9-1, 1-5, 5-10, 10-15, so on and so forth, 95-100, 100-200, 200-300, etc., more preferably 0.1-1, even more preferably 0.1705.

34. The method of embodiment 33, wherein there are improvements in complete response rates, objective response rates, and CAR or TCR T cell expansion for those subjects above the selected cutoff of 0.1705.

35. A method of patient stratification whereby subjects with low levels of CD27+CD28+ naïve Th cells (e.g., levels of around 0.1, 0.2, 0.3, 0.4, 0.5, 0.6, 0.7, 0.8, 0.9, 1, 1-5, 5-10, 10-20, preferably between 0.05-0.2, 0.2-0.25, 0.25-0.5, 0.5-0.6, 0.6-0.7, 0.7-0.8, 0.8-0.9, 0.9-1, 1-5, 5-10, 10-15, more preferably 0.1-1, even more preferably 0.1705), may benefit/are recommended for another form of therapy (combination therapy, allogeneic CAR T cells, etc) or manufacturing optimization to improve their likelihood of survival.

36. A method of predicting objective response in a subject in need of CAR T cell therapy comprising measuring the levels of CD27+CD28+ Naïve Th levels and low intermediate monocytes, whereby a level of CD27+CD28+ Naïve Th levels of/above 0.08% (level above the median, or above 0.05%, 0.1%, 0.2-1%, 1-5%, 5-10%, 10-15%, 15-20%, etc., 95-100%) and/or a level of intermediate monocytes of/below 3% (below the median, or below 1-5%, 5-10%, 10-15%, 15-20%, 20-25%, etc., 95%-100%) indicates an increase likelihood of objective response.

37. The method of embodiment 36, wherein these levels are used for stratifying patients which could benefit from off the shelf/allogeneic CAR or TCR T cells, immunomodulators, bispecific engagers, combination therapies, etc).

38. A method whereby the levels of intermediate monocytes in the pre-treatment apheresis PBMCs and CAR or TCR T cell expansion are measured and used to actively track patients after infusion to estimate what the long-term response will be and if supplemental therapeutics may be useful, wherein high level of intermediate monocytes in the pre-manufacturing PBMC population (wherein high level is a level above the median of intermediate monocytes in the general population, where the median may be between 0-1%, 1-2%, 2-3%, 3-4%, 4-5%, 5-6%, 6-7%, 7-8%, 8-9%, 9-10%, 10-15%, 15-20%, so on and so forth, preferably about 1.7-1.8%) and low level of CAR T cell expansion (wherein low level is a level below the median level of CAR T cell expansion in the general population, where the median is between 0-10, 10-20, 20-30, 30-40, 40-50, 50-60, 60-70, 70-80, 80-90, 90-100) correlates with the highest rate of non-responders.

39. The method of embodiment 38, wherein the method of estimate response based on the baseline intermediate monocyte levels and CAR or TCR expansion post infusion.

40. The method of embodiment 39, wherein subjects that have increased CAR T-cell peak expansion (wherein increased level is a level above the median level of CAR T cell expansion in the general CAR T cell treatment population, where the median is between 0-10, 10-20, 20-30, 30-40, 40-50, 50-60, 60-70, 70-80, 80-90, 90-100, preferably between 40-50) and lower intermediate monocyte levels (wherein a low level is a level below the median of intermediate monocytes in the general population, where the median may be between 0-1%, 1-2%, 2-3%, 3-4%, 4-5%, 5-6%, 6-7%, 7-8%, 8-9%, 9-10%, 10-15%, 15-20%, so on and so forth, preferably about 1.7-1.8%) there were increased ongoing response rates and reduced relapse or non-responder rates compared to the other quadrants.

41. A method whereby the levels of intermediate monocytes in the pre-treatment apheresis PBMCs and CAR T cell expansion are measured and used to actively track patients after infusion to estimate what the ongoing response, likelihood of relapse will be and if supplemental therapeutics may be useful based on the above correlation.

42. The method of embodiment 41, wherein if the subject has a baseline tumor burden above the median level, high intermediate monocytes (above the median, wherein the median may be around 1%, 2%, 3%, 4%, 5%, 6%, 7%, 8%, 9%, 10%, 10-15%, 15-20%, 20-25%, etc., 95-100%, preferably around 1.1%) and low CAR T-cell peak expansion (below the median, wherein the median may be around 5-10%, 10-15%, 15-20%, 20-25%, 25-30%, 30-35%, 35-40%, 40-45%, 45-50%, 50-55%, 55-60%, 60-65%, 65-70%, etc., 95-100%, preferably around 43%), the likelihood of response is low (between 1%-10%, 10-20%, 20-30%, 30-40%, 40-50% ongoing response and bet ween 1%-10%, 10-20%, 20-30%, 30-40%, 40-50% objective response rate).

43. The method of embodiment 42, wherein the levels of intermediate monocytes in the pre-treatment apheresis PBMCs, baseline tumor burden, and CAR or TCR T cell expansion are measured and used to actively track patients after infusion to estimate what the ongoing response and likelihood of objective response will be and if supplemental therapeutics may be useful, based on the above correlation.

44. A method of predicting the likelihood of response to CAR or TCR T cell treatment in a subject in need thereof, comprising measuring the level of CD27+CD28+ Naïve Th (% of Leukocyte) in the pre-manufacturing PBMC population and predicting a high likelihood of response when the level is above an optimal cut-off point (e.g., 0.1036%, 0-0.1%, 0.1%-0.5%, 0.5%-1.0%, 1.0-5%, 5-10%, 10-15%, 10-20%, 20-30%, 30-40%, 40-50%) or above median (e.g. 0.89%, 0-0.1%, 0.1%-0.5%, 0.5%-1.0%, 1.0-5%, 5-10%, 10-15%, 10-20%, 20-30%, 30-40%, 40-50%).

45. A method of selecting a patient for manufacturing optimization, combination therapy, or off-the-shelf/allogeneic CAR or TCR T cell therapy when the levels of CD27+CD28+ Naïve Th (% of Leukocyte) in the pre-manufacturing PBMC population are below the selected cut-off point or median range, which is also an indication of a lower likelihood of ongoing response.

46. A method of predicting the likelihood of response to CAR or TCR T cell treatment in a subject in need thereof, comprising measuring the level of intermediate monocytes (% of leukocyte) in the pre-manufacturing PBMC population and predicting a high likelihood of response when the level is below optimal cutpoint (e.g., 3.02%, 0-0.1%, 0.1%-0.5%, 0.5%-1.0%, 1.0-5%, 5-10%, 10-15%, 10-20%, 20-30%, 30-40%, 40-50%) or below median (e.g., 1.77%, 0-0.1%, 0.1%-0.5%, 0.5%-1.0%, 1.0-5%, 5-10%, 10-15%, 10-20%, 20-30%, 30-40%, 40-50%), wherein intermediate monocytes (% of leukocyte) in the pre-manufacturing PBMC population levels are lower in those subjects that have an ongoing (durable) response as compared to those that undergo relapse or are non-responders.

47. A method whereby levels of intermediate monocytes (% of leukocyte) in the pre-manufacturing PBMC population are measured and used in a method for selecting manufacturing optimization, combination therapy, or off-the-shelf/allogeneic CAR or TCR T cell therapy for subjects above range which have a lower likelihood of ongoing response.

48. A method of predicting response to CAR or TCR T cell therapy based on the levels of CD27+CD28+ Naïve Th cells in the pre-manufacturing PBMC population, whereby patients whom have higher levels of these cells are more likely than not to be responsive to CAR T therapy and less likely than not to need intervention, wherein those with lower levels may need to consider additional modifications to treatment such as combination therapies, optimized manufacturing approaches, off-the-shelf/allogeneic CAR or TCR T cells, next generation CAR constructs, etc 49. A method of predicting response to CAR or TCR T cell therapy whereby patients whom have higher levels of CD27+CD28+ Naïve Th cells (above 0-0.005%, 0.005-0.010%, 0.01%-0.05%, 0.05-0.1%, 0.1-0.5%, 0.5%-1.0%, 1-5%, 5-10%, 10-15%, preferably, above 0.1%) are predicted to be more responsive to CAR T therapy and less likely to need intervention.

50. A method of stratifying patients whereby those with lower levels (below 0-0.005%, 0.005-0.010%, 0.01%-0.05%, 0.05-0.1%, 0.1-0.5%, 0.5%0-1%, 1-5%, 5-10%, 10-15%, preferably below 0.08%) of CD27+CD28+ Naïve Th cells are considered for additional modifications to treatment such as combination therapies, optimized manufacturing approaches, off-the-shelf/allogeneic CAR T cells, next generation CAR constructs, etc.

51. A method of treatment whereby otherwise prior chemotherapeutics, which greatly reduce CD27+CD28+ Naïve Th cells, are moved to later lines of therapy to preserve CD27+CD28+ Naïve Th cells in the pre-manufacturing apheresis PBMC product and the peripheral/tumor environment for CAR T therapy.

52. A method whereby the levels of CD27+CD28+ Naïve Th cells in the pre-manufacturing apheresis PBMC product, along with the positive impact of these cells at the time of apheresis on product fitness, indicate that before any therapies are started for subjects with cancer, apheresis bags are frozen to obtain the best incoming cells for CAR or TCR T-cell therapy.

53. A method of predicting response to CAR or TCR T therapy and need for additional intervention whereby patients whom have lower levels of intermediate monocytes (below 0-1%, 1-5%, 5-10%, 10-15%, 15-20%, preferably below 3%) of these cells are more responsive to CAR T therapy and less likely to need additional intervention. In one embodiment, those patients with higher levels may need to consider additional modifications to treatment such as combination therapies, optimized manufacturing approaches, off-the-shelf/allogeneic CAR or TCR T cells, next generation CAR constructs, etc.

54. The method of embodiment 53, wherein prior chemotherapeutics, which increase these cells, are moved to later lines of therapy to prevent these cells from increasing in the peripheral/TME before CAR or TCR T therapy, wherein before any therapies are started for subjects with cancer, apheresis bags should be frozen to obtain the best incoming cells for CAR T-cell therapy.

55. A method of assessing prognosis, wherein the International Prognostic Index (IPI) score and the level of intermediate monocytes in the apheresis product are positively associated, further indicating that these cells are associated with subjects that have a worse prognosis, and wherein Intermediate monocytes were positively associated with baseline tumor burden. A 56. The method of embodiment 55, wherein the levels of intermediate monocytes are indicative of a less optimal state for CAR or TCR T cell effectiveness and additional interventions/optimizations may be needed to improve the efficacy of CAR T therapy when the levels of these cells are above 3% (or above 0-1%, 1-5%, 5-10%, 10-15%, 15-20%, 20-25%).

57. The method of any one of embodiments 55 and 56, wherein the patients are stratified for manufacturing optimization to remove int. monocytes and increase levels of naïve product cells, for use of next generation CAR constructs, and/or for use of combination therapies with immunomodulators or checkpoint blockade, off-the-shelf/allogeneic CAR or TCR T cells, etc based on the levels of intermediate monocytes.

58. A method of predicting OS and PFS to CAR or TCR T cell treatment in a subject in need thereof comprising measuring the level of CD27-CD28+ TEMRA Treg cells (% of leukocytes) in the apheresis product and determining the likelihood of survival and the PFS based on whether the level is above or below a cutoff, wherein the level of CD27-CD28+ TEMRA Treg cells (% of leukocytes) in the apheresis product associated positively with and is a predictive marker for OS and PFS.

59. The method of embodiment 58, wherein for CD27-CD28+ TEMRA Tregs, subjects with higher levels of these cells (e.g., above a threshold of 0.17%) have higher complete, objective, and ongoing response rates.

60. The method of embodiment 59, wherein, the cutoff threshold is 0.17%.

61. The method of embodiment 59, wherein the cutoff is around 0.1, 0.2, 0.3, 0.4, 0.5, 0.6, 0.7, 0.8, 0.9, 1, 1-5, 5-10, 10-20, preferably between 0.05-0.2, 0.2-0.25, 0.25-0.5, 0.5-0.6, 0.6-0.7, 0.7-0.8, 0.8-0.9, 0.9-1, 1-5, 5-10, 10-15, so on and so forth, 95-100, 100-200, 200-300, etc., more preferably around 0.1705.

62. The method of any one of embodiments 59 through 61, wherein patients are stratified, whereby subjects with low levels of CD27-CD28+ TEMRA Tregs may benefit from another form of therapy (combination therapy, allogeneic CAR or TCR T cells, etc), manufacturing optimization, next generation CAR, etc to improve their likelihood of survival with CAR therapy.

63. A method of predicting CAR or TCR T cell expansion and treatment response, whereby CD27+CD28+ Naïve Th cells positively associate with CAR T peak expansion, which in turn has been shown to positively correlate with response, indicating that these cells have a positive influence on response.

64. The method of embodiment 63, wherein low levels of both CD27+CD28+ Naïve Th cells and CAR T-cell peak expansion correlate with higher non-responder rates while increasing levels of both lead to higher response rates.

65. A method whereby the levels of intermediate monocytes are used to stratify patients for manufacturing optimization to decrease this population in the product to enhance the final CAR T cells, whereby the method improves CAR or TCR expansion and response rate, wherein there is an association between the level of intermediate monocytes in the apheresis product vs. CAR-T peak and CAR-T peak/baseline tumor burden; there is a negative association between the level of intermediate monocytes and CAR T-cell peak expansion (normalized by tumor burden); the levels of intermediate monocytes negatively associate with CAR T peak expansion (CAR/TB) which has been shown to be a positively correlate with response, indicating that these cells should have a negative influence on response and CAR function post infusion; and high int. monocytes are an indicator of utilization of additional therapeutics, next generation CAR constructs, off-the-shelf/allogeneic CAR or TCR T-cells, or manufacturing optimizations to improve efficacy.

66. A method to predict response to CAR or TCR T cell therapy by measuring the levels of intermediate monocytes and the CAR T peak expansion levels, whereby high levels (above median, or above 0-1%, 1-5%, 5-10%, 10-15%, 15-20%, preferably above 3%) of intermediate monocytes in the apheresis product and low (below the median, or below 5-10%, 10-15%, 15-20%, 20-25%, 25-30%, 30-35%, 35-40%, 40-45%, 45-50%, 50-55%, 55-60-%, preferably below 43%) CAR-T peak levels correlate with higher non-responder rates while decreasing intermediate monocyte levels and increased CAR T peak expansion lead to higher response rates.

67. A method of predicting the likelihood of complete response, objective response, and ongoing response to CAR or TCR T cell treatment in a subject in need thereof comprising measuring the ratio of Lymphocyte to Leukocytes in baseline hematology cell counts and predicting the likelihood of complete response, objective response, and ongoing response based on the ratio. In one embodiment, if the ratio is above the optimal cutoff (e.g., where the optimal cutoff may be about 0-5%, 5-10%, 10-15%, 15-20%, 20-25%, 25-30%, 30-35%, 35-40%, 40-45%, 45-50%, etc.) the likelihood of complete response, objective response, and ongoing response is higher than if the ratio is below cutoff (e.g., where the cutoff may be about 0-5%, 5-10%, 10-15%, 15-20%, 20-25%, 25-30%, 30-35%, 35-40%, 40-45%, 45-50%, etc).

68. A method of patient stratification whereby subjects with low levels of lymphocytes to leukocytes are treated with another form of therapy (combination therapy, allogeneic CAR T cells, next generation CAR construct, etc) to improve their likelihood of survival/response and/or are subjected to optimized manufacturing to improve product fitness.

69. A method of patient stratification whereby low levels (or below median, or below 1%, 1-5%, 5-10%, 10-15%, 15-20%, 20-25%, 25-30%, 30-35%, etc, preferably below 5.2) of lymphocytes to leukocytes indicates a higher likelihood of having a toxic event and the prophylactic administration of anti-inflammatory medications (e.g. tocilizumab, steroids) to the patient to prevent toxicity.

70. A method of predicting response to CAR or TCR T cell therapy by measuring the ratio of Lymphocyte to Leukocytes in baseline hematology cell counts, whereby the ratio is negatively associated with tumor burden and thereby positively associated with response.

71. method of stratifying patients for additional intervention to improve efficacy if the pre-manufacturing PBMC lymphocyte to leukocyte ratio is low (or below median, or below 1%, 1-5%, 5-10%, 10-15%, 15-20%, 20-25%, 25-30%, 30-35%, etc, preferably below 5.2) and/or the patient has high tumor burden.

72. A method of estimating the level of inflammatory cytokines CRP, Ferritin, IL6. CRP, ferritin, and IL6 in a cancer patient, which associate with a worse prognosis, by measuring the ratio of Lymphocyte to Leukocytes in baseline hematology cell counts, wherein the ratio of Lymphocyte to Leukocytes in baseline hematology cell counts is negatively associated with the cytokines, which have previously been shown to be pharmacodynamic markers that are negatively correlated with response in DLBCL, optionally wherein if low levels of lymphocytes to leukocytes are quantified, the patient is selected for administration of anti-inflammatory medications pre-during- and/or post CAR T cell therapy.

73. A method of predicting the levels of myeloid cells in a patient, wherein the ratio of Lymphocyte to Leukocytes in baseline hematology cell counts is negatively associated with myeloid cells (more specifically, intermediate monocytes, which are negatively associated with response) and positively associated with CD8 and EM/Effector T-cells.

74. The method of embodiment 73, wherein patients whom have a low ratio of lymphocyte to leukocytes (or below median, or below 1%, 1-5%, 5-10%, 10-15%, 15-20%, 20-25%, 25-30%, 30-35%, etc, preferably below 5.2) are considered for combination therapeutics that attempt to negate the activity of the myeloid compartment and/or for optimization of the manufacturing process to deplete those populations in the product.

75. A method of stratification in cancer treatment wherein subjects with low levels of lymphocytes to monocytes are administered another form of therapy in addition to or alternatively to CAR T cell therapy (e.g., combination therapy, allogeneic CAR T cells, next generation CAR construct, etc) to improve their likelihood of survival and/or wherein the subject is subjected to optimized manufacturing of CAR T cell products to improve product fitness, wherein the ratio of Lymphocyte to Monocytes in baseline hematology cell counts associated positively with and may serve as a predictive biomarker for OS and PFS.

76. A method of predicting response whereby a higher complete, objective, and ongoing response rates is observed in subjects whose ratio of lymphocyte to monocytes is above 0.79, or the ratio is between 0 and 0.5, 0.5-1.0, 1.0-1.5, 1.5-2.0, 2-5, 5-10, 10-15, etc.

77. A method of predicting response to immunotherapy (e.g., CAR T cells), wherein low levels (or below median, or below 1%, 1-5%, 5-10%, 10-15%, 15-20%, 20-25%, 25-30%, 30-35%, preferably below 8%) of lymphocytes to monocytes indicate higher likelihood of having a toxic event and indicate prophylactic use of anti-inflammatory medications (e.g. tocilizumab, steroids) to prevent toxicity.

78. A method of quantifying the ratio of Lymphocyte to Monocytes in baseline hematology cell counts that allow for estimation of the patient's tumor burden, which has been shown to be a negative indicator of clinical efficacy of CAR T-cells.

79. The method of embodiment 78, wherein the ratio of Lymphocyte to Monocytes in baseline hematology cell counts may indicate the use of additional therapeutics to help overcome larger estimated tumor burden such as chemo-, radio-antibody and small molecule based therapies, immunotherapies (including by not limited to check point inhibitors, bispecific engagers), and cell therapies (including but limited to CAR-T, TCR-based and tumor infiltrating lymphocytes) in which tumor burden had shown to be a negative prognostic and/or predictive biomarker.

80. A method of estimating the levels of CRP and IL6 in the serum of a cancer patient, and/or immunotherapy (e.g., CAR T cell therapy) prognosis, by measuring the ratio of Lymphocyte to Monocytes in baseline hematology cell counts, wherein the levels of CRP and IL6 associate negatively with the levels of ratio of Lymphocyte to Monocytes in baseline hematology cell counts and positively with a worse prognosis.

81. A method of stratification of patients wherein if low levels (or levels below median, or levels below 0.05%, 0.05-0.1%, 0.1-0.5%, 0.5-1.0%, 1-5%, 5-10%, 10-15%, preferably below 0.78) of lymphocytes to monocytes are quantified, the patient is administered anti-inflammatory medications.

82. A method of predicting the level of myeloid cells, CD8, and/or EM/Effector cells in the final infusion product by measuring the ratio of Lymphocyte to Monocytes in baseline hematology cell counts, wherein the ratio of Lymphocyte to Monocytes in baseline hematology cell counts associates negatively with myeloid cells and positively with CD8 and EM/Effector T-cells; optionally, this method is further used to stratify patients for combination therapeutics that attempt to negate the activity of the myeloid compartment and/or for optimization of the pre-manufacturing material to deplete those populations.

83. A method of predicting T cell product fitness and response in a cancer patient, wherein the ratio of Lymphocyte to Monocytes in baseline hematology cell counts is negatively associated with intermediate monocytes and correlates with apheresis populations associated with response, including CD27−CD28+ TEMRA and Treg and CD27+CD28+ Naïve and Th cells, wherein high levels (or above median, or above between 0 and 0.5, 0.5-1.0, 1.0-1.5, 1.5-2.0, 2-5, 5-10, 10-15, preferably above 0.8%) of lymphocytes to monocytes in the pre-manufacturing PBMC population are indicative of incoming apheresis material which tracks positively with product fitness and response; wherein low levels (below median, or below between 0 and 0.5, 0.5-1.0, 1.0-1.5, 1.5-2.0, 2-5, 5-10, 10-15, preferably below 0.78%) indicate the need for manufacturing optimization, combination therapy, or next generation CAR therapies or TCR therapies.

An embodiment of the disclosure relates to a method of predicting a likelihood of survival of a patient in need of chimeric antigen receptor (CAR) T cell therapy including: measuring a level of CD27+CD28+ naïve Th cells in an apheresis product from the patient; and determining the likelihood of survival of the patient at least in part from the level of CD27+CD28+ naïve Th cells in the apheresis product. In such an embodiment, the patient is determined to have an increased likelihood of survival if the level of CD27+CD28+ naïve Th cells is over a cut-off percentage value measured as a percentage of total leukocytes, and the patient is determined to have a decreased likelihood of survival if the level of CD27+CD28+ naïve Th cells is below the cut-off percentage value.

An embodiment of the disclosure relates to a method of predicting a likelihood of survival of a patient in need of chimeric antigen receptor (CAR) T cell therapy described above, where the cut-off percentage value is around 0-0.1%, 0.1%-0.5%, 0.5%-1.0%, 1.0-5%, 5-10%, 10-15%, 10-20%, 20-30%, 30-40%, 40-50%, or more preferably around 0.27%.

An embodiment of the disclosure relates to a method of predicting a likelihood of survival of a patient in need of chimeric antigen receptor (CAR) T cell therapy described above, further including: measuring a level of intermediate monocytes in the apheresis product from the patient; and determining the likelihood of survival of the patient at least in part from the level of intermediate monocytes in the apheresis product. In such a method, the patient is determined to have an increased likelihood of survival if the level intermediate monocytes is below a cut-off percentage value measured as a percentage of total leukocytes, and the patient is determined to have a decreased likelihood of survival if the level of intermediate monocytes is above the cut-off percentage value.

An embodiment of the disclosure relates to a method of predicting a likelihood of survival of a patient in need of chimeric antigen receptor (CAR) T cell therapy described above, where the cut-off percentage value is around 1%, 2%, 3%, 4%, 5%, 6%, 7%, 8%, 9%, 10%, 15%, or 20%, preferably between 1 and 5%, and even more preferably below around 3%.

An embodiment of the disclosure relates to a method of predicting a likelihood of survival of a patient in need of chimeric antigen receptor (CAR) T cell therapy described above, further including: measuring a level of CD27−CD28+ TEMRA Treg cells in the apheresis product from the patient; and determining the likelihood of survival of the patient at least in part from the level of CD27−CD28+ TEMRA Treg cells in the apheresis product. In such a method, the patient is determined to have an increased likelihood of survival if the level CD27−CD28+ TEMRA Treg cells is above a cut-off percentage value measured as a percentage of total leukocytes, and the patient is determined to have a decreased likelihood of survival if the level of CD27-CD28+ TEMRA Treg cells is below the cut-off percentage value.

An embodiment of the disclosure relates to a method of predicting a likelihood of survival of a patient in need of chimeric antigen receptor (CAR) T cell therapy described above, where the cut-off percentage value is around 0.1%, 0.2%, 0.3%, 0.4%, 0.5%, 0.6%, 0.7%, 0.8%, 0.9%, 1%, 1-5%, 5-10%, 10-20%, preferably between 0.05-0.2%, 0.2-0.25%, 0.25-0.5%, 0.5-0.6%, 0.6-0.7%, 0.7-0.8%, 0.8-0.9%, 0.9-1%, 1-5%, 5-10%, 10-15%, and more preferably around 0.1705%.

An embodiment of the disclosure relates to a method of predicting a likelihood of survival of a patient in need of chimeric antigen receptor (CAR) T cell therapy described above, further including: measuring a lymphocyte to leukocyte ratio in a baseline hematology count of the patient; and determining the likelihood of survival of the patient at least in part from the lymphocyte to leukocyte ratio. In such a method, the patient is determined to have an increased likelihood of survival if the lymphocyte to leukocyte ratio is above a cut-off value, and the patient is determined to have a decreased likelihood of survival if the lymphocyte to leukocyte ratio is below the cut-off value.

An embodiment of the disclosure relates to a method of predicting a likelihood of survival of a patient in need of chimeric antigen receptor (CAR) T cell therapy described above, where the cut-off value is 1%, 1-5%, 5-10%, 10-15%, 15-20%, 20-25%, 25-30%, 30-35%, and preferably below 5.2%.

An embodiment of the disclosure relates to a method of predicting a likelihood of survival of a patient in need of chimeric antigen receptor (CAR) T cell therapy described above, further including: measuring a lymphocyte to monocyte ratio in a baseline hematology count of the patient; and determining the likelihood of survival of the patient at least in part from the lymphocyte to monocyte ratio. In such a method, the patient is determined to have an increased likelihood of survival if the lymphocyte to monocyte ratio is above a cut-off value, and the patient is determined to have a decreased likelihood of survival if the lymphocyte to monocyte ratio is below the cut-off value.

An embodiment of the disclosure relates to a method of predicting a likelihood of survival of a patient in need of chimeric antigen receptor (CAR) T cell therapy described above, where the cut-off value is between 0 and 0.5, 0.5-1.0, 1.0-1.5, 1.5-2.0, 2-5, 5-10, 10-15, and preferably 0.79.

An embodiment of the disclosure relates to a method for manufacturing an immunotherapy product including: preparing an apheresis product from a blood sample from a subject; measuring a level of CD27+CD28+ naïve Th cells in the apheresis product; and increasing an amount of CD27+CD28+ naïve Th cells collected for processing if the level of CD27+CD28+ naïve Th cells in the apheresis product is below a cut-off percentage value measured as a percentage of total leukocytes in the apheresis product.

An embodiment of the disclosure relates to the method for manufacturing an immunotherapy product described above, where the cut-off percentage value is around 0-0.1%, 0.1%-0.5%, 0.5%-1.0%, 1.0-5%, 5-10%, 10-15%, 10-20%, 20-30%, 30-40%, 40-50%, or more preferably around 0.27%.

An embodiment of the disclosure relates to the method for manufacturing an immunotherapy product described above, further including: measuring a level of intermediate monocytes in the apheresis product; and decreasing the level of intermediate monocytes in the apheresis product prior to further processing if the level of intermediate monocytes in the apheresis product is above a cut-off percentage value measured as a percentage of total leukocytes in the apheresis product.

An embodiment of the disclosure relates to the method for manufacturing an immunotherapy product described above, where the cut-off percentage value is around 1%, 2%, 3%, 4%, 5%, 6%, 7%, 8%, 9%, 10%, 15%, or 20%, preferably between 1 and 5%, and even more preferably around 3%.

An embodiment of the disclosure relates to the method for manufacturing an immunotherapy product described above, further including: measuring a level of CD27-CD28+ TEMRA Treg cells in the apheresis product; and increasing an amount of CD27-CD28+ TEMRA Treg cells collected for processing if the level of CD27-CD28+ TEMRA Treg cells in the apheresis product is below a cut-off percentage value measured as a percentage of total leukocytes in the apheresis product.

An embodiment of the disclosure relates to the method for manufacturing an immunotherapy product described above, where the cut-off percentage value is around 0.1%, 0.2%, 0.3%, 0.4%, 0.5%, 0.6%, 0.7%, 0.8%, 0.9%, 1%, 1-5%, 5-10%, 10-20%, preferably between 0.05-0.2%, 0.2-0.25%, 0.25-0.5%, 0.5-0.6%, 0.6-0.7%, 0.7-0.8%, 0.8-0.9%, 0.9-1%, 1-5%, 5-10%, 10-15%, and more preferably around 0.1705%.

An embodiment of the disclosure relates to a method for treating a malignancy in a patient including: measuring a level of CD27+CD28+ naîve Th cells in an apheresis product from the patient; determining whether the patient should be administered an effective dose of T cells including a chimeric receptor, or an effective dose of T cells including a chimeric receptor and a combination therapy at least in part from the level of CD27+CD28+ naîve Th cells in the apheresis product; and administering the effective dose of T cells including a chimeric receptor, or the effective dose of T cells and the combination therapy based on the determining step. In such a method, the patient is administered the effective dose of T cells including a chimeric receptor if the level of CD27+CD28+ naîve Th cells is over a cut-off percentage value measured as a percentage of total leukocytes, and the patient is administered the effective dose of T cells including a chimeric receptor and the combination therapy if the level of CD27+CD28+ naîve Th cells is below the cut-off percentage value.

An embodiment of the disclosure relates to the method for treating a malignancy in a patient described above, where the cut-off percentage value is around 0-0.1%, 0.1%-0.5%, 0.5%-1.0%, 1.0-5%, 5-10%, 10-15%, 10-20%, 20-30%, 30-40%, 40-50%, or more preferably around 0.27%.

An embodiment of the disclosure relates to the method for treating a malignancy in a patient described above, further including: measuring a level of intermediate monocytes in the apheresis product from the patient; determining whether the patient should be administered an effective dose of T cells including a chimeric receptor, or an effective dose of T cells including a chimeric receptor and a combination therapy at least in part from the level of intermediate monocytes in the apheresis product; and administering the effective dose of T cells including a chimeric receptor, or the effective dose of T cells and the combination therapy based on the determining step. In such a method, the patient is administered the effective dose of T cells including a chimeric receptor if the level of intermediate monocytes is below a cut-off percentage value measured as a percentage of total leukocytes, and the patient is administered the effective dose of T cells including a chimeric receptor and the combination therapy if the level of intermediate monocytes is above the cut-off percentage value.

An embodiment of the disclosure relates to the method for treating a malignancy in a patient described above, where the cut-off percentage value is around 1%, 2%, 3%, 4%, 5%, 6%, 7%, 8%, 9%, 10%, 15%, or 20%, preferably between 1 and 5%, and even more preferably around 3%.

An embodiment of the disclosure relates to the method for treating a malignancy in a patient described above, further including: measuring a level of CD27-CD28+ TEMRA Treg cells in the apheresis product from the patient; determining whether the patient should be administered an effective dose of T cells including a chimeric receptor, or an effective dose of T cells including a chimeric receptor and a combination therapy at least in part from the level of CD27-CD28+ TEMRA Treg cells in the apheresis product; and administering the effective dose of T cells including a chimeric receptor, or the effective dose of T cells and the combination therapy based on the determining step. In such a method, the patient is administered the effective dose of T cells including a chimeric receptor if the level of CD27-CD28+ TEMRA Treg cells is above a cut-off percentage value measured as a percentage of total leukocytes, and the patient is administered the effective dose of T cells including a chimeric receptor and the combination therapy if the level of CD27-CD28+TEMRA Treg cells is below the cut-off percentage value.

An embodiment of the disclosure relates to the method for treating a malignancy in a patient described above, where the cut-off percentage value is around 0.1%, 0.2%, 0.3%, 0.4%, 0.5%, 0.6%, 0.7%, 0.8%, 0.9%, 1%, 1-5%, 5-10%, 10-20%, preferably between 0.05-0.2%, 0.2-0.25%, 0.25-0.5%, 0.5-0.6%, 0.6-0.7%, 0.7-0.8%, 0.8-0.9%, 0.9-1%, 1-5%, 5-10%, 10-15%, and more preferably around 0.1705%.

An embodiment of the disclosure relates to the method for treating a malignancy in a patient described above, further including: measuring a lymphocyte to leukocyte ratio in a baseline hematology count of the patient; determining whether the patient should be administered an effective dose of T cells including a chimeric receptor, or an effective dose of T cells including a chimeric receptor and a combination therapy at least in part from the lymphocyte to leukocyte ratio; and administering the effective dose of T cells including a chimeric receptor, or the effective dose of T cells and the combination therapy based on the determining step. In such a method, the patient is administered the effective dose of T cells including a chimeric receptor if the lymphocyte to leukocyte ratio is above a cut-off value, and the patient is administered the effective dose of T cells including a chimeric receptor and the combination therapy if the lymphocyte to leukocyte ratio is below the cut-off value.

An embodiment of the disclosure relates to the method for treating a malignancy in a patient described above, where the cut-off value is 1%, 1-5%, 5-10%, 10-15%, 15-20%, 20-25%, 25-30%, 30-35%, and preferably 5.2%.

An embodiment of the disclosure relates to the method for treating a malignancy in a patient described above, further including: measuring a lymphocyte to monocyte ratio in a baseline hematology count of the patient; determining whether the patient should be administered an effective dose of T cells including a chimeric receptor, or an effective dose of T cells including a chimeric receptor and a combination therapy at least in part from the lymphocyte to monocyte ratio; and administering the effective dose of T cells including a chimeric receptor, or the effective dose of T cells and the combination therapy based on the determining step. In such a method, the patient is administered the effective dose of T cells including a chimeric receptor if the lymphocyte to monocyte ratio is above a cut-off value, and the patient is administered the effective dose of T cells including a chimeric receptor and the combination therapy if the lymphocyte to monocyte ratio is below the cut-off value.

An embodiment of the disclosure relates to the method for treating a malignancy in a patient described above, where the cut-off value is between 0 and 0.5, 0.5-1.0, 1.0-1.5, 1.5-2.0, 2-5, 5-10, 10-15, and preferably 0.79.

An embodiment of the disclosure relates to the method for treating a malignancy in a patient described above, where the combination therapy includes immunotherapies, SRC kinase inhibitors, T cell bi-specific antibodies, anti-CD20 monoclonal antibody, anti-4-1BB, anti-CD47, TGF-beta inhibitors or dominant negative TGF-beta, mTOR/AKT agonists, histone deacetylase inhibitors, cyclophosphamide, fluorouracil, gemcitabine, doxorubicin, taxanes, chemo- or radio-therapies, small molecule inhibitors, antibodies targeted towards enhancing anti-tumor immunity, or anti-inflammatory medications.

DETAILED DESCRIPTION

Figure 1A:
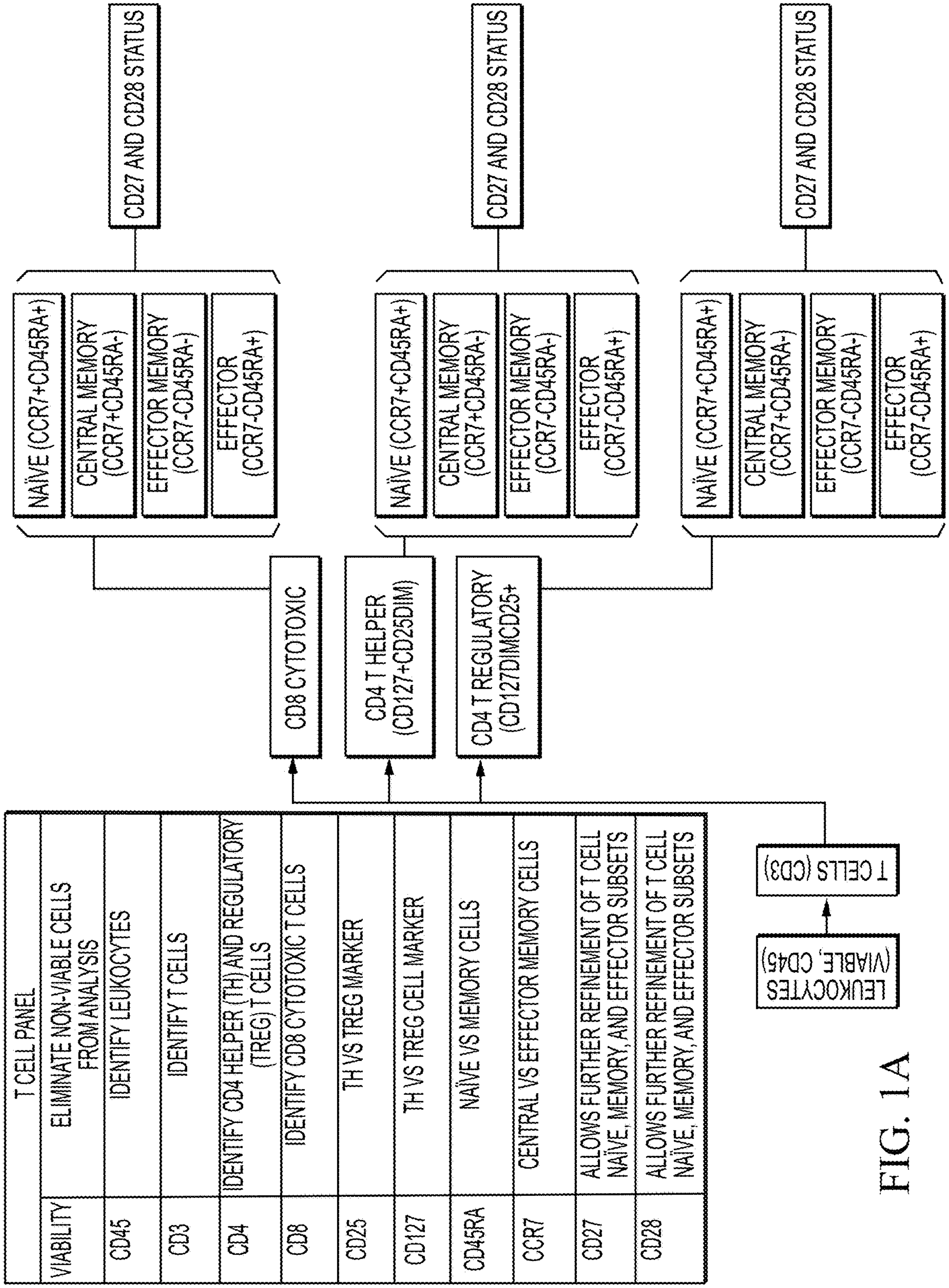
FIG. 1A An overview of flow cytometry markers utilized for analysis of apheresis material from a clinical study.

The present disclosure is based in part on the discovery that pre-infusion attributes (e.g., T cell fitness) of apheresis material and engineered CAR T cells, as well as pre-treatment characteristics of patients' immune factors that may be associated with clinical efficacy and toxicity including durable responses, grade ≥3 cytokine release syndrome, and grade ≥3 neurologic events.

Definitions

In order for the present disclosure to be more readily understood, certain terms are first defined below. Additional definitions for the following terms and other terms are set forth throughout the Specification.

As used in this Specification and the appended embodiments, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 1920, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" may mean within one or more than one standard deviation per the practice in the art. "About" or "approximately" may mean a range of up to 10% (i.e., ±10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Systéme International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. Exemplary routes of administration for the compositions disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering may also be performed, for example, once, a plurality of times, and/or over one or more extended periods. In one embodiment, the CAR T cell treatment is administered via an "infusion product" comprising CAR T cells.

The term "antibody" (Ab) includes, without limitation, a glycoprotein immunoglobulin which binds specifically to an antigen. In general, an antibody may comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD19. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocks a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. In this application, the term cancer is synonymous with malignancy. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, [add other solid tumors] multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of the cancers. In some embodiments, the cancer is multiple myeloma. In some embodiments, the cancer is NHL. The particular cancer may be responsive to chemo- or radiation therapy or the cancer may be refractory. A refractory cancer refers to a cancer that is not amenable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

As used herein, "chimeric receptor" refers to an engineered surface expressed molecule capable of recognizing a particular molecule. Chimeric antigen receptors (CARs) and engineered T cell receptors (TCRs), which comprise binding domains capable of interacting with a particular tumor antigen, allow T cells to target and kill cancer cells that express the particular tumor antigen. In one embodiment, the T cell treatment is based on T cells engineered to express a chimeric antigen receptor (CAR) or a T cell receptor (TCR), which comprises (i) an antigen binding molecule, (ii) a costimulatory domain, and (iii) an activating domain. The costimulatory domain may comprise an extracellular domain, a transmembrane domain, and an intracellular domain, wherein the extracellular domain comprises a hinge domain, which may be truncated.

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. Such terms can be used interchangeably. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy may include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. Nos. 7,741,465, 6,319,494, 5,728,388, and International Publication No. WO 2008/081035. In some embodiments, the immunotherapy comprises CAR T cell treatment. In some embodiments, the CAR T cell treatment product is administered via infusion.

The T cells of the immunotherapy may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by reference in its entirety.

The term "engineered Autologous Cell Therapy," or "eACT™," also known as adoptive cell transfer, is a process by which a patient's own T cells are collected and subsequently genetically altered to recognize and target one or more antigens expressed on the cell surface of one or more specific tumor cells or malignancies. T cells may be engineered to express, for example, chimeric antigen receptors (CAR). CAR positive (+) T cells are engineered to express an extracellular single chain variable fragment (scFv) with specificity for a particular tumor antigen linked to an intracellular signaling part comprising at least one costimulatory domain and at least one activating domain. The CAR scFv may be designed to target, for example, CD19, which is a transmembrane protein expressed by cells in the B cell lineage, including all normal B cells and B cell malignances, including but not limited to diffuse large B-cell lymphoma (DLBCL) not otherwise specified, primary mediastinal large B-cell lymphoma, high grade B-cell lymphoma, and DLBCL arising from follicular lymphoma, NHL, CLL, and non-T cell ALL. Example CAR T cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell may include a T cell. The term "in vivo" means within the patient.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that may comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex that specifically binds with a cognate stimulatory ligand present on an antigen present cell. A "stimulatory ligand" is a ligand that when present on an antigen presenting cell (e.g., an APC, a dendritic cell, a B-cell, and the like) may specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. In certain embodiments, a co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD33, CD45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD11a, CD11b, CD11c, CD11d, CDS, CEACAM1, CRT AM, DAP-10, DNAM1 (CD226), Fc gamma receptor, GADS, GITR, HVEM (LIGHTR), IA4, ICAM-1, ICOS, Ig alpha (CD79a), IL2R beta, IL2R gamma, IL7R alpha, integrin, ITGA4, ITGA6, ITGAD, ITGAE, ITGAL, ITGAM, ITGAX, ITGB2, ITGB7, ITGB1, KIRDS2, LAT, LFA-1, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions. Similarly, the term "increasing" indicates any change that is higher than the original value. "Increasing," "higher," and "lower" are relative terms, requiring a comparison between pre- and post-measurements and/or between reference standards. In some embodiments, the reference values are obtained from those of a general population, which could be a general population of patients. In some embodiments, the reference values come quartile analysis of a general patient population.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some embodiments, "treatment" or "treating" includes a partial remission. In another embodiment, "treatment" or "treating" includes a complete remission.

As used herein, the term "polyfunctional T cells" refers to cells co-secreting at least two proteins from a pre-specified panel per cell coupled with the amount of each protein produced (i.e., combination of number of proteins secreted and at what intensity). In some embodiments, a single cell functional profile is determined for each evaluable population of engineered T cells. Profiles may be categorized into effector (Granzyme B, IFN-γ, MIP-1α, Perforin, TNF-α, TNF-β), stimulatory (GM-CSF, IL-2, IL-5, IL-7, IL-8, IL-9, IL-12, IL-15, IL-21), regulatory (IL-4, IL-10, IL-13, IL-22, TGF-β1, sCD137, sCD40L), chemoattractive (CCL-11, IP-10, MIP-10, RANTES), and inflammatory (IL-1b, IL-6, IL-17A, IL-17F, MCP-1, MCP-4) groups. In some embodiments, the functional profile of each cell enables the calculation of other metrics, including a breakdown of each sample according to cell polyfunctionality (i.e., what percentage of cells are secreting multiple cytokines versus non-secreting or monofunctional cells), and a breakdown of the sample by functional groups (i.e., which mono- and polyfunctional groups are being secreted by cells in the sample, and their frequency).

As used herein, the term "quartile" or "quadrant" is a statistical term describing a division of observations into four defined intervals based upon the values of the data and how they compare to the entire set of observations.

As used herein, the term "Study day 0" is defined as the day the subject received the first CAR T cell infusion. The day prior to study day 0 will be study day −1. Any days after enrollment and prior to study day −1 will be sequential and negative integer-valued.

As used herein, the term "objective response" refers to complete response (CR), partial response (PR), or non-response. Criteria are based on the revised IWG Response Criteria for Malignant Lymphoma.

As used herein, the term "complete response" refers to complete resolution of disease, which becomes not detectable by radio-imaging and clinical laboratory evaluation. No evidence of cancer at a given time.

As used herein, the term "partial response" refers to a reduction of greater than 30% of tumor without complete resolution. Criteria are based on the revised IWG Response Criteria for Malignant Lymphoma where PR is defined as "At least a 50% decrease in sum of the product of the diameters (SPD) of up to six of the largest dominant nodes or nodal masses. These nodes or masses should be selected according to all of the following: they should be clearly measurable in at least 2 perpendicular dimensions; if possible they should be from disparate regions of the body; and they should include mediastinal and retroperitoneal areas of disease whenever these sites are involved As used herein, the term "non-response" refers to the subjects who had never experienced CR or PR post CAR T cell infusion.

As used herein, the term "durable response" refers to the subjects who were in ongoing response at least by one year follow up post CAR T cell infusion 6 months f/u is utilized only for Z1, C3 as there is no longer f/u available for this cohort. Nevertheless, the conclusions remain same.

As used herein, the term "relapse" refers to the subjects who achieved a complete response (CR) or partial response (PR) and subsequently experienced disease progression.

As used herein, the expansion and persistence of CAR T cells in peripheral blood may be monitored by qPCR analysis, for example using CAR-specific primers for the scFv portion of the CAR (e.g., heavy chain of a CD19 binding domain) and its hinge/CD28 transmembrane domain. Alternatively, it may be measured by enumerating CAR cells/unit of blood volume.

As used herein, the scheduled blood draw for CAR T cells may be before CAR T cell infusion, Day 7, Week 2 (Day 14), Week 4 (Day 28), Month 3 (Day 90), Month 6 (Day 180), Month 12 (Day 360), and Month 24 (Day 720).

As used herein, the "peak of CAR T cell" is defined as the maximum absolute number of CAR+ PBMC/μL in serum attained after Day 0.

As used herein, the "time to Peak of CAR T cell" is defined as the number of days from Day 0 to the day when the peak of CAR T cell is attained.

As used herein, the "Area Under Curve (AUC) of level of CAR T cell from Day 0 to Day 28" is defined as the area under the curve in a plot of levels of CAR T cells against scheduled visits from Day 0 to Day 28. This AUC measures the total levels of CAR T cells overtime.

As used herein, the scheduled blood draw for cytokines is before or on the day of conditioning chemotherapy (Day −5), Day 0, Day 1, Day 3, Day 5, Day 7, every other day if any through hospitalization, Week 2 (Day 14), and Week 4 (Day 28).

As used herein, the "baseline" of cytokines is defined as the last value measured prior to conditioning chemotherapy.

As used herein, the fold change from baseline at Day X is defined as $$\frac{\text{Cytokine level at Day } X - \text{Baseline}}{\text{Baseline}}$$

As used herein, the "peak of cytokine post baseline" is defined as the maximum level of cytokine in serum attained after baseline (Day −5) up to Day 28.

As used herein, the "time to peak of cytokine" post CAR T cell infusion is defined as the number of days from Day 0 to the day when the peak of cytokine was attained.

As used herein, the "Area Under Curve (AUC) of cytokine levels" from Day −5 to Day 28 is defined as the area under the curve in a plot of levels of cytokine against scheduled visits from Day −5 to Day 28. This AUC measures the total levels of cytokine overtime. Given the cytokine and CAR+ T cell are measured at certain discrete time points, the trapezoidal rule may be used to estimate the AUCs.

Various aspects of the disclosure are described in further detail in the following subsections.

Pre-Treatment Attributes

Pre-treatment attributes of the apheresis and engineered cells (T cell attributes) and patient immune factors measured from a patient sample may be used to assess the probability of clinical outcomes including response and toxicity. Pre-treatment attributes derived from the premanufacturing apheresis material, engineered CAR T-cells, and patient immune and clinical factors (including but not limited to cell populations, serum chemokines/cytokines, blood chemistry, etc) may be used to assess the probability of clinical outcomes including response and toxicity. This information may also be utilized to optimize the manufacturing process for Autologous CAR T cells, Allogeneic CAR T cells, iPSCs, and potentially TCRs and TILs for both hematological malignancies and solid tumor indications.

In one embodiment, the disclosure provides that the percentage of CD27+ CD28+ Th cells of naïve phenotype (CCR7+ CD45RA+) in the pre-manufacturing PBMC population (i.e., the population of PBMCs from which the T cell product is prepared) associated positively with phenotypic markers of product T cell fitness, including doubling time and viability, CD4/CD8 ratio, and percentage of CD8 and CD4 naïve T cells. Accordingly, the disclosure provides a method of manufacturing optimization that improves the product T cell population fitness by increasing the level of CD27+ CD28+ Th cells of naïve phenotype (CCR7+ CD45RA+) in the pre-manufacturing PBMC population. In one embodiment, this may be done by enriching for CD27+ CD28+ Th cells of naïve phenotype (CCR7+ CD45RA+) following subject apheresis, by increasing the amount of apheresis material collected until a threshold of CD27+ CD28+ Th cells of naïve phenotype (CCR7+ CD45RA+) is achieved to start the manufacturing process, by selecting the administered dose of CAR T-cells not through the total CAR count per kg but instead by utilizing a count of CD27+ CD28+ Th cells of naïve phenotype (CCR7+ CD45RA+) per kg, and/or by adjusting the T cells product manufacturing conditions (such as, without limitation, length of manufacturing and/or composition of growth media) to increase the levels of the CD27+ CD28+ Th cells of naïve phenotype (CCR7+ CD45RA+). In one embodiment, the disclosure also provides a method to stratify patients who may be better candidates for allogeneic/off-the-shelf CAR T-cells to overcome the lack of sufficient positive factors such as CD27+ CD28+ Th cells of naïve phenotype (CCR7+ CD45RA+) in the pre-manufacturing PBMC population. In one embodiment, the disclosure provides a method to stratify patients who may be better candidates for combination therapies which could enhance the activity of their CAR T-cells or reduce the impact of negative factors to improve on the clinical efficacy of the CAR T therapy. In one embodiment, the combination therapies may be selected from checkpoints inhibitors (including but not limited to anti-PD-1, anti-PD-L1, anti-CTLA-4, etc or any combination thereof), SRC kinase inhibitors (ex: dasatinib), anti-CD20 monoclonal antibody, anti-4-1BB, anti-CD47, lenzilumab, TGF-beta inhibitors or dominant negative TGF-beta, mTOR/AKT agonists, histone deacetylase inhibitors, cyclophosphamide, fluorouracil, gemcitabine, doxorubicin, taxanes In one embodiment, the disclosure provides that the patient is stratified for manufacturing optimization based on the percentage of CD27+CD28+ Th cells of naïve phenotype (CCR7+ CD45RA+) in the pre-manufacturing PBMC population or identification of subjects which would benefit from allogeneic/off-the-shelf CAR T cells or combination therapies to maximize the efficacy of CAR T-cells.

In one embodiment, the disclosure provides that the percentage of intermediate monocytes and total monocytes in pre-manufacturing PBMC population associated positively with pre-treatment inflammatory markers. Accordingly, the disclosure provides a method of quantifying simple biomarkers (intermediate monocytes and/or total monocytes) which allow for estimation of the inflammatory state of the patient which has been shown to be a negative indicator of clinical efficacy of CAR T-cells. In one embodiment, this method is used as an indicator of potential use of anti-inflammatory medications to negate the inflammatory signaling in the periphery. In one embodiment, the preferred anti-inflammatory medications are selected from antibodies against IL-6 (such as tocilizumab), corticosteroids, dexamethasone, siltuximab, etanercept, infliximab, anakinra, and anti-GM-CSF.

In one embodiment, the disclosure provides that the level of intermediate monocytes (% of leukocytes) in the pre-manufacturing PBMCs population is enriched in, and is a marker for, patients with higher IPI scores.

In one embodiment, the disclosure provides that the percentage of intermediate monocytes and total monocytes in pre-manufacturing PBMC population associated positively with tumor burden (baseline sum of product diameters). Accordingly, the disclosure provides a method of quantifying biomarkers (e.g., intermediate monocytes and/or total monocytes) that allow for estimation of the patient's tumor burden, which has been shown to be a negative indicator of clinical efficacy of CAR T-cells. In one embodiment, the level of intermediate monocytes and/or total monocytes may indicate the use of additional therapeutics to help overcome larger estimated tumor burden such as chemo-, radio-antibody and small molecule based therapies, immunotherapies (including by not limited to check point inhibitors, bispecific engagers), and cell therapies (including but limited to CAR-T, TCR-based and tumor infiltrating lymphocytes) in which tumor burden had shown to be a negative prognostic and/or predictive biomarker.

In one embodiment, the disclosure provides that the percentage of intermediate monocytes and total monocytes in pre-manufacturing PBMC population associated positively with hypoxia (indicated by serum LDH levels). Accordingly, the disclosure provides a method of quantifying biomarkers (e.g., intermediate monocytes and/or total monocytes) that allow for the estimation of the patient's hypoxic state, which has been shown to be a negative indicator of clinical efficacy of CAR T-cells. In one embodiment, the level of intermediate monocytes and/or total monocytes is used as an indicator of supplemental therapeutics to overcome the hypoxic environment. In one embodiment, the supplemental therapeutics are selected from metabolic modulators, HIF inhibitors, and LDH inhibitors that establish a more normoxic environment.

In one embodiment, the disclosure provides that monocytes, particularly intermediate monocytes, in pre-manufacturing PBMC population negatively associated with T-cell features in the tumor microenvironment (TME) while CD27+CD28+ Naïve Th cells and lymphocytes positively associate with T-cell features in the TME that have been associated with response. In one embodiment, the T-cell features in the TME that have been associated with response include activated CD8+ T cell subsets (CD3+CD8+PD-1+ Lag3+/−Tim3− cells) as well as genes associated with activated T cell signature (for example CXCL10, CXC11, GZMA, GZMB, GZMK and Immunosign21 Galon et al. ASCO, 2020. Accordingly, the disclosure provides a method of elucidating the overall status of the tumor microenvironment from peripheral blood biomarkers, allowing for estimation of the tumor immune contexture into varying classes such as immune desert, myeloid imbalanced, immunosuppressive, etc. These biomarkers may then be useful for selecting potential combinatory drugs that could help improve upon the tumor microenvironment, such as [checkpoints inhibitors (including but not limited to anti-PD-1, anti-PD-L1, anti-CTLA-4, etc or any combination thereof), lenzilumab, TGF-beta inhibitors or dominant negative TGF-beta, histone deacetylase inhibitors, amino acid deprivation, cyclophosphamide, fluorouracil, gemcitabine, doxorubicin, or taxanes] and/or protect the CAR T-cells from immune checkpoints or exhaustion, such as immune checkpoint inhibitors and SRC kinase inhibitors (ex: dasatinib).

In one embodiment, the disclosure provides that the levels of CD27+ CD28+ Th cells of the naïve phenotype in pre-manufacturing PBMC population associated positively with the percentage of naïve T cells in the product infusion bag and a T-cell rich tumor immune contexture (all markers displayed are markers of activated T-cells), and negatively with pre-treatment inflammatory (INTL8, PRF)/tumor hypoxic state (LDH). Accordingly, the disclosure provides a method of quantifying simple biomarkers (CD27+CD28+ naïve Th) which allow for estimation of the patients eventual infusion bag following manufacturing and a T-cell rich tumor immune contexture, these have both been shown to be positive indicators of clinical efficacy of CAR T-cells. Low levels of these CD27+CD28+ Naïve Th cells could indicate for potential use of anti-inflammatory medications or combination therapies which help modify the tumor microenvironment to improve CAR T cell efficacy.

In one embodiment, the disclosure provides that intermediate monocytes in the pre-manufacturing PBMC population, associated positively with pre-treatment inflammatory (INTL8, Ferritin, CRP, Amyloid A)/tumor hypoxic state (LDH), and negatively with a T-cell rich tumor immune contexture (e.g., activated T cell signatures, CD3+CD8+ PDI+LAG3−TIM3− cells; GZMA, TGIT, LAG3, CXCL10, GZMB, PRF1, STAT1, EOMES, CXCL9, GZMK, CXCL11, HAVCR2, CD3D, IS21) defined pre-treatment. Accordingly, the disclosure provides a method where high level of intermediate monocytes indicate the use of anti-inflammatory medications (such as corticosteroids or tocilizumab) and/or immunomodulatory drugs that help overcome the poor TIC (for example, or TME modulatory drugs [such as checkpoint inhibitors and drugs that target suppressive myeloid cells and enhance antigen presentation, drugs that stabilize the vasculature or normalize tumor metabolism. In one embodiment, the drugs are administered pre-immunotherapy. In one embodiment, the drugs are administered pre-, during and/or after immunotherapy.

In one embodiment, the disclosure provides that the level of intermediate monocytes in the pre-manufacturing PBMC population had a positive association with pretreatment tumor burden which itself is negatively associated with response. Accordingly, the disclosure provides a method of predicting whether a patient is likely to respond to CAR T cell therapy based on the level of intermediate monocytes in the pre-manufacturing PBMC population. Also, the disclosure provides a method of using the level of intermediate monocytes and/or total monocytes in the pre-manufacturing PBMC population to estimate the patient's tumor burden, which in turn has been shown to be a negative indicator of clinical efficacy of CAR T-cells. In one embodiment, the level of intermediate monocytes serves as an indicator to the use of additional therapeutics to help overcome larger estimated tumor burden such as chemo-, radio-antibody and small molecule based therapies, immunotherapies (including by not limited to check point inhibitors, bispecific engagers), and cell therapies (including but limited to CAR-T, TCR-based and tumor infiltrating lymphocytes) in which tumor burden had shown to be a negative prognostic and/or predictive biomarker.

In one embodiment, the disclosure provides that the level of CD27+CD28+ Naïve Th cells (% of leukocytes) in the apheresis product/pre-manufacturing PBMC population was a predictive marker for improved OS and PFS (optimal cutoff). There was a positive association between them, i.e., subjects with pre-treatment CD27+CD28+ naïve Th cells above the listed cutoff have a higher likelihood of survival than those below the selected cutoff. Accordingly, the disclosure provides a method of predicting the likelihood of survival of a patient in need of CAR T cell therapy based on the level of CD27+CD28+ Naïve Th cells (% of leukocytes) in the apheresis product that is used to prepare the CAR T cell product. Also accordingly, the disclosure provides a method of predicting the progression free survival of a patient in need of CAR T cell therapy based on the level of CD27+CD28+ Naïve Th cells (% of leukocytes) in the apheresis product that is used to prepare the CAR T cell product. Also, the disclosure also provides that there are improvements in complete response rates, objective response rates, and CAR T cell expansion for those subjects above the selected cutoff (see numbers below survival plots). In one embodiment, the disclosure provides a method of stratification whereby subjects with low levels (such as below 0.27%) of CD27+CD28+ naïve Th cells may benefit from another form of therapy (combination therapy, allogeneic CAR T cells, etc) to improve their likelihood of survival. In one embodiment, low levels are levels below median, or below between 0.1 and 0.5%, 0.5-1.0%, 1-1.5%, 1.5-2%, 2-5%, 5-10%, 10-15%, 15-20%, 20-25%, 25-50-% etc., or 95-100%.

In one embodiment, the disclosure provides that the level of intermediate monocytes in the apheresis product (% of leukocytes) was a predictive marker for OS and PFS (optimal cutoff). Accordingly, the disclosure provides a method whereby subjects with intermediate monocyte levels in the apheresis product (% of leukocytes) below a cutoff of around 1%, 2%, 3%, 4%, 5%, 6%, 7%, 8%, 9%, 10%, 15%, or 20%, preferably between 1 and 5%, even more preferably below around 3% are predicted to have a higher likelihood of survival than those above the cutoff. Accordingly, the disclosure provides a method of predicting OS and PFS in a subject in need of CAR T cell therapy comprising measuring the level of intermediate monocytes in the apheresis product (% of leukocytes) used to prepare the CAR T cell product and determining whether the level is above or below the cutoff. Also, the disclosure provides that there are improvements in complete response rates and objective response rates, as well as CAR T expansion for those subjects below a cutoff of around 3%. Also, the disclosure provides a method of patient stratification whereby subjects with high levels of intermediate monocytes (levels above around 1%, 2%, 3%, 4%, 5%, 6%, 7%, 8%, 9%, 10%, 15%, or 20%, preferably between 1 and 5%, even more preferably above around 3%) may benefit from another form of therapy (such as combination therapy with immunotherapies, allogeneic CAR T cells, etc) to improve their likelihood of survival.

In one embodiment, the disclosure provides that the ratio of CD27pCD28p Naïve Th cells in the apheresis product (% of leukocytes) to intermediate monocytes (% of leukocytes) showed a positive association with and serves as a predictive marker for OS and PFS. There were better survival/response/expansion rates for subjects with levels above the selected cutoff of around 0.1, 0.2, 0.3, 0.4, 0.5, 0.6, 0.7, 0.8, 0.9, 1, 1-5, 5-10, 10-20, preferably between 0.05-0.2, 0.2-0.25, 0.25-0.5, 0.5-0.6, 0.6-0.7, 0.7-0.8, 0.8-0.9, 0.9-1, 1-5, 5-10, 10-15, so on and so forth, 95-100, 100-200, 200-300, etc., more preferably, even more preferably 0.1705 as compared to those below it. Accordingly, the disclosure provides a method of predicting OS and PFS, response, and CAR T cell expansion rates in a subject in need of CAR T cell therapy comprising measuring the ratio of CD27pCD28p Naïve Th cells in the apheresis product (% of leukocytes) to intermediate monocytes (% of leukocytes) used to prepare the CAR T cell product and determining whether the level is above or below the cutoff of around 0.1, 0.2, 0.3, 0.4, 0.5, 0.6, 0.7, 0.8, 0.9, 1, 1-5, 5-10, 10-20, preferably between 0.05-0.2, 0.2-0.25, 0.25-0.5, 0.5-0.6, 0.6-0.7, 0.7-0.8, 0.8-0.9, 0.9-1, 1-5, 5-10, 10-15, so on and so forth, 95-100, 100-200, 200-300, etc., more preferably 0.1-1, even more preferably 0.1705. Also, the disclosure also provides that there are improvements in complete response rates, objective response rates, and CAR T cell expansion for those subjects above the selected cutoff of 0.1705. Accordingly, the disclosure provides a method of patient stratification whereby subjects with low levels of CD27+CD28+ naïve Th cells (e.g., levels of around 0.1, 0.2, 0.3, 0.4, 0.5, 0.6, 0.7, 0.8, 0.9, 1, 1-5, 5-10, 10-20, preferably between 0.05-0.2, 0.2-0.25, 0.25-0.5, 0.5-0.6, 0.6-0.7, 0.7-0.8, 0.8-0.9, 0.9-1, 1-5, 5-10, 10-15, more preferably 0.1-1, even more preferably 0.1705), may benefit from another form of therapy (combination therapy, allogeneic CAR T cells, etc) to improve their likelihood of survival.

In one embodiment, the disclosure provides that the level of CD27+CD28+ Naïve Th cells in the pre-manufacturing PBMC population has a negative association with the level of intermediate monocytes. Furthermore, subjects with high CD27+CD28+ Naïve Th levels and low intermediate monocytes levels had an increased proportion of objective responders. Accordingly, the disclosure provides a method of predicting objective response in a subject in need of CAR T cell therapy comprising measuring the levels of CD27+ CD28+ Naïve Th levels and low intermediate monocytes, whereby a level of CD27+CD28+ Naïve Th levels of/above 0.08% (level above the median, or above 0.05%, 0.1%, 0.2-1%, 1-5%, 5-10%, 10-15%, 15-20%, etc., 95-100%) and/or a level of intermediate monocytes of/below 3% (below the median, or below 1-5%, 5-10%, 10-15%, 15-20%, 20-25%, etc., 95%-100%) indicates an increase likelihood of objective response. In one embodiment, these levels are used for stratifying patients which could benefit from off the shelf/allogeneic CAR T cells, immunomodulators, bispecific engagers, combination therapies, etc).

In one embodiment, the disclosure provides that high level of intermediate monocytesin the pre-manufacturing PBMC population (wherein high level is a level above the median of intermediate monocytes in the general population, where the median may be between 0-1%, 1-2%, 2-3%, 3-4%, 4-5%, 5-6%, 6-7%, 7-8%, 8-9%, 9-10%, 10-15%, 15-20%, so on and so forth, preferably about 1.7-1.8%) and low level of CAR T cell expansion (wherein low level is a level below the median level of CAR T cell expansion in the general population, where the median is between 0-10, 10-20, 20-30, 30-40, 40-50, 50-60, 60-70, 70-80, 80-90, 90-100) correlates with the highest rate of non-responders. Accordingly, the disclosure provides a method of estimating response based on the baseline intermediate monocyte levels and CAR expansion post infusion. Accordingly, the disclosure provides a method whereby the levels of intermediate monocytes in the pre-treatment apheresis PBMCs and CAR T cell expansion are measured and used to actively track patients after infusion to estimate what the long-term response will be and if supplemental therapeutics may be useful.

In subjects that have increased CAR T-cell peak expansion (wherein increased level is a level above the median level of CAR T cell expansion in the general CAR T cell treatment population, where the median is between 0-10, 10-20, 20-30, 30-40, 40-50, 50-60, 60-70, 70-80, 80-90, 90-100, preferably between 40-50) and lower intermediate monocyte levels (wherein a low level is a level below the median of intermediate monocytes in the general population, where the median may be between 0-1%, 1-2%, 2-3%, 3-4%, 4-5%, 5-6%, 6-7%, 7-8%, 8-9%, 9-10%, 10-15%, 15-20%, so on and so forth, preferably about 1.7-1.8%.) there were increased ongoing response rates and reduced relapse or non-responder rates compared to the other quadrants. Accordingly, the disclosure provides a method whereby the levels of intermediate monocytes in the pre-treatment apheresis PBMCs and CAR T cell expansion are measured and used to actively track patients after infusion to estimate what the ongoing response, likelihood of relapse will be and if supplemental therapeutics may be useful based on the above correlation.

In one embodiment, if the subject has a baseline tumor burden above the median level, high intermediate monocytes (above the median, wherein the median may be around 1%, 2%, 3%, 4%, 5%, 6%, 7%, 8%, 9%, 10%, 10-15%, 15-20%, 20-25%, etc., 95-100%, preferably around 1.1%) and low CAR T-cell peak expansion (below the median, wherein the median may be around 5-10%, 10-15%, 15-20%, 20-25%, 25-30%, 30-35%, 35-40%, 40-45%, 45-50%, 50-55%, 55-60%, 60-65%, 65-70%, etc., 95-100%, preferably around 43%), the likelihood of response is low (between 1%-10%, 10-20%, 20-30%, 30-40%, 40-50% ongoing response and between 1%-10%, 10-20%, 20-30%, 30-40%, 40-50% objective response rate). Accordingly, the disclosure provides a method whereby the levels of intermediate monocytes in the pre-treatment apheresis PBMCs, baseline tumor burden, and CAR T cell expansion are measured and used to actively track patients after infusion to estimate what the ongoing response and likelihood of objective response will be and if supplemental therapeutics may be useful, based on the above correlation.

In one embodiment, the disclosure provides that there was an association between CD27+CD28+ Naïve Th (% of Leukocytes) in the pre-manufacturing PBMC population and response categories. CD27+CD28+ Naïve Th cell levels are higher in responding patients as compared to non-responding patients. Accordingly, the disclosure provides a method of predicting the likelihood of response to CAR T cell treatment in a subject in need thereof, comprising measuring the level of CD27+CD28+ Naïve Th (% of Leukocyte) in the pre-manufacturing PBMC population and predicting a high likelihood of response when the level is above an optimal cut-off point (e.g., 0.1036%, 0-0.1%, 0.1%-0.5%, 0.5%-1.0%, 1.0-5%, 5-10%, 10-15%, 10-20%, 20-30%, 30-40%, 40-50%) or above median (e.g. 0.89%, 0-0.1%, 0.1%-0.5%, 0.5%-1.0%, 1.0-5%, 5-10%, 10-15%, 10-20%, 20-30%, 30-40%, 40-50%). Accordingly, the disclosure provides a method of selecting a patient for manufacturing optimization, combination therapy, or off-the-shelf/allogeneic CAR T cell therapy when the levels of CD27+CD28+ Naïve Th (% of Leukocyte) in the pre-manufacturing PBMC population are below the selected cut-off point or median range, which is also an indication of a lower likelihood of ongoing response.

In one embodiment, the disclosure provides that there was an association between the level of intermediate monocytes (% of leukocyte) in the pre-manufacturing PBMC population and response categories. Intermediate monocytes are lower in responding patients as compared to non-responding patients. Accordingly, the disclosure provides a method of predicting the likelihood of response to CAR T cell treatment in a subject in need thereof, comprising measuring the level of intermediate monocytes (% of leukocyte) in the pre-manufacturing PBMC population and predicting a high likelihood of response when the level is below optimal cutpoint (e.g., 3.02%, 0-0.1%, 0.1%-0.5%, 0.5%-1.0%, 1.0-5%, 5-10%, 10-15%, 10-20%, 20-30%, 30-40%, 40-50%) or below median (e.g., 1.77%, 0-0.1%, 0.1%-0.5%, 0.5%-1.0%, 1.0-5%, 5-10%, 10-15%, 10-20%, 20-30%, 30-40%, 40-50%) Furthermore, intermediate monocytes (% of leukocyte) in the pre-manufacturing PBMC population levels are lower in those subjects that have an ongoing (durable) response as compared to those that undergo relapse or are non-responders. Accordingly, the disclosure provides a method whereby levels of intermediate monocytes (% of leukocyte) in the pre-manufacturing PBMC population, may be used in a method for selecting manufacturing optimization, combination therapy, or off-the-shelf/allogeneic CAR T cell therapy for subjects above range which have a lower likelihood of ongoing response.

In one embodiment, the levels of CD27+CD28+ Naïve Th cells track negatively with features that have been indicated to be associated with a worse prognosis (IPI score, tumor burden, prior lines of therapy). Accordingly, the disclosure provides a method of predicting response to CAR T cell therapy based on the levels of CD27+CD28+ Naïve Th cells in the pre-manufacturing PBMC population, whereby patients whom have higher levels of these cells are more likely than not to be responsive to CAR T therapy and less likely than not to need intervention. Those with lower levels may need to consider additional modifications to treatment such as combination therapies, optimized manufacturing approaches, off-the-shelf/allogeneic CAR T cells, next generation CAR constructs, etc In one embodiment, the disclosure provides that the level of naïve Th cells in the apheresis product was negatively associated with the number of prior line therapy. Front (Z12) or $2^{nd}$ (Z7) line DLBCL may have greater levels of naïve T cells at leukapheresis. The disclosure provides that subjects would have greater levels of these cells in their blood with fewer lines of therapy, indicating response rates could be improved if CAR T-cells were utilized as an earlier line of therapy ($1^{st}/2^{nd}$ line). Higher IPI scores trend with lower CD27+CD28+ Naïve Th cells. CD27+CD28+ Naïve Th cells show a weak negative association with baseline tumor burden. Accordingly, the disclosure provides that the levels of CD27+CD28+ Naïve Th cells in the pre-manufacturing apheresis PBMC product track negatively with features that have been indicated to be associated with a worse prognosis (IPI score, tumor burden, prior lines of therapy). Accordingly, the disclosure provides a method of predicting response to CAR T cell therapy whereby patients whom have higher levels (above 0-0.005%, 0.005-0.010%, 0.01%-0.05%, 0.05-0.1%, 0.1-0.5%, 0.5%-1.0%, 1-5%, 5-10%, 10-15%, preferably, above 0.1%) of these cells should be more responsive to CAR T therapy and less likely to need intervention. The disclosure also provides a method of stratifying patients whereby those with lower levels (below 0-0.005%, 0.005-0.010%, 0.01%-0.05%, 0.05-0.1%, 0.1-0.5%, 0.5%-1.0%, 1-5%, 5-10%, 10-15%, preferably below 0.08%) are considered for additional modifications to treatment such as combination therapies, optimized manufacturing approaches, off-the-shelf/allogeneic CAR T cells, next generation CAR constructs, etc. In addition, the disclosure provides a method of treatment whereby otherwise prior chemotherapeutics, which greatly reduce these cells, are moved to later lines of therapy to preserve CD27+CD28+ Naïve Th cells in the pre-manufacturing apheresis PBMC product and the peripheral/tumor environment for CAR T therapy. Accordingly, the disclosure provides a method whereby the levels of CD27+CD28+ Naïve Th cells in the pre-manufacturing apheresis PBMC product, along with the positive impact of these cells at the time of apheresis on product fitness, indicate that before any therapies are started for subjects with cancer, apheresis bags are frozen to obtain the best incoming cells for CAR T-cell therapy.

In one embodiment, the disclosure provides that the level of intermediate monocyte population in the apheresis product was associated with disease burden and moderately increased with the number of prior lines therapy. Accordingly, the disclosure provides that intermediate monocytes track positively with features that have been indicated to be associated with a worse prognosis (tumor burden, prior lines of therapy). Accordingly, the disclosure provides a method of predicting response to CAR T therapy and need for additional intervention whereby patients whom have lower levels (below 0-1%, 1-5%, 5-10%, 10-15%, 15-20%, preferably below 3%) of these cells are more responsive to CAR T therapy and less likely to need additional intervention. In one embodiment, those patients with higher levels may need to consider additional modifications to treatment such as combination therapies, optimized manufacturing approaches, off-the-shelf/allogeneic CAR T cells, next generation CAR constructs, etc. The disclosure provides that prior chemotherapeutics, which increase these cells, should be moved to later lines of therapy to prevent these cells from increasing in the peripheral/tumor environment before CAR T therapy. This data, along with the negative impact of these cells at the time of apheresis on product fitness, indicate that before any therapies are started for subjects with cancer, apheresis bags should be frozen to obtain the best incoming cells for CAR T-cell therapy.

In one embodiment, the disclosure provides that the level of intermediate monocytes in the apheresis product is positively associated with number of prior lines of therapy. Subjects would be expected to have lower levels of intermediate monocytes with fewer prior lines of therapy, and due to the negative association of these cells with response this also indicates that CAR T-cell response rates could be even higher if utilized as an earlier line of therapy ($1^{st}/2^{nd}$ line).

In one embodiment, the disclosure provides that the International Prognostic Index (IPI) score and the level of intermediate monocytes in the apheresis product were positively associated, further indicating that these cells are associated with subjects that have a worse prognosis. Intermediate monocytes were positively associated with baseline tumor burden. Accordingly, the disclosure provides that the levels of intermediate monocytes are indicative of a less optimal state for CAR T cell effectiveness and additional interventions/optimizations may be needed to improve the efficacy of CAR T therapy when the levels of these cells are above 3% (or above 0-1%, 1-5%, 5-10%, 10-15%, 15-20%, 20-25%). The disclosure also provides that patients may be stratified for manufacturing optimization to remove int. monocytes and increase levels of naïve product cells, for use of next generation CAR constructs, and/or for use of combination therapies with immunomodulators or checkpoint blockade, off-the-shelf/allogeneic CAR T cells, etc based on the levels of intermediate monocytes.

In one embodiment, the disclosure provides that the level of CD27−CD28+ TEMRA Treg cells (% of leukocytes) in the apheresis product associated positively with and may be a predictive marker for OS and PFS. The disclosure provides that for CD27−CD28+ TEMRA Tregs subjects with higher levels of these cells (e.g., above a threshold of 0.17) have higher complete, objective, and ongoing response rates. Accordingly, the disclosure provides a method of predicting OS and PFS to CAR T cell treatment in a subject in need thereof comprising measuring the level of CD27−CD28+ TEMRA Treg cells (% of leukocytes) in the apheresis product and determining the likelihood of survival and the PFS based on whether the level is above or below a cutoff. In one embodiment, the cutoff is 0.17. In one embodiment, the cutoff is around 0.1, 0.2, 0.3, 0.4, 0.5, 0.6, 0.7, 0.8, 0.9, 1, 1-5, 5-10, 10-20, preferably between 0.05-0.2, 0.2-0.25, 0.25-0.5, 0.5-0.6, 0.6-0.7, 0.7-0.8, 0.8-0.9, 0.9-1, 1-5, 5-10, 10-15, so on and so forth, 95-100, 100-200, 200-300, etc., more preferably around 0.1705. The disclosure provides a method of stratifying patients whereby subjects with low levels of CD27−CD28+ TEMRA Tregs may benefit from another form of therapy (combination therapy, allogeneic CAR T cells, etc), manufacturing optimization, next generation CAR, etc to improve their likelihood of survival with CAR therapy.

In one embodiment, the disclosure provides that there was an association between the level of CD27+CD28+ Naïve Th cells in the apheresis product vs. CAR-T peak and CAR-T peak/baseline tumor burden. A positive association between CD27+CD28+ Naïve Th cells and CAR T-cell peak expansion (normalized by tumor burden) was observed. Accordingly, the disclosure provides a method of predicting CAR T cell expansion, whereby CD27+CD28+ Naïve Th cells positively associate with CAR T peak expansion, which in turn has been shown to positively correlate with response, indicating that these cells have a positive influence on response.

In one embodiment, the disclosure provides that low levels of both CD27+CD28+Naïve Th cells and CAR T-cell peak expansion correlate with higher non-responder rates while increasing levels of both lead to higher response rates.

In one embodiment, the disclosure provides that there was an association between the level of intermediate monocytes in the apheresis product vs. CAR-T peak and CAR-T peak/baseline tumor burden. There was a negative association between the level of intermediate monocytes and CAR T-cell peak expansion (normalized by tumor burden). Accordingly, the disclosure provides that the levels of intermediate monocytes negatively associate with CAR T peak expansion (CAR/TB) which has been shown to be a positively correlate with response, indicating that these cells should have a negative influence on response and CAR function post infusion. The disclosure provides a method whereby the levels of intermediate monocytes are used to stratify patients for manufacturing optimization to decrease this population in the product to enhance the final CAR T cells, whereby the method improves CAR expansion and response rate. Also as has been mentioned previously indicates that high int. monocytes may be an indicator of utilization of additional therapeutics or next generation CAR constructs to improve efficacy.

In one embodiment, the disclosure provides a method to predict response to CAR T cell therapy by measuring the levels of intermediate monocytes and the CAR T peak expansion levels, whereby high levels (above median, or above 0-1%, 1-5%, 5-10%, 10-15%, 15-20%, preferably above 3%) of intermediate monocytes in the apheresis product and low (below the median, or below 5-10%, 10-15%, 15-20%, 20-25%, 25-30%, 30-35%, 35-40%, 40-45%, 45-50%, 50-55%, 55-60-%, preferably below 43%) CAR-T peak levels correlate with higher non-responder rates while decreasing intermediate monocyte levels and increased CAR T peak expansion lead to higher response rates.

In one embodiment, the disclosure provides that the ratio of Lymphocyte to Leukocytes in baseline hematology cell counts associated positively with and may serve as a predictive marker for OS and PFS (optimal cutoff). Lymphocyte to Leukocytes in baseline hematology cell counts was positively associated with complete response, objective, and ongoing response. Accordingly, the disclosure provides a method of predicting the likelihood of complete response, objective response, and ongoing response to CAR T cell treatment in a subject in need thereof comprising measuring the ratio of Lymphocyte to Leukocytes in baseline hematology cell counts and predicting the likelihood of complete response, objective response, and ongoing response based on the ratio. In one embodiment, if the ratio is above the optimal cutoff (e.g., where the optimal cutoff may be about 0-5%, 5-10%, 10-15%, 15-20%, 20-25%, 25-30%, 30-35%, 35-40%, 40-45%, 45-50%, etc.) the likelihood of complete response, objective response, and ongoing response is higher than if the ratio is below cutoff (e.g., where the cutoff may be about 0-5%, 5-10%, 10-15%, 15-20%, 20-25%, 25-30%, 30-35%, 35-40%, 40-45%, 45-50%, etc). In one embodiment, the disclosure provides a method of patient stratification whereby subjects with low levels of lymphocytes to leukocytes are treated with another form of therapy (combination therapy, allogeneic CAR T cells, next generation CAR construct, etc) to improve their likelihood of survival/response and/or are subjected to optimized manufacturing to improve product fitness.

In one embodiment, the disclosure provides that the ratio of Lymphocyte to Leukocytes in baseline hematology cell counts had weak negative associations with worst grade of toxicity. Accordingly, the disclosure provides a method of patient stratification whereby ow levels (or below median, or below 1%, 1-5%, 5-10%, 10-15%, 15-20%, 20-25%, 25-30%, 30-35%, etc, preferably below 5.2) of lymphocytes to leukocytes indicates a higher likelihood of having a toxic event and the prophylactic administration of anti-inflammatory medications (e.g. tocilizumab, steroids) to the patient to prevent toxicity.

In one embodiment, the disclosure provides a method of predicting response to CAR T cell therapy by measuring the ratio of Lymphocyte to Leukocytes in baseline hematology cell counts, whereby the ratio is negatively associated with tumor burden and thereby positively associated with response. Accordingly, the disclosure provides a method of stratifying patients for additional intervention to improve efficacy if the pre-manufacturing PBMC lymphocyte to leukocyte ratio is low (or below median, or below 1%, 1-5%, 5-10%, 10-15%, 15-20%, 20-25%, 25-30%, 30-35%, etc, preferably below 5.2) and/or the patient has high tumor burden.

In one embodiment, the disclosure provides that the ratio of Lymphocyte to Leukocytes in baseline hematology cell counts was negatively associated with the number of lines of prior therapy. Accordingly, the disclosure provides that since the increased number of prior chemotherapeutics reduces these cells, CAR T therapy should be considered in the first or second line setting to have the best efficacy or chemotherapies that reduce these cells should be considered as potential options post CAR T cell therapy. This data, along with the positive impact of these cells at the time of apheresis on product fitness, indicate that before any therapies are started for subjects with cancer, apheresis bags could be frozen to obtain the best incoming cells for CAR T-cell therapy.

These data indicate that CAR T-cell utilization in earlier lines of therapy may lead to improved objective and durable responses due to positive predictors of response and product fitness being higher with fewer lines of therapy.

In one embodiment, the disclosure provides that the ratio of Lymphocyte to Leukocytes in baseline hematology cell counts was negatively associated with CRP, Ferritin, IL6. CRP, ferritin, and IL6 have previously been shown to be pharmacodynamic markers that are negatively correlated with response in DLBCL. Accordingly, the disclosure provides a method of estimating the level of these inflammatory cytokines, which associate with a worse prognosis, in a patient by measuring the ratio of Lymphocyte to Leukocytes in baseline hematology cell counts. Also, if low levels of lymphocytes to leukocytes are quantified, the patient is selected for administration of anti-inflammatory medications pre-during- and/or post CAR T cell therapy.

In one embodiment, the disclosure provides a method of predicting the levels of myeloid cells in a patient, wherein the ratio of Lymphocyte to Leukocytes in baseline hematology cell counts is negatively associated with myeloid cells (more specifically, intermediate monocytes, which are negatively associated with response) and positively associated with CD8 and EM/Effector T-cells. In addition, the method provides that patients whom have a low ratio of lymphocyte to leukocytes (or below median, or below 1%, 1-5%, 5-10%, 10-15%, 15-20%, 20-25%, 25-30%, 30-35%, etc, preferably below 5.2) are considered for combination therapeutics that attempt to negate the activity of the myeloid compartment and/or for optimization of the manufacturing process to deplete those populations in the product.

In one embodiment, the disclosure provides that the ratio of Lymphocyte to Monocytes in baseline hematology cell counts associated positively with and may serve as a predictive biomarker for OS and PFS. Accordingly, the disclosure provides a method of stratification in cancer treatment wherein subjects with low levels of lymphocytes to monocytes are administered another form of therapy in addition to or alternatively to CAR T cell therapy (e.g., combination therapy, allogeneic CAR T cells, next generation CAR construct, etc) to improve their likelihood of survival and/or wherein the subject is subjected to optimized manufacturing of CAR T cell products to improve product fitness. The disclosure also provides a method of predicting response whereby a higher complete, objective, and ongoing response rates is observed in subjects whose ratio of lymphocyte to monocytes is above 0.79. In one embodiment, the ratio is between 0 and 0.5, 0.5-1.0, 1.0-1.5, 1.5-2.0, 2-5, 5-10, 10-15, etc.

Figure 29:
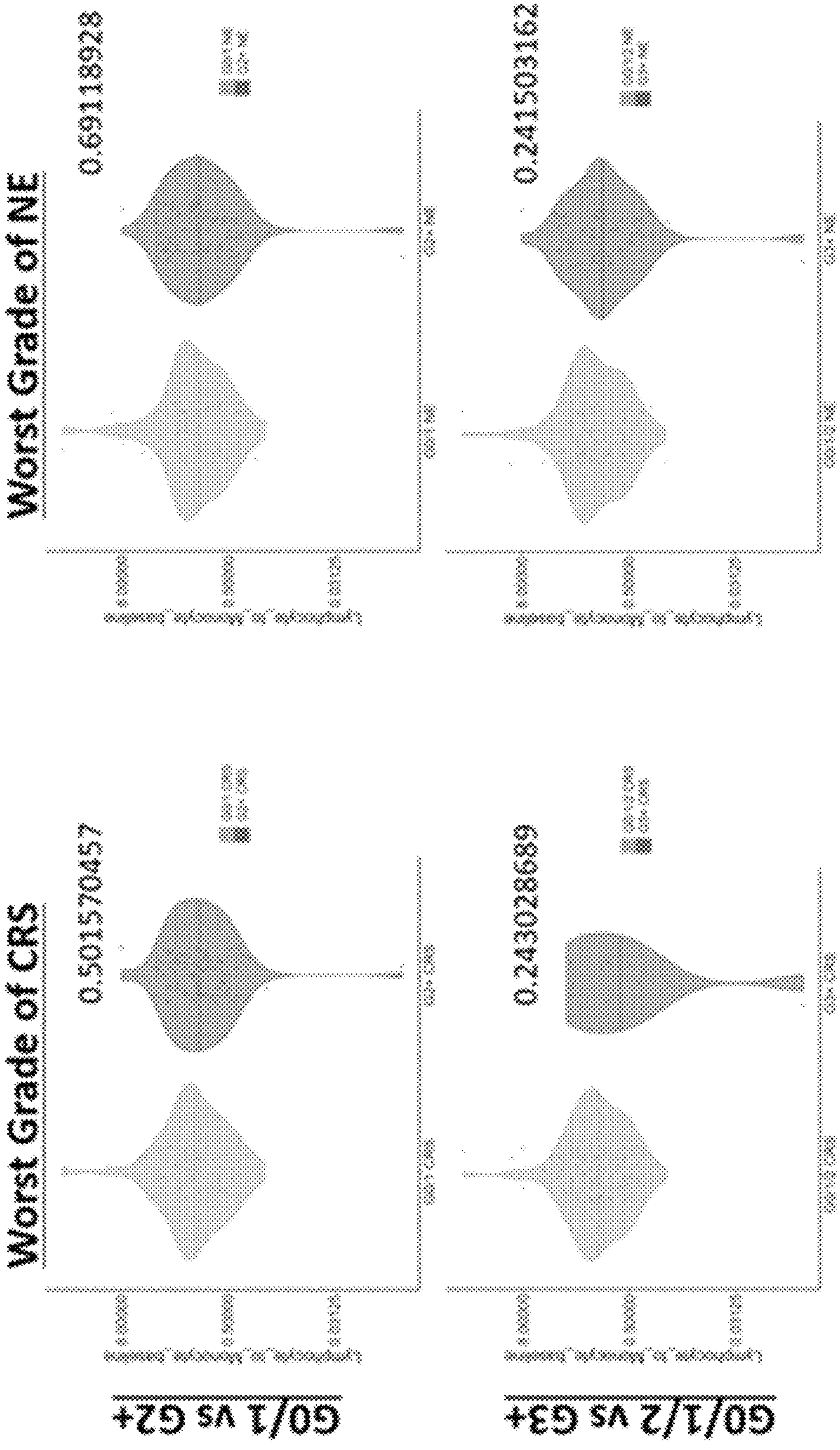
FIG. 29 Violin plots of the ratio lymphocyte to monocytes at baseline grouped by worst grade of toxicity. The ratio of lymphocytes to monocytes in baseline hematology cell counts trends toward a negative association with worst grade of toxicity. CRS-cytokine Release Syndrome. NE—Neurologic Events.

In one embodiment, the disclosure provides that the ratio of Lymphocyte to Monocytes in baseline hematology cell counts had weak negative associations with worst grade of toxicity. FIG. 29. Accordingly, the disclosure provides a method of predicting response to immunotherapy (e.g., CAR T cells), wherein low levels (or below median, or below 1%, 1-5%, 5-10%, 10-15%, 15-20%, 20-25%, 25-30%, 30-35%, preferably below 8%) of lymphocytes to monocytes indicate higher likelihood of having a toxic event and indicate prophylactic use of anti-inflammatory medications (e.g. tocilizumab, steroids) to prevent toxicity.

Figure 30:
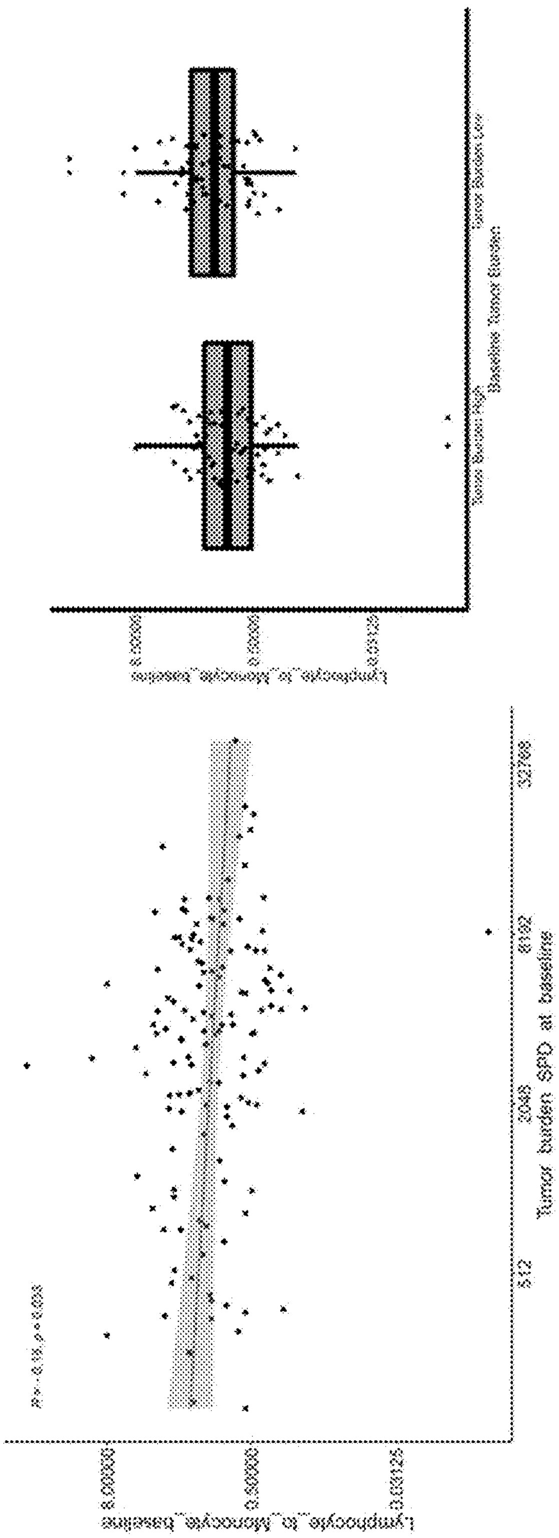
FIG. 30 Association between the ratio of lymphocytes to monocytes in baseline hematology cell counts and tumor burden by SPD at baseline. The ratio of lymphocytes to monocytes are negatively associated with tumor burden as shown by scatterplot (left) and boxplot grouped by category of tumor burden SPD at baseline.

In one embodiment, the disclosure provides that the ratio of Lymphocyte to Monocytes in baseline hematology cell counts was negatively associated with tumor burden. FIG. 30. Accordingly, Similar to prior tumor burden mentions (negatively tracking biomarker for a negative feature of response, potential for additional intervention to improve efficacy if low L to L and high TB. Accordingly, the disclosure provides a method of quantifying the ratio of Lymphocyte to Monocytes in baseline hematology cell counts that allow for estimation of the patient's tumor burden, which has been shown to be a negative indicator of clinical efficacy of CAR T-cells. In one embodiment, the ratio of Lymphocyte to Monocytes in baseline hematology cell counts may indicate the use of additional therapeutics to help overcome larger estimated tumor burden such as chemo-, radio-antibody and small molecule based therapies, immunotherapies (including by not limited to check point inhibitors, bispecific engagers), and cell therapies (including but limited to CAR-T, TCR-based and tumor infiltrating lymphocytes) in which tumor burden had shown to be a negative prognostic and/or predictive biomarker.

Figure 31:
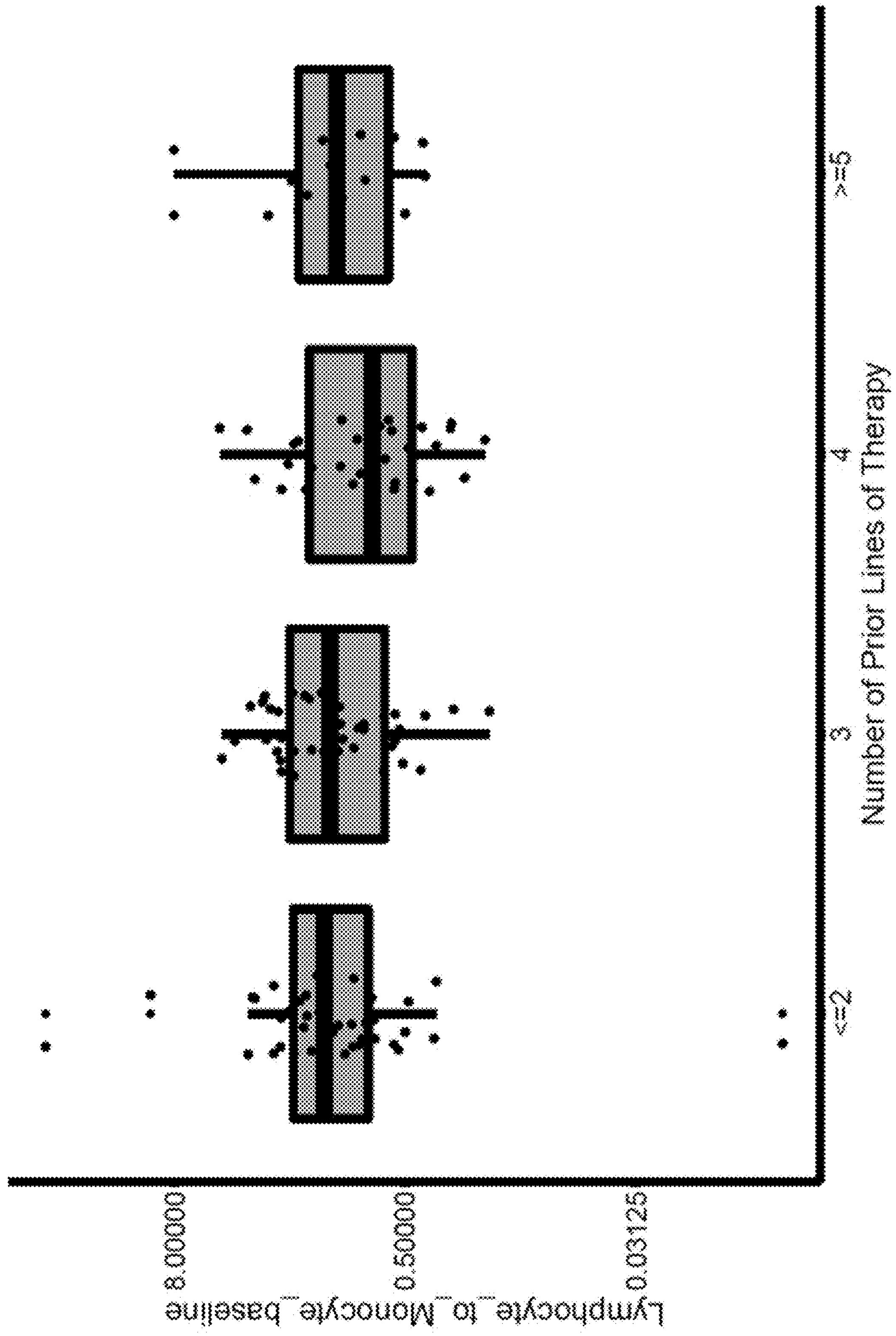
FIG. 31 Boxplot of the relationship between the ratio of lymphocytes to monocytes in baseline hematology cell counts and grouped number of prior lines of therapy. The ratio of lymphocytes to monocytes negatively associated with number of lines of prior therapy.

In one embodiment, the disclosure provides that the ratio of Lymphocyte to Monocytes in baseline hematology cell counts was negatively associated with the number of lines of prior therapy. FIG. 31. This suggests that use of CAR-T cells as first or second line of therapy may lead to even better response rates. Accordingly, Since the increased number of prior chemotherapeutics reduce these cells, CAR T therapy should be considered in the first or second line setting to have the best efficacy or chemotherapies that reduce these cells should be considered as potential options post CAR T cell therapy. This data, along with the positive impact of these cells at the time of apheresis on product fitness, indicate that before any therapies are started for subjects with cancer, apheresis bags could be frozen to obtain the best incoming cells for CAR T-cell therapy. That way if subjects do undergo therapies in advance of CAR T therapy they will still have a more effective starting material than those subjects which have undergone other therapies in advance of collecting the CAR T apheresis material.

Figure 32:
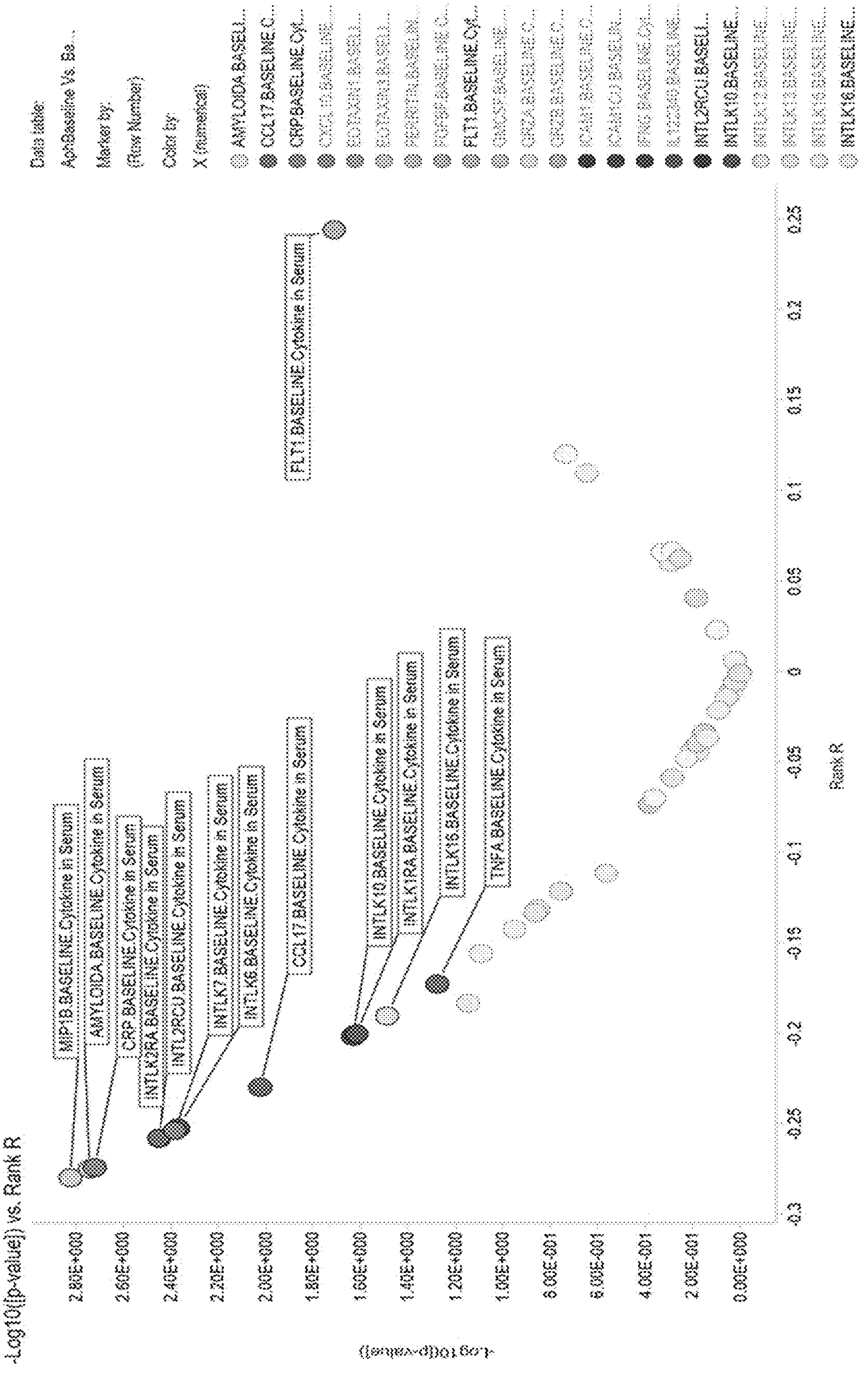
FIG. 32 Volcano plot of baseline serum cytokines and their Spearman Rank-Order correlation with the ratio of lymphocyte to monocytes in baseline hematology cell counts. The ratio of lymphocyte to monocytes is negatively associated with inflammatory and acute phase cytokines such as CRP and IL6.

In one embodiment, the disclosure provides that the ratio of Lymphocyte to Monocytes in baseline hematology cell counts was negatively associated with CRP and IL6. FIG. 32. Accordingly, the disclosure provides a method of estimating the levels of CRP and IL6 in the serum of a cancer patient, and/or immunotherapy (e.g., CAR T cell therapy) prognosis, by measuring the ratio of Lymphocyte to Monocytes in baseline hematology cell counts, wherein the levels of CRP and IL6 associate negatively with the levels of ratio of Lymphocyte to Monocytes in baseline hematology cell counts and positively with a worse prognosis. Also, the disclosure provides a method of stratification of patients wherein if low levels (or levels below median, or levels below 0.05%, 0.05-0.1%, 0.1-0.5%, 0.5-1.0%, 1-5%, 5-10%, 10-15%, preferably below 0.78) of lymphocytes to monocytes are quantified, the patient is administered anti-inflammatory medications.

Figure 33:
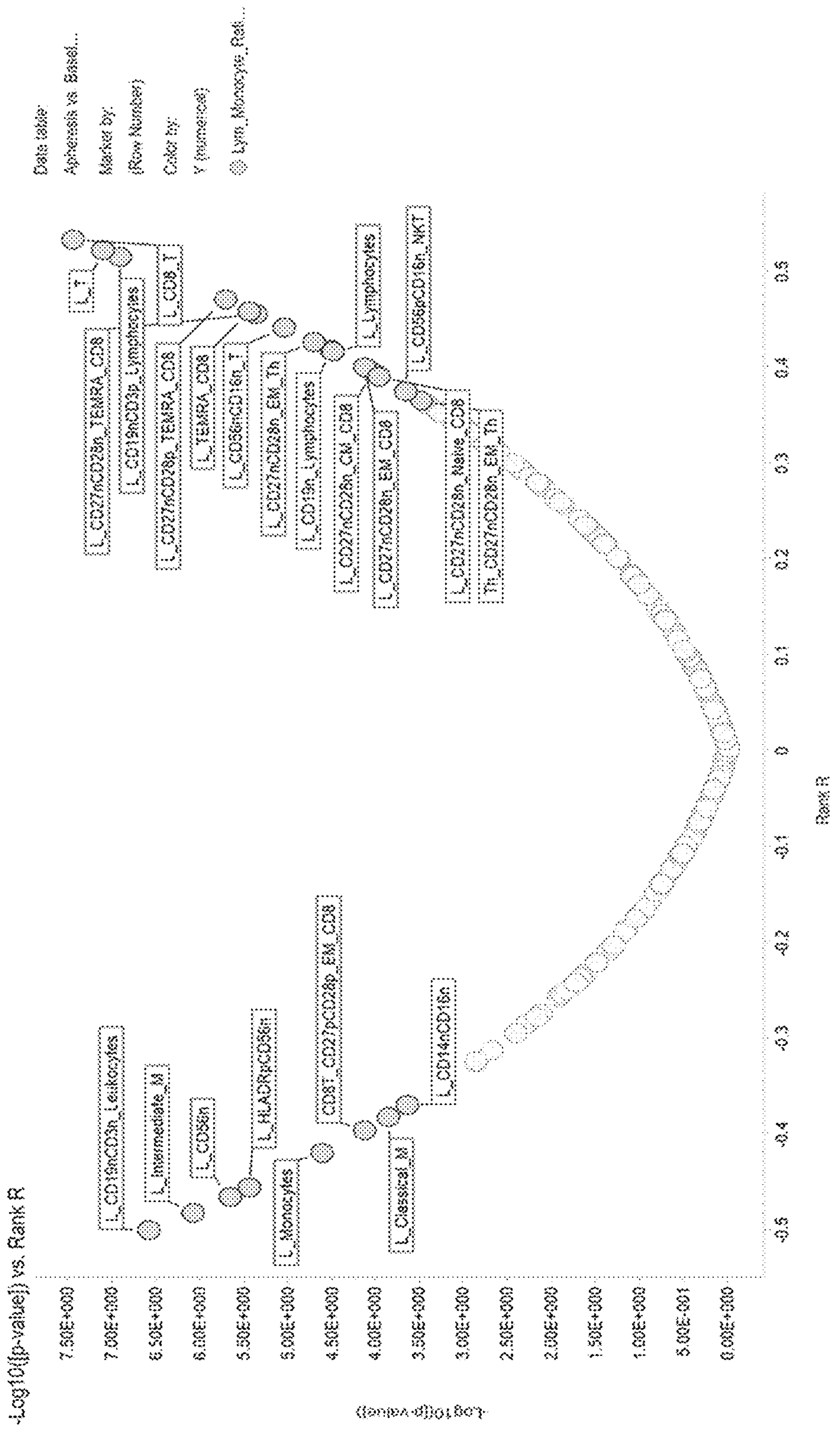
FIG. 33 Volcano plot of pre-manufacturing PBMC populations and their Spearman Rank-Order correlation with the ratio of lymphocytes to monocytes in baseline hematology cell counts. The ratio of lymphocytes to monocytes in baseline hematology cell counts is negatively associated myeloid cells and positively associated with CD8 and EM/Effector T-cells.

In one embodiment, the disclosure provides that the ratio of Lymphocyte to Monocytes in baseline hematology cell counts was negatively associated with myeloid cells and positively associated with CD8 and EM/Effector T-cells. FIG. 33. The disclosure provides that myeloid cells, CD8, and EM/Effector T-cells negatively associate with response. Accordingly, the disclosure provides a method of predicting the level of myeloid cells, CD8, and/or EM/Effector cells in the final infusion product by measuring the ratio of Lymphocyte to Monocytes in baseline hematology cell counts, wherein the ratio of Lymphocyte to Monocytes in baseline hematology cell counts associates negatively with myeloid cells and positively with CD8 and EM/Effector T-cells This method could further be used to stratify patients for combination therapeutics that attempt to negate the activity of the myeloid compartment and/or for optimization of the pre-manufacturing material to deplete those populations.

In one embodiment, the disclosure provides that the ratio of Lymphocyte to Monocytes in baseline hematology cell counts was negatively associated with intermediate monocytes and showed weak correlations with apheresis populations associated with response, including CD27−CD28+ TEMRA and Treg and CD27+CD28+ Naïve and Th cells. Accordingly, high levels (or above median, or above between 0 and 0.5, 0.5-1.0, 1.0-1.5, 1.5-2.0, 2-5, 5-10, 10-15, preferably above 0.8%) of lymphocytes to monocytes in the pre-manufacturing PBMC population may be indicative of incoming apheresis material which tracks positively with product fitness and response. Low levels (below median, or below between 0 and 0.5, 0.5-1.0, 1.0-1.5, 1.5-2.0, 2-5, 5-10, 10-15, preferably below 0.78%) may indicate the need for manufacturing optimization, combination therapy, or next generation CAR therapies T Cell Fitness In some embodiments, the intrinsic cell fitness is assessed based on the capacity of the CAR T cells to expand during nonspecific stimulation in vitro (e.g., shorter doubling time), the differentiation state of the CAR T cells (favorable juvenile phenotype), the levels of specialized CAR T-cell subsets in the CAR T-cell population (e.g., the numbers of CD8 and naïve-like CD8 cells (e.g., CD8+ CCR7+ CD45RA+ T Cells) in the infusion product), and the in vivo CAR T cell expansion rate.

In one embodiment, T cell fitness is the capability of cells to rapidly expand. In the context of engineered T cells, in one embodiment, T cell fitness is a measurement of how fast the engineered T cell population expand pre-treatment. As described herein, T cell fitness is an attribute of engineered T cells that associates with clinical outcome. In some embodiments, T cell fitness is measured by doubling time or expansion rate. An exemplary derivation of T cell "fitness" measured as T cell population doubling time (DT) during the manufacturing process is shown below.

$$\text{Doubling Time} = \frac{\ln(2)\times \text{duration}}{\ln\left(\frac{\text{total viable cells at harvest}}{\text{total viable cells at Day 3}}\right)}$$

Duration may be defined as total manufacturing timeframe MINUS three days (essentially the number of days for the product cells in culture post transduction and before harvest and cryopreservation). Recombinant IL-2 (after nonspecific stimulation with, for example, anti-CD3 antibodies) may be used to drive polyclonal T cell expansion towards achieving the target dose. The shorter the DT, the higher engineered T cell fitness. In vitro expansion rate may be calculated using the formula below.

$$\text{Expansion rate} = \ln(2)/\text{Doubling Time}$$

In the instances described above, the expansion rate is provided in units of "rate/day" or "/day."

In some embodiments, in vivo expansion rate is measured by enumerating CAR cells/unit of blood volume. In some embodiments, the in vivo expansion rate is measured by the number of CAR gene copies/μg of host DNA. In some embodiments, the in vivo expansion rate is measured by of enumerating CAR cells/unit of blood volume.

As described herein, during manufacturing, T cells may be initially non-specifically stimulated with anti-CD3 antibodies in the presence of IL2 and then expanded with growth medium supplemented with IL2. As described herein, low doubling time associates positively with objective response as compared to nonresponse. The median DT in responders was 1.6 days, while nonresponders had a median DT time of 2.1 days. Quartile analysis of response by DT showed that all patients (100%) in the lowest DT quartile achieved an objective response, while 80% of all nonresponders were in the third and fourth quartile of DT. Accordingly, the disclosure provides a method to assess primary treatment resistance comprising (a) measuring the doubling time of the population of T-cells in the infusion product to obtain a value and (b) assessing primary treatment resistance based on the value. In some embodiments, the assessment involves determining in which quartile of the population does the patient fall. In some embodiments, the assessment is done relative to a reference standard. In some embodiments, the method further comprises administering an effective dose of CAR T-cells to the patient, wherein the effective dose is determined using said/the value. In some embodiments, the higher doubling time is associated with primary treatment resistance. In some embodiments, a product doubling time >1.6 days is associated with non-response. In some embodiments, in patients with high tumor burden, patients with objective response or a durable response have doubling times <2 days. In some embodiments, a doubling time >2 days is associated with relapse or non-response. In some embodiments, the higher the number of CD28+CD27+ $T_N$ cells in the apheresis starting material the better (shorter) the infusion product doubling time.

As described herein, higher peak expansion of CAR T cells in the peripheral blood, generally occurring within 2 weeks of post-CAR T-cell infusion, associates with both objective response and durable response, defined as ongoing response with a minimum follow-up of 1 year. Peak number of CAR T cells in the blood correlated with response. Cumulative CAR T-cell levels over the first 28 days, as measured in blood by area under the curve (AUC), were also associated with better objective and durable response to therapy. Accordingly, the disclosure provides a method to assess response to CAR T cell treatment comprising (a) measuring the peak expansion of CAR T cells in the peripheral blood to obtain a value and (b) assessing treatment response based on the value. In another aspect, the disclosure provides a method of determining whether a patient will respond to CAR T cell therapy comprising: (a) measuring the peak CAR T-cell levels in the blood post CAR T-administration to obtain a value (b) normalizing the value to pretreatment tumor burden; and (c) determining if the patient will achieve durable response based on the normalized value. In some embodiments, the value is positively associated with durable response and separates subsets of patients with higher (~60%) vs. lower (~10%) probability of achieving a durable response. In some embodiments, the CAR T-cell levels are calculated by enumerating the number of CAR T-cells per unit of blood volume. In one embodiment, higher peak expansion of CAR T cells in the peripheral blood means peak expansion values falling within the higher quartiles. In some embodiments, in vivo expansion rate is measured by enumerating CAR cells/unit of blood volume. In some embodiments, the in vivo expansion rate is measured by the number of CAR gene copies/μg of host DNA. In some embodiments, the assessment or determination involves determining in which quartile of the population does the patient fall. In some embodiments, the assessment is done relative to a reference standard As described herein, higher peak CAR T-cell expansion is associated with severe neurotoxicity but not CRS. Accordingly, in one embodiment, the disclosure provides a method of predicting severe neurotoxicity comprising (a) measuring the peak CAR T-cell expansion after CAR T cell treatment and to obtain a value and (b) predicting neurotoxicity based on the value. In one embodiment, the method further comprises administering an agent that prevents or reduces neurotoxicity in combination with the CAR T cell treatment.

As described herein, higher expansion rate of CAR T cells during manufacturing associates with greater in vivo CAR T-cell expansion and higher probability of durable remission (durable remission/durable response means being in response at 1 year and beyond). As described herein, product doubling time negatively associates with expansion of CAR T cells in vivo after infusion. As described herein, product doubling time negatively associates with peak CAR T cells normalized to tumor burden. As described herein, product doubling time negatively associates with CAR T-cell AUC. In some embodiments, in vivo expansion rate is measured by enumerating CAR cells/unit of blood volume. In some embodiments, the in vivo expansion rate is measured by the number of CAR gene copies/μg of host DNA. Accordingly, in some embodiments, the disclosure provides a method of determining whether a patient will respond to CAR T cell therapy comprising: (a) measuring the expansion rate of CAR T cells during manufacturing or peak CAR T-cell levels in the blood post CAR T-administration to obtain a value (b) determining whether the patient will achieve durable response based on the value.

As described herein, among patients with high tumor burden, a greater proportion of patients who achieved an objective response or a durable response have a shorter product doubling time (<2 days) compared with patients who relapsed or had no response. Accordingly, in some embodiments, the disclosure provides a method of determining whether a patient will respond to CAR T cell therapy comprising: (a) measuring the peak CAR T-cell levels in the blood post CAR T-administration to obtain a value (b) normalizing the value to pretreatment tumor burden; and (c) determining if the patient will achieve durable response based on the normalized value. In some embodiments, the value is positively associated with durable response and separates subsets of patients with higher (~60%) vs. lower (~10%) probability of achieving a durable response. In some embodiments, the CAR T-cell levels are calculated by enumerating the number of CAR T-cells per unit of blood volume. In some embodiments, the assessment involves determining in which quartile of the population does the patient fall. In some embodiments, the assessment is done relative to a reference standard.

As described herein, doubling time positively associates with the frequency of T-cell differentiation subsets in the final infusion bag. Doubling time is positively associated with the frequency of effector memory T ($T_{EM}$) cells and negatively associated with the frequency of naïve-like T ($T_N$) cells. As described herein, intrinsic product T-cell fitness, as measured by the product doubling time, is positively associated with a less differentiated product and influences the ability of CAR T cells to expand in vivo to a sufficient effector-to-target ratio that supports tumor eradication. Accordingly, in one embodiment, the disclosure provides a method for improving response to CAR T cell treatment in a patient with an infusion product comprising manipulating the cell population to decrease the doubling time of the infusion product and/or administering to the patient an infusion product with a lower doubling time relative to a reference value.

As described herein, the intrinsic capability of T-cell expansion measured pretreatment, as measured by product doubling time, is a major attribute of product T-cell fitness. Relative to other product characteristics, DT was most strongly associated with the frequency of T-cell differentiation subsets in the final infusion bag. Specifically, DT was positively associated with the frequency of effector memory T (TEM) cells and negatively associated with the frequency of naïve-like T (TN) cells. As described herein, baseline tumor burden is positively associated with the differentiation phenotype in the final infusion product. As described herein, product composition and clinical performance associate with the pretreatment immune status of the patient. Accordingly, in one embodiment, the disclosure provides a method of reducing post-treatment tumor burden with treatment with CAR T cells comprising administering an infusion product comprising increased frequency of naïve-like T (TN) cells in the infusion product relative to a reference value. In another embodiment, the disclosure provides a method to predict or estimate the differentiation phenotype of the final infusion product comprising measuring the baseline tumor burden in the patient to obtain a value and estimating or predicting the differentiation phenotype based on the value. In one embodiment, the measure further comprises preparing an effective dose of CAR T cells in the final product based on the value.

T Cell Phenotypes

As described herein, the T cell phenotypes in manufacturing starting material (apheresis) may be associated with T cell fitness (DT). Total % of Tn-like and Tcm cells (CCR7+ cells) is inversely related to DT. The % of Tem (CCR7− CD45RA−) cells is directly associated with DT. Accordingly, in some embodiments, the pre-treatment attribute is the % of Tn-like and Tcm cells. In some embodiments, the % of Tn-like and Tcm cells is determined by the percentage of CCR7+ cells. In some embodiments, the percentage of CCR7+ cells is measured by flow cytometry.

In some embodiments, the pre-treatment attribute is the % of Tem (CCR7− CD45RA−) cells. In some embodiments, the % of Tem cells is determined by the percentage of CCR7− CD45RA− cells. In some embodiments, the percentage of CCR7− CD45RA− cells is measured by flow cytometry.

As described herein, manufacturing doubling time and product T-cell fitness associate directly with the differentiation state of patients' T cells prior to enrollment in CAR T cell treatment. Accordingly, the disclosure provides a method of predicting the T-cell fitness of the manufactured product comprising determining the differentiation state of the patients' T cells prior to CAR T cell treatment (e.g., in the apheresis product) and predicting T-cell fitness during manufacturing based on the differentiation state.

As described herein, the greater the proportions of effector memory T cells in the apheresis product, within total CD3+ T cells or CD4 and CD8 subsets, the higher the product doubling time. As described herein, the more juvenile the T-cell phenotype in the starting material but better the product T-cell fitness. As described herein, CD27+CD28+ $T_N$ cells, which represent immunologically competent subset of $T_N$ cells that express key costimulatory molecules, associate positively with product doubling time. As described herein, there is a direct association across all major phenotypic groups, including proportions of T-cell subsets defined by differentiation markers in CD3, CD4, and CD8 subpopulations, in the apheresis product relative to the final product phenotype. As described herein, the proportion of T cells with $CD25^{hi}$ CD4 expression, possibly representing regulatory T cells in the apheresis material, negatively correlates with the CD8 T-cell output in the product. As described herein, tumor burden after CAR T cell treatment is positively associated with the differentiation phenotype of the final product.

As described herein, the number of infused CD8+ T cells normalized to tumor burden is associated with durable response and expansion of CAR T cells relative to tumor burden. More specifically, quartile analysis of the number of infused CD8 T cells/pretreatment tumor burden, showed a durable response rate of 16% in the lowest quartile vs. 58% in the top quartile.

As described herein, the number of infused specialized T cells, primarily the CD8+ $T_N$-cell population, has a positive influence on durable clinical efficacy with CAR T-cell therapy. As described herein, higher numbers of product CD8+ T cells are needed to achieve complete tumor resolution and establish a durable response in patients with higher tumor burden. As described herein, in patients with high tumor burden, durable response is associated with significantly higher number of infused CD8 T cells compared with patients who respond and then relapse. As described herein, the number of infused TN cells normalized to tumor burden positively associates with durable response. As described herein, the CD4:CD8 ratio positively associates with durable response. As described herein, the total number of CD8 T cells in the product normalized to pretreatment tumor burden positively associates with durable response. Among CD8 T cells, the number of $T_N$ cells is most significantly associated with durable response. The disclosure provides some additional associations, which may be used for one or more of methods of improvement of CAR T cell infusion product, determination of effective dose, and/or predicting durable response based on one or more of these associations. See Table 1.

TABLE 1

Association between product phenotypes and ongoing response or peak CAR T-cell levels. P values were calculated using logistic regression for durable response and by Spearman correlation for CAR T-cell levels.

| | Association With Durable Response | | Association With Peak CAR T-cell Levels | |
|---|---|---|---|---|
| Parameter | P value | Direction of association | P value | Direction of association |
| CD3 infused (%) | 0.201 | Negative | 0.762 | Positive |
| Number of CD3 infused[a] | 0.654 | Positive | 0.441 | Positive |
| Number of CD3 infused/ tumor burden[a] | 0.030 | Positive | 0.443 | Positive |
| $T_n$ infused (%) | 0.454 | Positive | 0.099 | Positive |
| Number of Tn infused[a] | 0.182 | Positive | 0.091 | Positive |
| Number of Tn infused/tumor burden[a] | 0.025 | Positive | 0.114 | Positive |
| % CD8 infused | 0.21 | Positive | 0.126 | Positive |
| Number of CD8[a] | 0.116 | Positive | 0.154 | Positive |
| Number of CD8 infused/tumor burden[a] | 0.009 | Positive | 0.273 | Positive |
| CD4 infused (%) | 0.21 | Negative | 0.124 | Negative |
| Number of CD4 infused[a] | 0.930 | Negative | 0.257 | Negative |
| Number of CD4 infused/tumor burden[a] | 0.059 | Positive | 0.841 | Positive |

[a]Denote analytes in LOG2 transformation.

Accordingly, the disclosure provides a method of improving durable clinical efficacy (e.g., durable response) of CAR T-cell therapy in a patient comprising preparing and/or administering to the patient an effective dose of CAR T cell treatment, wherein the effective dose is determined based on the number of specialized T cells in the infusion product and/or the CD4:CD8 ratio. In some embodiments, the specialized T cells are CD8+ T cells, preferably $T_N$ cells.

In another embodiment, the disclosure provides a method of determining how a patient will respond to treatment comprising (a) characterizing the number of specialized T cells in the infusion product to obtain one or more values and (b) determining how the patient will respond based on the one or more values. In another embodiment, the present disclosure provides a method of treating a malignancy in a patient comprising measuring the T cell phenotypes in a population of T cells obtained from a patient (e.g., apheresis material). In some embodiments, the method further comprises determining whether the patient will respond to chimeric antigen receptor treatment based on the measured percentage of specific T cell types. In some embodiments, the T cell phenotype is measured prior to engineering the cells to express a chimeric antigen receptor (CAR) (e.g., apheresis material). In some embodiments, the T cell phenotype is measured after engineering the cells to express a chimeric antigen receptor (CAR) (e.g., engineered T cells comprising a CAR).

Tumor Burden

Tumor related parameters (e.g., tumor burden, serum LDH as hypoxic/cell death marker, inflammatory markers associated with tumor burden and myeloid cell activity) may be associated with clinical outcomes. In one aspect, the present disclosure provides a method of treating a malignancy in a patient comprising measuring the tumor burden in a patient prior to administration of a CAR T cell treatment. In some embodiments, the method further comprises determining whether the patient will respond to CAR T cell treatment based on the levels of tumor burden compared to a reference level. In some embodiments, the reference level is less than about 1,000 $mm^2$, about 2,000 $mm^2$, about 3,000 $mm^2$, about 4,000 $mm^2$.

As described herein, the higher the tumor burden, the higher the probability of relapse within 1 year post treatment in subjects who achieved an OR, and the higher the probability of grade 3+ neurotoxicity. In some embodiments, tumor burden may be used to assess the probability of relapse in patients who respond, if the pre-treatment tumor burden is greater than about 4,000 $mm^2$, about 5,000 $mm^2$, about 6,000 $mm^2$, about 7,000 $mm^2$, or about 8,000 $mm^2$.

As described herein, low tumor burden pre-CAR T-cell therapy is a positive predictor of durable response. As described herein, in the highest tumor burden quartile, patients who achieved a durable response had a greater than 3-fold higher peak CAR T-cell expansion compared with patients who relapsed or had no response. As described herein, there is a lower durable response rate at comparable peak CAR T-cell levels in patients with higher tumor burden compared with patients who had lower tumor burden. As described herein, durable responders had a higher peak CAR T-cell/tumor burden ratio compared with nonresponders or responders who subsequently relapsed within one year post-treatment. As described herein, complete responders had a higher peak CAR T-cell/tumor burden ratio compared with partial responders or nonresponders. Accordingly, the disclosure also provides a method of determining whether or not a patient will be a nonresponder, have a durable response, or relapse within one year after administration of CAR T cell treatment comprising measuring the peak CAR T-cell/tumor burden ratio and making the determination based on those levels. As described herein, objective and durable response rate correlate with increasing peak CAR T-cell levels. As described herein, there is a lower durable response rate (12%) in patients within the lowest quartile of peak CAR T-cell/tumor burden ratio than in the top quartiles (>50%). As described herein, durable response in refractory large cell lymphoma treated with anti-CD19 CAR T-cell therapy containing a CD28 costimulatory domain, benefits from early CAR T cell expansion, commensurate with tumor burden.

As described herein, tumor burden positively associates with severe neurotoxicity: while rates increase from quartile 1 to quartile 3, they decline in the highest quartile, generally mirroring the association between CAR T-cell expansion and tumor burden in the overall population.

As described herein, peak CAR T-cell levels that are normalized to either pretreatment tumor burden or body weight associate strongly with efficacy, and the latter associate with grade ≥3 NE. Accordingly, the disclosure also provides a method of determining whether or not a patient will show durable response after administration of CAR T cell treatment comprising measuring the peak CAR T-cell levels normalized to either pretreatment tumor burden or body weight and making the determination based on those levels. Also, the disclosure also provides a method of determining whether or not a patient will show grade ≥3 NE after administration of CAR T cell treatment comprising measuring the peak CAR T-cell levels normalized to pre-treatment tumor body weight and making the determination based on those levels.

Measuring Response and Efficacy

In some embodiments, methods described herein may provide a clinical benefit to a subject. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, approximately 1%, 2%, 3%, 4%, 5%, 6%, 7%, 8%, 9%, 10%, 15%, 20%, 25%, 30%, 35%, 40%, 45%, 0%, 55%, 60%, 65%, 70%, 75%, 80%, 85%, 90% or 95% and any unenumerated % in between of patients achieve a clinical benefit. In some embodiments, the response rate is 1%, 2%, 3%, 4%, 5%, 6%, 7%, 8%, 9%, 9.5%, 10.5%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 25 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81, 82, 83, 84, 85, 86, 87, 88, 89, 90, 91, 92, 93, 94, 95, 96, 97, 98, 99, or 100% or some other unenumerated percentage and range in between 1% and 100%. In some embodiments, the response rate is between 0%-10%, 10%-20%, 20%-30%, 30%-40%, 40%-50%, 50%-60%, 60%-70%, 70%-80%, 80%-90%, or 90%-100%. In some embodiments, the response rate is between 0%-1.%, 1%-1.5%, 1.5%-2%, 2%-3%, 3%-4%, 4%-5%, 5%-6%, 6%-7%, 7%-8%, 8%-9%, 9%-10%, 10%-15%, 15%-20%, 20-25%, 25%-30%, 35-40%, and so one and so forth, through 95%-100%.

In some embodiments, the quartiles for peak CAR T cells ranges are those in the FIGS. and Tables and 0-15, 15-35, and so on and so forth, 40-100, 0-40 40-50 40-60 40-70, 40-80, 40-90, 40-100, 40-110, 40-120, 40-130, 40-140, 40-150, 40-300, 40-1000, 80-160, 50-100, 50-110, 50-120, 50-130, 50-140, 50-150, 50-160, 50-170, 50-180, 50-190, 50-200, 60-100, 60-110, 60-120, 60-130, 60-140, 60-150, 60-160, 60-170, 60-180, 60-190, 60-200, 70-100, 70-110, 70-120, 70-130, 70-140, 70-150, 70-160, 70-170, 70-180, 70-190, 70-200, 80-100, 80-110, 80-120, 80-130, 80-140, 80-150, 80-160, 80-170, 80-180, 80-190, 80-200, 90-100, 90-110, 90-120, 90-130, 90-140, 90-150, 90-160, 90-170, 90-180, 90-190, 90-200, 100-110, 100-120, 100-130, 100-140, 100-150, 100-160, 100-170, 100-180, 100-190, 100-200, and so on and so forth, 50-70, 60-80, 70-90, 80-100, 90-110, 100-120, 110-130, 120-150, 130-160, 140-170, 150-180, 160-190, 170-200, 180-210, 190-210, 200-220, 210-230, 220-240, or 230-250, and so on and so forth, and any unenumerated ranges in between. In some embodiments, the quartiles for CCL2 and CXCL10 ranges are those in the FIGS. and Tables and 0-100, 100-200, 200-300, 400-500 500-600 600-700, or so on and so forth or any other unenumerated ranges in between, 0-50, 50-100, 100, 150, 200, 300, 400, 500, 549, 549-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, 1900-2000, 2000-2200, 2200-2300, 2300-2400, 2400-2600, 2600-2800, 2800-3000, or so on and so forth, or any other unenumerated ranges in between. In some embodiments, the quartiles for Tumor Burden are those in the FIGS. and Tables and 0-500, 500-1000, 1000-1500 and so on and so forth, 1000-2000, 2000-3000, 3000-4000, 4000-5000, 5000-6000, 6000-7000 and so on and so forth, 8000-10000, 10000-20000 and so on and so forth, and any other unenumerated ranges in between. In some embodiments, the quartiles for Ferritin ranges are those in the FIGS. and Tables and 0-50, 50-100, 100, 150, 200, 300, 400, 500, 549, 549-600, 600-650, 650-700, 700-750, 750-800, 800-850, 850-900, 900-950, 950-1000, 1000-1100, 1100-1200 and so on and so forth, 100,000-200,000, 200,000-500,000, 500,000, or 400,000-500,000, and so on and so forth, 1000000-1500000, 1500000-1600000, and so on and so forth, 2000000-10000000, 2000000-15000000, and so on and so forth, and any other unenumerated ranges in between. In some embodiments, the quartiles for IFNγ, Infused Naïve-like T Cells, Infused CD8 T Cells, Infused CD4 T cells ranges, are those in the FIGS. and Tables an <0.1, 0.1-0.2, 0.2-0.3, 0.3-0.4, 0.4-0.5, 0.6-0.7, 0.7-0.8, 0.8-0.9, 0.91-1.0, 1.0-1.1 so on and so forth through 99.9-100, 1-5, 5-10, 10-15, 15-20, 25-30, 30-35, 35-40, 40-45, 45-50, 50-60, 60-70, 70-80, 80-90, 90-100, 100-125, 125-150, 150-175, or 175-200, 10-30 30-50 50-70, 70-90 and so on and so forth, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60 and so on and so forth units and so on and so forth, and any other unenumerated ranges in between. In some embodiments, the quartiles for peak CAR T cells/tumor burden, peak CAR T cells/body weight, Infused Naïve-like T Cells/Tumor Burden, Infused CD8 T Cells/Tumor Burden, Infused CD4 T Cells/Tumor Burden, and Infused CD3 T Cells/Tumor Burden ranges are those in the FIGS. and Tables and 0.001-0.005, 0.005-0.010, 0.010-0.020, 0.020-0.030, 0.030-0.040, 0.040-0.050, 0.05-0.06, 0.06-0.07, 0.07-0.08, 0.08-0.09, 0.09-0.10, 0.1-0.11, 0.11-0.12, 0.12-0.13, 0.13-0.14, 0.14-0.15, 0.15-0.16, 0.16-0.17, 0.17-0.18, 0.18-0.19, 0.19-0.20, 0.5-2.5, 0.05-0.1, 0.1-0.2, 0.2-0.3, 0.3-0.4, 0.4-0.5, 0.5-0.6, 0.6-0.7, 0.7-0.8, 0.8-0.9, 0.9-1.0, 1-2, 2-3, 3-4, 4-5, and so on and so forth, and any unenumerated ranges in between, and the median is 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, or 10 units and any other values in between. In some embodiments, the quartiles for LDH and Infused CD3 T Cells ranges are those in the FIGS. and Tables and 0-50, 50-100, 100-150, 150-200, 200-250, 250-300, 300-350, 350-400, 400-450 or 450-500 and so on and so forth up to 1000, 150-250, 250-350, 350-450, 450-550, and so on and so forth, 1-500, 1-1000, 25-100, 25-200, 25-300, 25-400, 25-500, 25-1000, 100-150, 100-200, 100-300, 100-400, 100-500, 100-1000 and so on and so forth, 100-5000, 100-4900, 100-4800, 100-4700, 100-4600, 100-4500, 100-

4400, 100-4300, 100-4200, 100-4100, 100-4000, 100-3900, 100-3800, 100-3700, 100-3600, 100-3500, 100-3400, 100-3300, 100-3200, 100-3100, 100-3000, 100-2900, 100-2800, 100-2700, 100-2600, 100-2500, 100-2400, 100-2300, 100-2200, 100-2100, 100-2000, 100-1900, 100-1800, 100-1700, 100-1600, 100-1500, 100-1400, 100-1300, 100-1200, 100-1100, 100-1000, 100-900, 100-800, 100-700, 100-600, 100-500, 100-400, 100-300, 100-200, 500-10,000, 500-7500, 500-5000, 500-4900, 500-4800, 500-4700, 500-4600, 500-4500, 500-4400, 500-4300, 500-4200, 500-4100, 500-4000, 500-3900, 500-3800, 500-3700, 500-3600, 500-3500, 500-3400, 500-3300, 500-3200, 500-3100, 500-3000, 500-2900, 500-2800, 500-2700, 500-2600, 500-2500, 500-2400, 500-2300, 500-2200, 500-2100, 500-2000, 500-1900, 500-1800, 500-1700, 500-1600, 500-1500, 500-1400, 500-1300, 500-1200, 500-1100, 500-1000, 500-900, 500-800, 500-700, or 500-600, and so on and so forth, and any other unenumerated ranges in between. In some embodiments, the quartiles for IL-6 ranges are those in the FIGS. and Tables and 0-1, 1-2, 2-3, 3-4, 4-5, 5-6, 6-7, 7-8, 8-9, 9-10, and so on and so forth, 3-4, 3-5, 3-6, 3-7, 3-8, 3-9, and so on and so forth, 6-1, 6-2, 6-3, 6-4, 6-6, 6-6, 6-7 and so on and so forth, 6.7-10, 6.7-20, 6.7-30, 6.7-80, 6.7-90, 6.7-100, 6.7-110, 6.77-120, 6.7-130, and so on and so forth, and any other unenumerated ranges in between. In some embodiments, the quartiles for Infused CD3 T cells ranges are those in the FIGS. and Tables and 0-100, 100-200, 200-300, 300-400, 400-500, 500-600, 600-700, and so on and so forth, 100-240, 100-150, 100-260, and so on and so forth, 300-400, 300-500, 300-600, 300-700, 300-800, and so on and so forth, and any other unenumerated ranges in between. In some embodiments, the quartiles for Doubling Time are those in the FIGS. and Tables and <2, <2.1, <2.2, <2.3, <2.4, <2.5 and so on and so forth, more than 1.1, 1.2, 1.3, 1.4, 1.5, 16, 1.7, 1.8, 1.9 and less than 2, and so on and so forth, and any other ranges in between. In some embodiments, the quartiles for IFNγ in coculture ranges are 200-300, 300-400, 400-500, 500-600 and so on and so forth, 300-500, 300-1000, 300-1500, 300-2000, 300-2500, 300-3000, 300-3500, 300-3600 and so on and so forth, 2000-3000, 3000-4000, 4000-5000, 4000-6000, and so on and so forth, 6000-7000, 6000-8000, 6000-9000 and so on and so forth, 8000-15000, 8000-16000, 8000-17000, 8000-18000 and so on and so forth and any other unenumerated ranges in between. In some embodiments, any of these ranges can be qualified by the terms about or approximately.

Clinical benefit may be objective response or durable clinical response defined as ongoing response at a median follow up time of 1 year. In some embodiments, response, levels of CAR T cells in blood, or immune related factors is determined by follow up at about 1 day, about 2 days, about 3 days, about 4 days, about 5 days, about 6 days, or about 7 days after administration of engineered CAR T cells. In some embodiments, response, levels of CAR T cells in blood, or immune related factors is determined by follow up at about 1 week, about 2 weeks, about 3 weeks, or about 4 weeks after administration of engineered CAR T cells. In some embodiments, response, levels of CAR T cells in blood and/or immune related factors are determined by follow up at about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months after administration of a engineered CAR T cells. In some embodiments, response, levels of CAR T cells in blood and/or immune related factors are determined by follow up at about 1 year, about 1.5 years, about 2 years, about 2.5 years, about 3 years, about 4 years, or about 5 years after administration of engineered CAR T cells.

Measuring Response and Efficacy

In some embodiments, methods described herein may provide a clinical benefit to a subject. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, approximately 1%, 2%, 3%, 4%, 5%, 6%, 7%, 8%, 9%, 10%, 15%, 20%, 25%, 30%, 35%, 40%, 45%, 0%, 55%, 60%, 65%, 70%, 75%, 80%, 85%, 90% or 95% and any unenumerated % in between of patients achieve a clinical benefit. In some embodiments, the response rate is 1%, 2%, 3%, 4%, 5%, 6%, 7%, 8%, 9%, 9.5%, 10.5%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 25 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81, 82, 83, 84, 85, 86, 87, 88, 89, 90, 91, 92, 93, 94, 95, 96, 97, 98, 99, or 100% or some other unenumerated percentage and range in between 1% and 100%. In some embodiments, the response rate is between 0%-10%, 10%-20%, 20%-30%, 30%-40%, 40%-50%, 50%-60%, 60%-70%, 70%-80%, 80%-90%, or 90%-100%. In some embodiments, the response rate is between 0%-1.%, 1%-1.5%, 1.5%-2%, 2%-3%, 3%-4%, 4%-5%, 5%-6%, 6%-7%, 7%-8%, 8%-9%, 9%-10%, 10%-15%, 15%-20%, 20-25%, 25%-30%, 35-40%, and so one and so forth, through 95%-100%.

In some embodiments, the quartiles for peak CAR T cells ranges are those in the FIGS. and Tables and 0-15, 15-35, and so on and so forth, 40-100, 0-40 40-50 40-60 40-70, 40-80, 40-90, 40-100, 40-110, 40-120, 40-130, 40-140, 40-150, 40-300, 40-1000, 80-160, 50-100, 50-110, 50-120, 50-130, 50-140, 50-150, 50-160, 50-170, 50-180, 50-190, 50-200, 60-100, 60-110, 60-120, 60-130, 60-140, 60-150, 60-160, 60-170, 60-180, 60-190, 60-200, 70-100, 70-110, 70-120, 70-130, 70-140, 70-150, 70-160, 70-170, 70-180, 70-190, 70-200, 80-100, 80-110, 80-120, 80-130, 80-140, 80-150, 80-160, 80-170, 80-180, 80-190, 80-200, 90-100, 90-110, 90-120, 90-130, 90-140, 90-150, 90-160, 90-170, 90-180, 90-190, 90-200, 100-110, 100-120, 100-130, 100-140, 100-150, 100-160, 100-170, 100-180, 100-190, 100-200, and so on and so forth, 50-70, 60-80, 70-90, 80-100, 90-110, 100-120, 110-130, 120-150, 130-160, 140-170, 150-180, 160-190, 170-200, 180-210, 190-210, 200-220, 210-230, 220-240, or 230-250, and so on and so forth, and any unenumerated ranges in between. In some embodiments, the quartiles for CCL2 and CXCL10 ranges are those in the FIGS. and Tables and 0-100, 100-200, 200-300, 400-500 500-600 600-700, or so on and so forth or any other unenumerated ranges in between, 0-50, 50-100, 100, 150, 200, 300, 400, 500, 549, 549-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, 1900-2000, 2000-2200, 2200-2300, 2300-2400, 2400-2600, 2600-2800, 2800-3000, or so on and so forth, or any other unenumerated ranges in between. In some embodiments, the quartiles for Tumor Burden are those in the FIGS. and Tables and 0-500, 500-1000, 1000-1500 and so on and so forth, 1000-2000, 2000-3000, 3000-4000, 4000-5000, 5000-6000, 6000-7000 and so on and so forth, 8000-10000, 10000-20000 and so on and so forth, and any other unenumerated ranges in between. In some embodiments, the quartiles for Ferritin ranges are those in the FIGS. and Tables and 0-50, 50-100, 100, 150, 200, 300, 400, 500, 549, 549-600, 600-650, 650-700, 700-750, 750-800, 800-850, 850-900, 900-950, 950-1000, 1000-1100, 1100-1200 and so on and so forth, 100,000-200,000, 200,000-500,000, 500,000, or 400,000-500,000, and so on and so forth, 1000000-1500000, 1500000-1600000, and so on and so forth, 2000000-10000000, 2000000-15000000, and so on and so forth, and any other unenumerated ranges in between. In some embodiments, the quartiles for IFNγ, Infused Naïve-like T Cells, Infused CD8 T Cells, Infused CD4 T cells ranges, are those in the FIGS. and Tables an <0.1, 0.1-0.2, 0.2-0.3, 0.3-0.4, 0.4-0.5, 0.6-0.7, 0.7-0.8, 0.8-0.9, 0.91-1.0, 1.0-1.1 so on and so forth through 99.9-100, 1-5, 5-10, 10-15, 15-20, 25-30, 30-35, 35-40, 40-45, 45-50, 50-60, 60-70, 70-80, 80-90, 90-100, 100-125, 125-150, 150-175, or 175-200, 10-30 30-50 50-70, 70-90 and so on and so forth, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60 and so on and so forth units and so on and so forth, and any other unenumerated ranges in between. In some embodiments, the quartiles for peak CAR T cells/tumor burden, peak CAR T cells/body weight, Infused Naïve-like T Cells/Tumor Burden, Infused CD8 T Cells/Tumor Burden, Infused CD4 T Cells/Tumor Burden, and Infused CD3 T Cells/Tumor Burden ranges are those in the FIGS. and Tables and 0.001-0.005, 0.005-0.010, 0.010-0.020, 0.020-0.030, 0.030-0.040, 0.040-0.050, 0.05-0.06, 0.06-0.07, 0.07-0.08, 0.08-0.09, 0.09-0.10, 0.1-0.11, 0.11-0.12, 0.12-0.13, 0.13-0.14, 0.14-0.15, 0.15-0.16, 0.16-0.17, 0.17-0.18, 0.18-0.19, 0.19-0.20, 0.5-2.5, 0.05-0.1, 0.1-0.2, 0.2-0.3, 0.3-0.4, 0.4-0.5, 0.5-0.6, 0.6-0.7, 0.7-0.8, 0.8-0.9, 0.9-1.0, 1-2, 2-3, 3-4, 4-5, and so on and so forth, and any unenumerated ranges in between, and the median is 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 01, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, or 10 units and any other values in between. In some embodiments, the quartiles for LDH and Infused CD3 T Cells ranges are those in the FIGS. and Tables and 0-50, 50-100, 100-150, 150-200, 200-250, 250-300, 300-350, 350-400, 400-450 or 450-500 and so on and so forth up to 1000, 150-250, 250-350, 350-450, 450-550, and so on and so forth, 1-500, 1-1000, 25-100, 25-200, 25-300, 25-400, 25-500, 25-1000, 100-150, 100-200, 100-300, 100-400, 100-500, 100-1000 and so on and so forth, 100-5000, 100-4900, 100-4800, 100-4700, 100-4600, 100-4500, 100-4400, 100-4300, 100-4200, 100-4100, 100-4000, 100-3900, 100-3800, 100-3700, 100-3600, 100-3500, 100-3400, 100-3300, 100-3200, 100-3100, 100-3000, 100-2900, 100-2800, 100-2700, 100-2600, 100-2500, 100-2400, 100-2300, 100-2200, 100-2100, 100-2000, 100-1900, 100-1800, 100-1700, 100-1600, 100-1500, 100-1400, 100-1300, 100-1200, 100-1100, 100-1000, 100-900, 100-800, 100-700, 100-600, 100-500, 100-400, 100-300, 100-200, 500-10,000, 500-7500, 500-5000, 500-4900, 500-4800, 500-4700, 500-4600, 500-4500, 500-4400, 500-4300, 500-4200, 500-4100, 500-4000, 500-3900, 500-3800, 500-3700, 500-3600, 500-3500, 500-3400, 500-3300, 500-3200, 500-3100, 500-3000, 500-2900, 500-2800, 500-2700, 500-2600, 500-2500, 500-2400, 500-2300, 500-2200, 500-2100, 500-2000, 500-1900, 500-1800, 500-1700, 500-1600, 500-1500, 500-1400, 500-1300, 500-1200, 500-1100, 500-1000, 500-900, 500-800, 500-700, or 500-600, and so on and so forth, and any other unenumerated ranges in between. In some embodiments, the quartiles for IL-6 ranges are those in the FIGS. and Tables and 0-1, 1-2, 2-3, 3-4, 4-5, 5-6, 6-7, 7-8, 8-9, 9-10, and so on and so forth, 3-4, 3-5, 3-6, 3-7, 3-8, 3-9, and so on and so forth, 6-1, 6-2, 6-3, 6-4, 6-6, 6-6, 6-7 and so on and so forth, 6.7-10, 6.7-20, 6.7-30, 6.7-80, 6.7-90, 6.7-100, 6.7-110, 6.77-120, 6.7-130, and so on and so forth, and any other unenumerated ranges in between. In some embodiments, the quartiles for Infused CD3 T cells ranges are those in the FIGS. and Tables and 0-100, 100-200, 200-300, 300-400, 400-500, 500-600, 600-700, and so on and so forth, 100-240, 100-150, 100-260, and so on and so forth, 300-400, 300-500, 300-600, 300-700, 300-800, and so on and so forth, and any other unenumerated ranges in between. In some embodiments, the quartiles for Doubling Time are those in the FIGS. and Tables and <2, <2, <2.1, <2.2, <2.3, <2.4, <2.5 and so on and so forth, more than 1.1, 1.2, 1.3, 1.4, 1.5, 1.6, 1.7, 1.8, 1.9 and less than 2, and so on and so forth, and any other ranges in between. In some embodiments, the quartiles for IFNγ in coculture ranges are 200-300, 300-400, 400-500, 500-600 and so on and so forth, 300-500, 300-1000, 300-1500, 300-2000, 300-2500, 300-3000, 300-3500, 300-3600 and so on and so forth, 2000-3000, 3000-4000, 4000-5000, 4000-6000, and so on and so forth, 6000-7000, 6000-8000, 6000-9000 and so on and so forth, 8000-15000, 8000-16000, 8000-17000, 8000-18000 and so on and so forth and any other unenumerated ranges in between. In some embodiments, any of these ranges can be qualified by the terms about or approximately.

Clinical benefit may be objective response or durable clinical response defined as ongoing response at a median follow up time of 1 year. In some embodiments, response, levels of CAR T cells in blood, or immune related factors is determined by follow up at about 1 day, about 2 days, about 3 days, about 4 days, about 5 days, about 6 days, or about 7 days after administration of engineered CAR T cells. In some embodiments, response, levels of CAR T cells in blood, or immune related factors is determined by follow up at about 1 week, about 2 weeks, about 3 weeks, or about 4 weeks after administration of engineered CAR T cells. In some embodiments, response, levels of CAR T cells in blood and/or immune related factors are determined by follow up at about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months after administration of a engineered CAR T cells. In some embodiments, response, levels of CAR T cells in blood and/or immune related factors are determined by follow up at about 1 year, about 1.5 years, about 2 years, about 2.5 years, about 3 years, about 4 years, or about 5 years after administration of engineered CAR T cells.

Chimeric Antigen Receptors

Chimeric antigen receptors (CARs) are genetically engineered receptors. These engineered receptors may be inserted into and expressed by immune cells, including T cells and other lymphocytes in accordance with techniques known in the art. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci. Transl. Med. 3:95 (2011); Porter et al., N. Engl. J. Med. 365:725-33 (2011), and Gross et al., Annu. Rev. Pharmacol. Toxicol. 56:59-83 (2016).

In some embodiments, a costimulatory domain which includes a truncated hinge domain ("THD") further comprises some or all of a member of the immunoglobulin family such as IgG1, IgG2, IgG3, IgG4, IgA, IgD, IgE, IgM, or fragment thereof.

In some embodiments, the THD is derived from a human complete hinge domain ("CHD"). In other embodiments, the THD is derived from a rodent, murine, or primate (e.g., non-human primate) CHD of a costimulatory protein. In some embodiments, the THD is derived from a chimeric CHD of a costimulatory protein.

The costimulatory domain for the CAR of the disclosure may further comprise a transmembrane domain and/or an intracellular signaling domain. The transmembrane domain may be fused to the extracellular domain of the CAR. The costimulatory domain may similarly be fused to the intracellular domain of the CAR. In some embodiments, the transmembrane domain that naturally is associated with one of the domains in a CAR is used. In some instances, the transmembrane domain is selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this disclosure may be derived from (i.e., comprise) 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1; CD11a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Optionally, short linkers may form linkages between any or some of the extracellular, transmembrane, and intracellular domains of the CAR. In some embodiments, the linker may be derived from repeats of glycine-glycine-glycine-glycine-serine (SEQ ID NO: 2) (G4S)n (SEQ ID NO: 2) or GSTSGSGKPGSGEGSTKG (SEQ ID NO: 1). In some embodiments, the linker comprises 3-20 amino acids and an amino acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to GSTSGSGKPGSGEGSTKG (SEQ ID NO: 1).

The linkers described herein, may also be used as a peptide tag. The linker peptide sequence may be of any appropriate length to connect one or more proteins of interest and is preferably designed to be sufficiently flexible so as to allow the proper folding and/or function and/or activity of one or both of the peptides it connects. Thus, the linker peptide may have a length of no more than 10, no more than 11, no more than 12, no more than 13, no more than 14, no more than 15, no more than 16, no more than 17, no more than 18, no more than 19, or no more than 20 amino acids. In some embodiments, the linker peptide comprises a length of at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids. In some embodiments, the linker comprises at least 7 and no more than 20 amino acids, at least 7 and no more than 19 amino acids, at least 7 and no more than 18 amino acids, at least 7 and no more than 17 amino acids, at least 7 and no more than 16 amino acids, at least 7 and no more 15 amino acids, at least 7 and no more than 14 amino acids, at least 7 and no more than 13 amino acids, at least 7 and no more than 12 amino acids or at least 7 and no more than 11 amino acids. In certain embodiments, the linker comprises 15-17 amino acids, and in particular embodiments, comprises 16 amino acids. In some embodiments, the linker comprises 10-20 amino acids. In some embodiments, the linker comprises 14-19 amino acids. In some embodiments, the linker comprises 15-17 amino acids. In some embodiments, the linker comprises 15-16 amino acids. In some embodiments, the linker comprises 16 amino acids. In some embodiments, the linker comprises 3, 4, 5, 6, 7, 8, 9, 10, 11, 12, 13, 14, 15, 16, 17, 18, 19 or 20 amino acids.

In some embodiments, a spacer domain is used. In some embodiments, the spacer domain is derived from CD4, CD8a, CD8b, CD28, CD28T, 4-1BB, or other molecule described herein. In some embodiments, the spacer domains may include a chemically induced dimerizer to control expression upon addition of a small molecule. In some embodiments, a spacer is not used.

The intracellular (signaling) domain of the engineered T cells of the disclosure may provide signaling to an activating domain, which then activates at least one of the normal effector functions of the immune cell. Effector function of a T cell, for example, may be cytolytic activity or helper activity including the secretion of cytokines.

In certain embodiments, suitable intracellular signaling domain include (i.e., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, ligand that specifically binds with CD83, LIGHT, LTBR, Ly9 (CD229), Ly108), lymphocyte function-associated antigen-1 (LFA-1; CD11a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Antigen Binding Molecules

Suitable CARs may bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment ("scFv"). A scFv is a single chain antibody fragment having the variable regions of the heavy and light chains of an antibody linked together. See U.S. Pat. Nos. 7,741,465 and 6,319,494, as well as Eshhar et al., Cancer Immunol Immunotherapy (1997) 45: 131-136. A scFv retains the parent antibody's ability to interact specifically with target antigen. scFv's are useful in chimeric antigen receptors because they may be engineered to be expressed as part of a single chain along with the other CAR components. Id See also Krause et al., J. Exp. Med., Volume 188, No. 4, 1998 (619-626); Finney et al., *Journal of Immunology,* 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the disclosure, with specificity to more than one target of interest.

In some embodiments, the polynucleotide encodes a CAR comprising a (truncated) hinge domain and an antigen binding molecule that specifically binds to a target antigen. In some embodiments, the target antigen is a tumor antigen. In some embodiments, the antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGFI)-1, intestinal carboxyl esterase, kappa chain, LAGA-la, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the Al domain of tenascin-C (TnC Al), thyroglobulin, tumor stromal antigens, vascular endothelial growth factor receptor-2 (VEGFR2), virus-specific surface antigen such as an HIV-specific antigen (such as HIV gpl20), as well as any derivate or variant of these surface antigens.

Engineered T Cells and Uses

The cell of the present disclosure may be obtained through T cells obtained from a subject. T cells may be obtained from, e.g., peripheral blood mononuclear cells, bone marrow, lymph node tissue, cord blood, thymus tissue, tissue from a site of infection, ascites, pleural effusion, spleen tissue, tumors, or differentiated in vitro. In addition, the T cells may be derived from one or more T cell lines available in the art. T cells may also be obtained from a unit of blood collected from a subject using any number of techniques known to the skilled artisan, such as FICOLL™ separation and/or apheresis. In some embodiments, the cells collected by apheresis are washed to remove the plasma fraction, and placed in an appropriate buffer or media for subsequent processing. In some embodiments, the cells are washed with PBS. As will be appreciated, a washing step may be used, such as by using a semi-automated flow through centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Pub. No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection may be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected may be used. For example, to enrich for CD4+ cells by negative selection, a monoclonal antibody cocktail typically includes antibodies to CD8, CD11b, CD14, CD16, CD20, and HLA- DR. In some embodiments, flow cytometry and cell sorting are used to isolate cell populations of interest for use in the present disclosure.

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, CD8+ cells are further sorted into naive, central memory, and effector cells by identifying cell surface antigens that are associated with each of these types of CD8+ cells. In some embodiments, the expression of phenotypic markers of central memory T cells includes expression of CCR7, CD3, CD28, CD45RO, CD62L, and CD127 and negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+ T helper cells may be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is the Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In some embodiments, the T cells are obtained from a donor subject. In some embodiments, the donor subject is human patient afflicted with a cancer or a tumor. In some embodiments, the donor subject is a human patient not afflicted with a cancer or a tumor.

In some embodiments, a composition comprising engineered T cells comprises a pharmaceutically acceptable carrier, diluent, solubilizer, emulsifier, preservative and/or adjuvant. In some embodiments, the composition comprises an excipient.

In some embodiments, the composition is selected for parenteral delivery, for inhalation, or for delivery through the digestive tract, such as orally. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In some embodiments, the vehicle for parenteral injection is sterile distilled water in which composition described herein, with or without at least one additional therapeutic agent, is formulated as a sterile, isotonic solution, properly preserved. In some embodiments, the preparation involves the formulation of the desired molecule with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

In some embodiments, the methods of treating a cancer in a subject in need thereof comprise a T cell therapy. In some embodiments, the T cell therapy disclosed herein is engineered Autologous Cell Therapy (eACT™). According to this embodiment, the method may include collecting blood cells from the patient. The isolated blood cells (e.g., T cells) may then be engineered to express a CAR disclosed herein. In a particular embodiment, the CAR T cells are administered to the patient. In some embodiments, the CAR T cells treat a tumor or a cancer in the patient. In some embodiments the CAR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient. In certain embodiments, the T cell is a tumor-infiltrating lymphocyte (TIL), engineered autologous T cell (eACT™), an allogeneic T cell, a heterologous T cell, or any combination thereof.

In some embodiments, the engineered T cells are administered at a therapeutically effective amount. For example, a therapeutically effective amount of the engineered T cells may be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, the therapeutically effective amount of the engineered viable T cells is between about $1\times10^6$ and about $2\times10^6$ engineered viable T cells per kg body weight up to a maximum dose of about $1\times10^8$ engineered viable T cells.

Methods of Treatment

The methods disclosed herein may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, Waldenstrom macroglobulinemia, or a combination thereof.

In some embodiments, the cancer is a myeloma. In some embodiments, the cancer is multiple myeloma. In some embodiments, the cancer is leukemia. In some embodiments, the cancer is acute myeloid leukemia.

In some embodiments, the cancer is Non-Hodgking lymphoma. In some embodiments, the cancer is relapsed/refractory NHL. In some embodiments, the cancer is mantle cell lymphoma.

In some embodiments, the methods further comprise administering a chemotherapeutic. In some embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 and U.S. Pat. Nos. 9,855,298 and 10,322,146, which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient. Another embodiment comprises serum cyclophosphamide and fludarabine at days −4, −3, and −2 prior to T cell administration at a dose of of 500 mg/m of body surface area of cyclophosphamide per day and a dose of 30 mg/m$^2$ of body surface area per day of fludarabine during that period of time. Another embodiment comprises cyclophosphamide at day −2 and fludarabine at days −4, −3, and −2 prior to T cell administration, at a dose of 900 mg/m$^2$ of body surface area of cyclophosphamide and a dose of 25 mg/m$^2$ of body surface area per day of fludarabine during that period of time. In another embodiment, the conditioning comprises cyclophosphamide and fludarabine at days −5, −4 and −3 prior to T cell administration at a dose of 500 mg/m$^2$ of body surface area of cyclophosphamide per day and a dose of 30 mg/m$^2$ of body surface area of fludarabine per day during that period of time.

In some embodiments, the antigen binding molecule, transduced (or otherwise engineered) cells (such as CARs), and the chemotherapeutic agent are administered each in an amount effective to treat the disease or condition in the subject.

In some embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylol melamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; Polysaccharide K (PSK); razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone, R-CHOP (CHOP plus Rituximab), and G-CHOP (CHOP plus obinutuzumab).

In some embodiments, the chemotherapeutic agent is administered at the same time or within one week after the administration of the engineered cell. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pidilizumab (CureTech), and atezolizumab (Roche).

Additional therapeutic agents suitable for use in combination with the compositions and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib), inhibitors of GM-CSF, CSF1, GM-CSFR, or CSF1R, in addition to anti-thymocyte globulin, lenzilumab and mavrilimumab.

In some embodiments, the treatment further comprises bridging therapy, which is therapy between conditioning and the compositions disclosed herein. In some embodiments, the bridging therapy comprises, CHOP, G-CHOP, R-CHOP (rituximab, cyclophosphamide, doxorubicin, vincristine, and prednisolone), corticosteroids, bendamustine, platinum compounds, anthracyclines, and/or phosphoinositide 3-kinase (PI3K) inhibitors. In some embodiments, the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032). In some embodiments, the AKT inhibitor is perifosine, MK-2206. In one embodiment, the mTOR inhibitor is selected from everolimus, sirolimus, temsirolimus, ridaforolimus. In some embodiments, the dual PI3K/mTOR inhibitor is selected from BEZ235, XL765, and GDC-0980. In some embodiments, the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032).

In some embodiments, the bridging therapy comprises acalabrutinib, brentuximab vedotin, copanlisib hydrochloride, nelarabine, belinostat, bendamustine hydrochloride, carmustine, bleomycin sulfate, bortezomib, zanubrutinib, carmustine, chlorambucil, copanlisib hydrochloride, denileukin diftitox, dexamethasone, doxorubicin hydrochloride, duvelisib, pralatrexate, obinutuzumab, ibritumomab tiuxetan, ibrutinib, idelalisib, recombinant interferon alfa-2b, romidepsin, lenalidomide, mechloretamine hydrochloride, methotrexate, mogamulizumab-kpc, prerixafor, nelarabine, obinutuzumab, denileukin diftitox, pembrolizumab, plerixafor, polatuzumab vedotin-piiq, mogamulizumab-kpc, prednisone, rituximab, hyaluronidase, romidepsin, bortezomib, venetoclax, vinblastine sulfate, vorinostat, zanubrutinib, CHOP, COPP, CVP, EPOCH, R-EPOCH, HYPER-CVAD, ICE, R-ICE, R-CHOP, R-CVP, and combinations of the same.

In some embodiments, a composition comprising engineered CAR T cells are administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO, Epogen®, Procrit®); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (TLs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

Monitoring

In some embodiments, administration of chimeric receptor T cell immunotherapy occurs at a certified healthcare facility.

In some embodiments, the methods disclosed herein comprise monitoring patients at least daily for 7 days at the certified healthcare facility following infusion for signs and symptoms of CRS and neurologic toxicities and other adverse reactions to CAR T cell treatment. In some embodiments, the symptom of neurologic toxicity is selected from encephalopathy, headache, tremor, dizziness, aphasia, delirium, insomnia, and anxiety. In some embodiments, the symptom of adverse reaction is selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia. In some embodiments, patients are instructed to remain within proximity of the certified healthcare facility for at least 4 weeks following infusion.

Clinical Outcomes

In some embodiments, the clinical outcome is complete response. In some embodiments, the clinical outcome is durable response. In some embodiments, the clinical outcome is complete response. In some embodiments, the clinical outcome is no response. In some embodiments, the clinical outcome is partial response. In some embodiments, the clinical outcome is objective response. In some embodiments, the clinical outcome is survival. In some embodiments, the clinical outcome is relapse.

In some embodiments, objective response (OR) is determined per the revised IWG Response Criteria for Malignant Lymphoma (Cheson, 2007) and determined by IWG Response Criteria for Malignant Lymphoma (Cheson et al. Journal of Clinical Oncology 32, no. 27 (September 2014) 3059-3067). Duration of Response is assessed. The Progression-Free Survival (PFS) by investigator assessment per Lugano Response Classification Criteria is evaluated.

Prevention or Management of Severe Adverse Reactions

In some embodiments, the present disclosure provides methods of preventing the development or reducing the severity of adverse reactions based on the levels of one or more attributes. In this respect, the disclosed method may comprise administering a "prophylactically effective amount" of tocilizumab, a corticosteroid therapy, or an anti-seizure medicine for toxicity prophylaxis. In some embodiments, the method comprises administering inhibitors of GM-CSF, CSF1, GM-CSFR, or CSF1R, lenzilumab, mavrilimumab, cytokines, and/or anti-inflammatory agents. The pharmacologic and/or physiologic effect may be prophylactic, i.e., the effect completely or partially prevents a disease or symptom thereof. A "prophylactically effective amount" may refer to an amount effective, at dosages and for periods of time necessary, to achieve a desired prophylactic result (e.g., prevention of onset of adverse reactions).

In some embodiments, the method comprises management of adverse reactions. In some embodiments, the adverse reaction is selected from the group consisting of cytokine release syndrome (CRS), a neurologic toxicity, a hypersensitivity reaction, a serious infection, a cytopenia and hypogammaglobulinemia.

In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

Cytokine Release Syndrome (CRS)

In some embodiments, the method comprises preventing or reducing the severity of CRS in a chimeric receptor treatment. In some embodiments, the engineered CAR T cells are deactivated after administration to the patient.

In some embodiments, the method comprises identifying CRS based on clinical presentation. In some embodiments, the method comprises evaluating for and treating other causes of fever, hypoxia, and hypotension. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered.

In some embodiments, the method comprises monitoring patients at least daily for 7 days at the certified healthcare facility following infusion for signs and symptoms of CRS. In some embodiments, the method comprises monitoring patients for signs or symptoms of CRS for 4 weeks after infusion. In some embodiments, the method comprises counseling patients to seek immediate medical attention should signs or symptoms of CRS occur at any time. In some embodiments, the method comprises instituting treatment with supportive care, tocilizumab or tocilizumab and corticosteroids as indicated at the first sign of CRS.

Neurologic Toxicity (NT)

In some embodiments, the method comprises monitoring patients for signs and symptoms of neurologic toxicities. In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life-threatening neurologic toxicities. In some embodiments, the symptom of neurologic toxicity is selected from encephalopathy, headache, tremor, dizziness, aphasia, delirium, insomnia, and anxiety.

In some embodiments, the method comprises monitoring patients at least daily for 7 days at the certified healthcare facility following infusion for signs and symptoms of neurologic toxicities. In some embodiments, the method comprises monitoring patients for signs or symptoms of neurologic toxicities for 4 weeks after infusion.

Secondary Malignancies

In some embodiments, patients treated with CAR T cells (e.g., CD19-directed) or other genetically modified autologous T cell immunotherapy may develop secondary malignancies. In certain embodiments, patients treated with CAR T cells (.e.g, CD19-directed) or other genetically modified allogeneic T cell immunotherapy may develop secondary malignancies. In some embodiments, the method comprises monitoring life-long for secondary malignancies.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present disclosure. To the extent that any of the definitions or terms provided in the references incorporated by reference differ from the terms and discussion provided herein, the present terms and definitions control.

The present disclosure is further illustrated by the following examples, which should not be construed as further limiting. The contents of all references cited throughout this application are expressly incorporated herein by reference.

The disclosures provided by this application may be used in a variety of methods in additional to, or as a combination of, the methods described above. The following is a compilation of exemplary methods that can be derived from the disclosures provided in this application.

Methods and Compositions to Generate and Optimize a Product for Increased Clinical Efficacy and/or Decreased Toxicity See earlier sections titled "SUMMARY" and "BRIEF DESCRIPTION OF THE DRAWINGS", and the Examples section below.

Methods of Increasing the Efficacy and/or Diminishing the Toxicity of T cell Therapy In one embodiment, the disclosure provides a method of increasing the efficacy and/or reducing the toxicity of T cell immunotherapy (e.g., CAR T cell immunotherapy) comprising decreasing the subject's tumor burden prior to CAR T-cell immunotherapy. In one embodiment, the decrease of the subject's tumor burden comprises administration of bridging therapy. In one embodiment, bridging therapy comprises therapy between conditioning and T cell administration. In one embodiment, the bridging therapy comprises CHOP, R-CHOP (rituximab, cyclophosphamide, doxorubicin, vincristine, and prednisolone), G-CHOP (obinutuzumab, cyclophosphamide, doxorubicin, vincristine, and prednisolone), corticosteroids, bendamustine, platinum compounds, anthracyclines, venetoclax, zanubrutinib, and/or phosphoinositide 3-kinase (PI3K) inhibitors, and inhibitors of the PI3K/Akt/mTOR pathway. In one embodiment, the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032). In one embodiment, the bridging therapy comprises acalabrutinib, brentuximab vedotin, copanlisib hydrochloride, nelarabine, belinostat, bendamustine hydrochloride, carmustine, bleomycin sulfate, bortezomib, zanubrutinib, carmustine, chlorambucil, copanlisib hydrochloride, denileukin diftitox, dexamethasone, doxorubicin hydrochloride, duvelisib, pralatrexate, obinutuzumab, ibritumomab tiuxetan, ibrutinib, idelalisib, recombinant interferon alfa-2b, romidepsin, lenalidomide, mechloretamine hydrochloride, methotrexate, mogamulizumab-kpc, prerixafor, nelarabine, obinutuzumab, denileukin diftitox, pembrolizumab, plerixafor, polatuzumab vedotin-piiq, mogamulizumab-kpc, prednisone, rituximab, hyaluronidase, romidepsin, bortezomib, venetoclax, vinblastine sulfate, vorinostat, zanubrutinib, CHOP, COPP, CVP, EPOCH, R-EPOCH, HYPER-CVAD, ICE, R-ICE, R-CHOP, R-CVP, and combinations of the same.

In one embodiment, the disclosure provides a method of increasing the efficacy and/or reducing the toxicity of T cell immunotherapy (e.g., CAR T cell immunotherapy) comprising decreasing the subject's systemic inflammatory state prior to T-cell immunotherapy. In one embodiment, the therapy is CAR T cell therapy. In one embodiment, the method comprises administering anti-inflammatory treatment to the subject prior to CAR T-cell immunotherapy. Examples of anti-inflammatory treatments are provided elsewhere in this disclosure.

In one embodiment, the disclosure provides a method of increasing the efficacy and/or reducing the toxicity of T cell immunotherapy (e.g., CAR T cell immunotherapy) comprising reducing myeloid cell activity in the subject prior to CAR T-cell immunotherapy. In one embodiment, the disclosure provides a method of increasing the efficacy and/or reducing the toxicity of T cell immunotherapy (e.g., CAR T cell immunotherapy) comprising reducing the MCP-1 and/or IL-6 activity prior to, or early after CAR T-cell administration. In one embodiment, reducing myeloid cell activity, MCP-1, and/or IL-6 activity comprises administering to the subject a monoclonal antibody against MCP-1, IL-6, IL-1, CSF1R, GM-CSF and/or a small molecule. Examples of such agents are described elsewhere in the disclosure. In one embodiment, the small molecule is a JAK/STAT inhibitor. In one embodiment, the JAK/STAT inhibitor is selected from tofacitinib, ruxolitinib, filgotinib, baricitinib, peficitinib, oclacitinib, upadicitinib, solcitinib, decernotinib, SHR0302, AC430, PF-06263276, BMS-986165, lestaurtinib, PF-06651600, PF-04965841, abrocitinib, sttatic, peptidomimetics, and combinations thereof.

In one embodiment, the disclosure provides a method of increasing the efficacy and/or reducing the toxicity of T cell immunotherapy (e.g., CAR T cell immunotherapy) comprising reducing the activity of activated T cells in the subject/product prior to CAR T-cell immunotherapy. In one embodiment, this can be achieved by separation/removal of differentiated cells (effector memory and/or effector cells, enriching the product for juvenile T cells (CCR7+), removing or diminishing the percentage and number of differentiated T cells in the T cell product infusion bag through separation techniques; and/or treating the product T cells during or after manufacturing process with pharmacological agents or biological response modifiers that would reduce excessive T cell activity (e.g. JAK/STAT inhibitors).

In one embodiment, the disclosure provides a method of increasing the efficacy and/or reducing the toxicity of T cell immunotherapy (e.g., CAR T cell immunotherapy) comprising increasing the dosage of the T cell immunotherapy in a manner commensurate with tumor burden and/or re-dosing patients with high tumor burden. Methods of measuring and classifying tumor burden are described elsewhere in the disclosure.

In one embodiment, the disclosure provides a method of increasing the efficacy and/or reducing the toxicity of T cell immunotherapy (e.g., CAR T cell immunotherapy) comprising (a) identifying a subject positive for marker(s) of toxicity in response to T-cell immunotherapy; and (b) reducing IL-15 elevation post-conditioning and pre-T cell immunotherapy in the subject. In one embodiment, the marker of toxicity in response to T-cell immunotherapy is high tumor burden. In one embodiment, the marker of toxicity in response to T-cell immunotherapy is increased pre-treatment levels of an inflammatory marker. In one embodiment, the inflammatory marker is selected from IL6, CRP, and ferritin. In one embodiment, reduction of IL-15 elevation post-conditioning and pre-T cell immunotherapy is accomplished by selection of a pre-conditioning protocol. In one embodiment, the pre-conditioning protocol comprises cyclophosphamide, fludarabine, bendamustine, Anti-Human Thymocyte Globulin, carmustine, radiation, etoposide, cytarabine, melphalan, rituximab, or combinations thereof.

Methods of Manipulating the Composition of Specific T Cell Subsets in a T Cell Product to Improve Methods of Treating a Subject with a T Cell Product In one embodiment, the disclosure provides methods of treatment of malignancies that combine any of the above methods of predicting response and/or toxicity, and methods of manipulating the composition of the T cell product with administration of T cell treatment (e.g., T cell infusion products).

In one embodiment, the disclosure provides a method of improving an infusion product comprising engineered lymphocytes and, optionally, treating a cancer in a subject with an infusion product comprising engineered lymphocytes comprising:

- measuring levels of one or more attributes in a population of lymphocytes from an apheresis product; and/or
- measuring levels of one or more attributes in a population of engineered lymphocytes (e.g., CAR T cells) during manufacturing of a final infusion product and/or in the final infusion product; and/or
- manipulating the composition of the T cell infusion product to improve effectiveness and reduce treatment-associated toxicity; and/or
- determining or predicting a patient's response to treatment with the engineered lymphocytes based on the measured levels of one or more attributes compared to a reference level; and, optionally,
- administering a therapeutically effective dose of the engineered lymphocytes to the subject, wherein the therapeutically effective dose is determined based on the levels of one or more attributes of the population of engineered lymphocytes in the infusion product and/or of the T cells in the apheresis product.

In one embodiment, the engineered lymphocytes target a tumor antigen. In one embodiment, the tumor antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGFI)-1, intestinal carboxyl esterase, kappa chain, LAGA-la, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, survivin and telomerase, TAG-72, the extra domain A (EDA) and extra domain B (EDB) of fibronectin and the Al domain of tenascin-C (TnC Al), thyroglobulin, tumor stromal antigens, vascular endothelial growth factor receptor-2 (VEGFR2), virus-specific surface antigen such as an HIV-specific antigen (such as HIV gpl20), as well as any derivate or variant of these surface antigens. In one embodiment, the target antigen is CD19.

In one embodiment, the cancer is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof. In one embodiment, the cancer is (relapsed or refractory) diffuse large B-cell lymphoma (DLBCL) not otherwise specified, primary mediastinal large B-cell lymphoma, high grade B-cell lymphoma, DLBCL arising from follicular lymphoma, or mantle cell lymphoma.

In one embodiment, the therapeutically effective amount or effective dose of the engineered lymphocytes (e.g., CAR T cells) may be at least about $10^4$ cells, at least about $10^5$ cells, at least about $10^6$ cells, at least about $10^7$ cells, at least about $10^8$ cells, at least about $10^9$, or at least about $10^{10}$ cells. In one embodiment, the therapeutically effective amount or effective dose of the engineered lymphocytes (e.g., CAR T cells) is about $10^4$ cells, about $10^5$ cells, about $10^6$ cells, about $10^7$ cells, or about $10^8$ cells. In one embodiment, the therapeutically effective amount or effective dose of the engineered lymphocytes (e.g., CAR T cells) may be about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In one embodiment, the therapeutically effective amount or effective dose of the engineered lymphocytes (e.g., CAR T cells) may be between about $1\times10^6$ and about $2\times10^6$ engineered viable lymphocytes (e.g., CAR T cells) per kg body weight up to a maximum dose of about $1\times10^8$ engineered viable lymphocytes (e.g., CAR T cells). In one embodiment, the therapeutically effective dose is between 75 and $200\times10^6$ engineered lymphocytes.

EXAMPLES

A clinical study wherein patients with relapsed/refractory NHL have been treated with axicabtagene ciloleucel was conducted. Axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

Patients may have had diffuse large B-cell lymphoma, primary mediastinal B-cell lymphoma, or transformed follicular lymphoma with refractory disease despite undergoing recommended prior therapy. Patients received a target dose of $2\times10^6$ anti-CD19 CAR T cells per kilogram of body weight after receiving a conditioning regimen of low-dose cyclophosphamide and fludarabine. (Neelapu, S S et al. 2017, *N Engl J Med* 2017; 377(26):2531-44).

In the following EXAMPLES, biomarker data from the clinical study patients were analyzed according to an expanded statistical analysis plan for correlates of response and parameters differentially associated with treatment efficacy and toxicities, as well as product fitness. Several correlations were revealed. Available samples from patients in the clinical study (NCT02348216) were analyzed. Safety and efficacy results were previously reported. (Neelapu, S S et al. 2017, *N Engl J Med* 2017; 377(26):2531-44; Locke F L et al. 2019; Lancet Oncol. 2019 January; 20(1):31-42. doi: 10.1016/S1470-2045(18)30864-7. Epub 2018 Dec. 2). Durable response refers to those patients who were in ongoing response at least 1 year post-axicabtagene ciloleucel infusion. Relapse refers to those patients who achieved a CR or PR and subsequently experienced disease progression. Patients who achieved stable or progressive disease as best response are included in no response category.

While conventional prognostic factors for LICL were not associated with outcomes in the pivotal clinical study (Neelapu et al. NEJM. 2017), other attributes like chimeric antigen receptor (CAR) T-cell fitness and composition (CCR7+CD45RA+ T cells), reduced preTx tumor burden, and immune tumor microenvironment (TME) with presence of activated CD8+PD 1+LAG-3+/−TIM-3− T cells were associated with efficacy (Locke et al., Blood Advances, 2020 and Galon et al., ASCO, 2020. By systemic interrogation of factors influencing CAR-T cell fitness and the TIC in LBCL, an association was uncovered between pre-treatment immune cell characteristics in blood on one side and key features of Axicabtagene ciloleucel product and the TIC respectively, that influence clinical response to CAR T cell intervention.

Figure 1B:
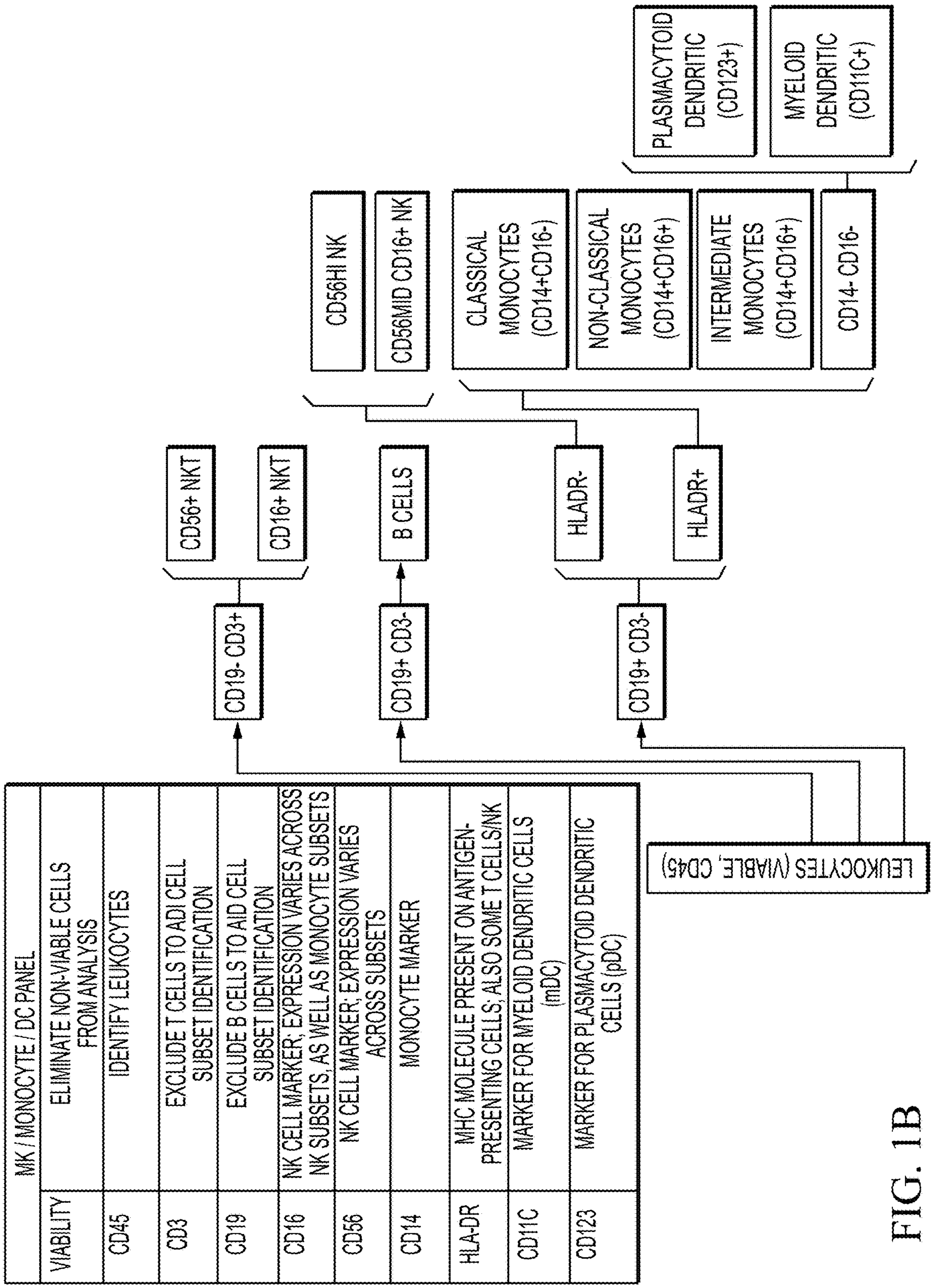
FIG. 1B Overview of NK/MONOCYTE/DC subsets flow cytometry markers and gating strategy utilized for analysis of apheresis material from the clinical study.

Pre-existing characteristics of the immune system were systematically analyzed by multiparametric flow cytometry of the apheresed peripheral blood mononuclear cells (PBMC) that served as the starting material for the Axicabtagene ciloleucel manufacturing process in the clinical study (N=101). The apheresed PBMC were kept at liquid nitrogen before thawing for antibody staining. The panels utilized for this analysis characterized the memory compartment of T-cells (CD27, CD28, CCR7, and CD45RA), subsets of myeloid cells, NK, NKT and B cells (FIGS. 1A and 1B). The analysis of pre-treatment TIC was performed by multiplex immunohistochemistry (N=18) and gene expression analysis (N=30) as previously described (Rossi et al, Cancer Res Jul. 1, 2018 (78) (13 Supplement) LB-016; DOI: 10.1158/1538-7445.AM2018-LB-016, Galon et al, Journal of Clinical Oncology 2020 (38) (15_suppl), 3022-3022 DOI: 10.1200/JCO.2020.38.15_suppl.3022 *Journal of Clinical Oncology* 38, no. 15_suppl (May 20, 2020) 3022-3022. Axicabtagene ciloleucel characteristics related to T-cell fitness were analyzed by measuring doubling time and viability during manufacturing (N=145), as well as end-product T cell phenotypes by flow cytometry (including percentage and total number of infused CCR7+CD45RA+ T cells). Correlative analyses between these covariates and parameters from routine hematology tests, as well as features from routine hematology testing, were performed by Spearman rank correlation and the Wilcoxon test. The effects of different variables on survival were assessed by the Kaplan-Meier method with optimal cutpoint selection.

Two key pre-existing features of the immune system were identified, consisting in the percentage of CD27+ CD28+ Th cells of naïve phenotype (CCR7+ CD45RA+) and intermediate monocytes (CD14+ CD16+), both measurable in the pre-manufacturing PBMC population, that associated positively and negatively respectively, with determinants of Axicabtagene ciloleucel clinical efficacy. More specifically, the frequency of CD27+ CD28+ Th cells of naïve phenotype in pre-manufacturing PBMC population associated positively with the pre-treatment T cell signature in the TME, as well as the percentage of product CCR7+ CD45RA+ T cells. In addition, this metric associated positively with ongoing response rate, progression free survival and overall response post Axicabtagene ciloleucel. Conversely, the percentage of intermediate monocytes (CD14+CD16+) in pre-manufacturing PBMC population associated directly with negative predictive markers such as pre-treatment serum levels of LDH, IL-6 and CRP and inversely with survival and T cell signature in the TME.

Figure 1C:
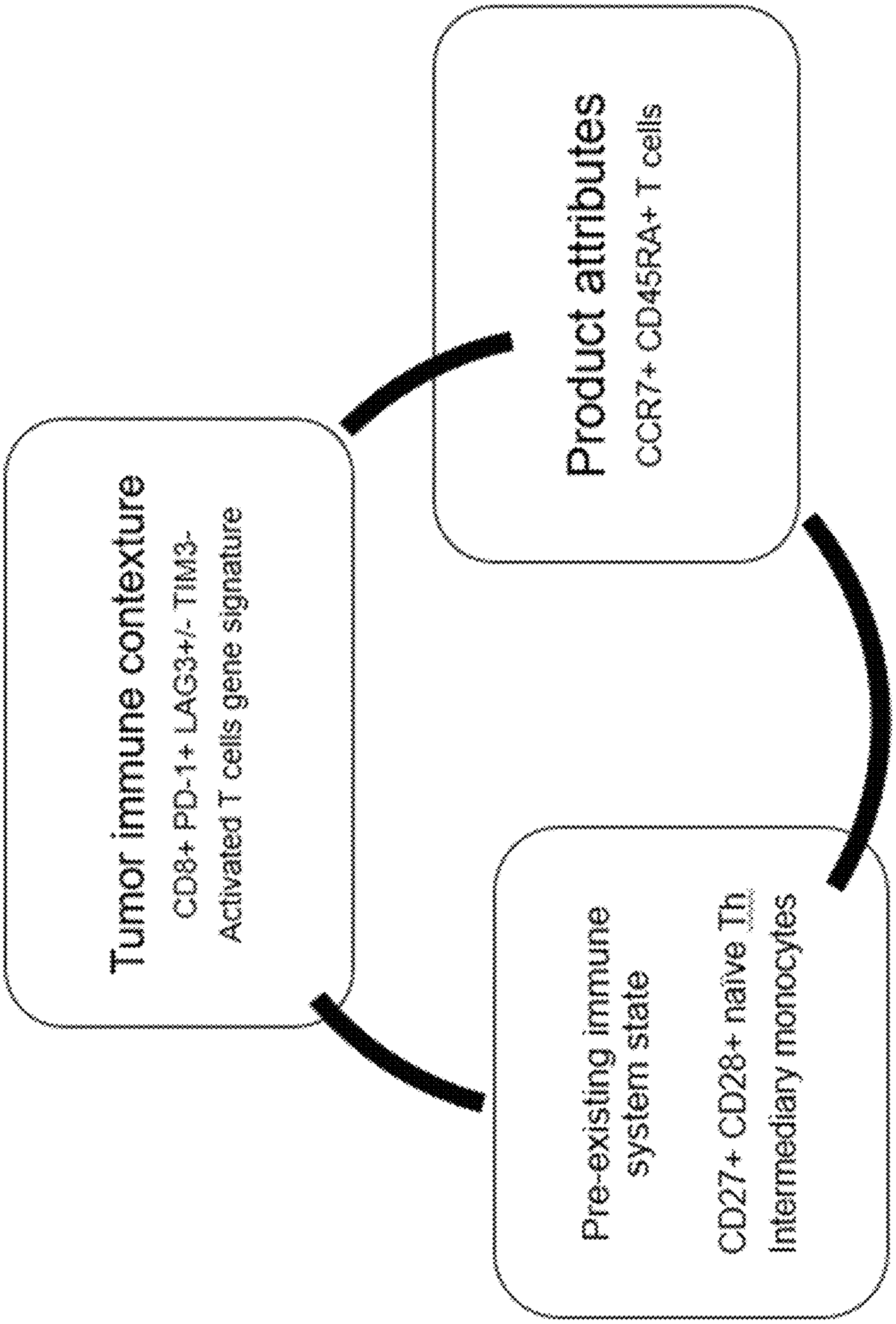
FIG. 1C Schematic overview of the comparisons and major findings between the pre-existing immune system state (as determined from blood), tumor immune contexture, and Axicabtagene ciloleucel product attributes.

The pre-existing state of the immune system probed by interrogation of pre-manufacturing PBMC, most notably the frequency of $CD27^{+}$ $CD28^{+}$ naïve Th cells and that of intermediate monocytes, influenced positively and negatively respectively, key tumor microenvironment and product determinants that favor clinical efficacy of Axicabtagene ciloleucel. Altogether, these results provide a key link between the pre-existing state of the immune system and clinical efficacy of autologous CAR T cell therapy in LBCL, and providing rationale as to how this treatment modality may overcome tumors associated with poor prognostic markers, or treatment optimizations to improve its performance. FIG. 1C.

Example 1

Figure 2:
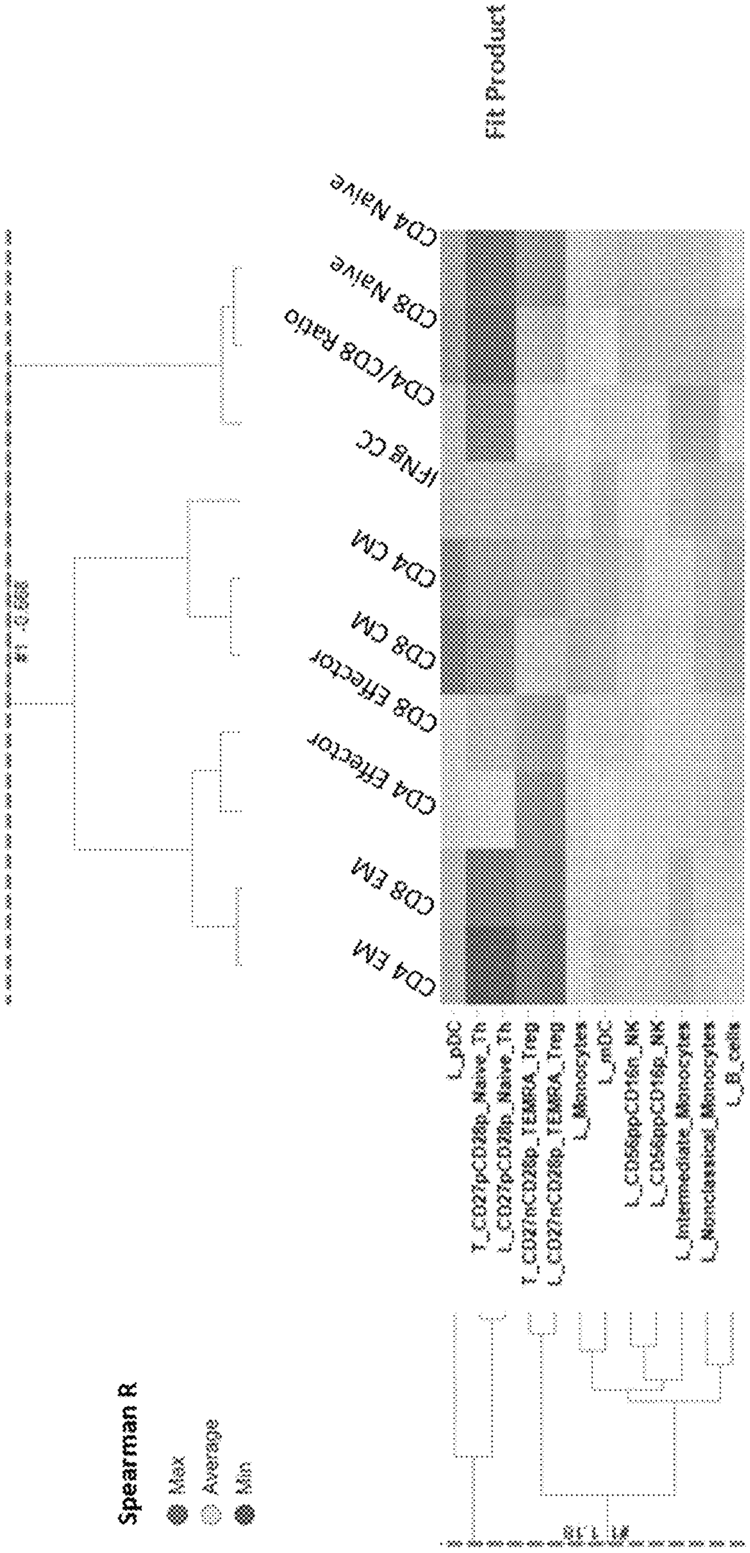
FIG. 2 Associations between pretreatment immune populations and major product attributes. Heatmap of select immune populations from the pre-manufacturing PBMC population of clinical study subjects (y-axis) compared against Axicabtagene ciloleucel product attributes (x-axis) by Spearman's Rank-Order correlation. Values in red are representative of a positive correlation while those in blue are representative of a negative correlation. The % of CD27+CD28+ Naïve Th cells in the pre-manufacturing PBMC population associates with a CD27+CD28+ naïve product phenotype.
Figure 3:
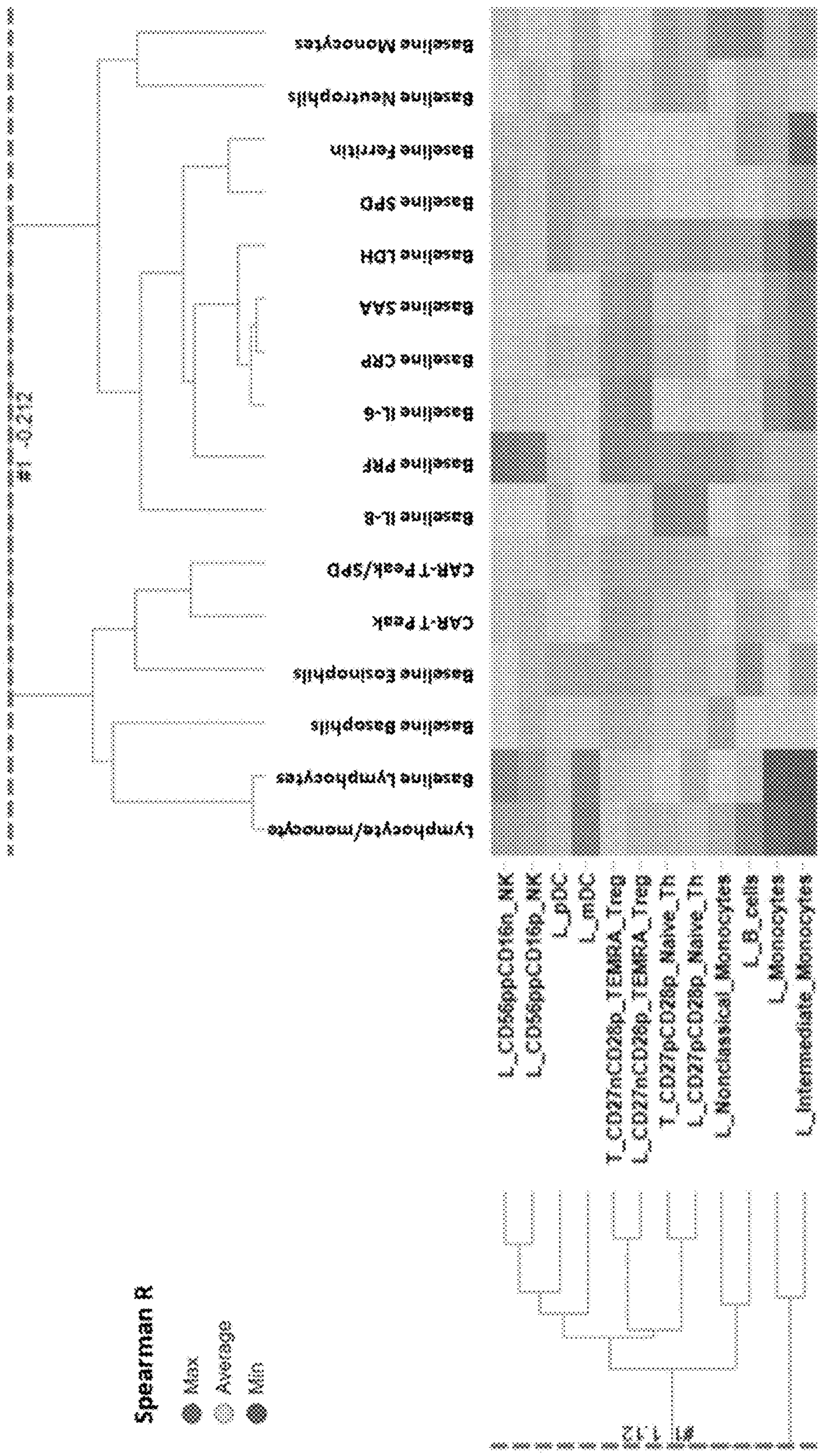
FIG. 3 Associations between pre-manufacturing immune populations and immune populations at baseline, inflammatory cytokines, CAR T cell expansion, and baseline tumor burden. Heatmap of select immune populations from the pre-manufacturing PBMC population of clinical study subjects (y-axis) compared against immune populations at baseline, inflammatory cytokines, CAR T cell expansion, and baseline tumor burden (x-axis) by Spearman's Rank-Order correlation. Values in red are representative of a positive correlation while those in blue are representative of a negative correlation. The % of intermediate monocytes and total monocytes in the pre-manufacturing PBMC population associate with pre-treatment circulating inflammatory markers, tumor burden and hypoxia (LDH) while CD27+CD28+ Naïve Th, CD27-CD28+ TEMRA Treg, and B cells positively associate with CAR T cell expansion.
Figure 4:
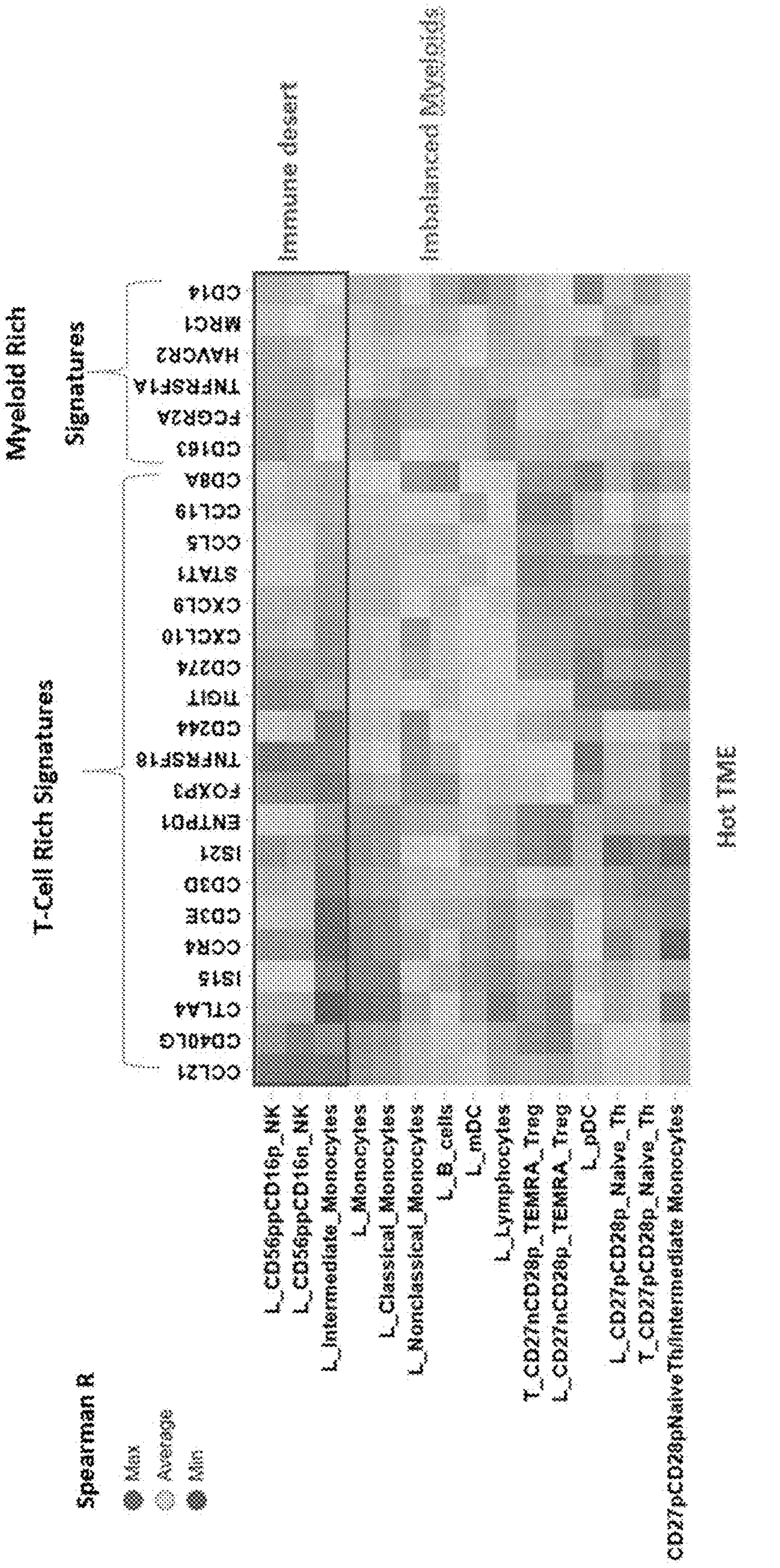
FIG. 4 Associations between pre-manufacturing immune populations and signatures of the tumor microenvironment. Heatmap of select immune populations from the pre-manufacturing PBMC population of clinical study subjects (y-axis) compared against gene expression profiling by nanostring of the tumor microenvironment (x-axis) by Spearman's Rank-Order correlation. Values in red are representative of a positive correlation while those in blue are representative of a negative correlation. The % of CD27+CD28+ Naïve Th and CD27-CD28+ TEMRA Treg cells in the pre-manufacturing PBMC population associate with a TME rich in T-cell ("hot" TME) and myeloid signatures while monocytic populations in the pre-manufacturing PBMC populations associate with an immune TME void of immune cells, i.e. immune desert (intermediate monocytes) or an imbalanced TME with a predominance of myeloid signatures.
Figure 5:
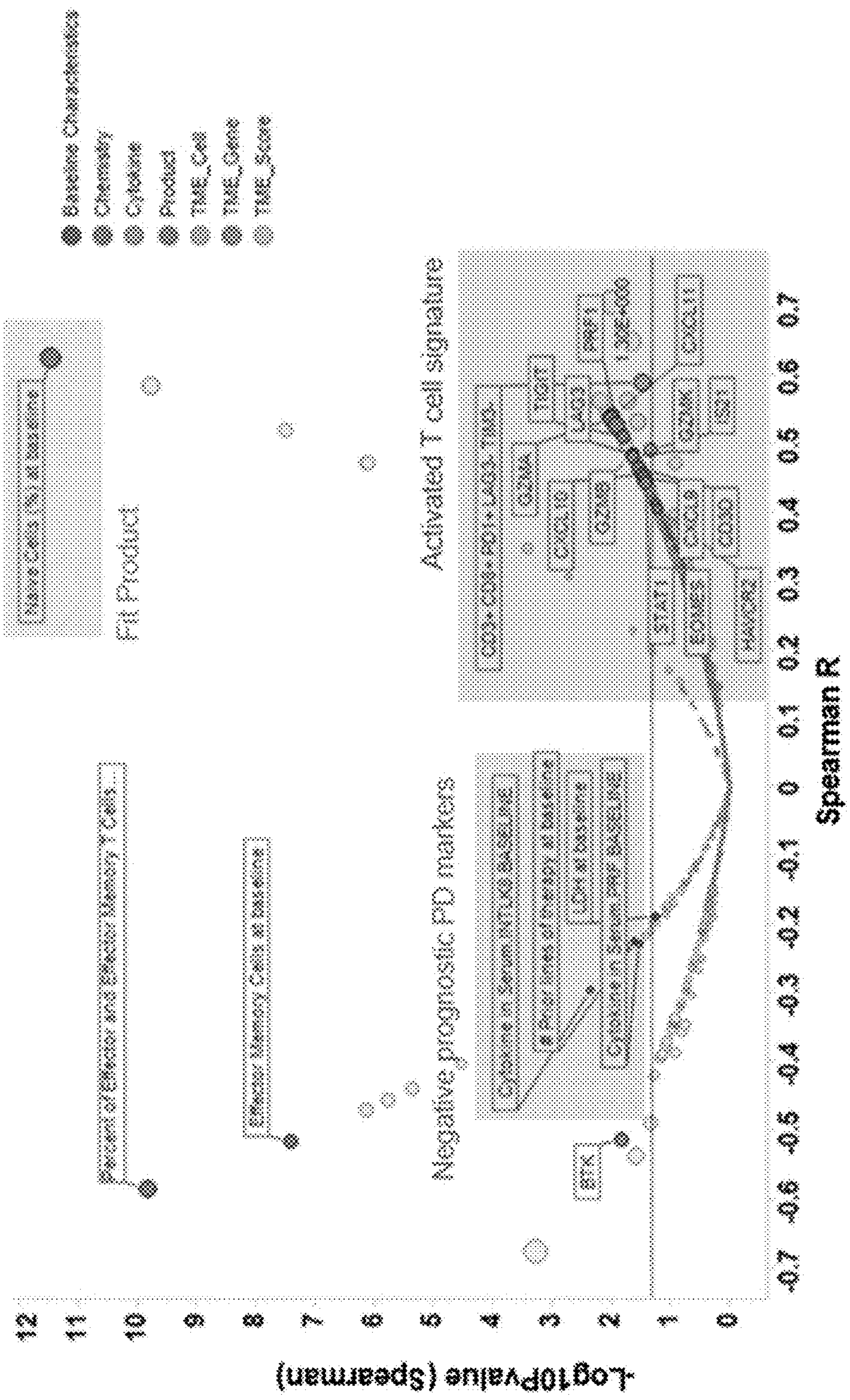
FIG. 5 Volcano plot of naïve Th cells in the pre-manufacturing PBMC population of clinical study subjects compared against baseline cytokines, baseline lab chemistry values, Axicabtagene ciloleucel product attributes, and baseline pretreatment TME signatures. The x-axis represents the Spearman's Rank-Order correlation between values while the y-axis represents the significance of the correlation. Naïve Th subsets pre-manufacturing, associate positively with % naïve T cells in the product infusion bag, a T-cell rich tumor immune contexture, and negatively with pre-treatment inflammatory/tumor hypoxic state. IS21, Immunosign 21 gene expression signature.
Figure 6:
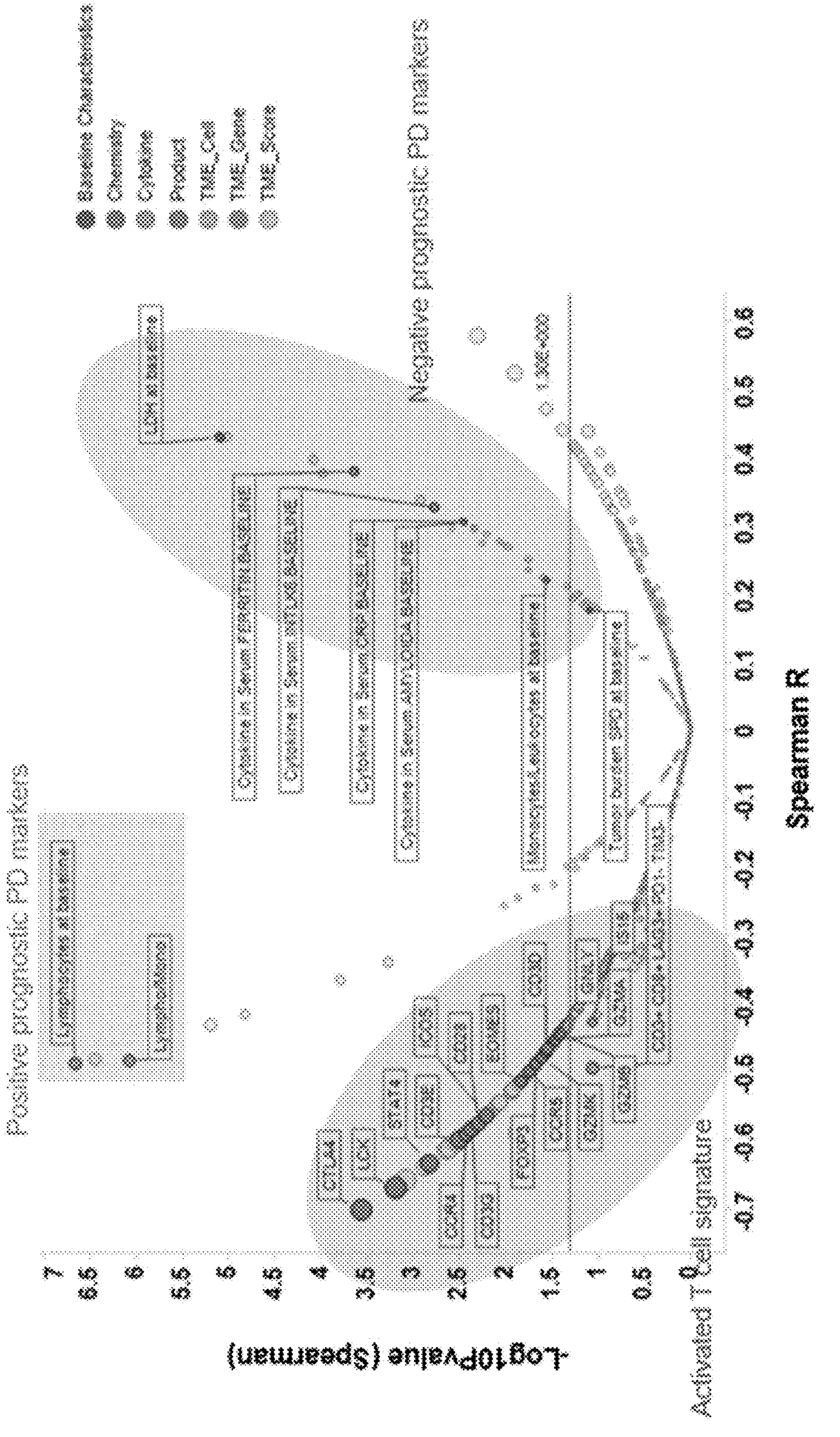
FIG. 6 Volcano plot of intermediate monocyte cells in the pre-manufacturing PBMC population of clinical study subjects compared against baseline cytokines, baseline lab chemistry values, Axicabtagene ciloleucel product attributes, and pretreatment TME signatures. The x-axis represents the Spearman's Rank-Order correlation between values while the y-axis represents the significance of the correlation. Intermediate monocytes pre-manufacturing associate positively with pre-treatment inflammatory/tumor hypoxic state, and negatively with a T-cell rich tumor immune contexture at pre-treatment.

The percentage of CD27+ CD28+ Th cells of naïve phenotype (CCR7+ CD45RA+) in the pre-manufacturing PBMC population associated positively with phenotypic markers of product T cell fitness, including doubling time and viability, CD4/CD8 ratio, and percentage of CD8 and CD4 naïve T cells. FIG. 2. Final product cells are characterized by the same parameters. The percentage of intermediate monocytes and total monocytes in pre-manufacturing PBMC population associated positively with pre-treatment inflammatory markers, tumor burden (baseline sum of product diameters (SPD) and hypoxia (indicated by serum LDH levels). FIG. 3. The relative proportion of T cell subsets versus myeloid cell subsets in pre-manufacturing PBMC population, associated differentially with the pre-treatment tumor immune contexture. FIG. 4. Monocytes, particularly intermediate monocytes, negatively associated with T-cell features in the TME while CD27+CD28+ Naïve Th cells and lymphocytes positively associate with T-cell features in the TME which have been associated with response. Naïve Th subsets pre-manufacturing, associated positively with percentage of naïve T cells in the product infusion bag, a T-cell rich tumor immune contexture (all markers displayed are markers of activated T-cells), and negatively with pre-treatment inflammatory (INTL8, PRF)/tumor hypoxic state (LDH) FIG. 5. Intermediate monocytes pre-manufacturing, associated positively with pre-treatment inflammatory (INTL8, Ferritin, CRP, Amyloid A)/tumor hypoxic state (LDH), and negatively with a T-cell rich tumor immune contexture (all markers displayed are markers of activated T-cells) defined pre-treatment. FIG. 6. Intermediate monocytes pre-manufacturing had a negative association with lymphocytes and the lymphocyte to monocyte ratio (shown later in this document to be correlated positively with response/survival). Also, a positive association with pre-treatment tumor burden which itself is negatively associated with response was observed.

Example 2

Figure 7A:
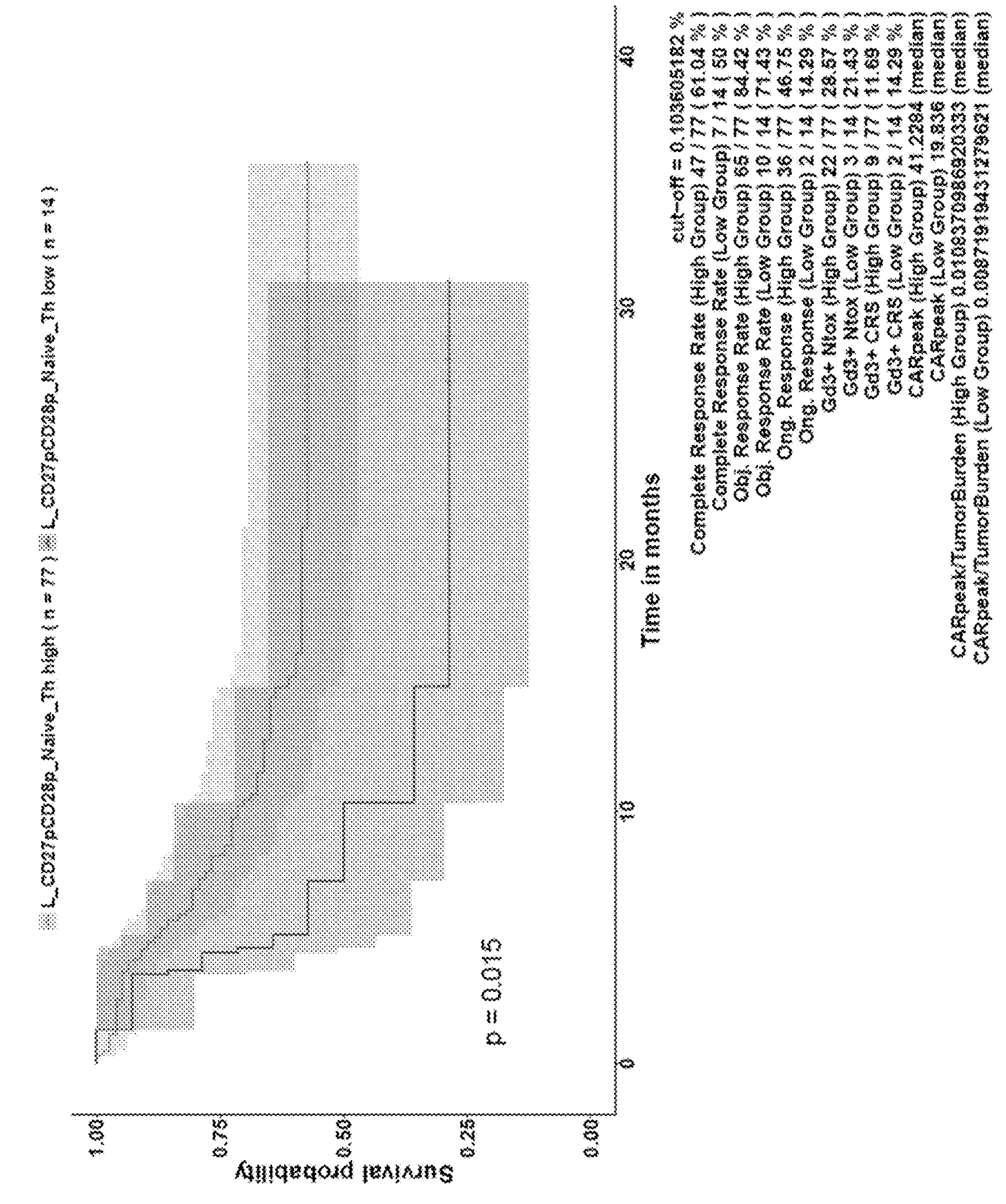
FIG. 7A Overall survival curve of clinical study subjects grouped by % CD27+CD28+Naïve Th cells pre-manufacturing. Kaplan-Meier overall survival curve with an optimal cut-off selection for % CD27+CD28+ Naïve Th cells in pre-manufacturing PBMC population with significance determined by the Log-Rank test. The rate of complete response, objective response, ongoing response, grade 3+ toxicity, and CAR T cell expansion were determined for subjects with % CD27+CD28+ Naïve Th cells in the pre-manufacturing PBMC populations above or below the optimal cut-off, FIG. 7B Progression-free survival curve of clinical study subjects grouped by % CD27+CD28+ Naïve Th cells pre-manufacturing. Kaplan-Meier progression-free survival curve with an optimal cut-off selection for % CD27+CD28+ Naïve Th cells in pre-manufacturing PBMC population with significance determined by the Log-Rank test. The rate of complete response, objective response, ongoing response, grade 3+ toxicity, and CAR T cell expansion were determined for subjects with % CD27+CD28+ Naïve Th cells in the pre-manufacturing PBMC populations above or below the optimal cut-off.
Figure 7B:
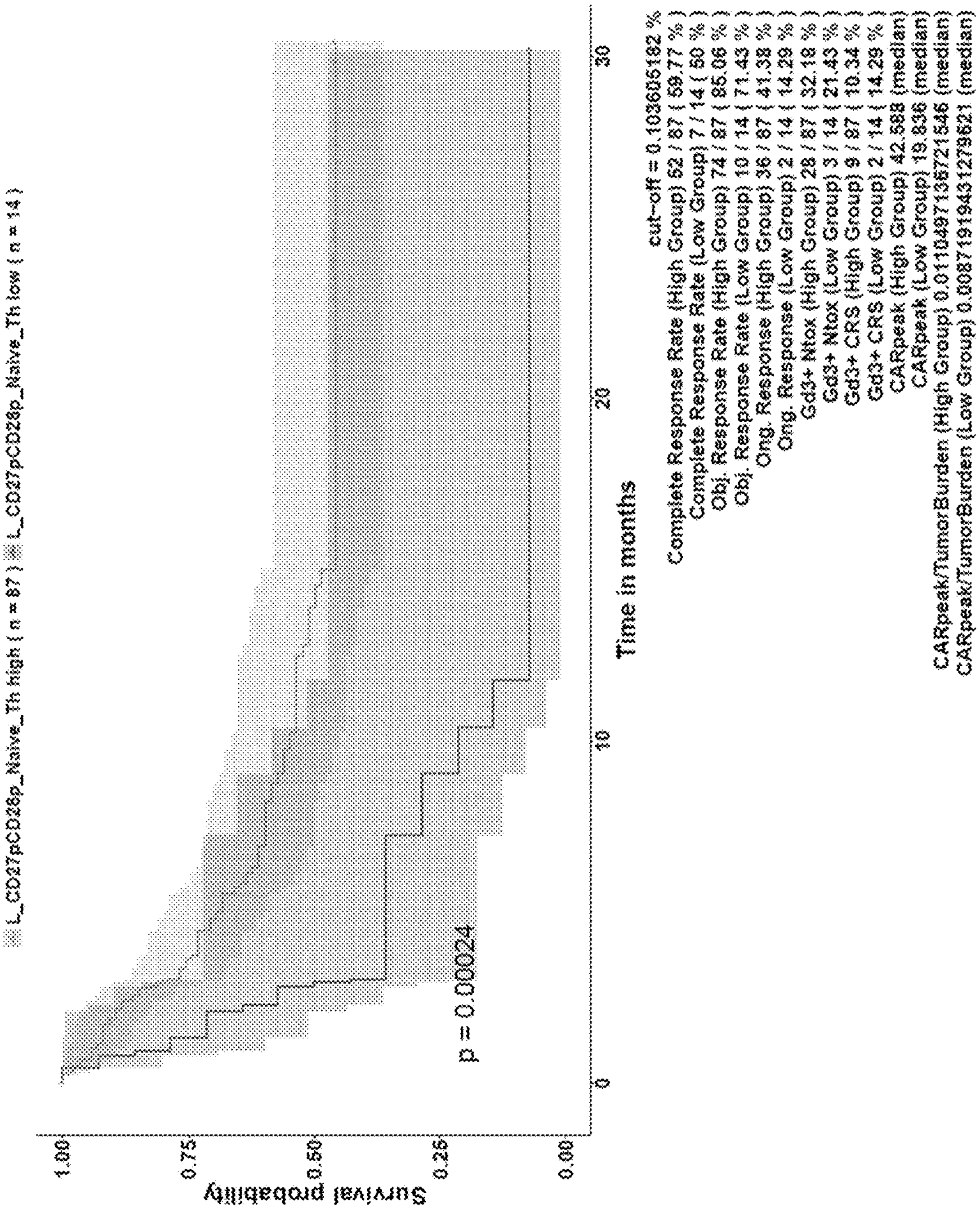
Figure 8B:
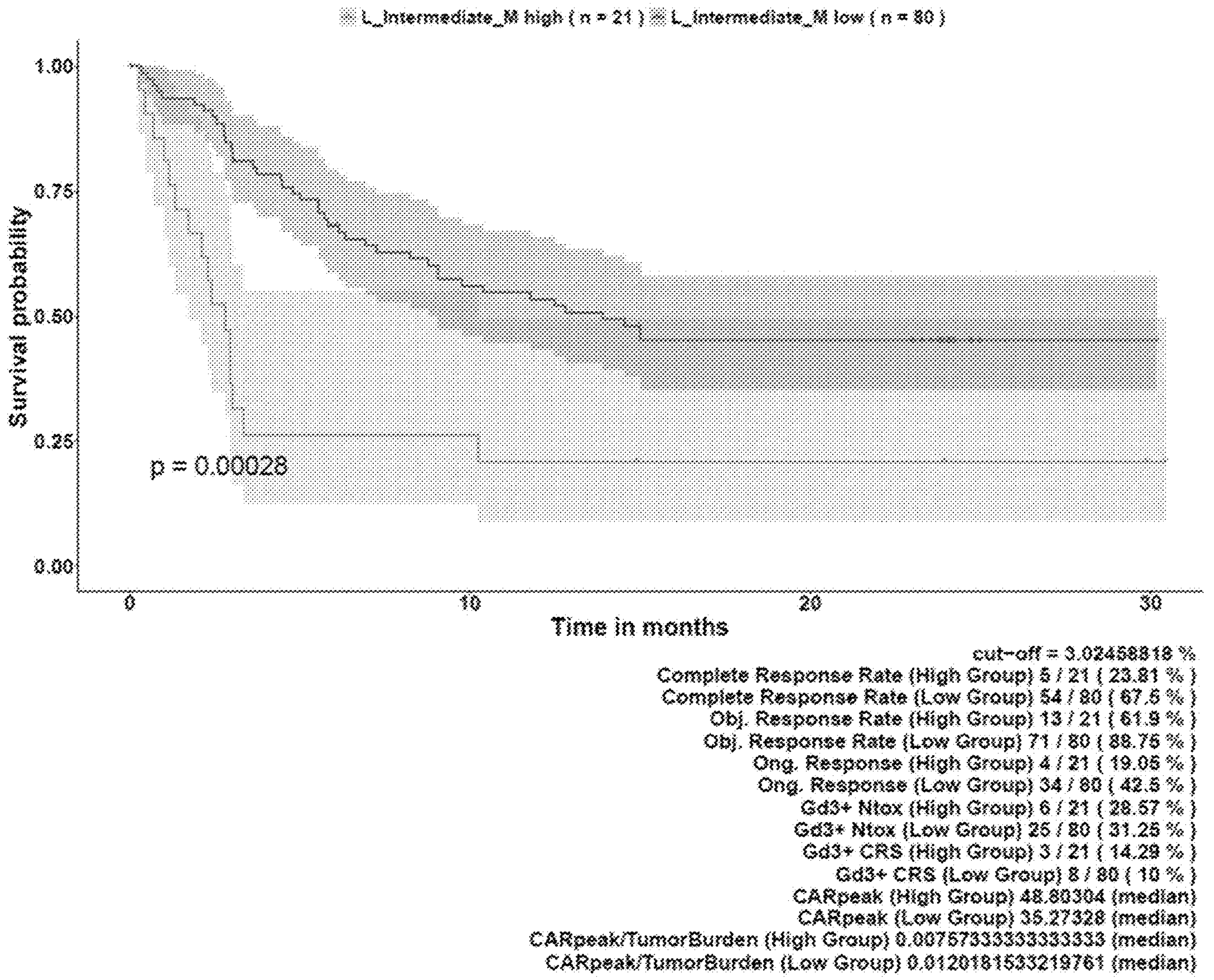
FIG. 8A Overall survival curve of clinical study subjects grouped by % Intermediate monocyte cells pre-manufacturing. Kaplan-Meier overall survival curve with an optimal cut-off selection for % Intermediate monocyte cells in pre-manufacturing PBMC population with significance determined by the Log-Rank test. The rate of complete response, objective response, ongoing response, grade 3+ toxicity, and CAR T cell expansion were determined for subjects with % Intermediate monocyte cells in the pre-manufacturing PBMC populations above or below the optimal cut-off, FIG. 8B Progression-free survival curve of clinical study subjects grouped by % Intermediate monocyte cells pre-manufacturing. Kaplan-Meier progression-free survival curve with an optimal cut-off selection for % Intermediate monocyte cells in pre-manufacturing PBMC population with significance determined by the Log-Rank test. The rate of complete response, objective response, ongoing response, grade 3+ toxicity, and CAR T cell expansion were determined for subjects with % Intermediate monocyte cells in the pre-manufacturing PBMC populations above or below the optimal cut-off.
Figure 9A:
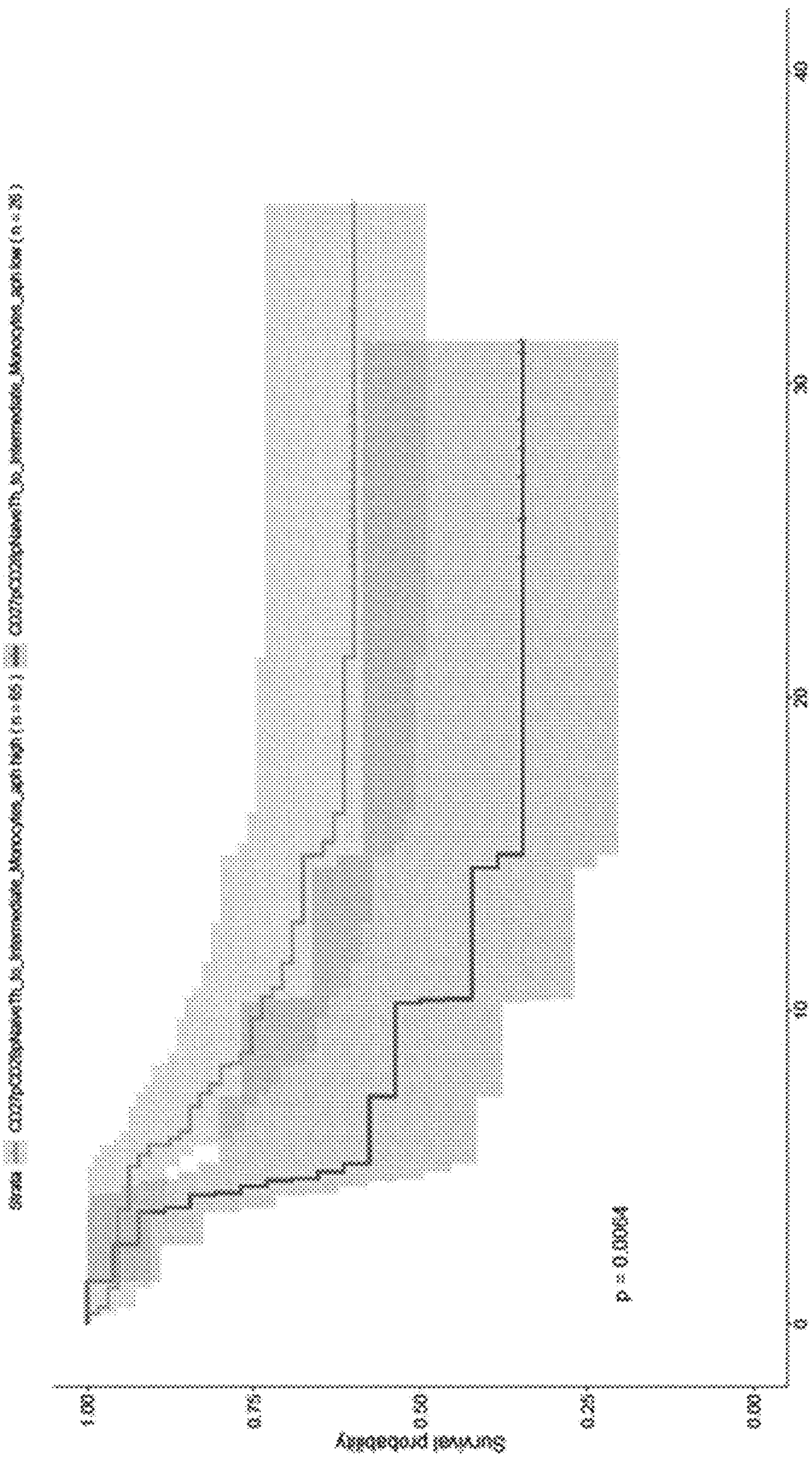
FIG. 9A Overall survival curve of clinical study subjects grouped by the ratio of CD27+CD28+ Naïve Th cells to intermediate monocytes pre-manufacturing. Kaplan-Meier overall survival curve with an optimal cut-off selection for the ratio of CD27+CD28+ Naïve Th cells to intermediate monocytes in pre-manufacturing PBMC population with significance determined by the Log-Rank test. The rate of complete response, objective response, ongoing response, grade 3+ toxicity, and CAR T cell expansion were determined for subjects above or below the optimal cut-off.
Figure 9B:
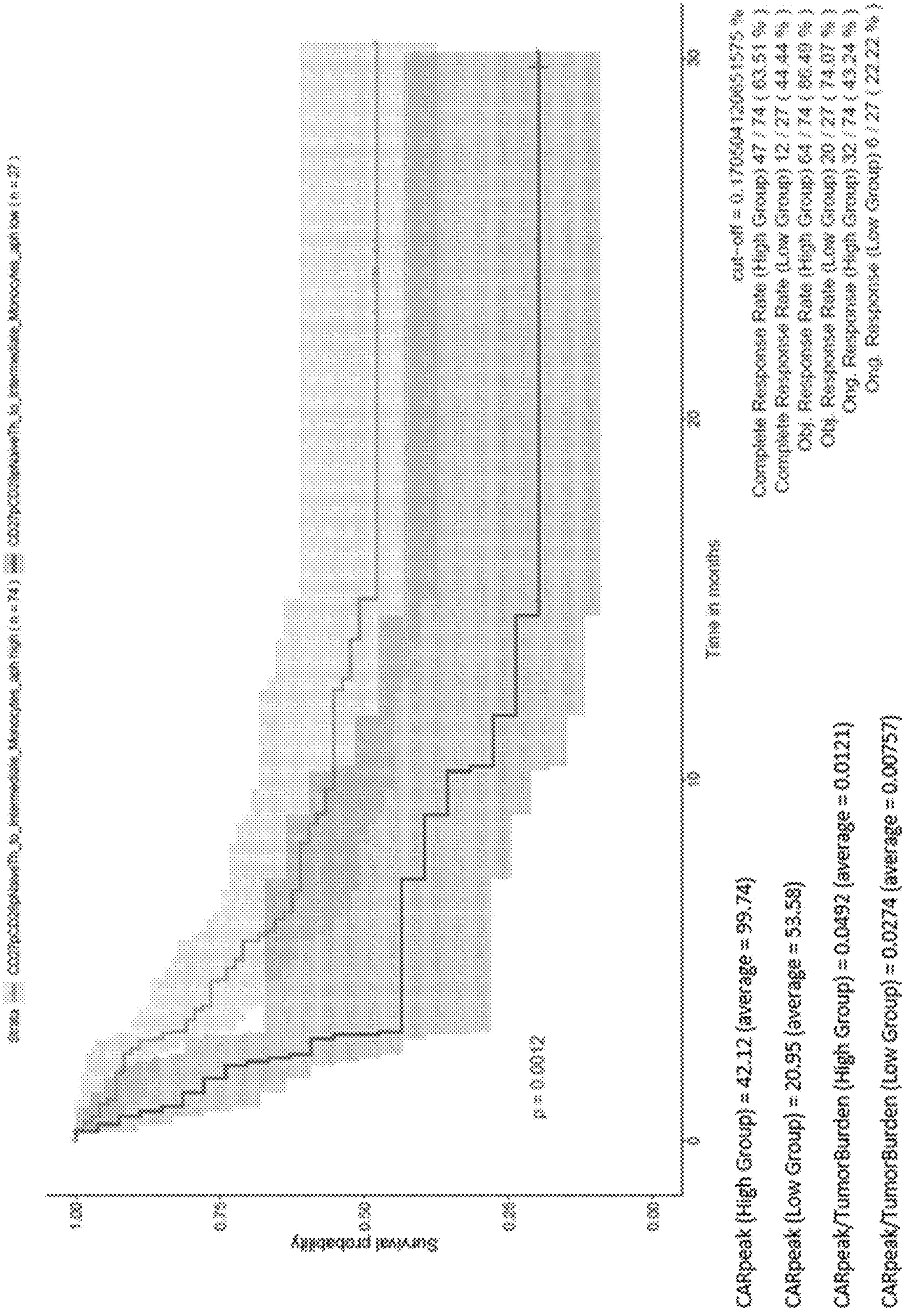
FIG. 9B Progression-free survival curve of clinical study subjects grouped by the ratio of CD27+CD28+ Naïve Th cells to intermediate monocytes pre-manufacturing. Kaplan-Meier progression-free survival curve with an optimal cut-off selection for the ratio of CD27+CD28+ Naïve Th cells to intermediate monocytes in pre-manufacturing PBMC population with significance determined by the Log-Rank test. The rate of complete response, objective response, ongoing response, grade 3+ toxicity, and CAR T cell expansion were determined for subjects above or below the optimal cut-off.
Figure 10A:
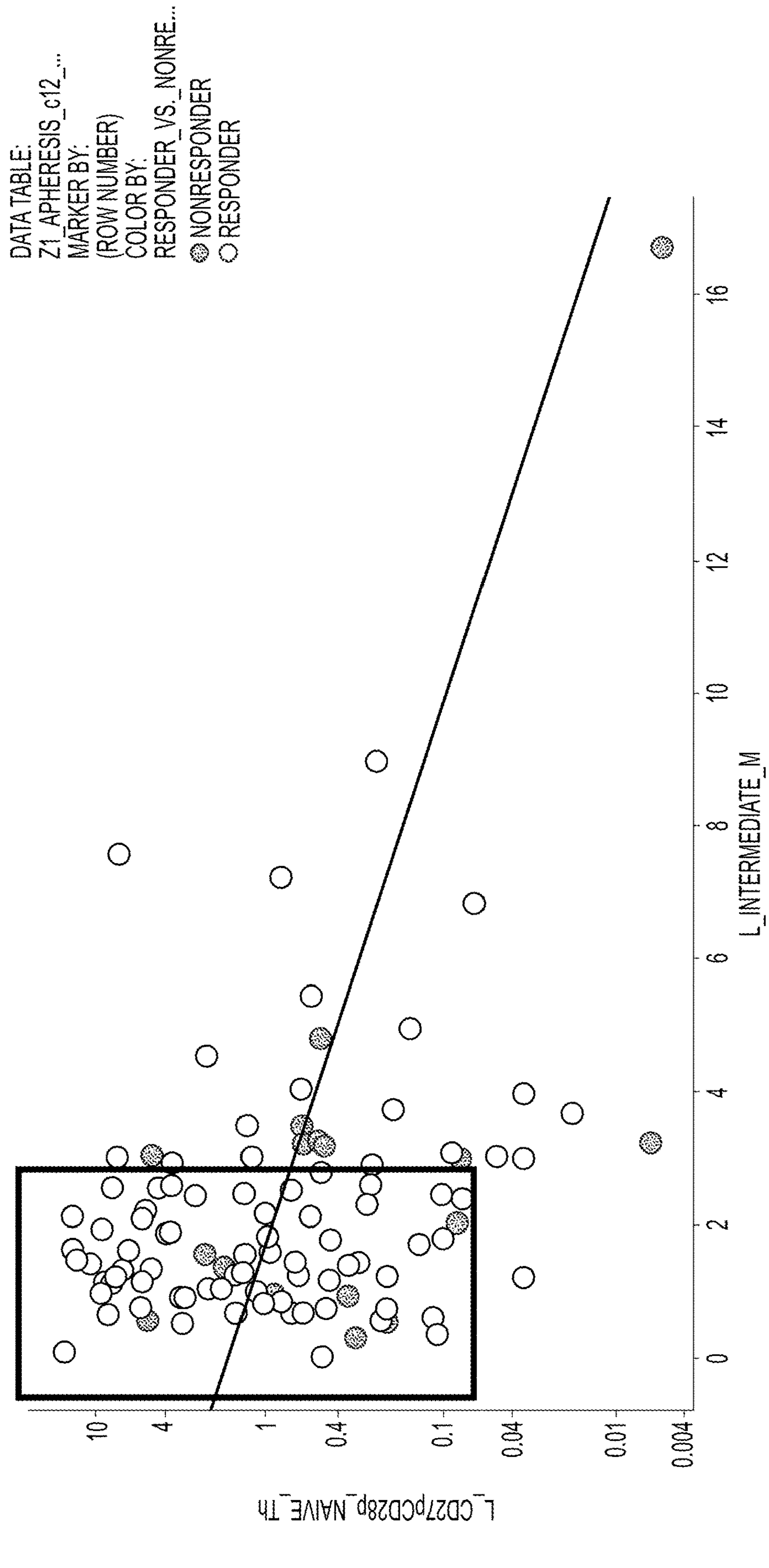
FIG. 10A Scatterplot of % CD27+CD28+ Naïve Th vs % Intermediate monocytes in the pre-manufacturing PBMC population colored by objective response status. Linear association (black line) between the % CD27+CD28+ Naïve Th and the % Intermediate monocytes in the pre-manufacturing PBMC population. A blue box surrounds a region showing that responders cluster on the curve with high % CD27+CD28+ Naïve Th cells and low % Intermediate monocytes.
Figure 10B:
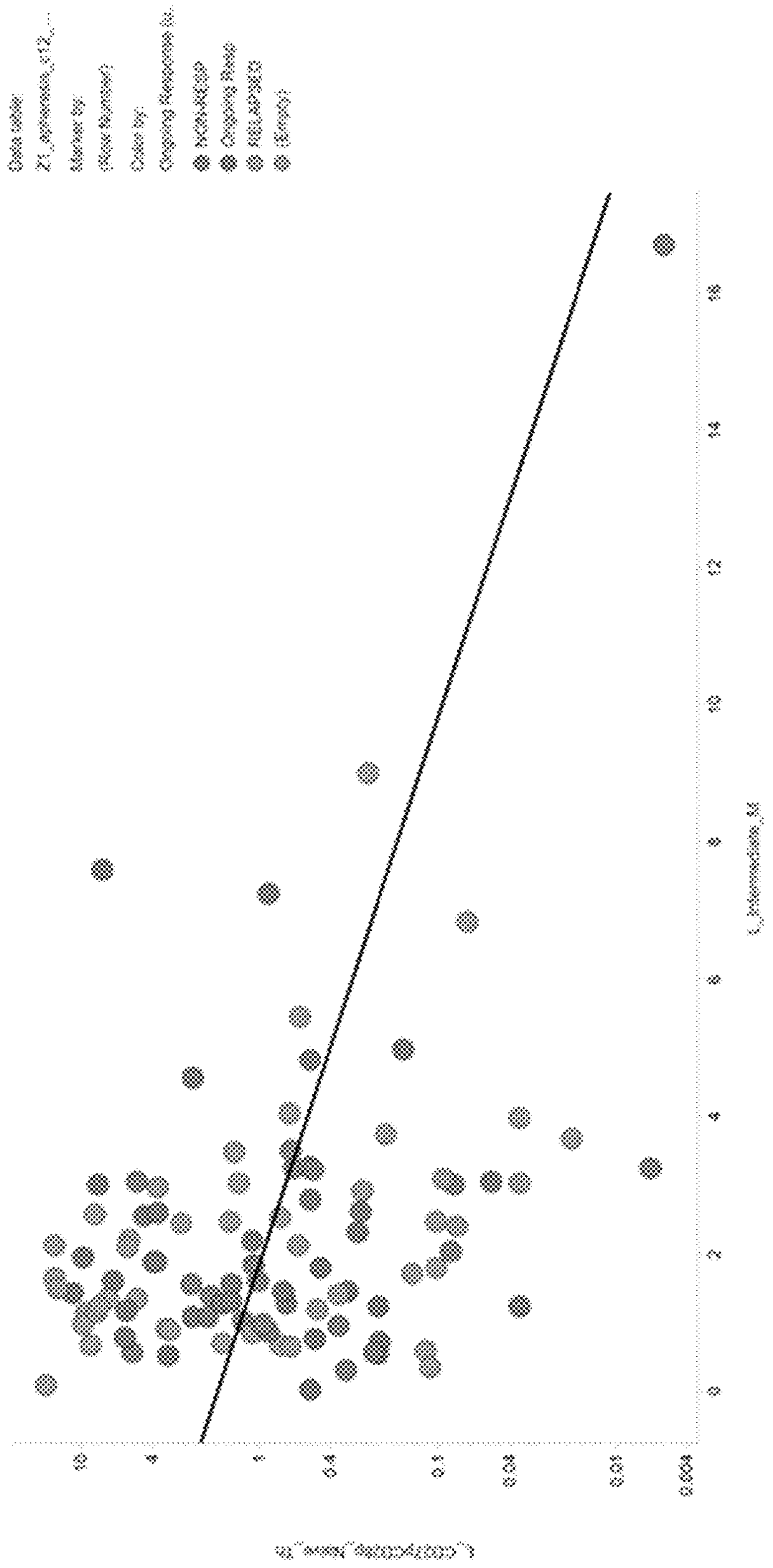
FIG. 10B Scatterplot of % CD27+CD28+ Naïve Th vs % Intermediate monocytes in the pre-manufacturing PBMC population colored by ongoing response status. Linear association (black line) between the % CD27+CD28+ Naïve Th and the % Intermediate monocytes in the pre-manufacturing PBMC population.
Figure 11:
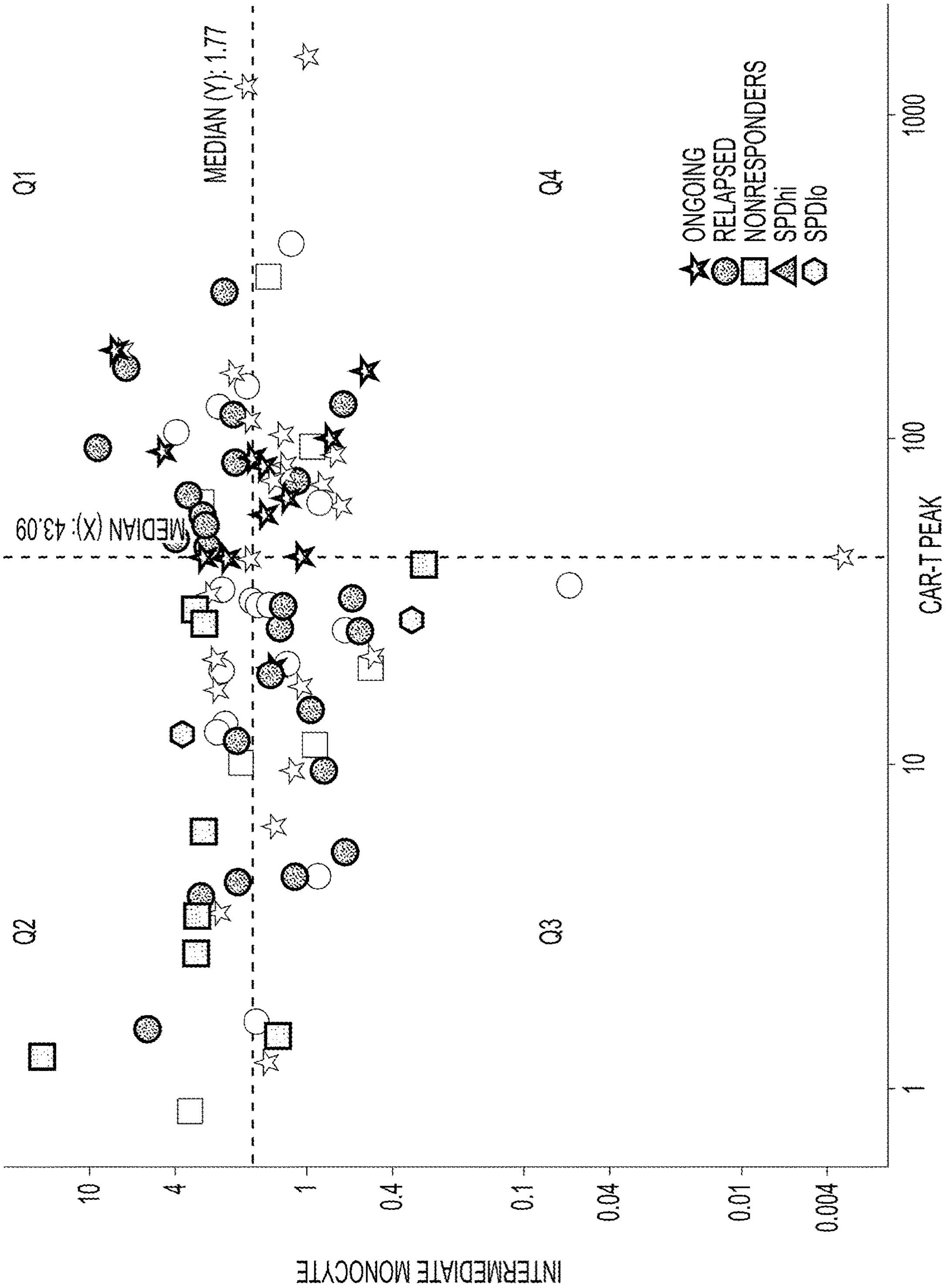
FIG. 11 Scatterplot of % Intermediate monocytes in the pre-manufacturing PBMC population vs. peak CAR T cell expansion colored by ongoing response status. The scatterplot is partitioned into quadrants (Q1-Q4) based on the status of intermediate monocytes and peak CAR T cell expansion above or below the median of each of those covariates. Note that non-responder of high SPD cluster with high intermediate monocytes and low CAR-T peak while responders with high SPD cluster with high CAR-T peak. SPD—sum of product diameters.
Figure 12A:
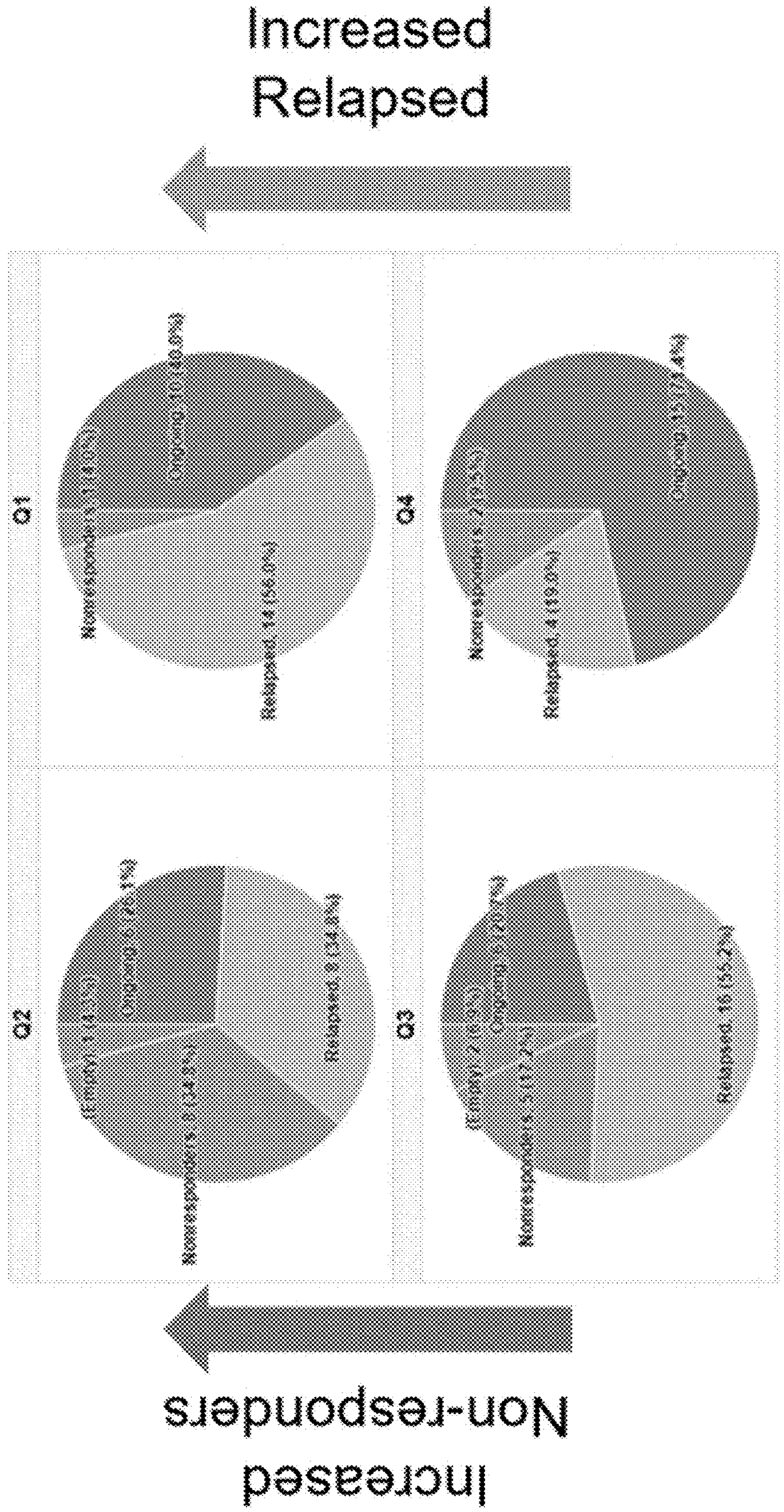
FIG. 12A Ongoing response rates from the quadrants of the % Intermediate monocytes to peak CAR T-cell expansion scatterplot from FIG. 11.
Figure 12B:
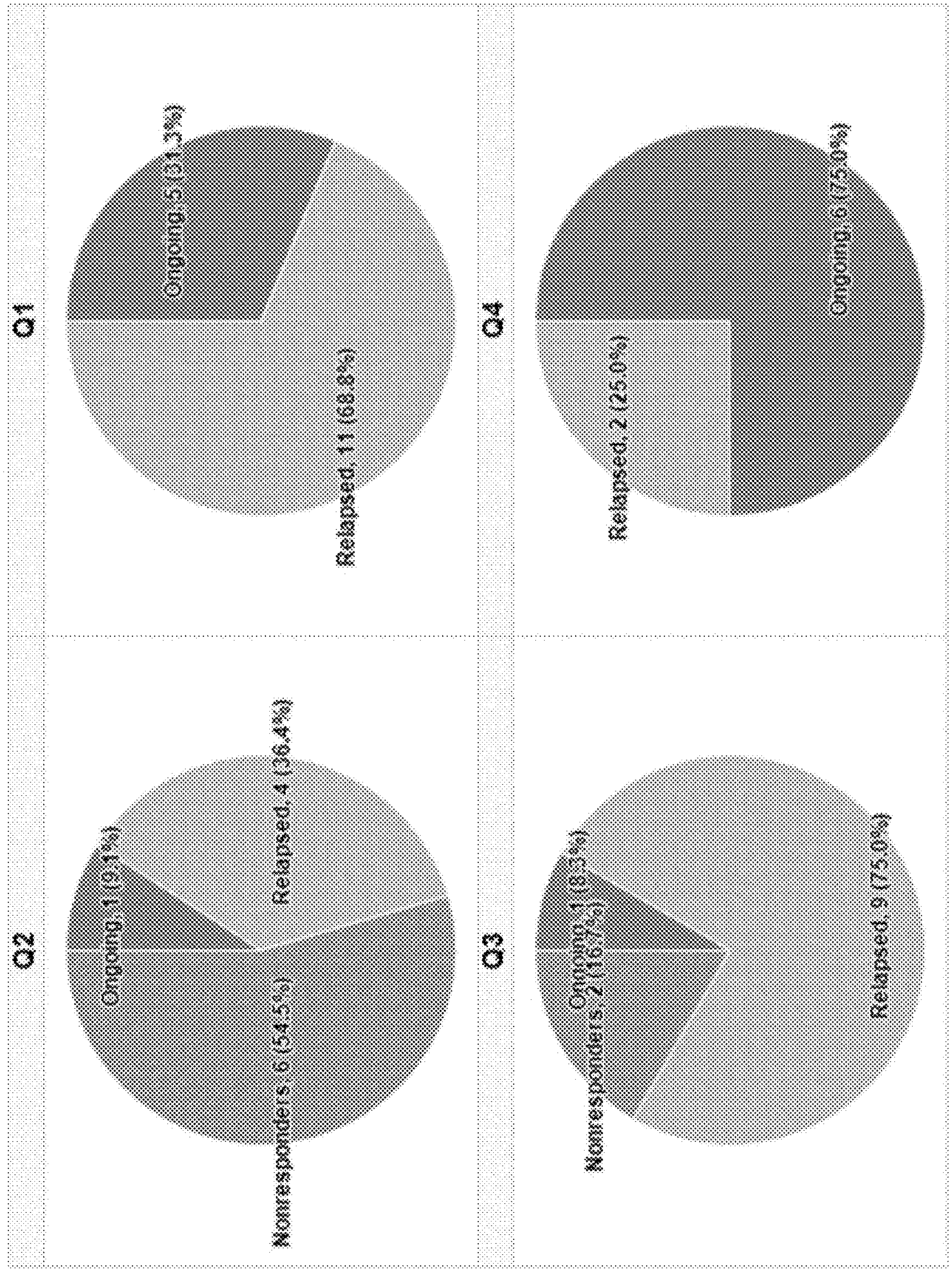
FIG. 12B Ongoing response rates from the quadrants of the % Intermediate monocytes to peak CAR T-cell expansion scatterplot from FIG. 11 for subjects that had a baseline tumor burden above the median level (SPDhi) FIG. 12C Ongoing response rates from the quadrants of the % Intermediate monocytes to peak CAR T-cell expansion scatterplot from FIG. 11 for subjects that had a baseline tumor burden below the median level (SPD 10).
Figure 12C:
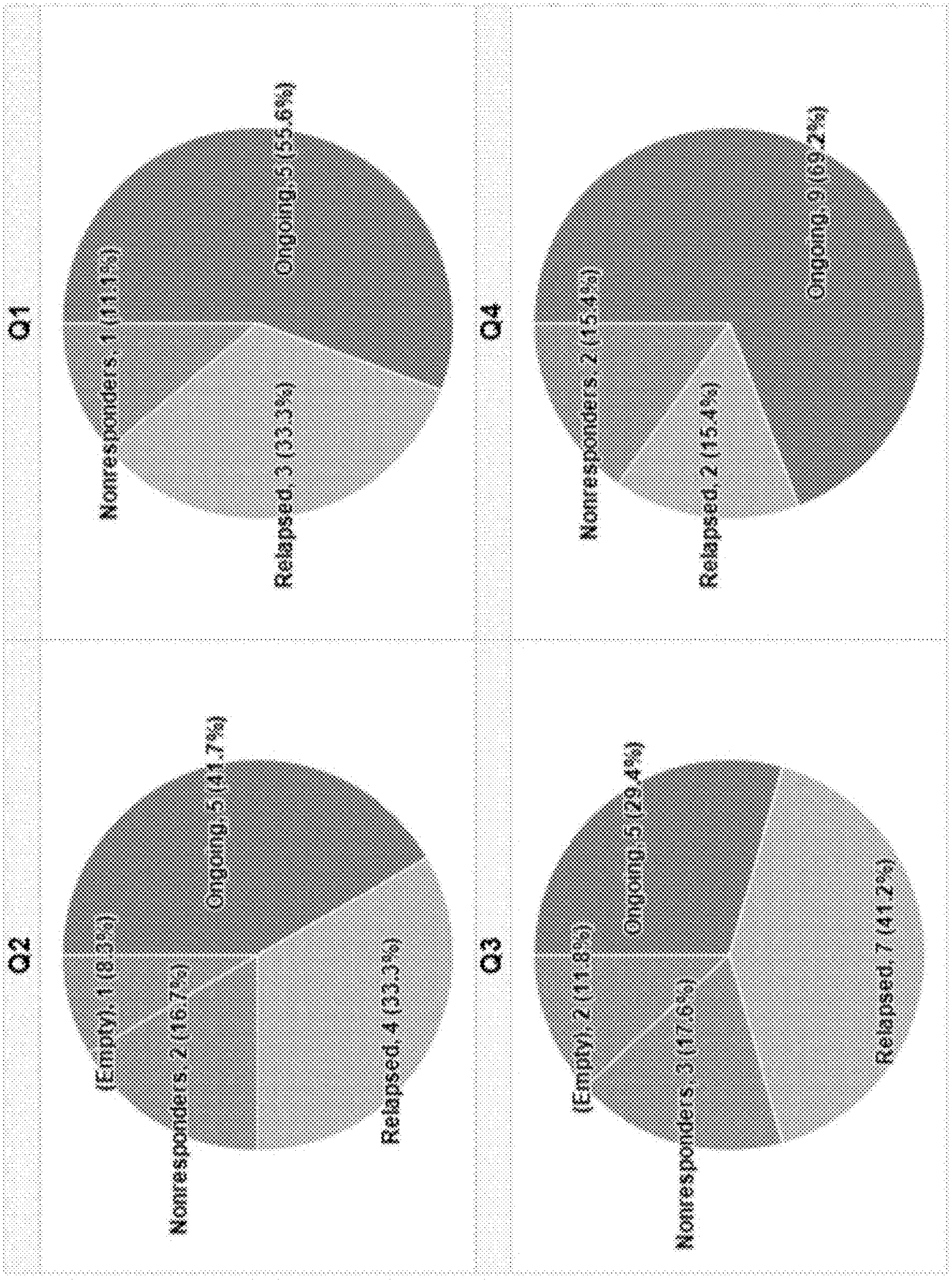

CD27+CD28+ Naïve Th cells (% of leukocytes) in the apheresis product were predictive markers for improved OS (FIG. 7A) and PFS (FIG. 7B) (optimal cutoff). There was a positive association between them, i.e., subjects with pre-treatment CD27+CD28+ naïve Th cells above the listed cutoff have a higher likelihood of survival than those below the selected cutoff. The level of intermediate monocytes in the apheresis product (% of leukocytes) were also predictive markers for OS (FIG. 8A) and PFS (optimal cutoff) (FIG. 8B). The current data suggests that subjects with intermediate monocyte levels below the listed cutoff have a higher likelihood of survival than those above the cutoff. The ratio of CD27pCD28p Naïve Th cells in the apheresis product (% of leukocytes) to Intermediate Monocytes (% of leukocytes) showed a positive association with and serves as a predictive marker for OS (FIG. 9A) and PFS (optimal cutoff) (FIG. 9B). There were better survival/response/expansion rates for subjects with levels above the selected cutoff as compared to those below it. The relationship between CD27+CD28+ Naïve Th cells (% of leukocytes) vs. Intermediate Monocytes (% of leukocytes, CD14+CD16+) in the apheresis product in non-responders, ongoing response, and relapsed patients was also studied. FIG. 10A and FIG. 10B. CD27+ CD28+ Naïve Th cells have a negative association with intermediate monocytes. Furthermore, subjects with high CD27+CD28+ Naïve Th levels and low intermediate monocytes levels have an increased proportion of objective responders (upper left section of FIG. 10B). The frequency of intermediate monocytes may have greater negative impact to efficacy in subjects having tumors with large sum of product diameter (SPD). FIG. 12B. It was observed in Q2 that high intermediate monocytes and low CAR T cell expansion correlates with the highest rate of non-responders. FIG. 11. In subjects that have increased CAR T-cell peak expansion and lower intermediate monocyte levels (Q4) there were increased ongoing response rates and reduced relapse or non-responder rates compared to the other quadrants. FIG. 11 and FIG. 12A. These quadrants of CAR T-cell peak expansion and intermediate monocytes can be viewed within the context of high (FIG. 12B) or low (FIG. 12C) tumor burden. When viewed with the additional context of high baseline tumor burden, the above trends are amplified where subjects with high intermediate monocytes and low CAR T-cell peak expansion have even lower ongoing response rates but again decreases in intermediate monocytes and increased CAR T-cell expansion correspond to increased ongoing response rates. FIG. 12B. Trends are still maintained within the context of low tumor burden but the ongoing response rates are higher due to needing to overcome a smaller tumor burden. FIGS. 12B and C.d Example 3

Figure 13:
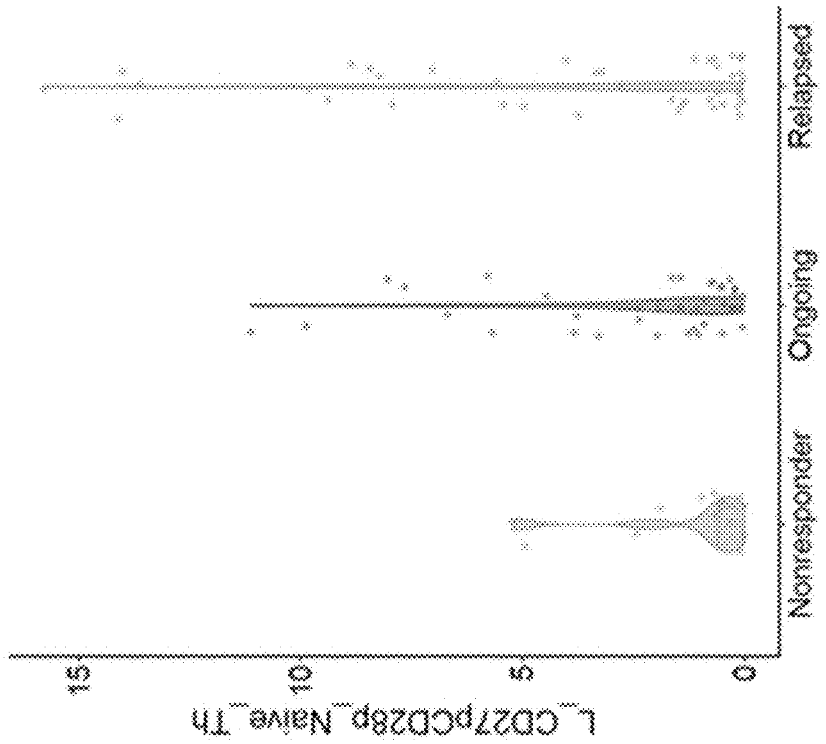
FIG. 13 Violin plots of CD27+CD28+ Naïve Th (% of Leukocyte) in pre-manufacturing PBMCs grouped by response categories FIG. 14 Violin plots of Intermediate Monocytes (% of Leukocyte) in pre-manufacturing PBMCs grouped by response categories.
Figure 13:
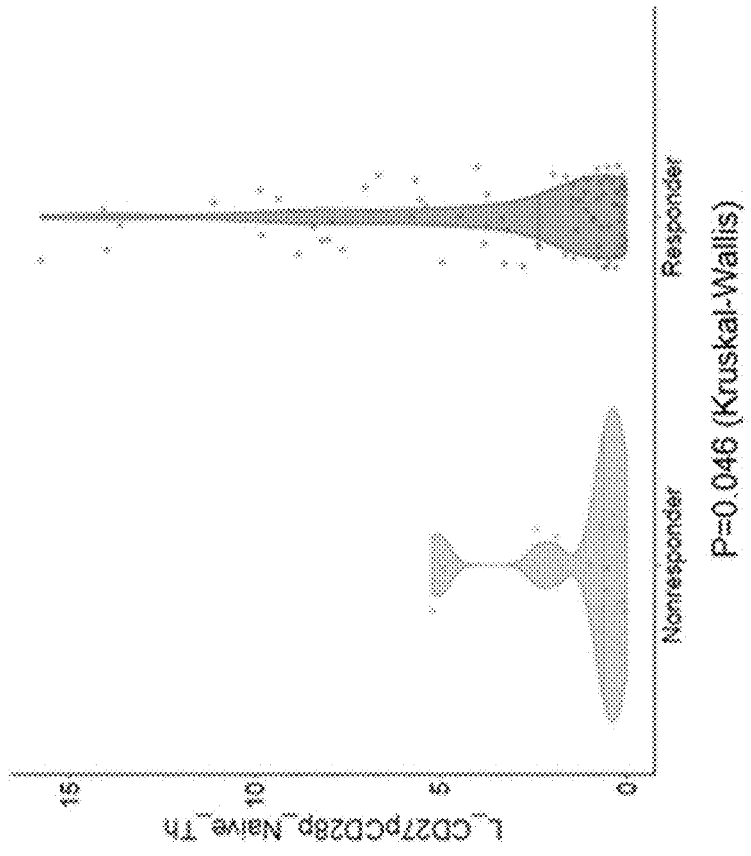
Figure 14:
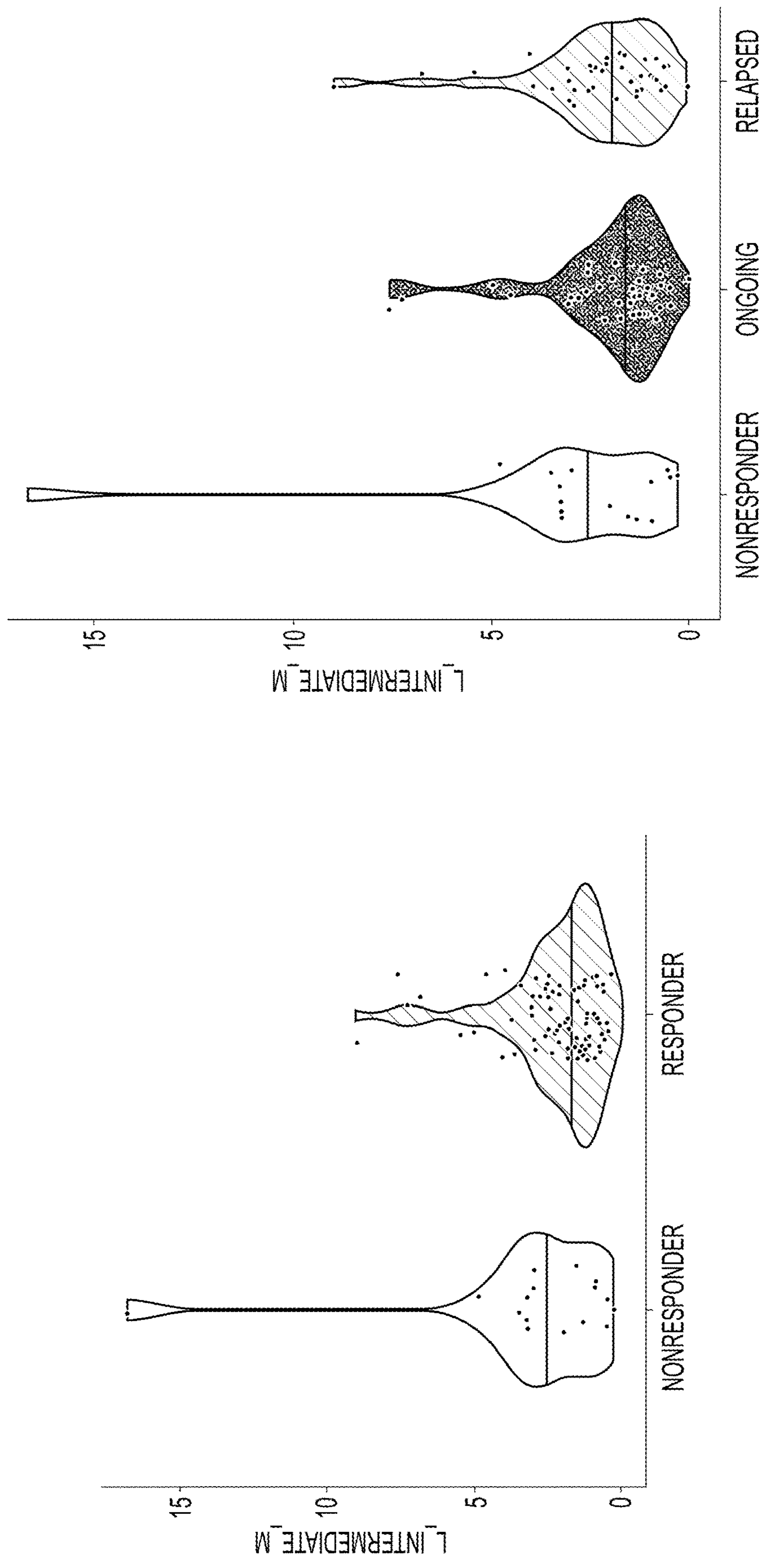

There was an association between CD27+CD28+ Naïve Th (% of Leukocyte) and response categories. FIG. 13. CD27+CD28+ Naïve Th cell levels are higher in responding patients as compared to non-responding patients. There was also an association between Intermediate Monocytes (% of Leukocyte) and response categories. FIG. 14. Intermediate monocytes are lower in responding patients as compared to non-responding patients. Furthermore, levels are lower in those subjects that have an ongoing (durable) response as compared to those that undergo relapse or are non-responders.

Example 4

The naïve Th cell population in the apheresis product was negatively associated with the number of prior line therapy.

Figure 15A:
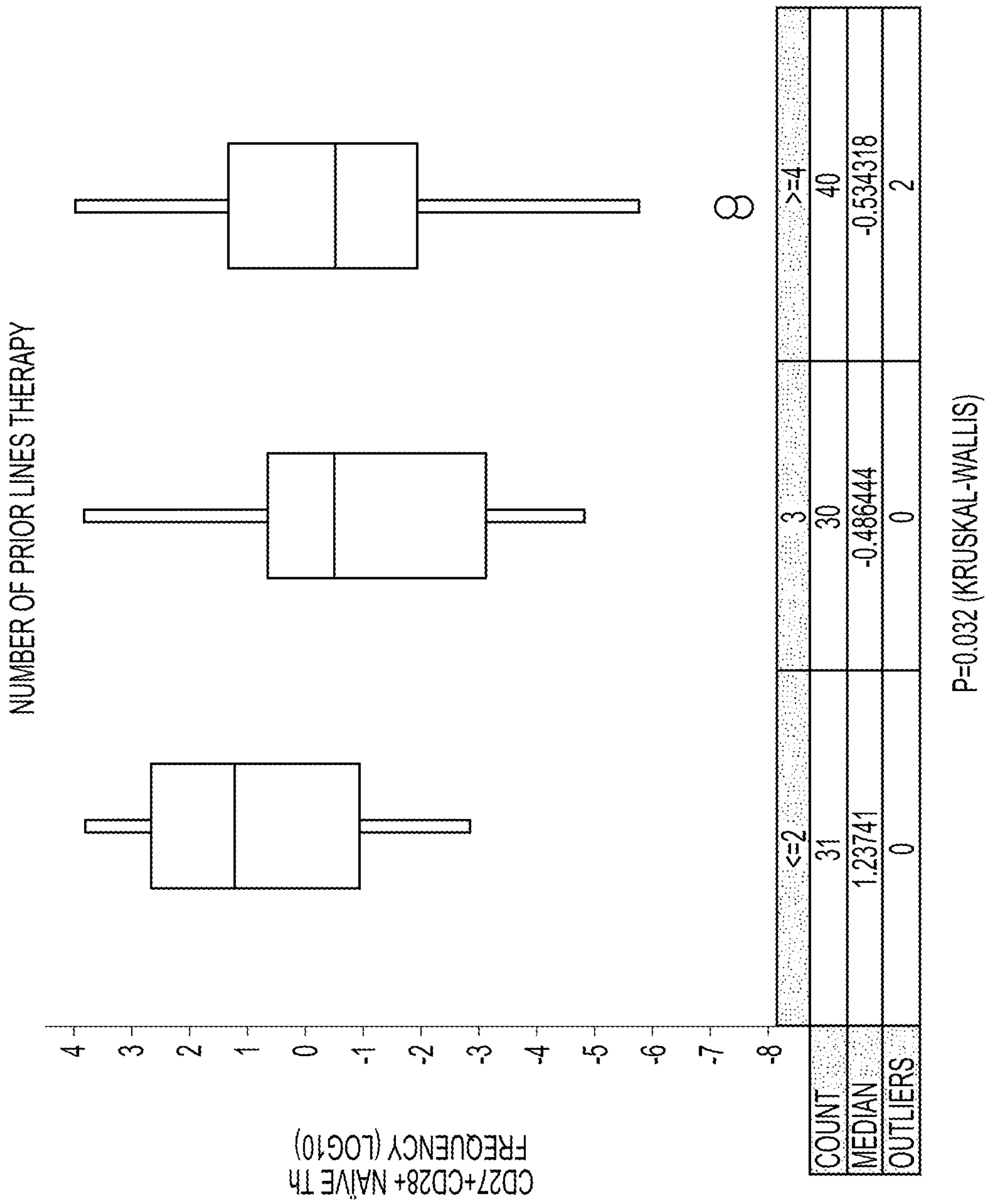
FIG. 15A Boxplot of CD27+CD28+ Naïve Th (% of Leukocytes) in pre-manufacturing PBMCs grouped by number of prior lines of therapy pointing to their enrichment in patients who received 2 or less lines of therapy.
Figure 15B:
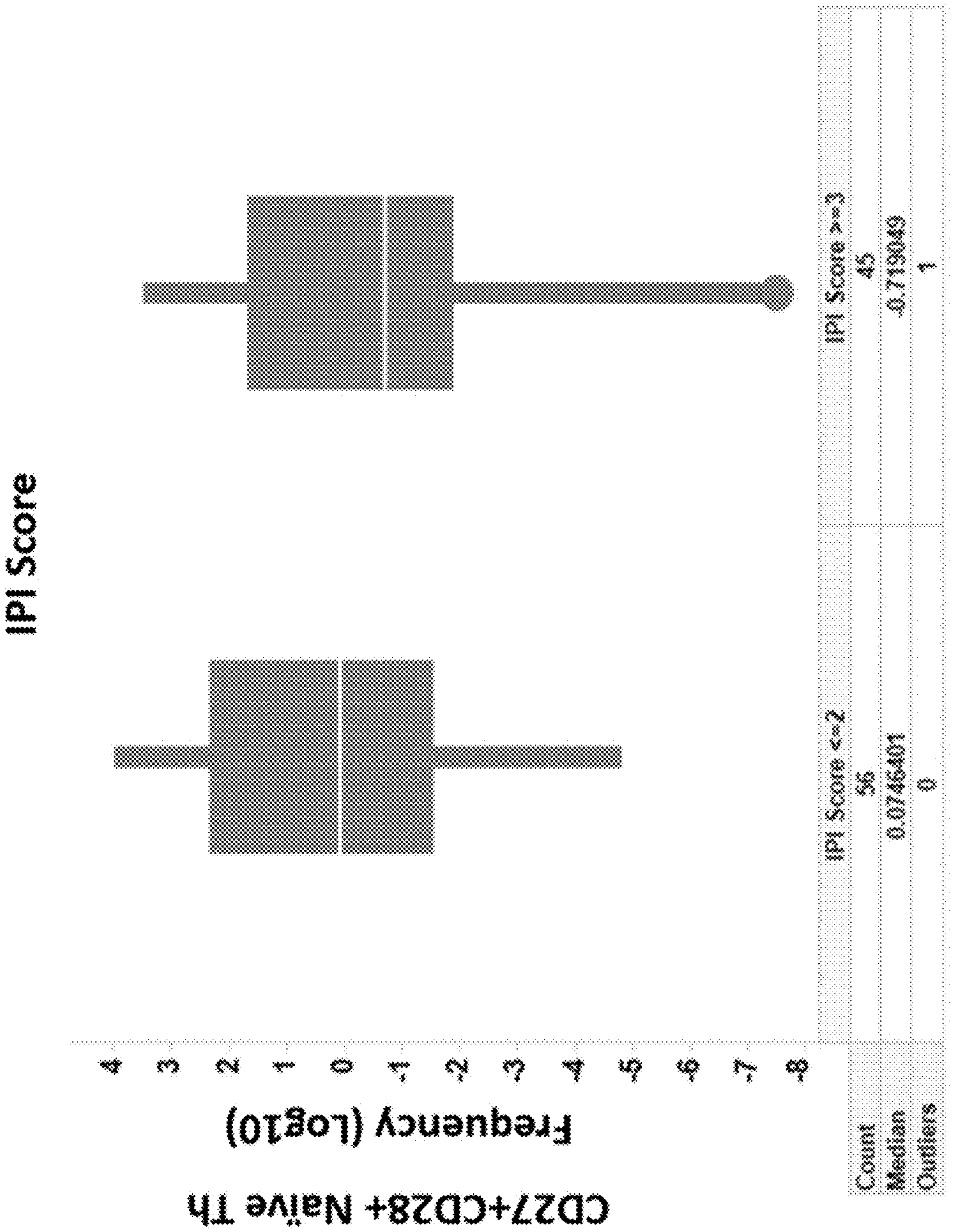
FIG. 15B Boxplot of CD27+CD28+ Naïve Th (% of Leukocytes) in pre-manufacturing PBMCs grouped by IPI Score.
Figure 15C:
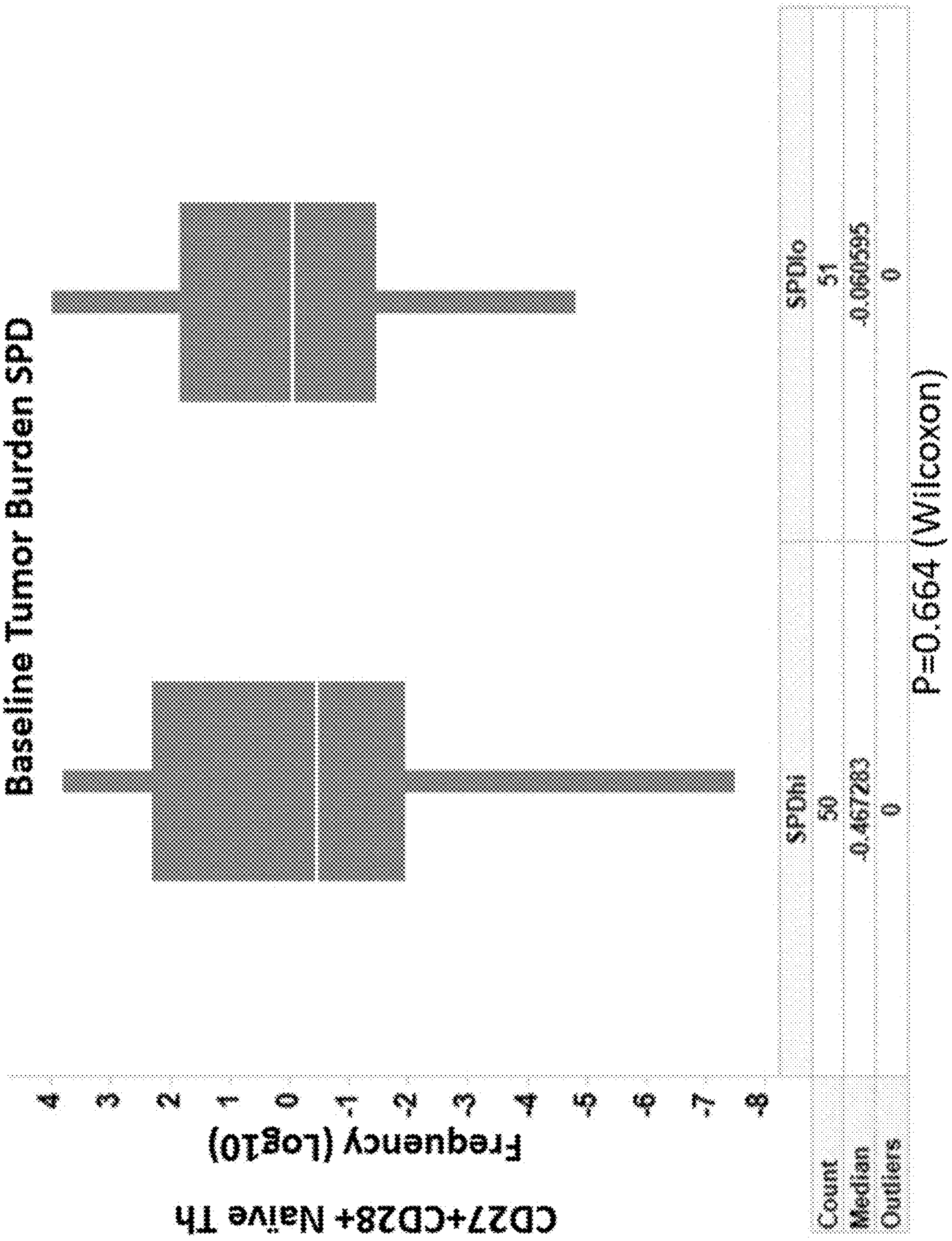
FIG. 15C Boxplot of CD27+CD28+ Naïve Th (% of Leukocytes) in pre-manufacturing PBMCs grouped by baseline tumor burden (SPD).

Front (Z12) or $2^{nd}$ (Z7) line DLBCL may have greater levels of naïve T cells at leukapheresis. FIG. 15A, FIG. 15B, FIG. 15C. The data in FIG. 15A may indicate that subjects would have greater levels of these cells in their blood with fewer lines of therapy, indicating response rates could be improved if CAR T-cells were utilized as an earlier line of therapy ($1^{st}/2^{nd}$ line). Higher IPI scores trend with lower CD27+CD28+ Naïve Th cells. CD27+CD28+ Naïve Th cells show a weak negative association with baseline tumor burden. FIG. 15B.

Example 5

Figure 16A:
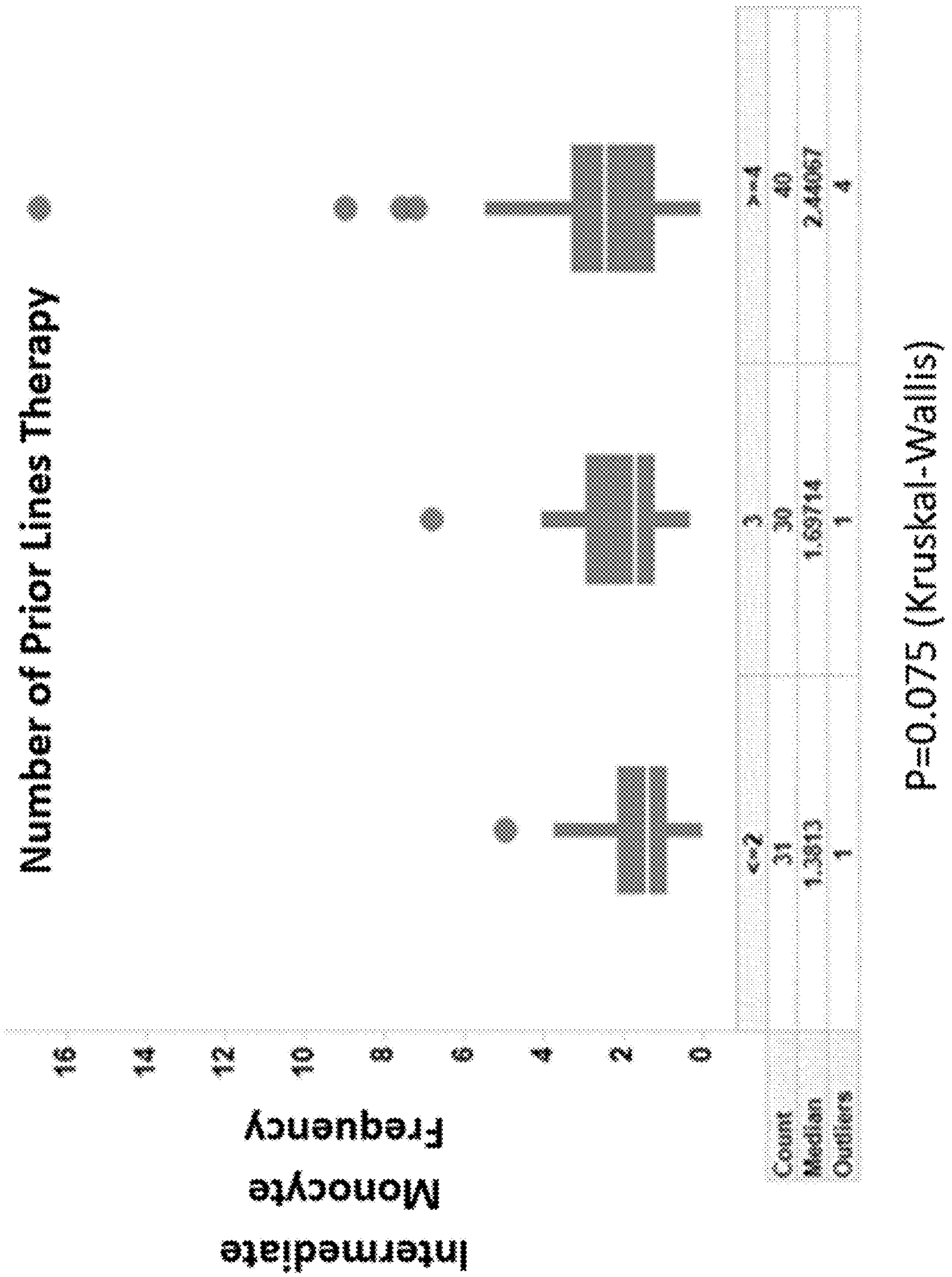
FIG. 16A Boxplot of Intermediate Monocytes FIG. 16B Boxplot of Intermediate Monocytes (% of Leukocytes) in pre-manufacturing PBMCs grouped by IPI Score pointing to their enrichment in patients with higher IPI scores (% of Leukocytes) in pre-manufacturing PBMCs grouped by number of prior lines of therapy.
Figure 16B:
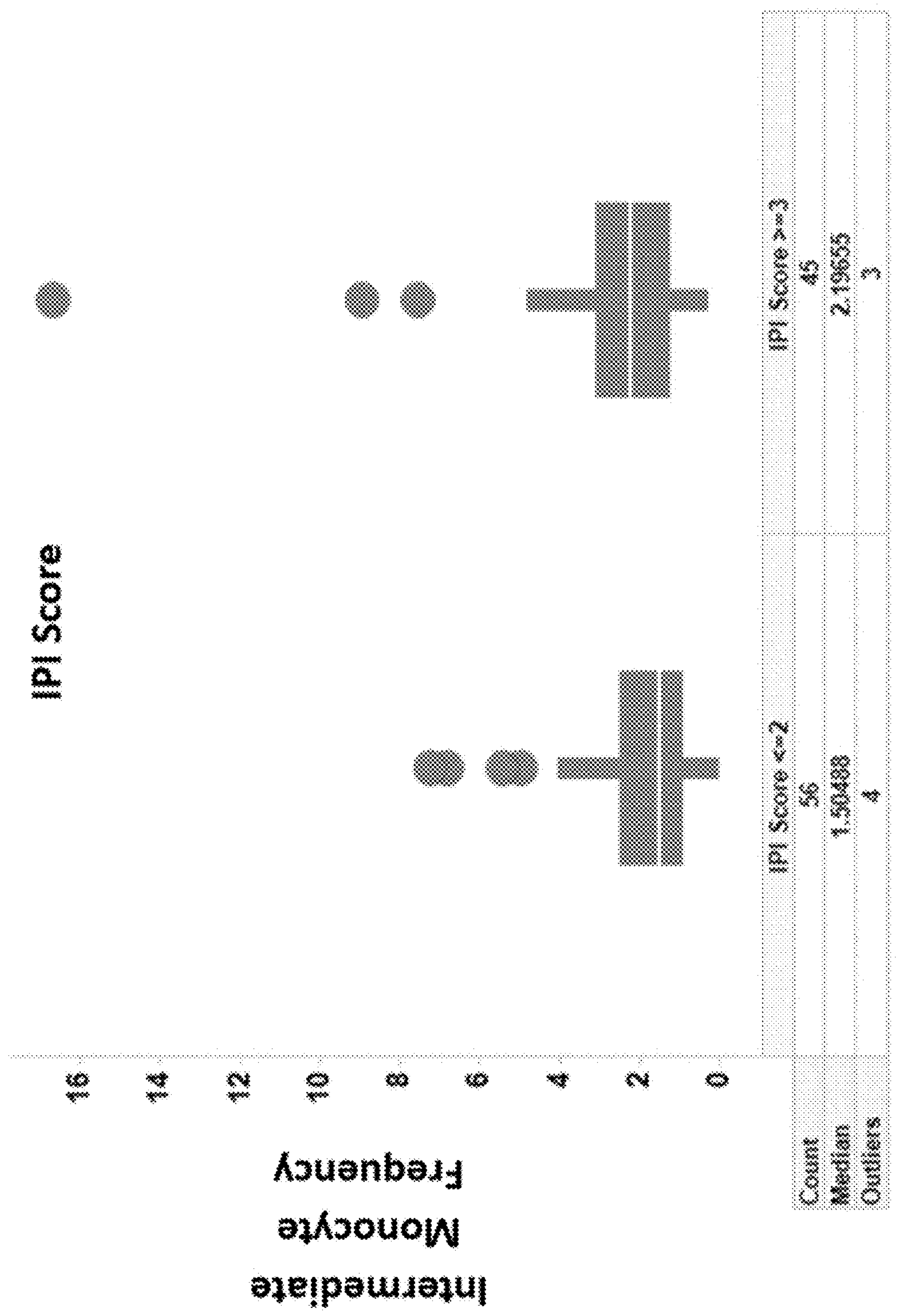
FIG. 16C Boxplot of Intermediate Monocytes (% of Leukocytes) in pre-manufacturing PBMCs grouped by baseline tumor burden (SPD).
Figure 16C:
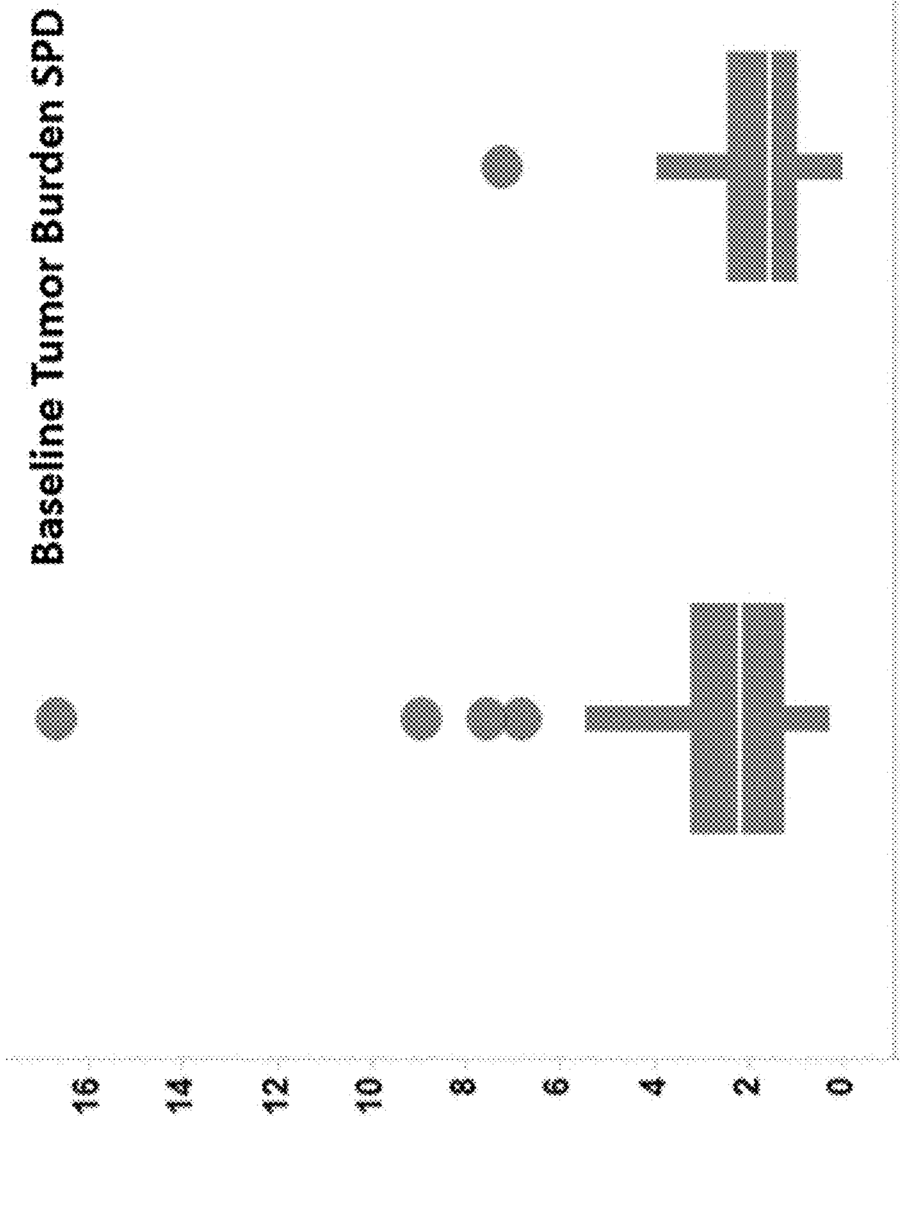

The intermediate monocyte population in the apheresis product was associated with disease burden (FIG. 16C) and moderately increased with the number of prior lines therapy. Intermediate monocytes are positively associated with number of prior lines of therapy. Subjects would be expected to have lower levels of intermediate monocytes with fewer prior lines of therapy, and due to the negative association of these cells with response this also indicates that CAR T-cell response rates could be even higher if utilized as an earlier line of therapy ($1^{st}/2^{nd}$ line). FIG. 16A. International Prognostic Index (IPI) score and intermediate monocytes were positively associated, further indicating that these cells are associated with subjects that have a worse prognosis. FIG. 16B. Intermediate monocytes were positively associated with baseline tumor burden. FIG. 16C.

Example 6

Figure 17A:
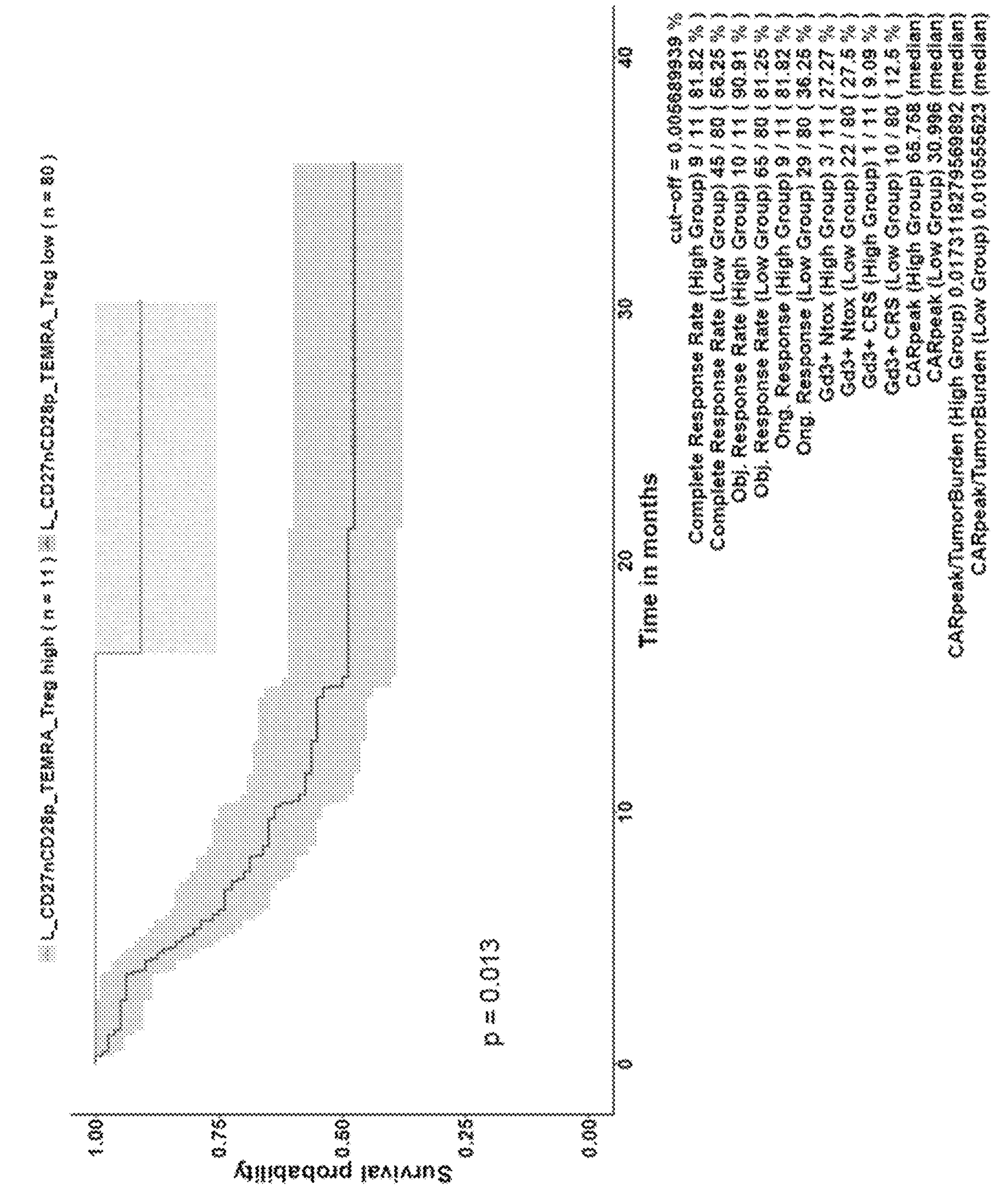
FIG. 17A Overall survival curve of clinical study subjects grouped by % CD27−CD28+ TEMRA Treg cells pre-manufacturing. Kaplan-Meier overall survival curve with an optimal cut-off selection for % CD27−CD28+ TEMRA Treg cells in pre-manufacturing PBMC population with significance determined by the Log-Rank test. The rate of complete response, objective response, ongoing response, grade 3+ toxicity, and CAR T cell expansion were determined for subjects with % CD27−CD28+ TEMRA Treg cells in the pre-manufacturing PBMC populations above or below the optimal cut-off.
Figure 17B:
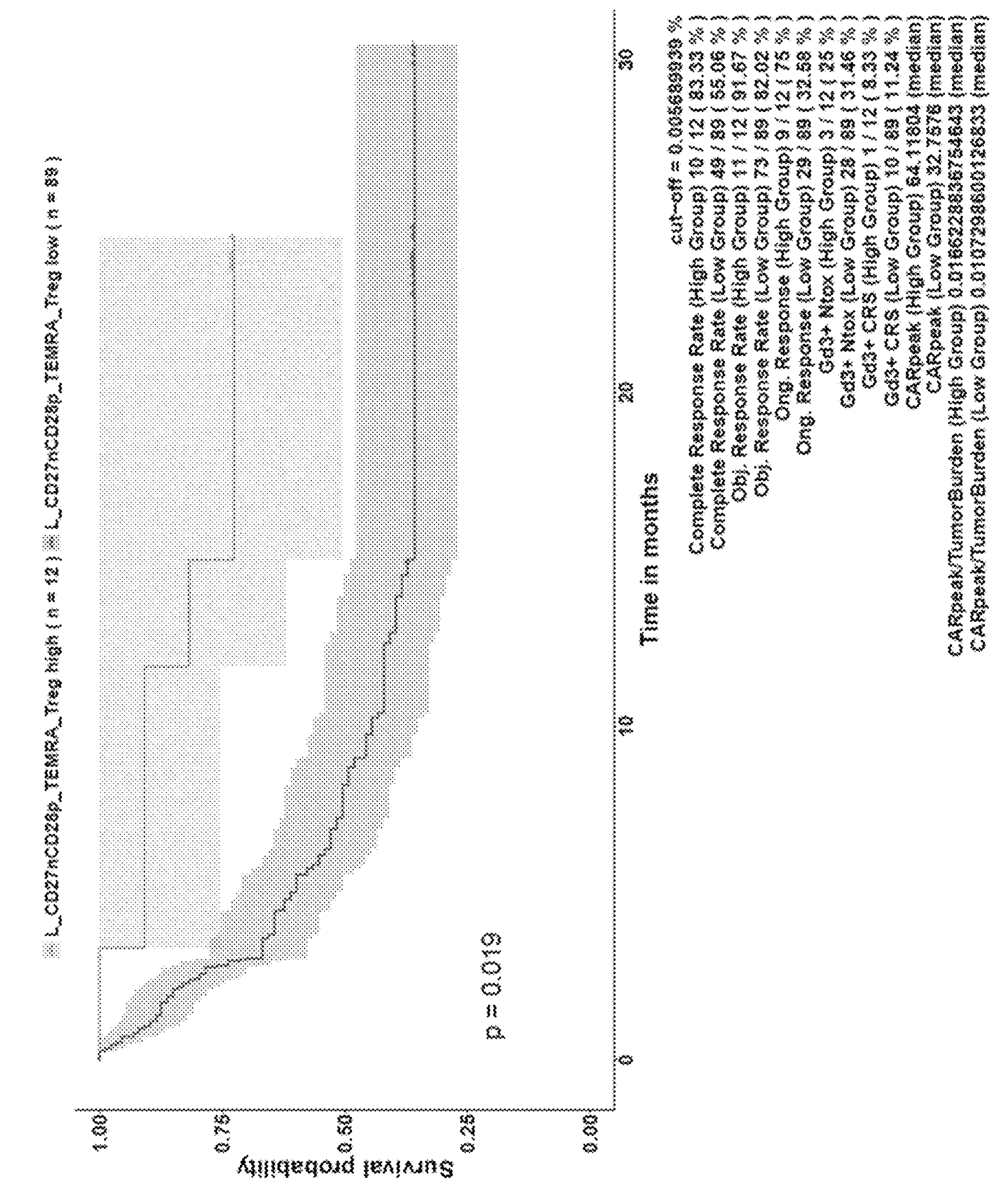
FIG. 17B Progression-free survival curve of clinical study subjects grouped by % CD27−CD28+ TEMRA Treg cells pre-manufacturing. Kaplan-Meier progression-free survival curve with an optimal cut-off selection for % CD27−CD28+ TEMRA Treg cells in pre-manufacturing PBMC population with significance determined by the Log-Rank test. The rate of complete response, objective response, ongoing response, grade 3+ toxicity, and CAR T cell expansion were determined for subjects with % CD27−CD28+ TEMRA Treg cells in the pre-manufacturing PBMC populations above or below the optimal cut-off.

The levels of CD27−CD28+ TEMRA Treg cells (% of leukocytes) in the apheresis product associated positively with and may be a predictive marker for OS (FIG. 17A) and PFS (FIG. 17B) (optimal cutoff). Utilizing this cutoff for CD27−CD28+ TEMRA Tregs subjects with higher levels of these cells have higher complete, objective, and ongoing response rates.

Example 7

Figure 18A:
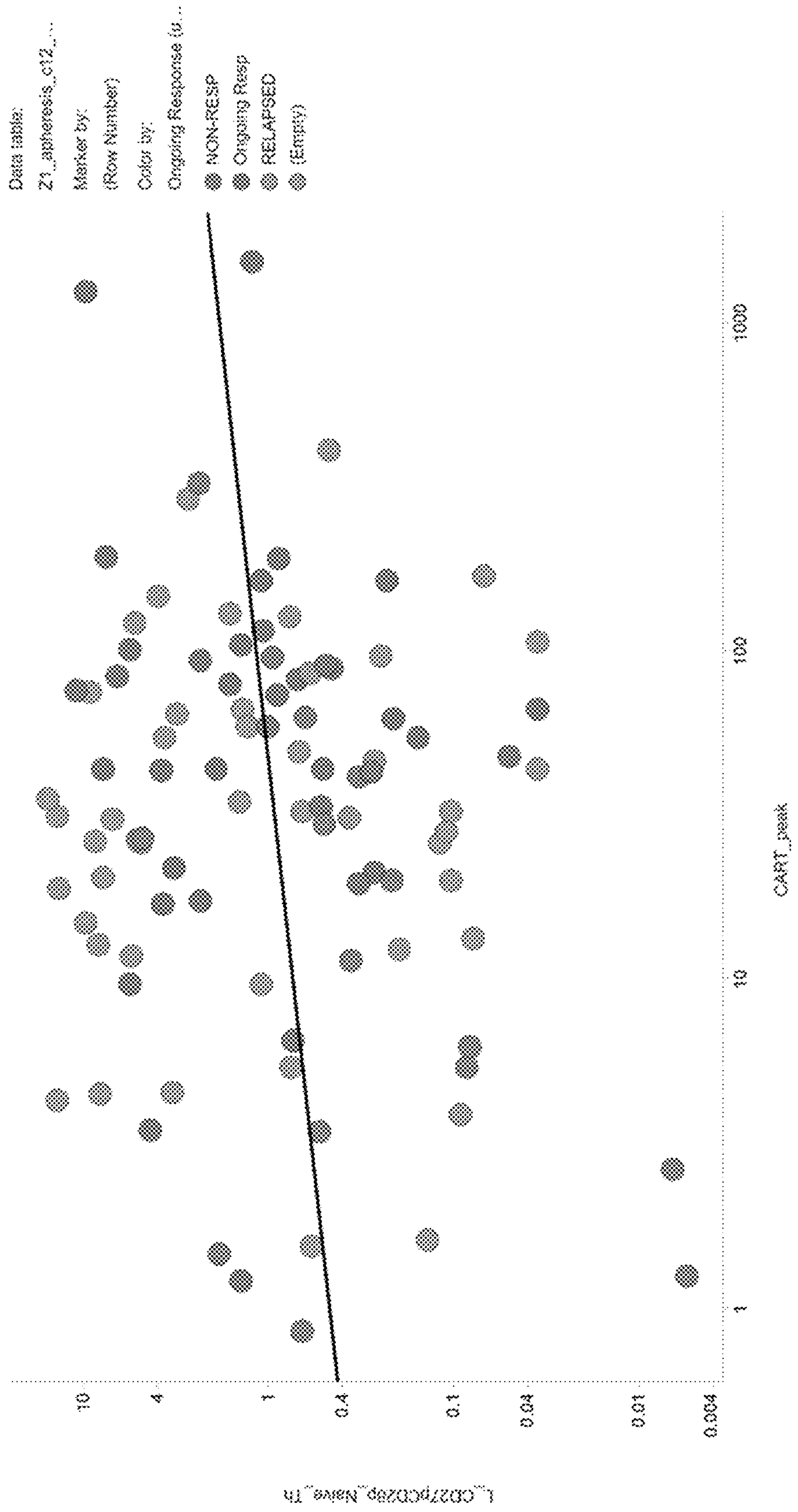
FIG. 18A Scatterplot of % CD27+CD28+ Naïve Th in the pre-manufacturing PBMC population vs peak CAR T-cell expansion colored by ongoing response status. Linear association (black line) between the % CD27+CD28+ Naïve Th in the pre-manufacturing PBMC population and peak CAR T-cell expansion.
Figure 18B:
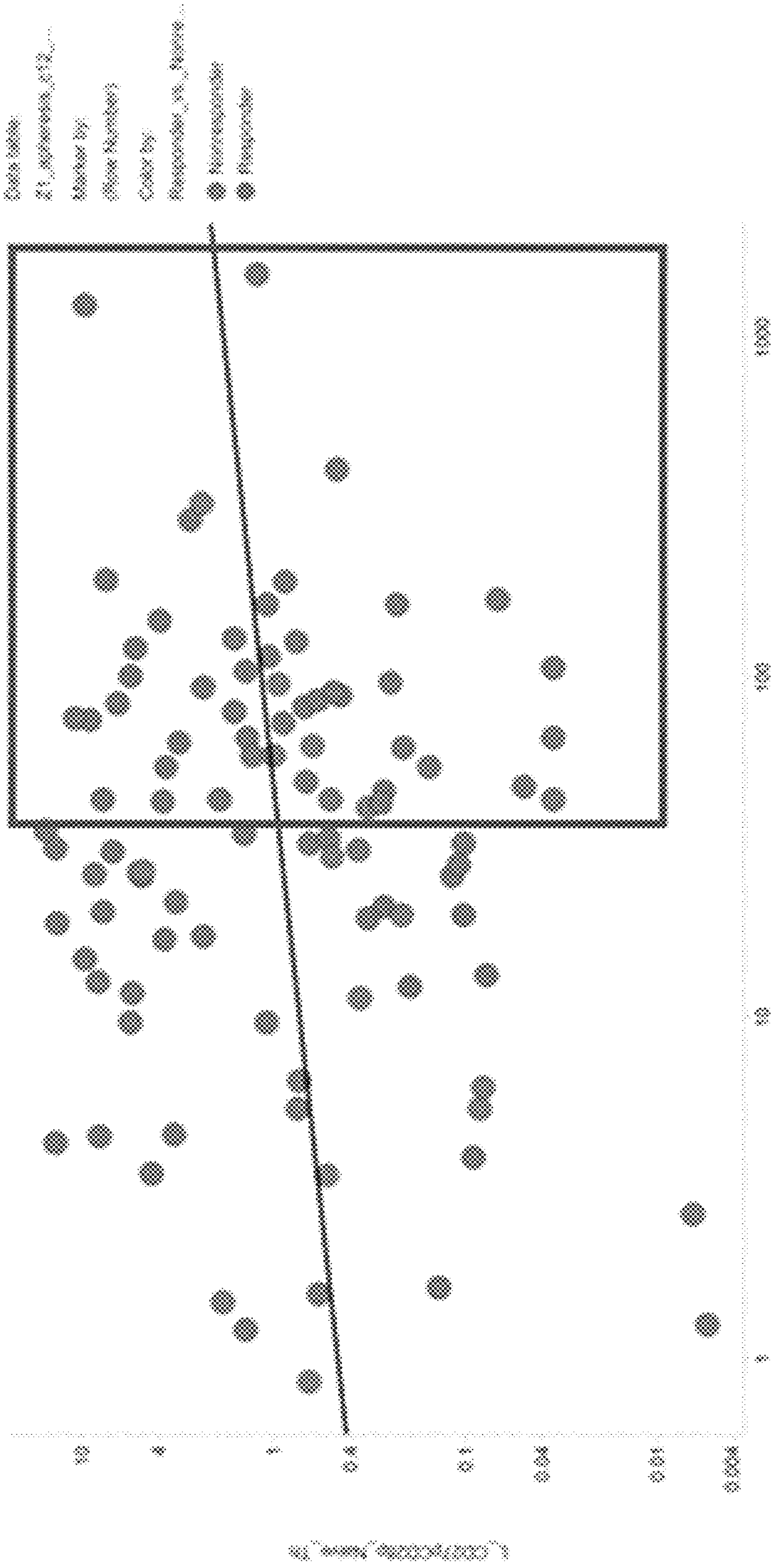
FIG. 18B Scatterplot of % CD27+CD28+ Naïve Th in the pre-manufacturing PBMC population vs peak CAR T-cell expansion colored by objective response status. Linear association (black line) between the % CD27+CD28+ Naïve Th in the pre-manufacturing PBMC population and peak CAR T-cell expansion. Blue box indicates a high response rate area with high peak CAR T-cell expansion and CD27+CD28+ Naïve Th cells.
Figure 18C:
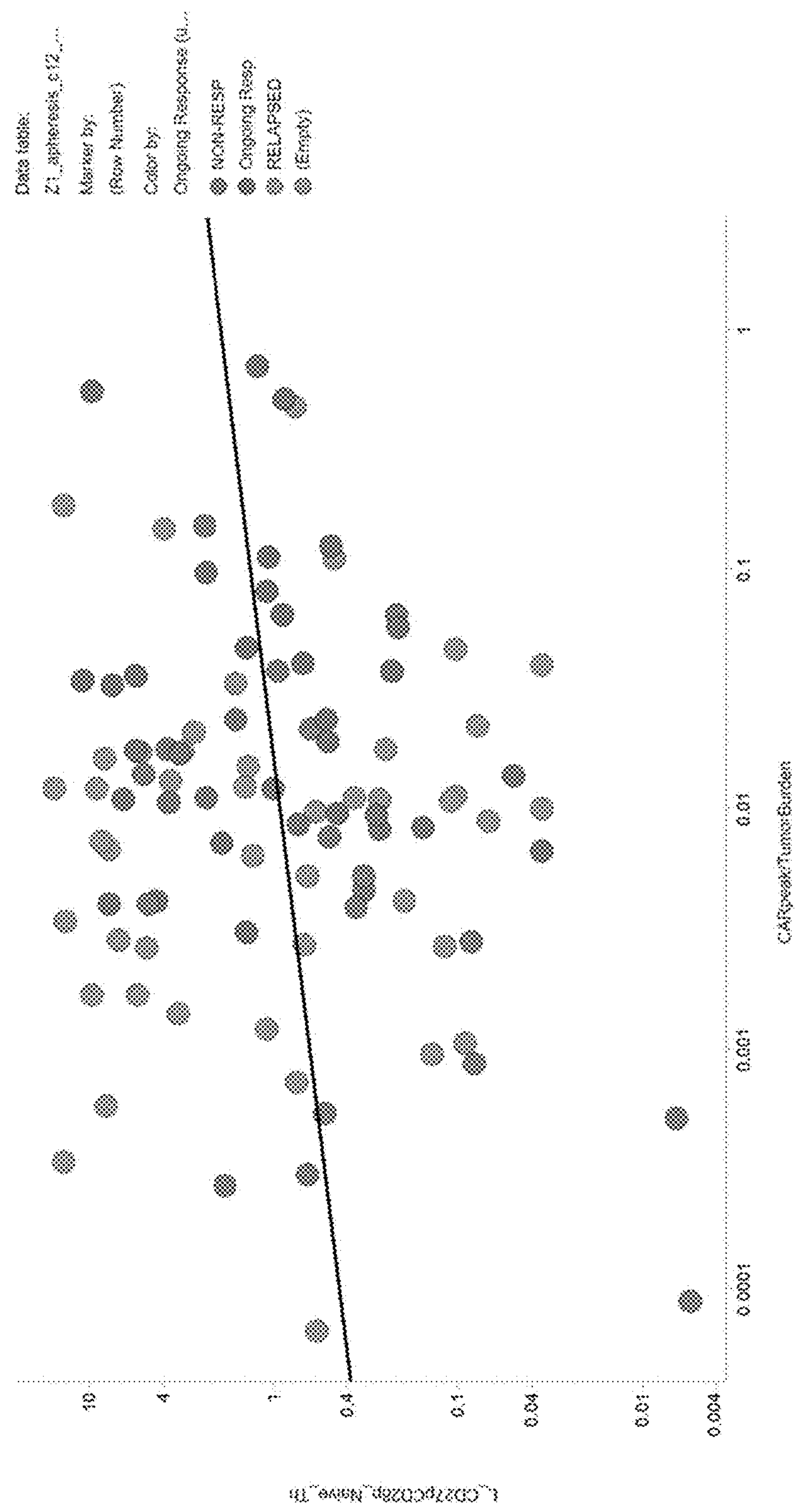
FIG. 18C Scatterplot of % CD27+CD28+ Naïve Th in the pre-manufacturing PBMC population vs peak CAR T-cell expansion/baseline tumor burden colored by ongoing response status. Linear association (black line) between the % CD27+CD28+ Naïve Th in the pre-manufacturing PBMC population and peak CAR T-cell expansion/baseline tumor burden (as determined by sum of product diameters, SPD)
Figure 18D:
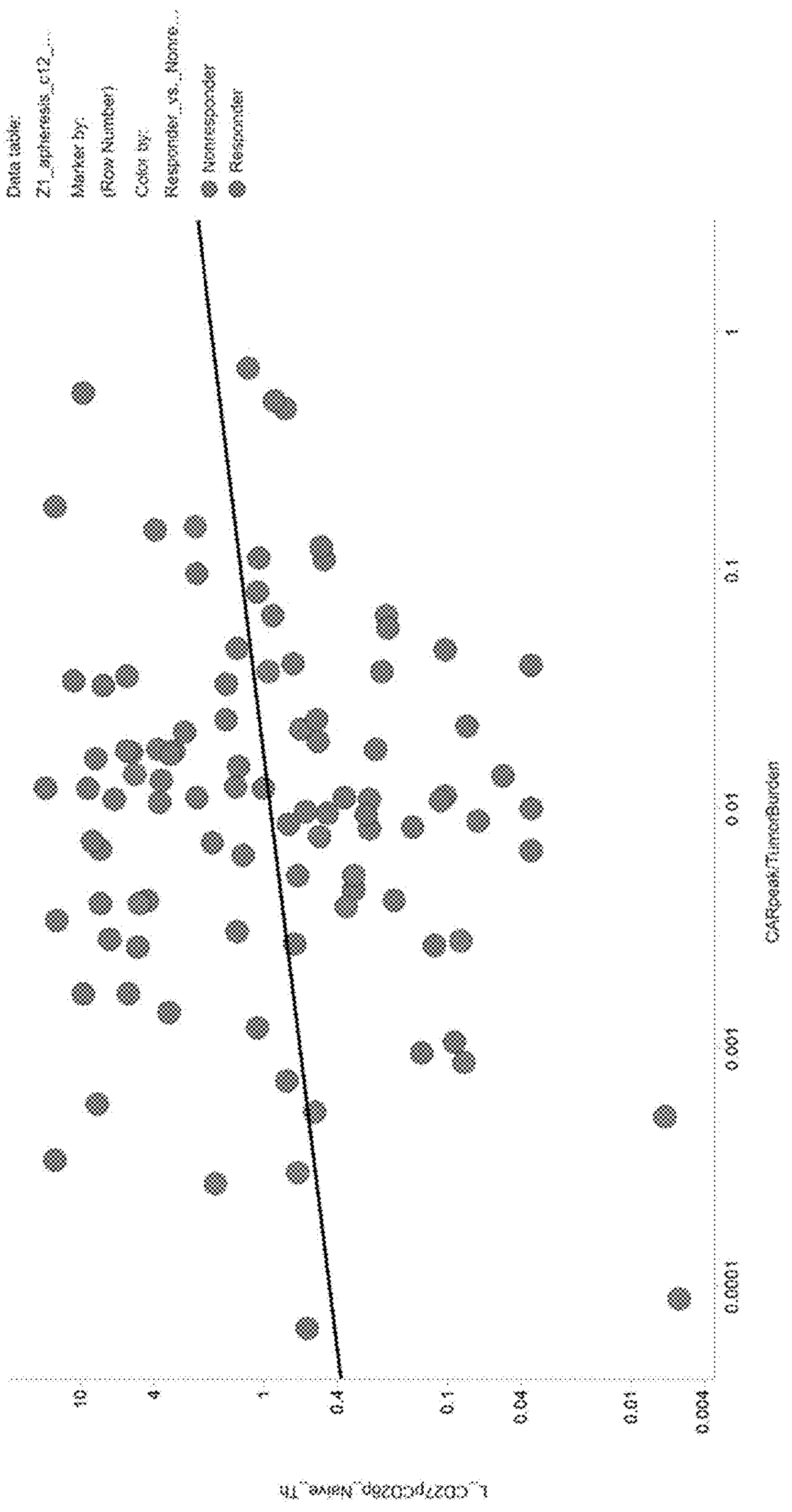
FIG. 18D Scatterplot of % CD27+CD28+ Naïve Th in the pre-manufacturing PBMC population vs peak CAR T-cell expansion/baseline tumor burden colored by objective response status. Linear association (black line) between the % CD27+CD28+ Naïve Th in the pre-manufacturing PBMC population and peak CAR T-cell expansion/baseline tumor burden. Blue box indicates a high response rate area with high peak CAR T-cell expansion/baseline tumor burden and CD27+CD28+ Naïve Th cells.
Figure 19A:
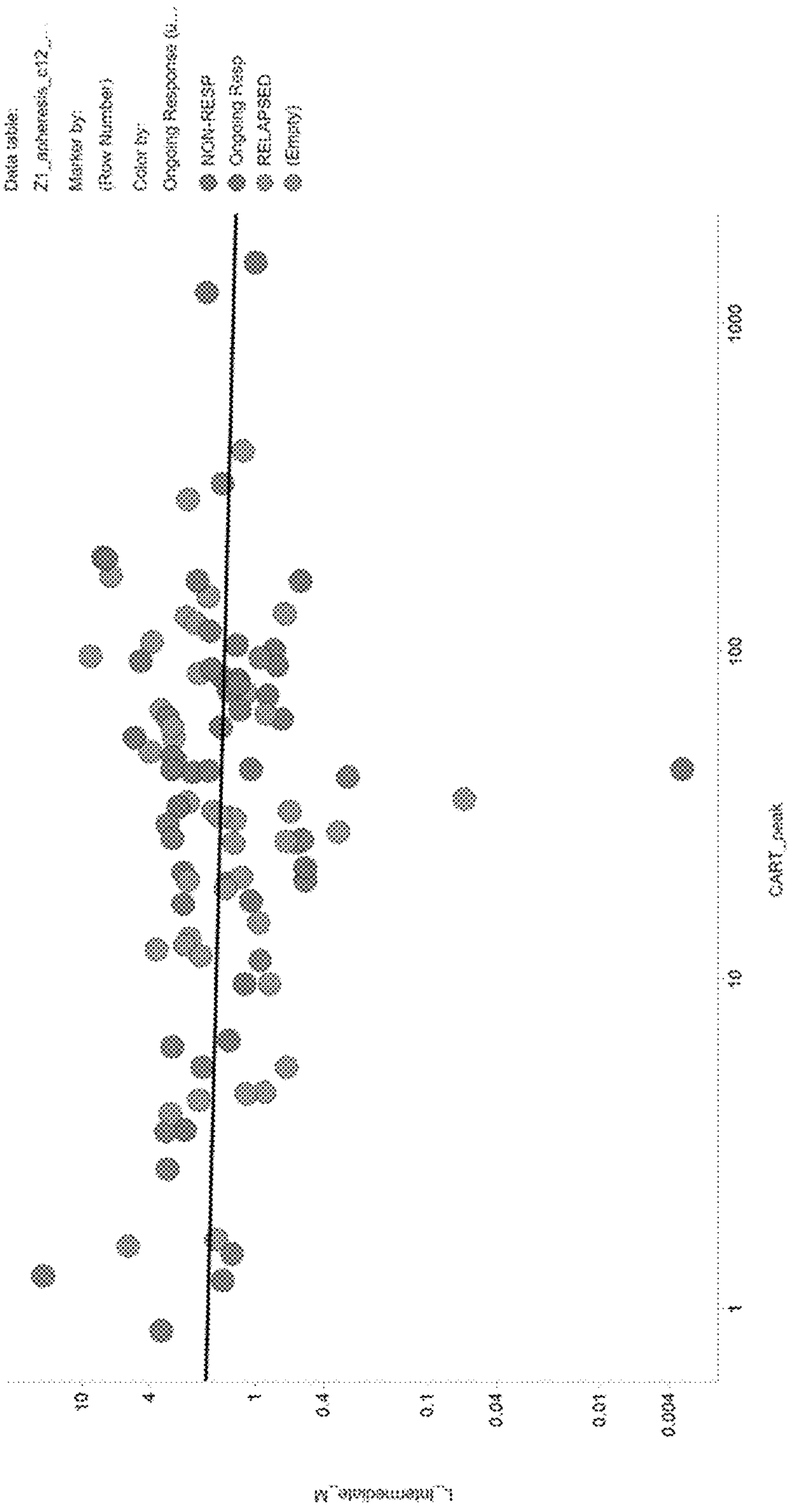
FIG. 19A Scatterplot of % Intermediate Monocytes in the pre-manufacturing PBMC population vs peak CAR T-cell expansion colored by ongoing response status. Linear association (black line) between the % Intermediate Monocytes in the pre-manufacturing PBMC population and peak CAR T-cell expansion. Blue box indicates the with a cluster of high ongoing response rates where there is high peak CAR T-cell expansion and low intermediate monocytes.
Figure 19B:
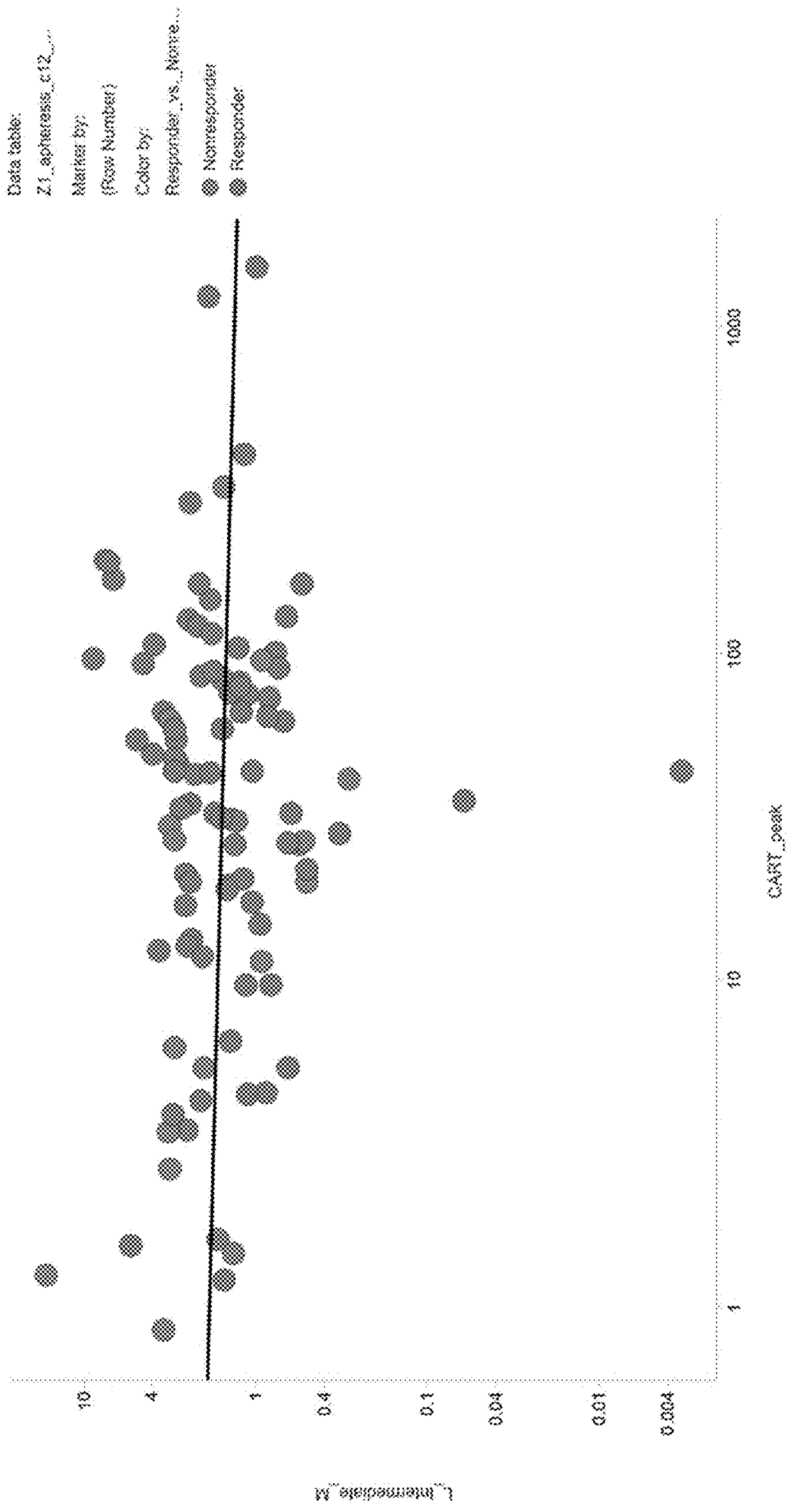
FIG. 19B Scatterplot of % Intermediate Monocytes in the pre-manufacturing PBMC population vs peak CAR T-cell expansion colored by objective response status. Linear association (black line) between the % Intermediate Monocytes in the pre-manufacturing PBMC population and peak CAR T-cell expansion. Blue box indicates with a cluster of high response rates where there is high peak CAR T-cell expansion and low intermediate monocytes.
Figure 19C:
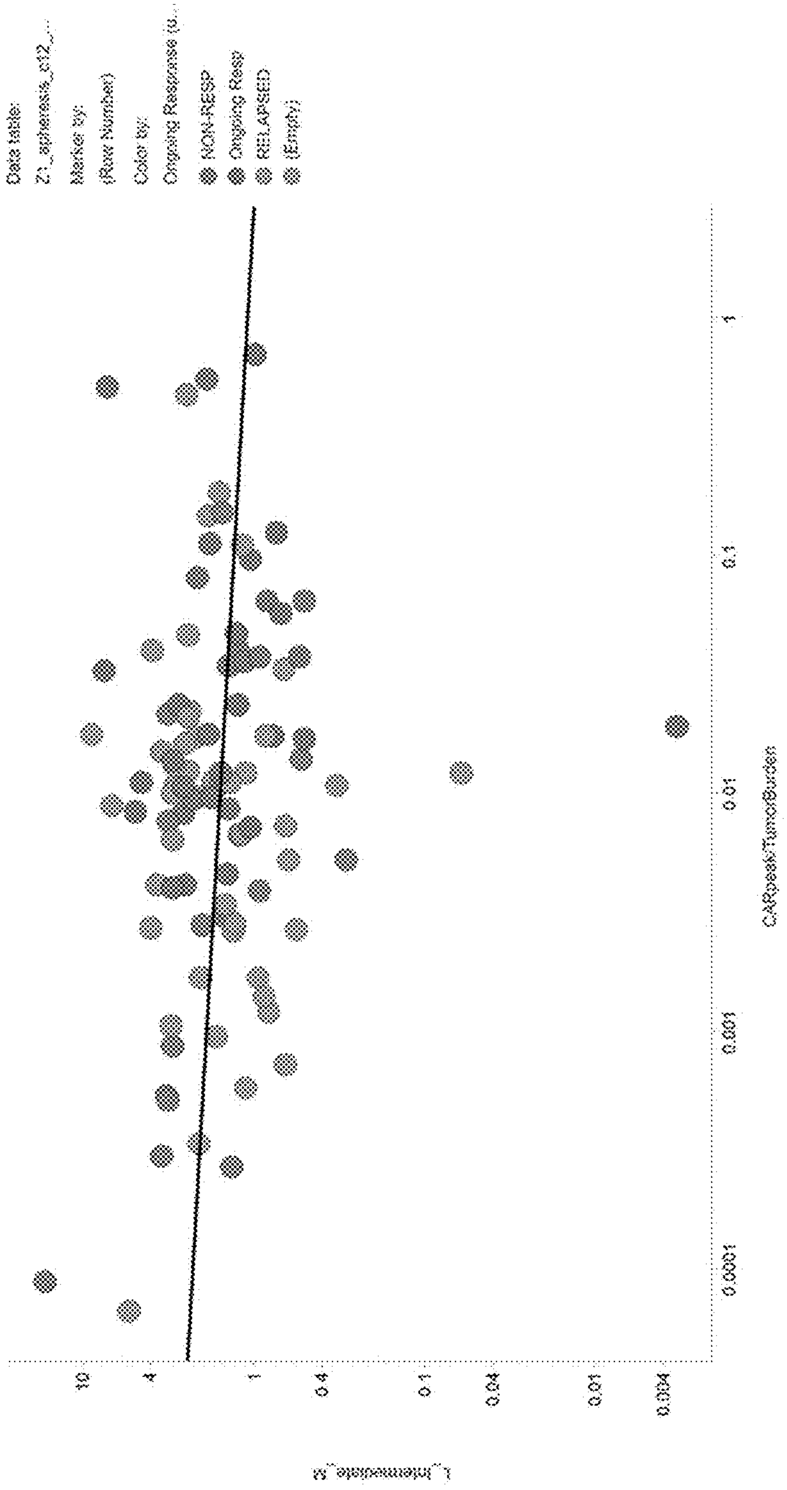
FIG. 19C Scatterplot of % Intermediate Monocytes in the pre-manufacturing PBMC population vs peak CAR T-cell expansion/baseline tumor burden colored by ongoing response status. Linear association (black line) between the % Intermediate Monocytes in the pre-manufacturing PBMC population and peak CAR T-cell expansion/baseline tumor burden. Blue box indicates with a cluster of high ongoing response rates where there is high peak CAR T-cell expansion/baseline tumor burden and low intermediate monocytes.
Figure 19D:
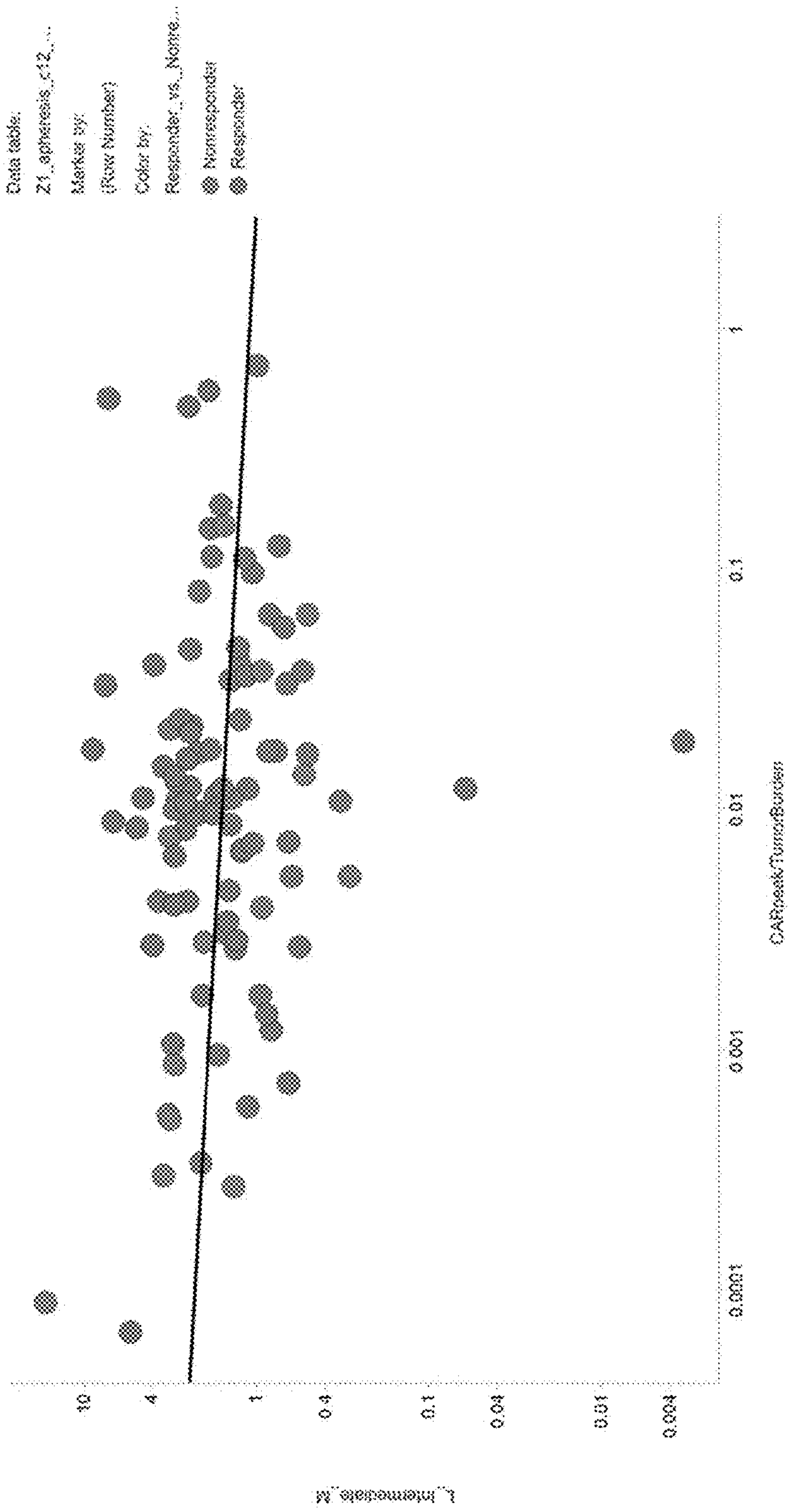
FIG. 19D Scatter-plot of % Intermediate Monocytes in the pre-manufacturing PBMC population vs peak CAR T-cell expansion/baseline tumor burden colored by objective response status. Linear association (black line) between the % Intermediate Monocytes in the pre-manufacturing PBMC population and peak CAR T-cell expansion/baseline tumor burden. Blue box indicates with a cluster of high response rates where there is high peak CAR T-cell expansion/baseline tumor burden and low intermediate monocytes.

There was an association between CD27+CD28+ Naïve Th cells in the apheresis product vs. CAR-T peak (FIG. 18A and FIG. 18B) and CAR-T peak/baseline tumor burden (FIG. 18C and FIG. 18D). A positive association between CD27+CD28+ Naïve Th cells and CAR T-cell peak expansion (normalized by tumor burden also FIG. 18C-D) was observed. Low levels of both correlate with higher non-responder rates while increasing levels of both lead to higher response rates. An association between intermediate monocytes vs. CAR-T peak and CAR-T peak/baseline tumor burden was observed. There was a positive association between intermediate monocytes and CAR T-cell peak expansion (normalized by tumor burden also FIG. 19C-D). Low levels of both correlate with higher non-responder rates while increasing levels of both lead to higher response rates. FIG. 19.

Example 8

Composition of apheresis and baseline hematology cell counts.

TABLE 1

| | Apheresis Product % of Leukocyte Parent | | | | | |
|---|---|---|---|---|---|---|
| Analyte | median | mean | min | max | range | N |
| Lymphocytes | 72.13559 | 69.63881 | 16.13167 | 99.00392 | 82.87226 | 101 |
| Bcells (CD3− CD19+) | 0.015625 | 0.804813 | 0.001611 | 16.94887 | 16.94726 | 101 |
| T cells (CD45+CD3+) | 49.67002 | 49.28159 | 2.655696 | 97.48279 | 94.8271 | 101 |
| Th (CD4+CD127+CD25dim) | 18.25844 | 20.0634 | 1.287762 | 65.47249 | 64.18472 | 101 |
| Naïve Th (CCR7+CD45RA+) | 0.914182 | 2.769145 | 0.006665 | 16.03658 | 16.02991 | 101 |
| CM Th (CCR7+CD45RA−) | 9.328898 | 10.71058 | 0.52022 | 37.6775 | 37.15728 | 101 |
| EM Th (CCR7− CD45RA−) | 4.769625 | 5.646541 | 0.27874 | 21.93252 | 21.65378 | 101 |
| TEMRA Th (CCR7- CD45RA+) | 0.16783 | 0.632719 | 0.002107 | 7.398687 | 7.39658 | 101 |
| CD8 T (CD8+) | 22.76942 | 24.10071 | 0.971329 | 69.65397 | 68.68264 | 101 |
| Naïve CD8 (CCR7+CD45RA+) | 0.685984 | 1.458885 | 0.022667 | 16.14957 | 16.1269 | 101 |
| CM CD8 (CCR7+CD45RA−) | 2.17137 | 3.310274 | 0.160992 | 47.31743 | 47.15644 | 101 |
| EM CD8 (CCR7- CD45RA−) | 6.592083 | 8.287809 | 0.205052 | 32.26761 | 32.06256 | 101 |
| TEMRA CD8 (CCR7− CD45RA+) | 7.328635 | 10.5934 | 0.217927 | 49.46025 | 49.24232 | 101 |
| Treg (CD4+CD127dimCD25+) | 1.626824 | 2.354672 | 0.104711 | 19.12081 | 19.0161 | 101 |
| Naïve Treg (CCR7+CD45RA+) | 0.073594 | 0.134119 | 0.000639 | 0.707633 | 0.706994 | 101 |
| CM Treg (CCR7+CD45RA−) | 0.81553 | 1.263328 | 0.059662 | 11.00624 | 10.94657 | 101 |
| EM Treg (CCR7− CD45RA−) | 0.53725 | 0.883234 | 0.037506 | 7.34346 | 7.305954 | 101 |
| TEMRA Treg (CCR7− CD45RA+) | 0.003054 | 0.013393 | 0 | 0.300936 | 0.300936 | 101 |
| NK (CD3−CD19−CD56+/− CD16+/−) | 6.720638 | 8.778434 | 0.046268 | 33.83903 | 33.79276 | 101 |
| CD56+CD16− NK | 1.407865 | 2.073451 | 0.015995 | 11.09515 | 11.07916 | 101 |

TABLE 1-continued

| Analyte | Apheresis Product % of Leukocyte Parent | | | | | |
|---|---|---|---|---|---|---|
| | median | mean | min | max | range | N |
| CD56++CD16− NK | 0.369796 | 0.689727 | 0.000107 | 6.681104 | 6.680997 | 101 |
| CD56++CD16+ NK | 0.138904 | 0.24675 | 0 | 1.947303 | 1.947303 | 101 |
| CD56+CD16++ NK | 4.488074 | 5.768506 | 0.030165 | 24.48757 | 24.4574 | 101 |
| NKT (CD3+CD56+/− CD16+/−) | 4.679279 | 6.581782 | 0.183656 | 31.73799 | 31.55433 | 101 |
| CD56−CD16+ NKT | 1.807404 | 3.072575 | 0.072626 | 17.10215 | 17.02952 | 101 |
| CD56+CD16− NKT | 1.557345 | 2.594318 | 0.050846 | 27.83969 | 27.78885 | 101 |
| CD56+CD16+ NKT | 0.36766 | 0.914889 | 0.008266 | 6.654513 | 6.646247 | 101 |
| Monocytes (CD3−CD19− CD56−CD11c+CD14+/− CD16+/−) | 27.66377 | 30.51524 | 0.121677 | 84.17273 | 84.05105 | 101 |
| Nonclassical Monocytes (CD16+CD14−) | 1.048348 | 1.579376 | 0.028551 | 9.702222 | 9.673671 | 101 |
| Classical Monocytes (CD16−CD14+) | 23.29715 | 26.56988 | 0.06823 | 81.34641 | 81.27818 | 101 |
| Intermediate Monocyte (CD16+CD14+) | 1.767519 | 2.285025 | 0.003411 | 16.68793 | 16.68452 | 101 |
| pDC (CD3−CD19−CD56− CD11c−CD123+) | 0.229742 | 0.289518 | 0.00882 | 1.587529 | 1.578708 | 101 |
| mDC (CD3−CD19−CD56− CD14−CD16− CD11c+HLADR+) | 5.012917 | 5.654447 | 0.233119 | 16.91714 | 16.68402 | 101 |

TABLE 2

| Analyte | Blood levels Baseline Hematology Cell Counts | | | | | |
|---|---|---|---|---|---|---|
| | median | mean | min | max | range | N |
| Basophils_at_baseline (10^9/L) | 0.01 | 0.031029 | 0 | 0.7 | 0.7 | 136 |
| Eosinophils_at_baseline (10^9/L) | 0.1 | 0.147246 | 0 | 1.97 | 1.97 | 138 |
| Erythrocytes_at_baseline (10^12/L) | 3.58 | 3.61875 | 2.34 | 9.6 | 7.26 | 144 |
| Leukocytes_at_baseline (10^9/L) | 5.37 | 6.156438 | 1.6 | 26.1 | 24.5 | 146 |
| Lymphocytes_at_baseline (10^9/L) | 0.6226 | 0.700651 | 0.076 | 2.9862 | 2.9102 | 146 |
| Monocytes_at_baseline (10^9/L) | 0.545 | 0.863841 | 0.03 | 40 | 39.97 | 138 |
| Neutrophils_at_baseline (10^9/L) | 3.65 | 4.648342 | 0.09 | 24.85 | 24.76 | 146 |
| Platelets_at_baseline (10^9/L) | 178 | 183.0616 | 31 | 877 | 846 | 146 |

Example 9

Figure 20A:
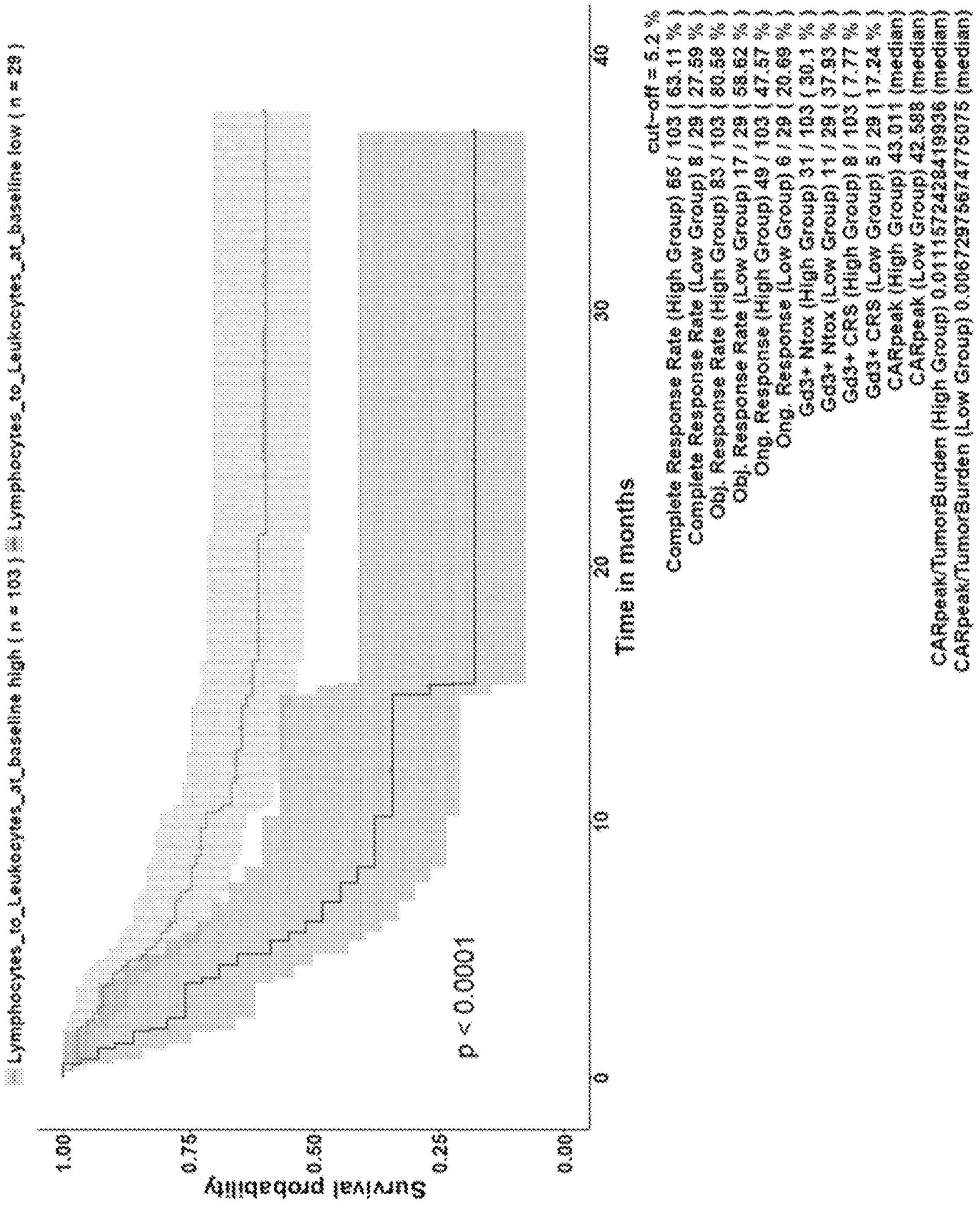
FIG. 20A Overall survival curve of clinical study subjects grouped by the % of lymphocytes to leukocytes at baseline. Kaplan-Meier overall survival curve with an optimal cut-off selection for the % of lymphocytes to leukocytes at baseline with significance determined by the Log-Rank test. The rate of complete response, objective response, ongoing response, grade 3+ toxicity, and CAR T cell expansion were determined for subjects above or below the optimal cut-off.
Figure 20B:
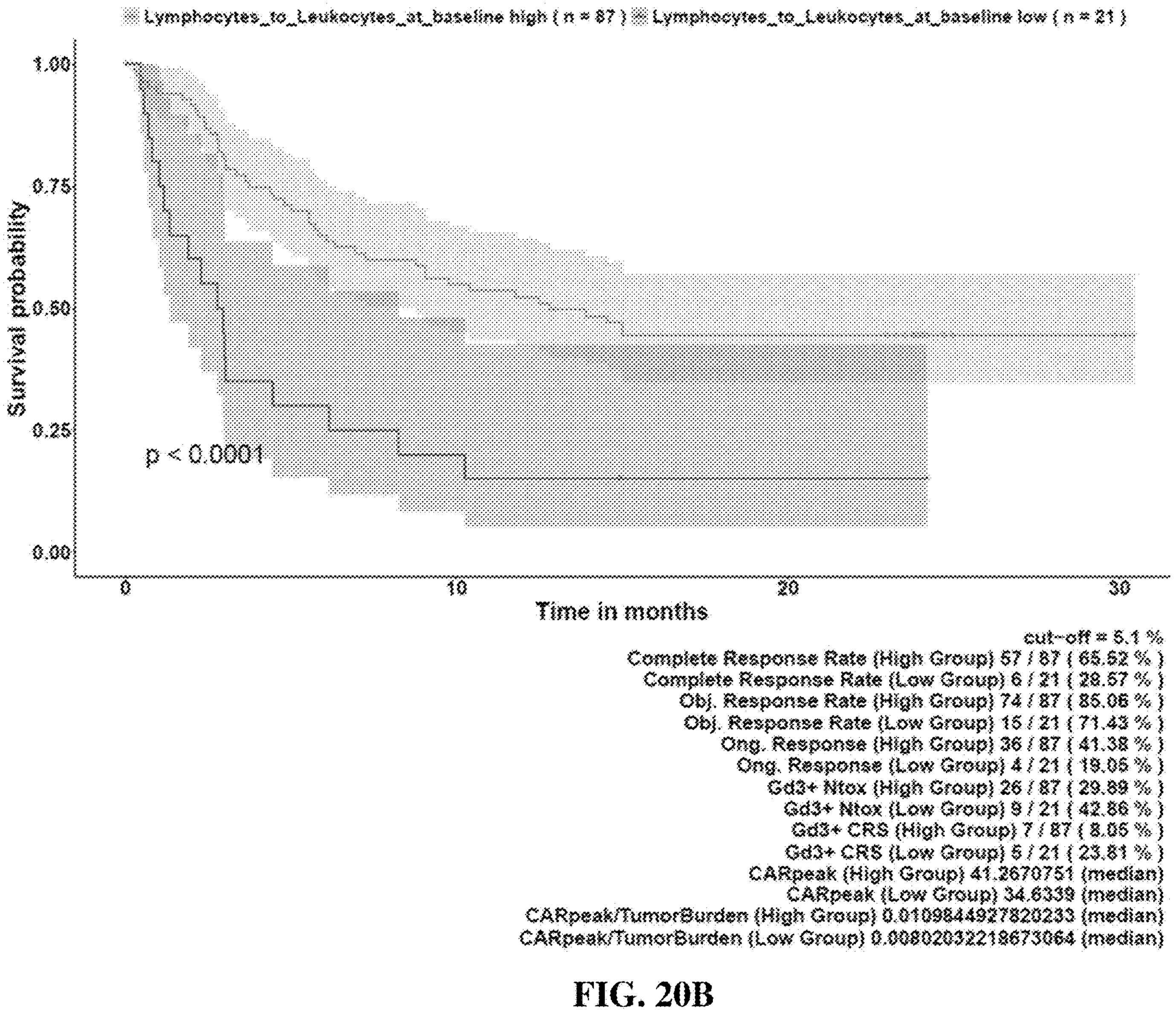
FIG. 20B Overall survival curve of clinical study subjects grouped by the % of lymphocytes to leukocytes at baseline. Kaplan-Meier overall survival curve with an optimal cut-off selection for the % of lymphocytes to leukocytes at baseline with significance determined by the Log-Rank test. The rate of complete response, objective response, ongoing response, grade 3+ toxicity, and CAR T cell expansion were determined for subjects above or below the optimal cut-off.
Figure 21:
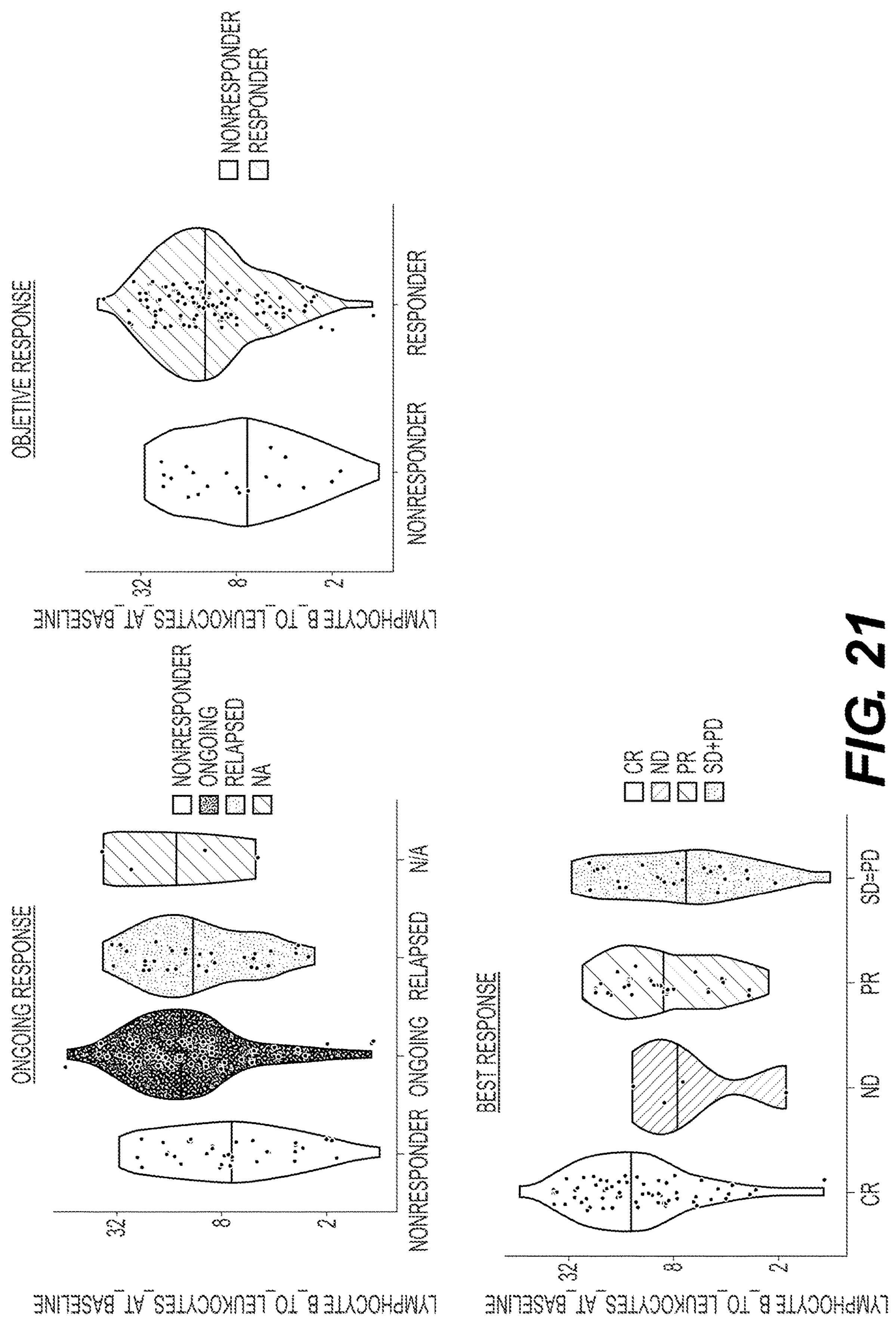
FIG. 21 Violin plots of the % lymphocyte to leukocytes at baseline grouped by response categories for evaluable clinical study subjects. The % lymphocytes to leukocytes positively associate with response.

Lymphocyte to Leukocytes in baseline hematology cell counts associated positively with and may serve as a predictive marker for OS (FIG. 20A) and PFS (FIG. 20B) (optimal cutoff). Lymphocyte to Leukocytes in baseline hematology cell counts was positively associated with complete response, objective, and ongoing response. FIG. 21.

Example 10

Figure 22:
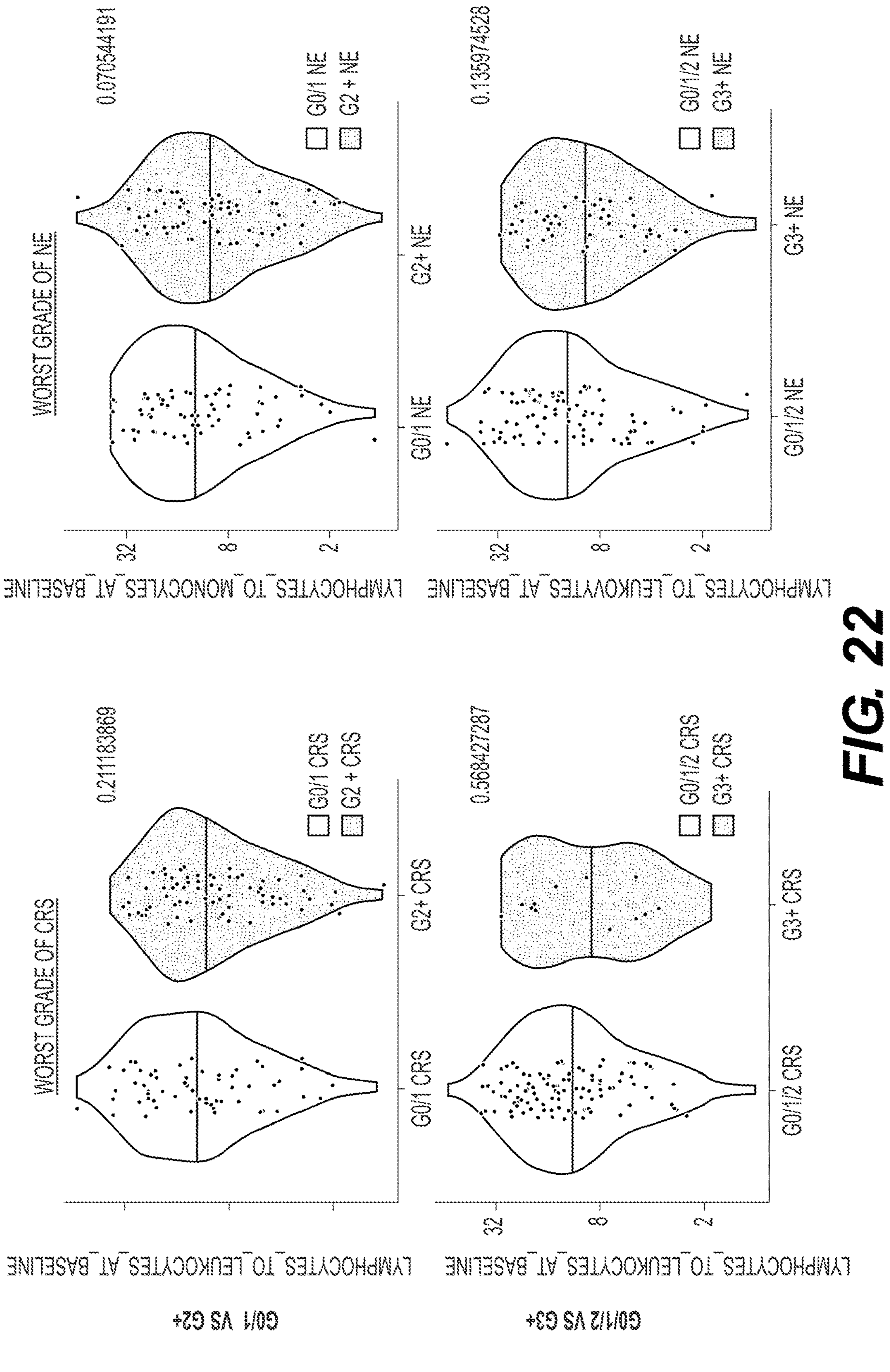
FIG. 22 Violin plots of the % lymphocyte to leukocytes at baseline grouped by worst grade of toxicity. Lymphocyte to Leukocytes in baseline hematology cell counts trends toward a negative association with worst grade of toxicity. CRS-cytokine Release Syndrome. NE—Neurologic Events.
Figure 23:
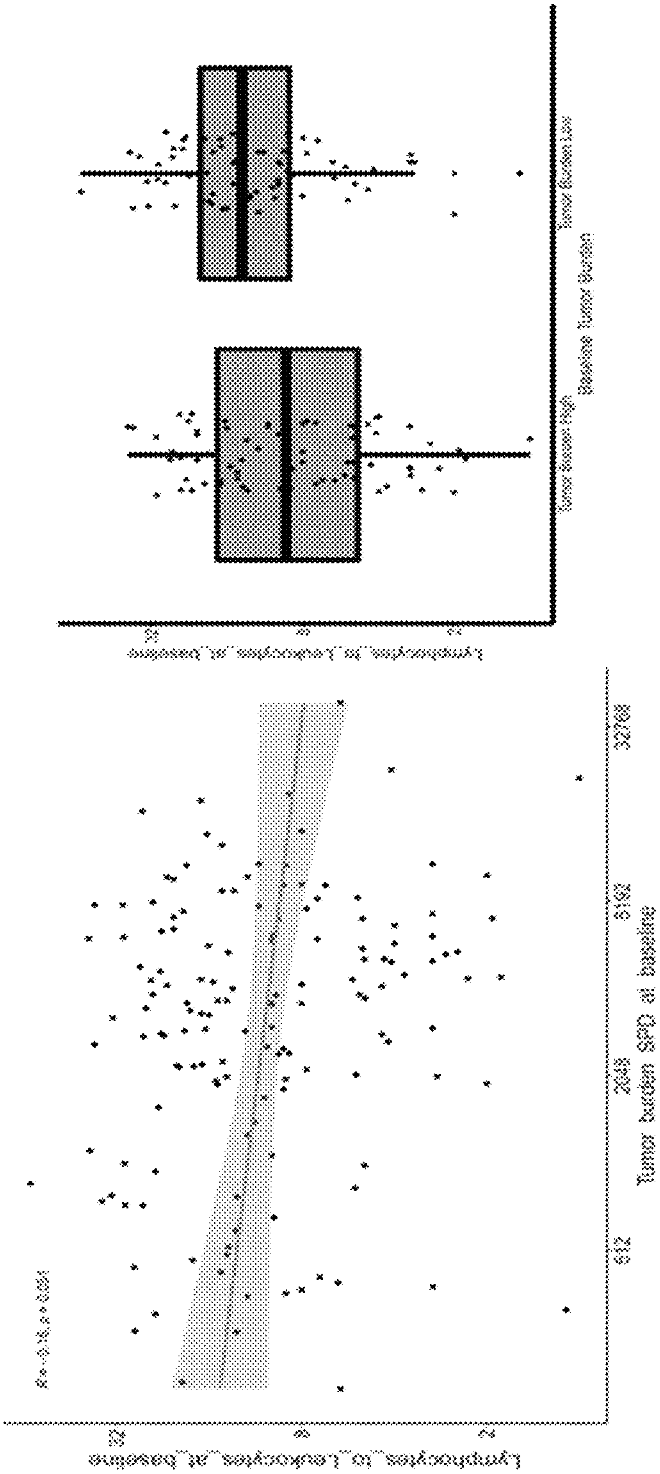
FIG. 23 Association between Lymphocyte to Leukocytes in baseline hematology cell counts and tumor burden by SPD at baseline. The % lymphocytes to leukocytes are negatively associated with tumor burden as shown by scatterplot (left) and boxplot grouped by category of tumor burden SPD at baseline.
Figure 24:
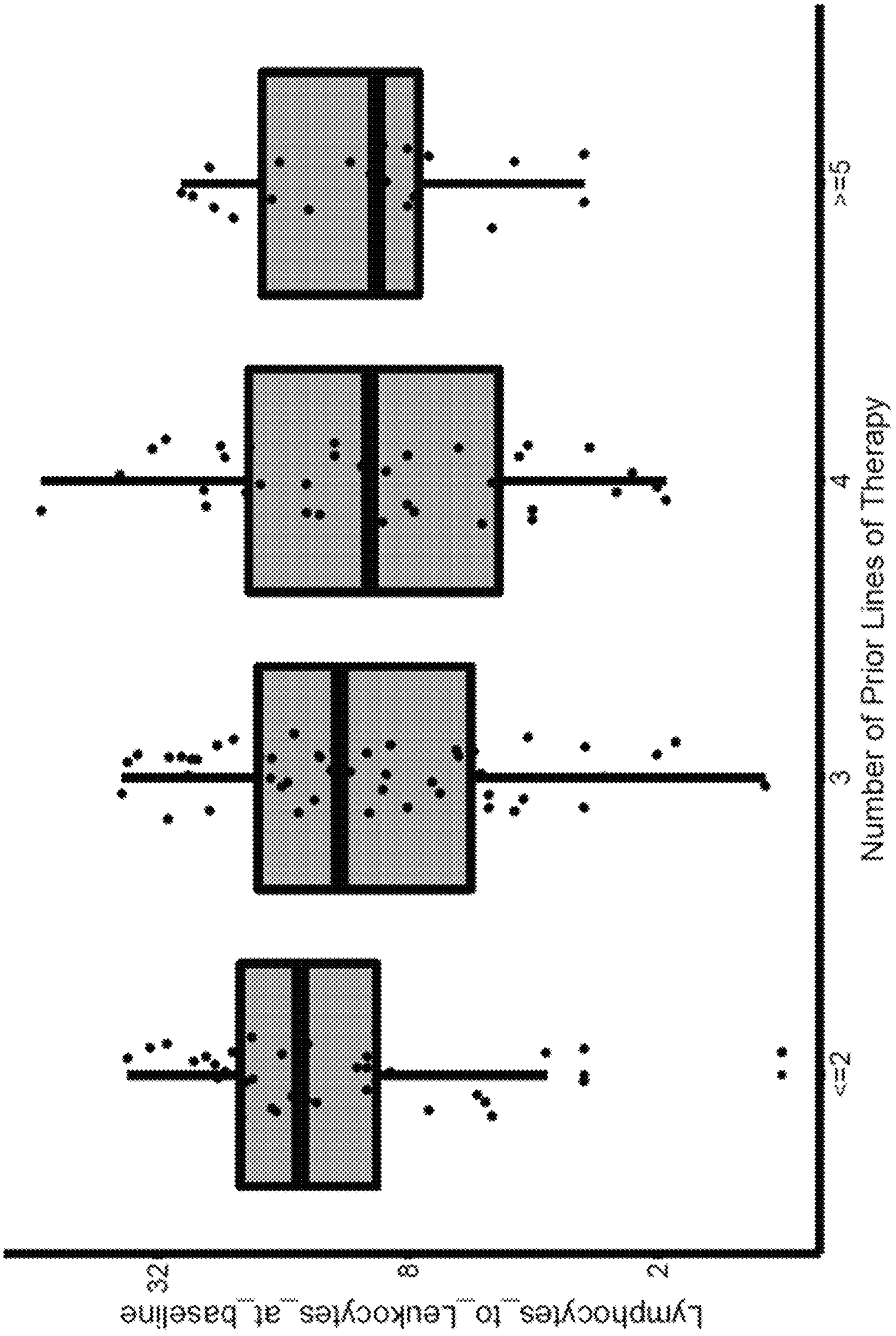
FIG. 24 Boxplot of the relationship between the % lymphocyte to leukocytes in baseline hematology cell counts and grouped number of prior lines of therapy. The % lymphocytes to leukocytes negatively associated with number of lines of prior therapy.
Figure 25:
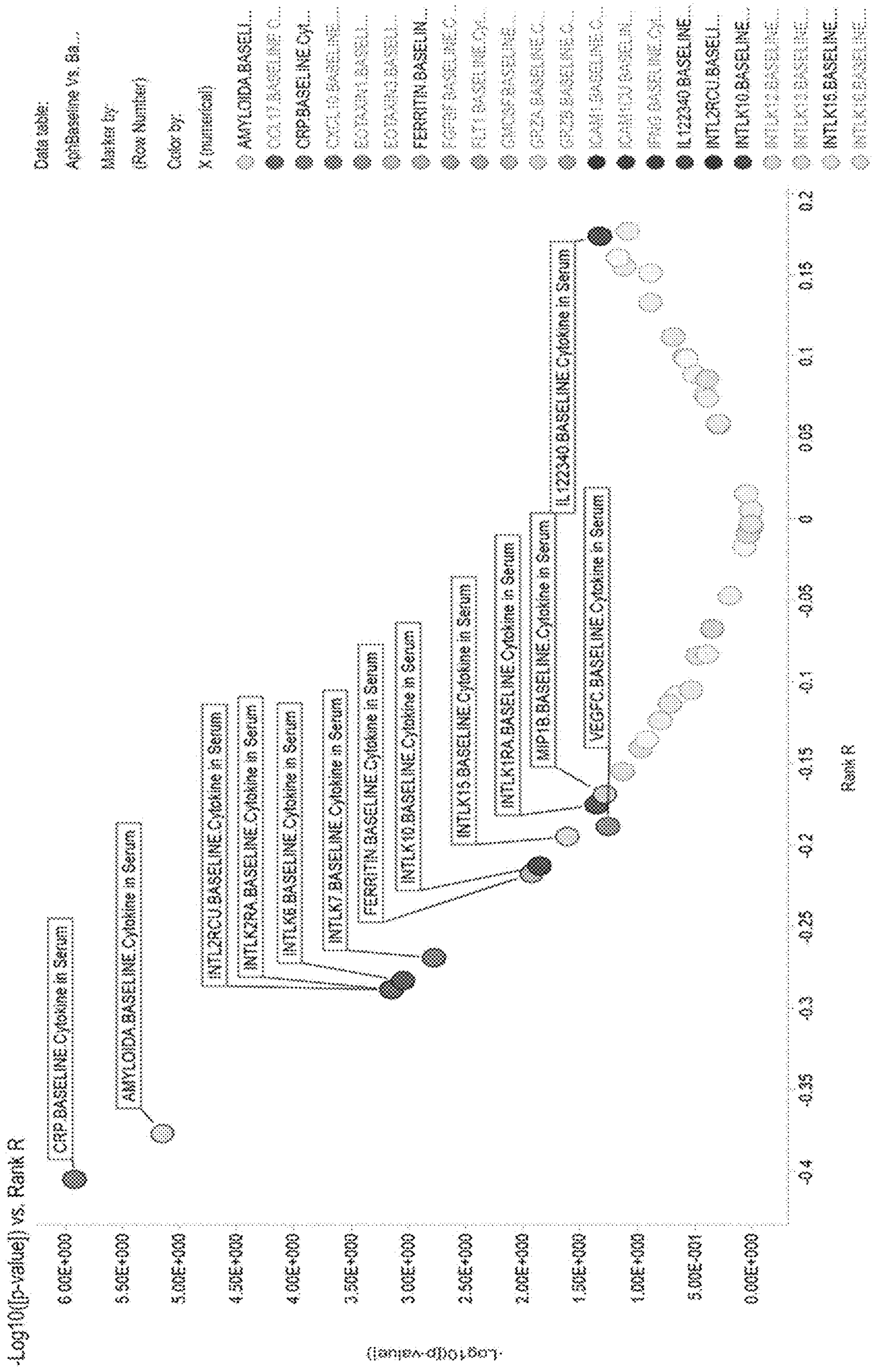
FIG. 25 Volcano plot of baseline serum cytokines and their Spearman Rank-Order correlation with the % Lymphocyte to Leukocytes in baseline hematology cell counts. The % lymphocytes to leukocytes is negatively associated with inflammatory and acute phase cytokines such as CRP, Ferritin, IL6.
Figure 26:
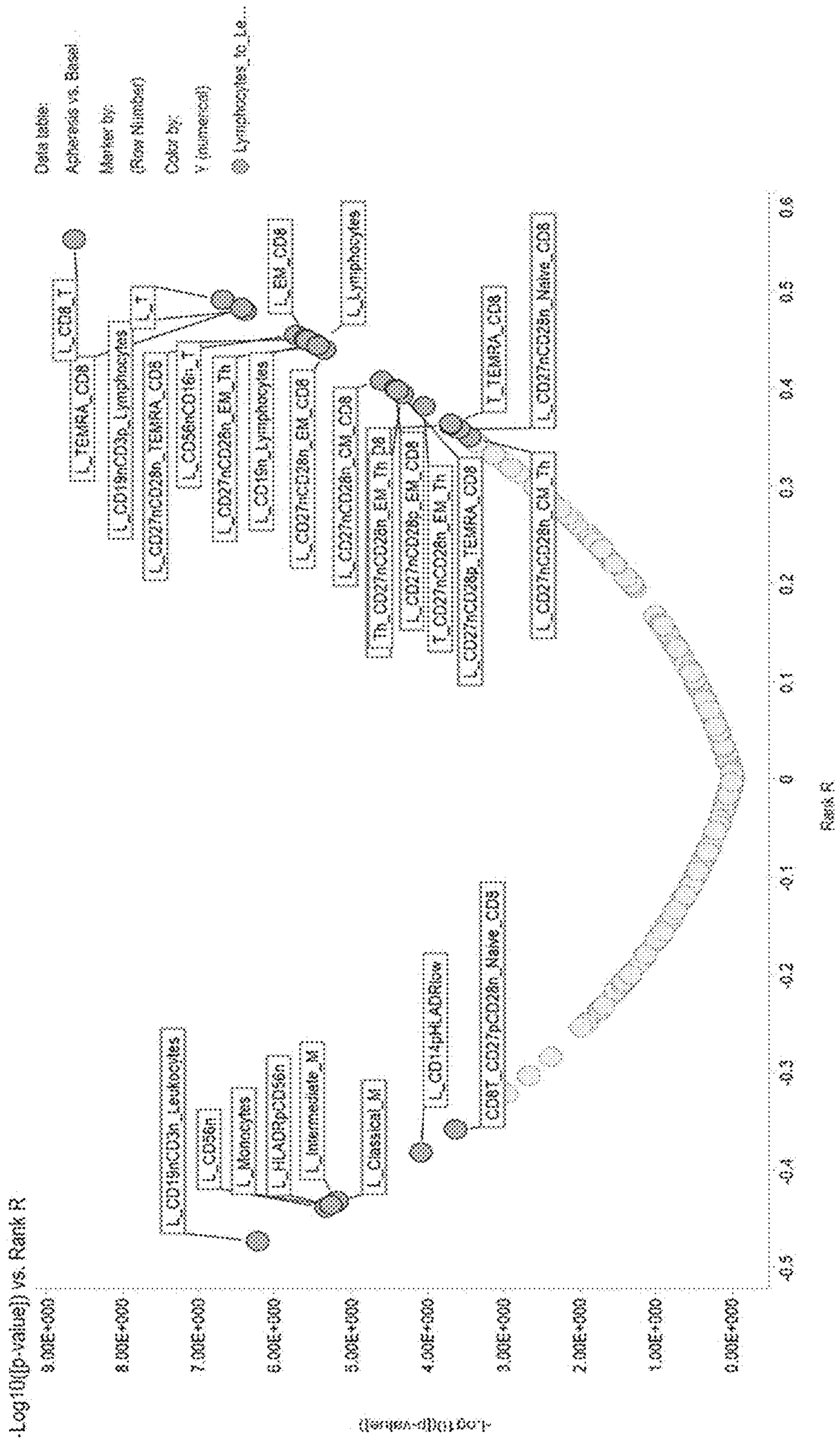
FIG. 26 Volcano plot of pre-manufacturing PBMC populations and their Spearman Rank-Order correlation with the % Lymphocyte to Leukocytes in baseline hematology cell counts. The % Lymphocyte to Leukocytes in baseline hematology cell counts is negatively associated myeloid cells and positively associated with CD8 and EM/Effector T-cells.

Lymphocyte to Leukocytes in baseline hematology cell counts had weak negative associations with worst grade of toxicity. FIG. 22. Lymphocyte to Leukocytes in baseline hematology cell counts was negatively associated with tumor burden. FIG. 23. Lymphocyte to Leukocytes in baseline hematology cell counts was negatively associated with the number of lines of prior therapy. FIG. 24. These data indicate that CAR T-cell utilization in earlier lines of therapy may lead to improved objective and durable responses due to positive predictors of response and product fitness being higher with fewer lines of therapy. Lymphocyte to Leukocytes in baseline hematology cell counts was positively associated with CD8 and effector cells in the product. Lymphocyte to Leukocytes in baseline hematology cell counts was negatively associated with CRP, Ferritin, IL6. CRP, ferritin, and IL6 have previously been shown to be pharmacodynamic markers that are negatively correlated with response in DLBCL. FIG. 25. Lymphocyte to Leukocytes in baseline hematology cell counts was negatively associated with myeloid cells (more specifically, intermediate monocytes, which are negatively associated with response) and positively associated with CD8 and EM/Effector T-cells. FIG. 26. Lymphocyte to Leukocytes in baseline hematology cell counts was negatively associated with intermediate monocytes and showed weak correlations with apheresis populations associated with response, including CD27−CD28+ TEMRA and Treg and CD27+CD28+Naïve and Th cells. B cells levels are most likely not the populations driving the lymphocyte levels due to the weak to no association shown. High B cell levels positively correlate with response. Lymphocyte to leukocyte in baseline hematology had limited or no association with CAR T peak cell expansion and naïve product T cells. Due to the limited association between these features, we can potentially use these in combination to better stratify patients.

Example 11

Figure 27A:
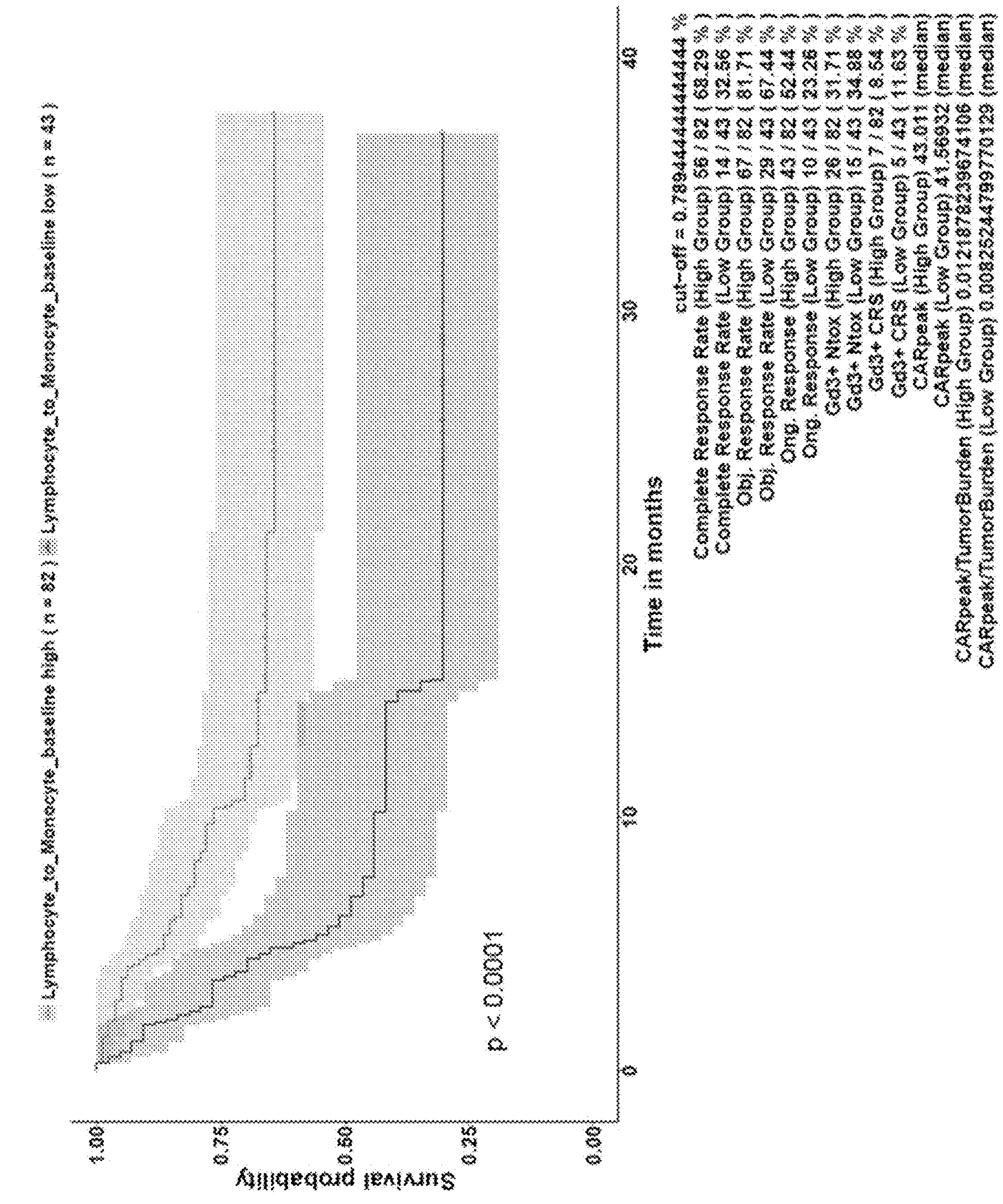
FIG. 27A Overall survival curve of clinical study subjects grouped by the ratio of lymphocytes to monocytes at baseline. Kaplan-Meier overall survival curve with an optimal cut-off selection for the ratio of lymphocytes to monocytes at baseline with significance determined by the Log-Rank test. The rate of complete response, objective response, ongoing response, grade 3+ toxicity, and CAR T cell expansion were determined for subjects above or below the optimal cut-off.
Figure 27B:
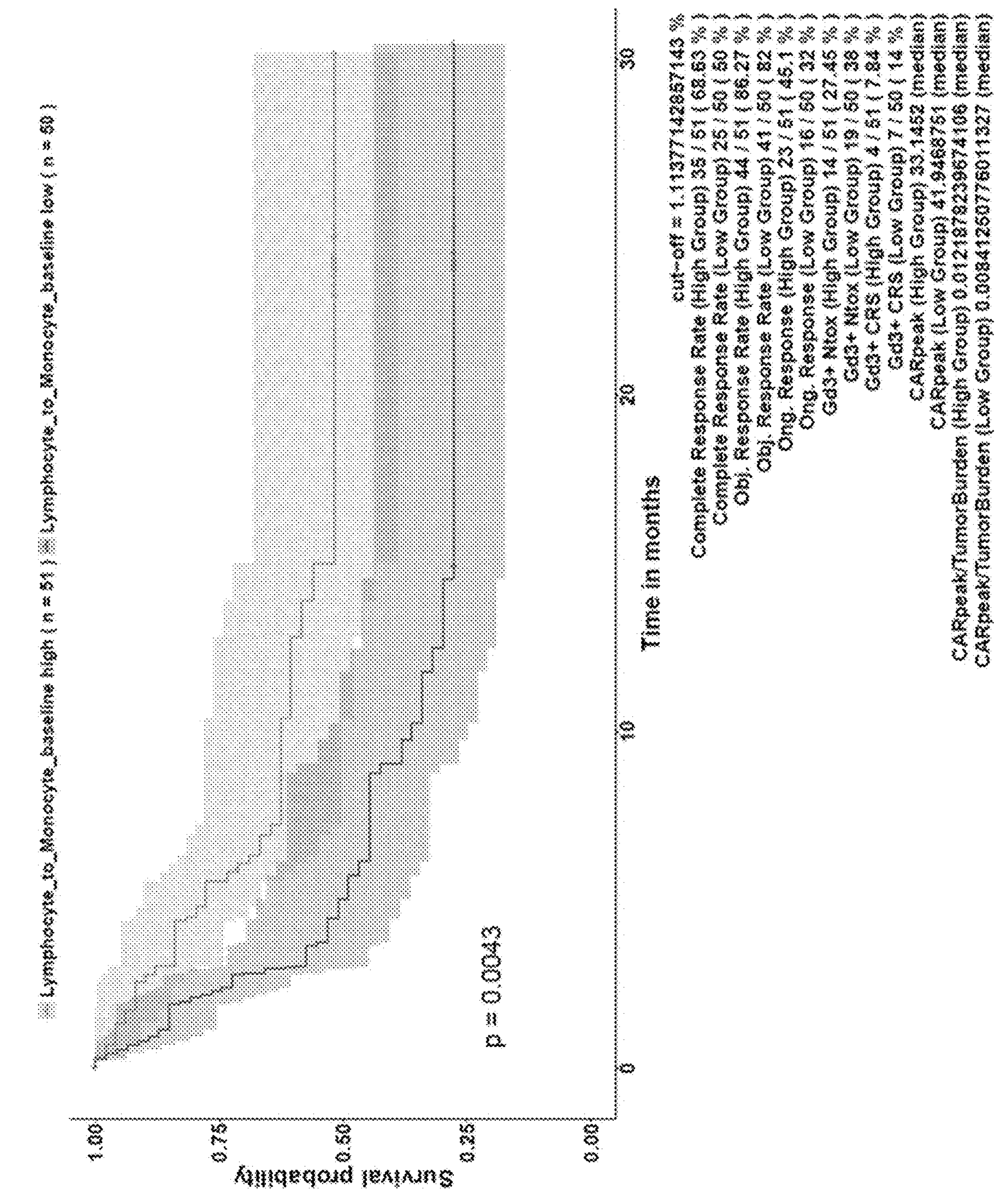
FIG. 27B Progression-freel survival curve of clinical study subjects grouped by the ratio of lymphocytes to monocytes at baseline. Kaplan-Meier progression-freel survival curve with an optimal cut-off selection for the ratio of lymphocytes to monocytes at baseline with significance determined by the Log-Rank test. The rate of complete response, objective response, ongoing response, grade 3+ toxicity, and CAR T cell expansion were determined for subjects above or below the optimal cut-off.
Figure 28:
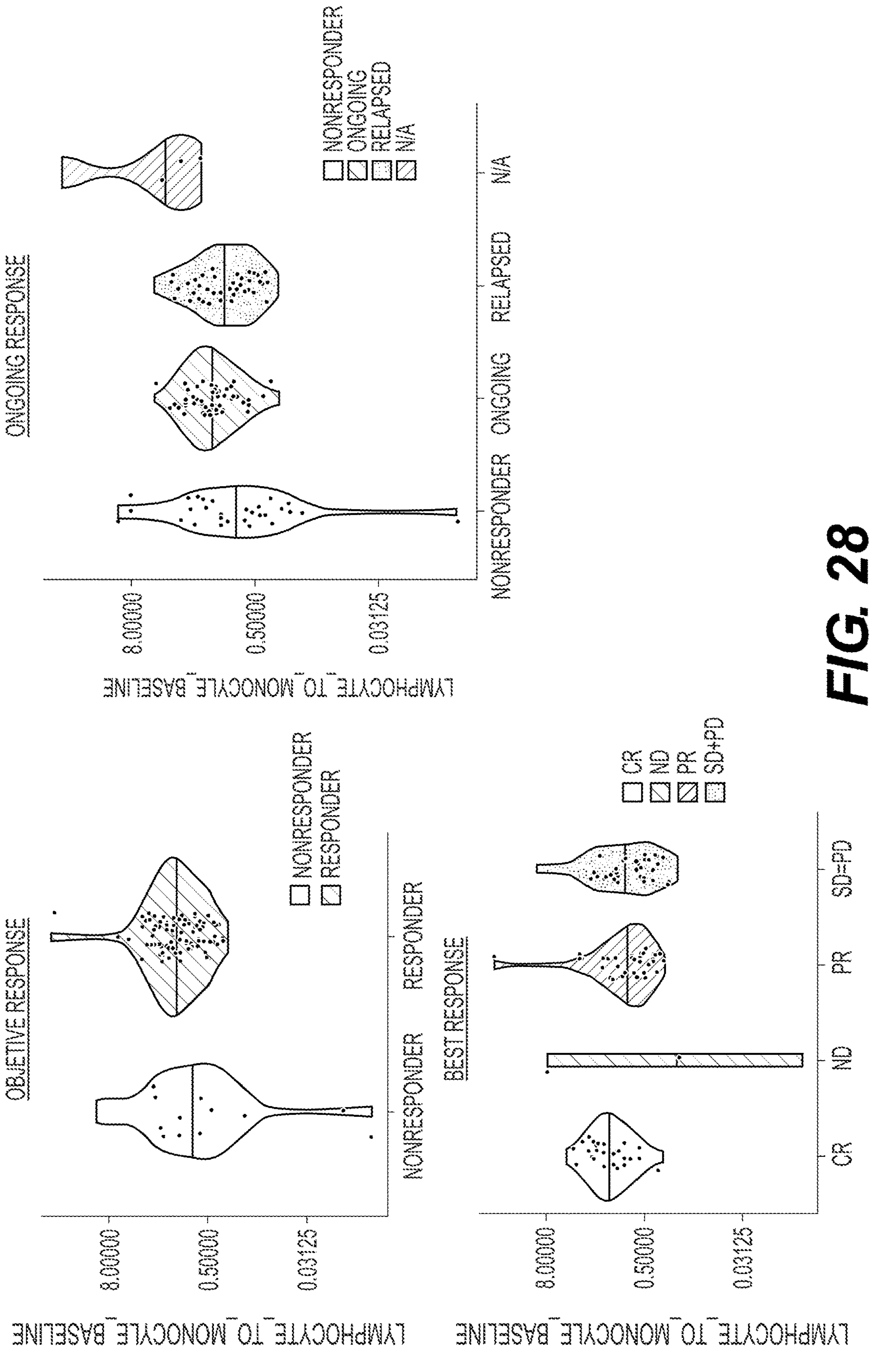
FIG. 28 Violin plots of the ratio of lymphocytes to monocytes at baseline grouped by response categories for evaluable clinical study subjects. The ratio of lymphocytes to monocytes positively associate with response.

Lymphocyte to Monocytes in baseline hematology cell counts associated positively with and may serve as a predictive biomarker for OS (FIG. 27A) and PFS (FIG. 27B) (optimal cutoff) (positive association). Lymphocyte to Monocytes in baseline hematology cell counts was positively associated with complete response, objective and ongoing response. FIG. 28. Lymphocyte to Monocytes in baseline hematology cell counts had weak negative associations with worst grade of toxicity. FIG. 29. Lymphocyte to Monocytes in baseline hematology cell counts was negatively associated with tumor burden. FIG. 30. Lymphocyte to Monocytes in baseline hematology cell counts was negatively associated with the number of lines of prior therapy. FIG. 31. This suggests that use of CAR-T cells as first or second line of therapy may lead to even better response rates. Lymphocyte to Monocytes in baseline hematology cell counts was positively associated with effector T cells. Lymphocyte to Monocytes in baseline hematology cell counts was negatively associated CRP and IL6. FIG. 32. Lymphocyte to Monocytes in baseline hematology cell counts was negatively associated with myeloid cells and positively associated with CD8 and EM/Effector T-cells. FIG. 33. Lymphocyte to Monocytes in baseline hematology cell counts was negatively associated with intermediate monocytes and showed weak correlations with apheresis populations associated with response, including CD27−CD28+ TEMRA and Treg and CD27+CD28+ Naïve and Th cells Lymphocyte to monocyte in baseline hematology had limited or no association with CAR T peak cell expansion and naïve product T cells.

Example 12

Axicabtagene ciloleucel is an autologous anti-CD19 chimeric antigen receptor (CAR) T-cell therapy approved for the treatment of relapsed or refractory LBCL after ≥2 lines of systemic therapy. A global Phase 3 randomized study, showed superiority of Axicabtagene ciloleucel vs standard-of-care 2L therapy (N=359; median event-free survival [EFS] 8.3 vs 2 months, [HR 0.398, P<0.0001]; estimated 2-year EFS 41% vs 16%; overall response rate [ORR] 83% vs 50%, Locke et al. NEJM 2021). This example discusses the Axicabtagene ciloleucel pharmacokinetics (PK), pharmacodynamics (PD), and product attributes associated with clinical outcomes.

Samples from patients who received Axicabtagene ciloleucel (n=170) were analyzed. P̈K, PD, and Axicabtagene ciloleucel T-cell composition (naïve, CCR7+CD45RA+; differentiated, CCR7−) were assessed for associations with safety and efficacy using previously described methodologies (Neelapu, et al. NEJM. 2017; Locke, et al. *Blood Adv.* 2020).

The median (Q1, Q3; n=162) peak CAR T-cell level, time to peak, and area under the curve within the first 28 days of treatment ($AUC_{0-28}$) were 25.8 cells/μl (8.2, 57.9), 8 days (8, 9), and 236.2 cells/μl*days (76.4, 758.0), respectively. CAR T-cell peak and $AUC_{0-28}$ positively correlated with ORR (P=0.0224 and 0.0054, respectively) and Grade (Gr)≥3 neurologic events (NEs; P=0.0006) but not with durability of response (P=0.4894) or Gr≥3 cytokine release syndrome (CRS; P=0.2040). Rapid transient increases in serum analytes, including granzyme B, ferritin, IL-6, IL-10, CXCL-10, IL-15, ICAM-1 and GM-CSF, occurred early (median peak ≤7 days) and were positively associated with Gr≥3 NEs and Gr≥3 CRS (P<0.05).

Infusion products richer in naive-like T cells expressing CD27 and CD28 positively associated with EFS, ORR, and complete response (P<0.05). In contrast, infusion products with higher % of differentiated T cells (CCR7−) and lower % of CCR7+CD45RA+ T cells associated positively with postinfusion peak levels and $AUC_{0-28}$ of several proinflammatory and immunomodulatory serum analytes. Increased rates of Gr≥3 NEs were found in patients who received Axicabtagene ciloleucel with >median number of CCR7− T cells (above median: 30% vs below median: 10%). Corroborating this, a trend of higher rates of Gr≥3 NEs and CRS were observed in patients who received Axicabtagene ciloleucel that secreted higher levels of IFN-7 in product co-culture with CD19-expressing targets.

In summary, Axicabtagene ciloleucel PK and PD profiles in the randomized phase 3 trial were associated with clinical outcomes. Pre-infusion product features and post-infusion PK/PD profiles associated with safety and efficacy outcomes, suggesting that optimizing product composition towards a juvenile T-cell phenotype (CCR7+CD45RA+) may improve Axicabtagene ciloleucel therapeutic index.

We claim:

1. A method for treating a hematological cancer in a patient comprising:

measuring a level of CD27+CD28+ naïve CD4+ T helper (Th) cells in an apheresis product from said patient; and administering an effective dose of T cells comprising a chimeric antigen receptor if the level of CD27+CD28+ naïve CD4+ Th cells is over a cut-off percentage value measured as a percentage of total leukocytes, or administering an effective dose of T cells comprising the chimeric antigen receptor and a combination therapy if the level of CD27+CD28+ naïve CD4+ Th cells is below said cut-off percentage value, wherein said cut-off percentage value is between 0.1%-0.5%, and wherein chimeric antigen receptor comprises an anti-CD19 single chain variable fragment (scFv).

2. The method of claim 1, wherein said cut-off percentage value is 0.27%.

3. The method of claim 1, further comprising:

measuring a level of intermediate monocytes in said apheresis product from said patient;

determining whether said patient should be administered an effective dose of T cells comprising a chimeric receptor, or an effective dose of T cells comprising a chimeric receptor and a combination therapy at least in part from said level of intermediate monocytes in said apheresis product; and administering said effective dose of T cells comprising a chimeric receptor, or said effective dose of T cells and said combination therapy based on said determining step, wherein said patient is administered said effective dose of T cells comprising a chimeric receptor if the level of intermediate monocytes is below a cut-off percentage value measured as a percentage of total leukocytes, and wherein said patient is administered said effective dose of T cells comprising a chimeric receptor and said combination therapy if the level of intermediate monocytes is above said cut-off percentage value.

4. The method of claim 3, wherein said cut-off percentage value is 1%, 2%, 3%, 4%, 5%, 6%, 7%, 8%, 9%, 10%, 15%, or 20%.

5. The method of claim 1, further comprising:

measuring a level of CD27-CD28+ TEMRA Treg cells in said apheresis product from said patient;

determining whether said patient should be administered an effective dose of T cells comprising a chimeric receptor, or an effective dose of T cells comprising a chimeric receptor and a combination therapy at least in part from said level of CD27−CD28+ TEMRA Treg cells in said apheresis product; and administering said effective dose of T cells comprising a chimeric receptor, or said effective dose of T cells and said combination therapy based on said determining step, wherein said patient is administered said effective dose of T cells comprising a chimeric receptor if the level of CD27−CD28+ TEMRA Treg cells is above a cut-off percentage value measured as a percentage of total leukocytes, and wherein said patient is administered said effective dose of T cells comprising a chimeric receptor and said combination therapy if the level of CD27−CD28+ TEMRA Treg cells is below said cut-off percentage value.

6. The method of claim 5, wherein said cut-off percentage value is 0.1%, 0.2%, 0.3%, 0.4%, 0.5%, 0.6%, 0.7%, 0.8%, 0.9%, 1%, 1-5%, 5-10%, or 10-20%.

7. The method of claim 1, further comprising:

measuring a lymphocyte to leukocyte ratio in a baseline hematology count of said patient;

determining whether said patient should be administered an effective dose of T cells comprising a chimeric receptor, or an effective dose of T cells comprising a chimeric receptor and a combination therapy at least in part from said lymphocyte to leukocyte ratio; and administering said effective dose of T cells comprising a chimeric receptor, or said effective dose of T cells and said combination therapy based on said determining step, wherein said patient is administered said effective dose of T cells comprising a chimeric receptor if the lymphocyte to leukocyte ratio is above a cut-off value, and wherein said patient is administered said effective dose of T cells comprising a chimeric receptor and said combination therapy if the lymphocyte to leukocyte ratio is below said cut-off value.

8. The method of claim 7, wherein said cut-off value is 1%, 1-5%, 5-10%, 10-15%, 15-20%, 20-25%, 25-30%, or 30-35%.

9. The method of claim 1, further comprising:

measuring a lymphocyte to monocyte ratio in a baseline hematology count of said patient; and administering an effective dose of T cells comprising the chimeric antigen receptor if the lymphocyte to monocyte ratio is above a cut-off value, or administering an effective dose of T cells comprising the chimeric antigen receptor and a combination therapy if the lymphocyte to monocyte ratio is below said cut-off value, wherein said cut-off value is between 0.5-1.0.

10. The method of claim 9, wherein said cut-off value is 0.79.

11. The methods of claim 1, wherein said combination therapy comprises immunotherapies, SRC kinase inhibitors, T cell bi-specific antibodies, anti-CD20 monoclonal antibody, anti-4-1BB, anti-CD47, TGF-beta inhibitors or dominant negative TGF-beta, mTOR/AKT agonists, histone deacetylase inhibitors, chemo- or radio-therapies, small molecule inhibitors, antibodies targeted towards enhancing anti-tumor immunity, or anti-inflammatory medications.

12. The method of claim 11, wherein said combination therapy is selected from the list consisting of cyclophosphamide, fluorouracil, gemcitabine, doxorubicin, taxanes, dasatinib, rituximab, tocilizumab, siltuximab, dexamethasone, etanercept, infliximab, anakinra, lenzilumab, bevacizumab, corticosteroids, and atezolizumab.

13. A method for treating a hematological cancer in a patient comprising:

measuring a level of CD27+CD28+ naïve CD4+ T helper (Th) cells in an apheresis product from said patient;

measuring a lymphocyte to monocyte ratio in a baseline hematology count of said patient; and administering an effective dose of T cells comprising a chimeric antigen receptor if the level of CD27+CD28+ naïve CD4+ Th cells is over a cut-off percentage value measured as a percentage of total leukocytes, or administering an effective dose of T cells comprising the chimeric antigen receptor and a combination therapy if the level of CD27+CD28+ naïve CD4+ Th cells is below said cut-off percentage value, wherein said cut-off percentage value is between 0.1%-0.5%, or administering an effective dose of T cells comprising the chimeric antigen receptor if the lymphocyte to monocyte ratio is above a cut-off value, or administering an effective dose of T cells comprising the chimeric antigen receptor and a combination therapy if the lymphocyte to monocyte ratio is below said cut-off value, wherein said cut-off value is 0.79, wherein chimeric antigen receptor comprises an anti-CD19 single chain variable fragment (scFv).

14. The method of claim 13, wherein said combination therapy comprises immunotherapies, SRC kinase inhibitors, T cell bi-specific antibodies, anti-CD20 monoclonal antibody, anti-4-1BB, anti-CD47, TGF-beta inhibitors or dominant negative TGF-beta, mTOR/AKT agonists, histone deacetylase inhibitors, chemo- or radio-therapies, small molecule inhibitors, antibodies targeted towards enhancing anti-tumor immunity, or anti-inflammatory medications.

15. The method of claim 14, wherein said combination therapy is selected from the list consisting of cyclophosphamide, fluorouracil, gemcitabine, doxorubicin, taxanes, dasatinib, rituximab, tocilizumab, siltuximab, dexamethasone, etanercept, infliximab, anakinra, lenzilumab, bevacizumab, corticosteroids, and atezolizumab.

* * * * *

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Thr Ser Gly Ser Gly Lys Pro Gly Ser Gly Glu Gly Ser Thr
1               5                   10                  15

Lys Gly


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Gly Gly Gly Gly Ser
1               5
```